(12) United States Patent
Ohto et al.

(10) Patent No.: US 7,501,268 B2
(45) Date of Patent: Mar. 10, 2009

(54) METHODS OF PRODUCING PRENYL ALCOHOLS

(75) Inventors: Chikara Ohto, Toyota (JP); Shusei Obata, Nagoya (JP); Masayoshi Muramatsu, Aichi (JP); Kiyohiko Nishi, Saga (JP); Kazuhiko Totsuka, Yamato (JP)

(73) Assignee: Toyota Jidosha Kabushiki Kaisha, Aichi-Ken (JP)

( * ) Notice: Subject to any disclaimer, the term of this patent is extended or adjusted under 35 U.S.C. 154(b) by 785 days.

(21) Appl. No.: 10/451,643

(22) PCT Filed: Dec. 20, 2001

(86) PCT No.: PCT/JP01/11214

§ 371 (c)(1),
(2), (4) Date: Jun. 24, 2003

(87) PCT Pub. No.: WO02/053746

PCT Pub. Date: Jul. 11, 2002

(65) Prior Publication Data

US 2007/0087425 A1 Apr. 19, 2007

(30) Foreign Application Priority Data

Dec. 28, 2000 (JP) ............................. 2000-403067

(51) Int. Cl.
*C12P 7/02* (2006.01)
*C12P 7/58* (2006.01)
*C12N 9/10* (2006.01)
*C12N 1/00* (2006.01)
*C12N 15/74* (2006.01)
*C12N 15/00* (2006.01)
*C07H 21/04* (2006.01)

(52) U.S. Cl. .................... 435/155; 435/193; 435/254.2; 435/254.21; 435/320.1; 435/483; 435/137; 536/23.2

(58) Field of Classification Search ........................ None
See application file for complete search history.

(56) References Cited

U.S. PATENT DOCUMENTS

| 5,460,949 | A | | 10/1995 | Saunders et al. ............... 435/55 |
| 5,578,466 | A | * | 11/1996 | Hayano et al. ............. 435/69.7 |
| 5,663,461 | A | | 9/1997 | Mori et al. .................. 568/886 |
| 5,773,273 | A | | 6/1998 | Nishino et al. .............. 435/193 |
| 6,040,165 | A | | 3/2000 | Narita et al. ................ 435/193 |
| 6,156,913 | A | | 12/2000 | Hyatt ......................... 549/408 |
| 6,225,096 | B1 | | 5/2001 | Narita et al. ................ 435/132 |
| 6,242,227 | B1 | | 6/2001 | Millis et al. ................. 435/125 |
| 6,262,279 | B1 | | 7/2001 | Hyatt ......................... 549/408 |

FOREIGN PATENT DOCUMENTS

| EP | 0 509 841 A2 | | 10/1992 |
| EP | 1 219 704 A2 | | 7/2002 |
| JP | 5-115298 | | 5/1993 |
| JP | 5-192184 | | 8/1993 |
| JP | 8-242861 | | 9/1996 |
| WO | WO00/01649 | | 1/2000 |
| WO | WO00/01650 | | 1/2000 |
| WO | WO 00/01650 | * | 1/2000 |
| WO | WO00/01685 | | 1/2000 |
| WO | WO00/01686 | | 1/2000 |

OTHER PUBLICATIONS

Anderson et al, Farnesyl Diphosphate Synthase, JBC., 1989, vol. 264(32): 19176-19184.*
Anderson et al., Farnesyl diphosphate synthetase. Molecular cloning, sequence and expression of an essential gene from *Saccharomyces cerevisiae*. J. Biol. Chem., 1989, vol. 264: 19176-19184. (Seq Align only).*
Fujisaki et al., Cloning and nucleotide sequence of the ispA gne responsible for farnesyl diphosate synthase activity in *Escherichia coli*. J. Biochem., 1990, vol. 108: 995-1000. (Seq Align only).*
Jiang et al., BTS1 encodes a geranylgeranyl diphosphate synthase in *Saccharomyces cerevisiae*. J. Biol. Chem., 1995, 270: 21793-21799. (Seq Align only).*
Broun et al., Catalytic plasticity of fatty acid modification enzymes underlying chemical diversity of plant lipids. Science, 1998, vol. 282: 1315-1317.*
Witkowski et al., Conversion of b-ketoacyl synthase to a malonyl decarboxylase by replacemnt of the active-site cysteine with glutamine. Biochemistry, 1999, vol. 38: 11643-11650.*
Seffernick et al., Melamine deaminase and Atrazine chlorohydrolase: 98 percent identical but functionally different. J. Bacteriol.,2001, vol. 183 (8): 2405-2410.*
Lindbladh et al., Metabolic studies on *Saccharomyces cerevisiae* containing fused citrate synthase/malate dehydrogenase. Biochemistry, 1994, vol. 33: 11684-11691.*
Mewes, H. W., et al., "Overview of the yeast genome", *Nature*, vol. 387, Supp., May 29, 1997, pp. 7-65.
Hahn, Frederick M, et al., "*Escherichia coli* Open Reading Fram 696 Is *idi*, a Nonessential Gene Encoding Isopentenyl Diphosphate Isomerase", *Journal of Bacteriology*, vol. 181, No. 15, Aug. 1999, pp. 4499-4504.
Chambon C., et al.: Isolation and Properties of Yeast Mutants . . . , Curr. Genet., vol. 18, p. 41-46 (1990).
N. Kamimura, et al.: Construction of Squalene-accumulating *Saccharomyces* . . . , Appl. Microbiol. Biotechnol., vol. 42, p. 353-357 (1994).
Thomas E. Meigs, et al.: Regulation of 3-Hydroxy-3-methylglutaryl-Coenzyme A Reductase . . . , Journal of Biological Chemistry, vol. 271, No. 14, p. 7916-7922 (1996).

(Continued)

*Primary Examiner*—Rebecca E. Prouty
*Assistant Examiner*—Ganapathirama Raghu
(74) *Attorney, Agent, or Firm*—Kenyon & Kenyon LLP

(57) ABSTRACT

A method of producing a prenyl alcohol, comprising creating a recombinant by transferring into a host a recombinant DNA for expression or a DNA for genomic integration each comprising a prenyl diphosphate synthase gene or a mutant thereof, culturing the resultant recombinant, and recovering the prenyl alcohol from the resultant culture.

16 Claims, 65 Drawing Sheets

OTHER PUBLICATIONS

R. Kennedy Keller, et al.: *Farnesol is not the Nonsterol Regulator* . . . , Archives of Biochemistry and Biophysics, vol. 328, No. 2, Article No. 0180, p. 324-330 (1996).

Anna Szkopinska, et al.: *Polyprenol Formation in the Yeast Saccharomyces cerevisiae*, Journal of Lipid Research, vol. 38, p. 962-968 (1997).

Polakowski T., et al.: *Overexpression of a Cytosolic Hydroxymethylglutaryl-CoA* . . . , Appl. Microbiol. Biotechnol., vol. 49, p. 66-71 (1998).

Dorota Grabowska, et al.: *Effect of Squalene Synthase Gene Disruption on* FEBS Letters, vol. 434, p. 406-408 (1998).

Kiyotaka Machida, et al.: *Farnesol-induced Growth Inhibition in Microbiology*, vol. 145, p. 293-299 (1999).

Anna Szkopinska, et al.: *The Regulation of Activity of Main Mevalonic Acid* . . . , Biochemical and Biophysical Research Communications, vol. 267, p. 473-477 (2000).

Michel E. Basson, et al.: "*Structural and Functional Conversation between Yeast and Human* . . . ", Molecular and Cellular Biology, vol. 8, No. 9, Sep. 1988, pp. 3797-3808.

Mary Thorsness, et al.: "*Positive and Negative Transcriptional Control by Heme of Genes* . . . ", Molecular and Cellular Biology, vol. 9, No. 12, Dec. 1989, pp. 5702-5712.

Joseph L. Goldstein & Michael S. Brown, "*Regulation of the mevalonate pathway*", Nature, vol. 343, Feb. 1990, pp. 425-430.

Christian Sengstag, et al., "*Genetic and Biochemical Evaluation and Eucaryotic Membrane* . . . ", Molecular and Cellular Biology, vol. 10, No. 2, Feb. 1990, pp. 672-680.

Christopher Chambon, et al. ,"*Sterol Pathway Yeast. Identification and Properties of Mutant* . . . ", Lipids, vol. 26, No. 8, 1991, pp. 633-636.

B. Behalova, et al., "Regulation of Sterol Biosynthesis in *Saccharomyces cerevisiae*", Folia Microbiol, vol. 39, No. 4, 1994, pp. 287-290.

Randolph Y. Hampton and Jasper Rine, *Regulated Degradation of HMG-CoA Reductase, an Integral* . . . , The Journal of Cell Biology, vol. 125, No. 2, Apr. 1994, pp. 299-312.

Shigeyuki Yamoto, et al., "*Metabolic Engineering for Production of β-Carotene and Lycopene in* . . . ", Biosci. Biotech Biochem., vol. 58, No. 6, 1994, pp. 1112-1114.

Susumu Kajiwara, et al., "*Expression of an exogenous isopentenyl diphosate isomerase* . . . ", Biochem. J., vol. 324, 1997, pp. 421-426.

K. Allen G. Donald, et al., "*Effects of Overproduction of the Catalytic Domain of* . . . ", Applied and Environmental Microbiology, vol. 63, No. 9, Sep. 1997, pp. 3341-3344.

Norihiko Misawa and Hisoshi Shimada, "*Metabolic engineering for the production of carotenoids in* . . . ", Journal of Biotechnology, vol. 59, 1998, pp. 169-181.

Randolph Y. Hampton, "*Genetic analysis of hydroxymethylglutaryl-coenzyme A* . . . ", Current Opinion in Lipidology, 1998, pp. 9397.

Yutaka Miura et al., "*Production of the Carotenoids Lycopene β-Carotene, and* . . . ", Environmental Microbiology, vol. 64, No. 4, Apr. 1998, pp. 1226-1229.

Yutaka Miura et al., "Production of Lycopene by the Food Yeast, *Canidida utilis* . . . ", Biotechnology and Bioengineering, vol. 58, Nos. 2&3, Apr./May 1998, pp. 306-308.

Hisashi Hemmi, et al., "Identification of Genes Affecting Lycopene Formation in *Escherichia* . . . ", J. Biochem., vol. 123, 1998, pp. 1088-1096.

Hiroshi Shimada, et al., "Increased Caratenoid Production by the Food Yeast *Candida utilis* . . . ", Applied and Environmental Microbiology, vol. 64, No. 7, Jul. 1998, pp. 2676-2680.

Richard Gardner, et al., "*Sequence Detriminants for Regulated Degradation of* . . . ", Molecular Biology of the Cell, vol. 9, 1998, pp. 2611-2626.

Chia-Wei Wang, et al., "*Engineered Isoprenoid Pathway Enhances Astaxanthin Production in* . . . ", Biotechnology and Bioengineering, vol. 62, No. 2, Jan. 1999, pp. 235-241.

Dago Dimster-Denk, et al., "*Comprehensive evaluation of isoprenoid biosynthesis* . . . ", Journal of Lipid Research, vol. 40, 1999, pp. 850-860.

Deborah A. Profant, et al., *The Role of the 3-Hydroxy 3-Methylglutaryl Coenzyme A Reductase* . . . , Molecular Biology of the Cell, vol. 10, Oct. 1999, pp. 3409-3423.

Richard G. Gardner and Randolph Y. Hampton, "*A Highly Conserved Signal Controls Degradation of* . . . ", The Journal of Biological Chemistry, vol. 274, No. 44, Oct. 1999, pp. 31671-31678.

William R. Farmer and James C. Liao, "Improving lycopene production in *Escherichia coli* by engineering . . . ", Nature Biotechnology, vol. 18 May 2000, pp. 533-537.

Deborah A. Profant, et al., *Mutational analysis of the karmellae-inducing signal in Hmglp, a yeast* . . . , Yeast 2000, vol. 16, 2000, pp. 811-827.

Danuta Plochocka, et al., "The role of *ERG20* gene (encoding yeast farnesyl dephosphate synthase) . . . ", Biochemie, vol. 82, 2000, pp. 733-738.

William R. Farmer and James C. Liao, "*Precursor Balancing for Metabolic Engineering of Lycopene Production* . . . ", Biotechnol. Prog., vol. 17, 2001, pp. 57-61.

Ahmad Oulmouden and Francis Karst, "Isolation of the *ERG12* gene of *Saccharomyces cerevisiae* encoding . . . ", Gene, vol. 88, 1990, pp. 253-257.

Shingo Fujisaki, et al., "Cloning and Nucleotide Sequence of the *ispA* Gene Responsible for . . . ", J. Biochem., vol. 108, 1990, pp. 995-1000.

Yim H. Tsay and Gordon W. Robinson, "Cloning and Characterization of *ERG8*, and Essential Gene of . . . ", Molecular and Cellular Biology, vol. 11, No. 2, 1991, pp. 620-631.

Matthias P. Mayer, et al., "Disruption and Mapping of *IDI* 1, the Gene for Isopentenyl Diphosphate . . . ", Yeast, vol. 8, 1992, pp. 743-748.

Laree Hiser, et al., "*ERG10* from *Saccharomyces cerevisiae* Encodes Acetoacetyl-CoA Thiolase", The Journal of Biological Chemistry, vol. 269, No. 50, Dec. 1994, pp. 31383-31389.

Yu Jiang, et al., "*BTS1* Encodes a Geranylgeranyl Diphosphate Synthase in . . . ", The Journal of Biological Chemistry, vol. 270, No. 37, Sep. 1995, pp. 21793-21799.

Matt S. Anderson, et al., "*Farnesyl Diphosphate Synthetase*", The Journal of Biological Chemistry, vol. 264, No. 32, Nov. 1989, pp. 19176-19184.

Laurence Blanchard and Francis Karst, "*Characterization of a lysine-to-glutamic acid mutation in a conservative* . . . ", Gene, vol. 125, 1993, pp. 185-189.

* cited by examiner

Fig.5

```
GGATCCTCTA GCTCCCTAAC ATGTAGGTGG CGGAGGGGAG ATATACAATA GAACAGATAC CAGACAAGAC
CCTAGGAGAT CGAGGGATTG TACATCCACC GCCTCCCCTC TATATGTTAT CTTGTCTATG GTCTGTTCTG
    10         20         30         40         50         60         70

ATAATGGGCT AAACAAGACT ACACCAATTA CACTGCCTCA TTGATGGTGG TACATAACGA ACTAATACTG
TATTACCCGA TTTGTTCTGA TGTGGTTAAT GTGACGGAGT AACTACCACC ATGTATTGCT TGATTATGAC
    80         90        100        110        120        130        140

TAGCCCTAGA CTTGATAGCC ATCATCATAT CGAAGTTTCA CTACCCTTTT TCCATTTGCC ATCTATTGAA
ATCGGGATCT GAACTATCGG TAGTAGTATA GCTTCAAAGT GATGGGAAAA AGGTAAACGG TAGATAACTT
   150        160        170        180        190        200        210

GTAATAATAG GCGCATGCAA CTTCTTTTCT TTTTTTTTCT TTTCTCTCTC CCCCGTTGTT GTCTCACCAT
CATTATTATC CGCGTACGTT GAAGAAAAGA AAAAAAAAGA AAAGAGAGAG GGGGCAACAA CAGAGTGGTA
   220        230        240        250        260        270        280

ATCCGCAATG ACAAAAAAAT GATGGAAGAC ACTAAAGGAA AAAATTAACG ACAAAGACAG CACCAACAGA
TAGGCGTTAC TGTTTTTTTA CTACCTTCTG TGATTTCCTT TTTTAATTGC TGTTTCTGTC GTGGTTGTCT
   290        300        310        320        330        340        350

TGTCGTTGTT CCAGAGCTGA TGAGGGGTAT CTCGAAGCAC ACGAAACTTT TTCCTTCCTT CATTCACGCA
ACAGCAACAA GGTCTCGACT ACTCCCCATA GAGCTTCGTG TGCTTTGAAA AAGGAAGGAA GTAAGTGCGT
   360        370        380        390        400        410        420

CACTACTCTC TAATGAGCAA CGGTATACGG CCTTCCTTCC AGTTACTTGA ATTTGAAATA AAAAAAGTTT
GTGATGAGAG ATTACTCGTT GCCATATGCC GGAAGGAAGG TCAATGAACT TAAACTTTAT TTTTTTCAAA
   430        440        450        460        470        480        490

GCTGTCTTGC TATCAAGTAT AAATAGACCT GCAATTATTA ATCTTTTGTT TCCTCGTCAT TGTTCTCGTT
CGACAGAACG ATAGTTCATA TTTATCTGGA CGTTAATAAT TAGAAAACAA AGGAGCAGTA ACAAGAGCAA
   500        510        520        530        540        550        560

CCCTTTCTTC CTTGTTTCTT TTTCTGCACA ATATTTCAAG CTATACCAAG CATACAATCA ACTGGTACCC
GGGAAAGAAG GAACAAAGAA AAAGACGTGT TATAAAGTTC GATATGGTTC GTATGTTAGT TGACCATGGG
   570        580        590        600        610        620        630

GGGTCGACTC GAGCTCTAGA GGTTAACTAA GCGAATTTCT TATGATTTAT GATTTTTATT ATTAAATAAG
CCCAGCTGAG CTCGAGATCT CCAATTGATT CGCTTAAAGA ATACTAAATA CTAAAAATAA TAATTTATTC
   640        650        660        670        680        690        700

TTATAAAAAA AATAAGTGTA TACAAATTTT AAAGTGACTC TTAGGTTTTA AAACGAAAAT TCTTATTCTT
AATATTTTTT TTATTCACAT ATGTTTAAAA TTTCACTGAG AATCCAAAAT TTTGCTTTTA AGAATAAGAA
   710        720        730        740        750        760        770

GAGTAACTCT TTCCTGTAGG TCAGGTTGCT TTCTCAGGTA TAGCATGAGG TCGCTCTTAT TGACCACATC
CTCATTGAGA AAGGACATCC AGTCCAACGA AAGAGTCCAT ATCGTACTCC AGCGAGAATA ACTGGTGTAG
   780        790        800        810        820        830        840

TCTACCGGCA TGCCGAGCAA ATGCCTGCAA ATCGCTCCCC ATTTCACCCA ATTGTAGATA TGCTAACTCC
AGATGGCCGT ACGGCTCGTT TACGGACGTT TAGCGAGGGG TAAAGTGGGT TAACATCTAT ACGATTGAGG
   850        860        870        880        890        900        910

AGCAATGAGT TGATGAATCT CGGTGTGTAT TTTATGTCCT CAGAGGACAA CACCTGTTGT AATCGTTCTT
TCGTTACTCA ACTACTTAGA GCCACACATA AAATACAGGA GTCCTGTT GTGGACAACA TTAGCAAGAA
   920        930        940        950        960        970        980

CCACACGGAT CC
GGTGTGCCTA GG
   990
```

Fig.11
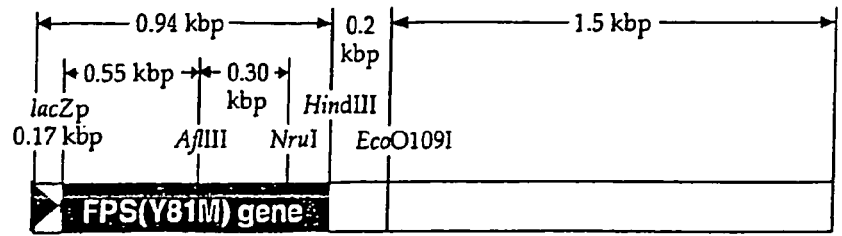
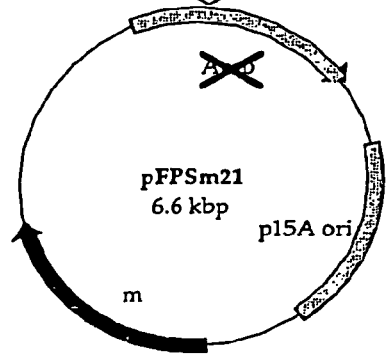
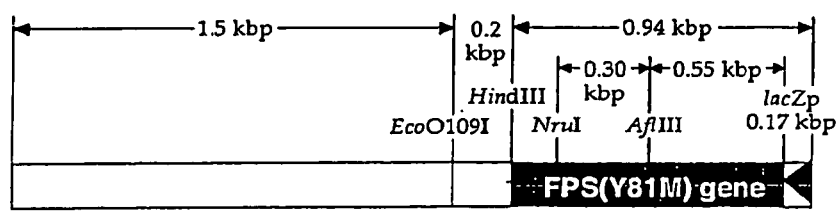
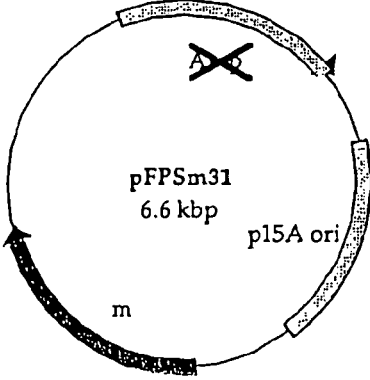

Fig.15A
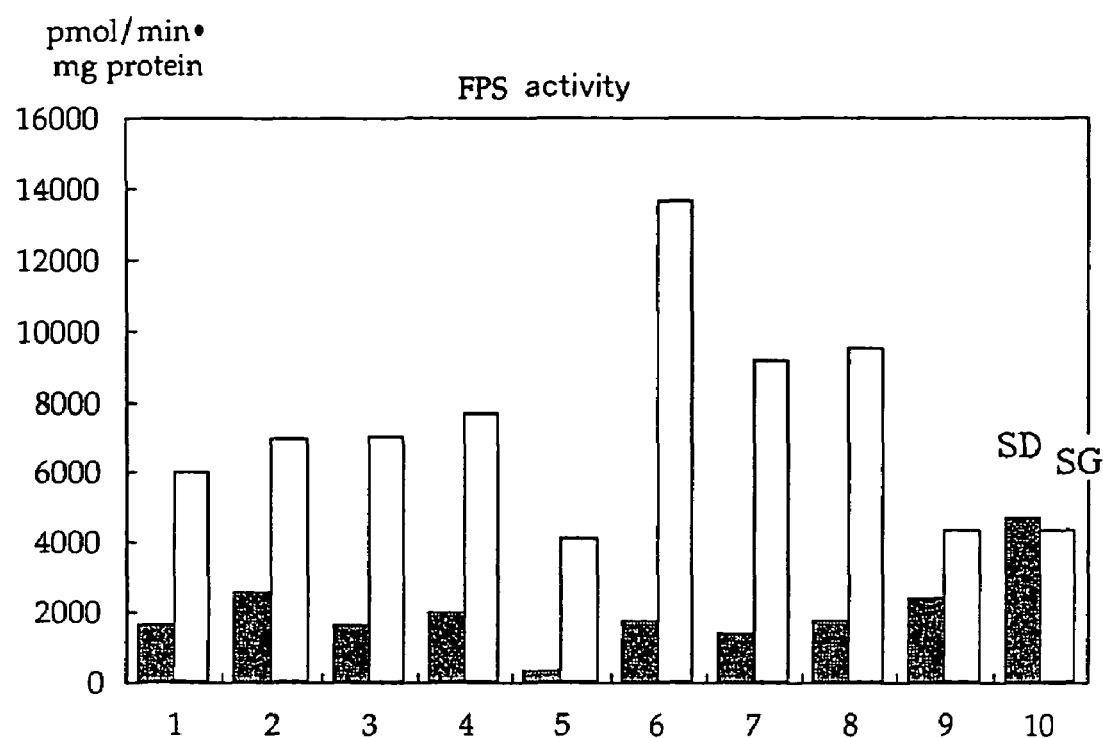
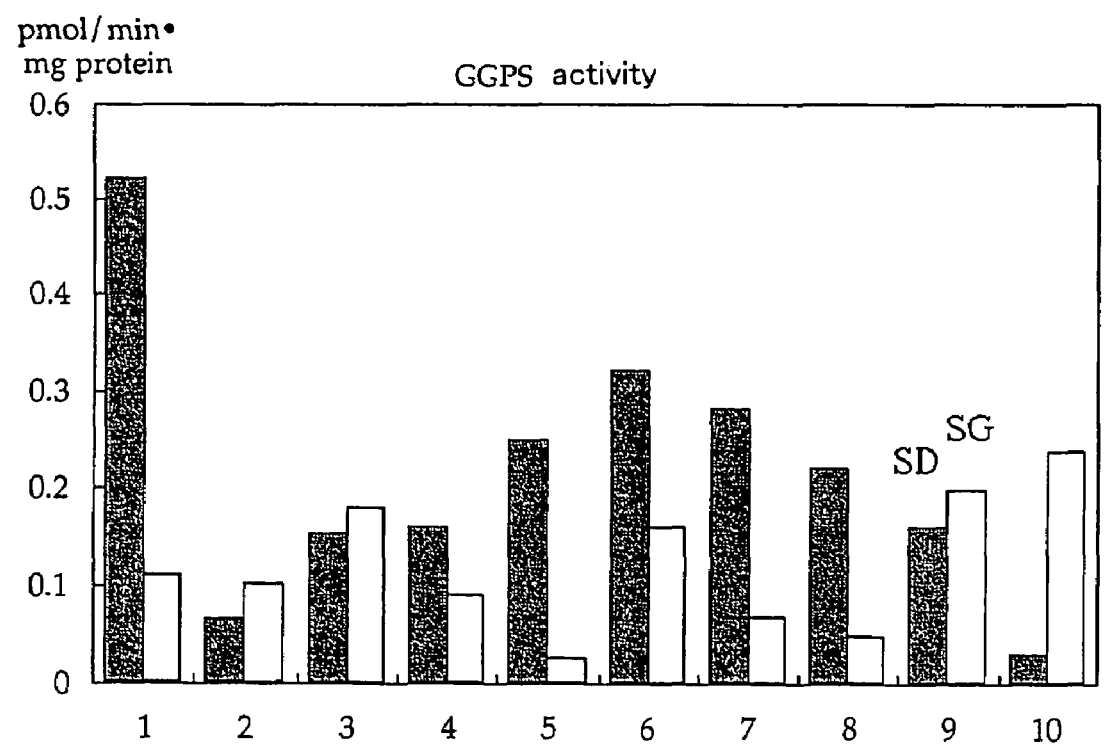

Fig. 15B
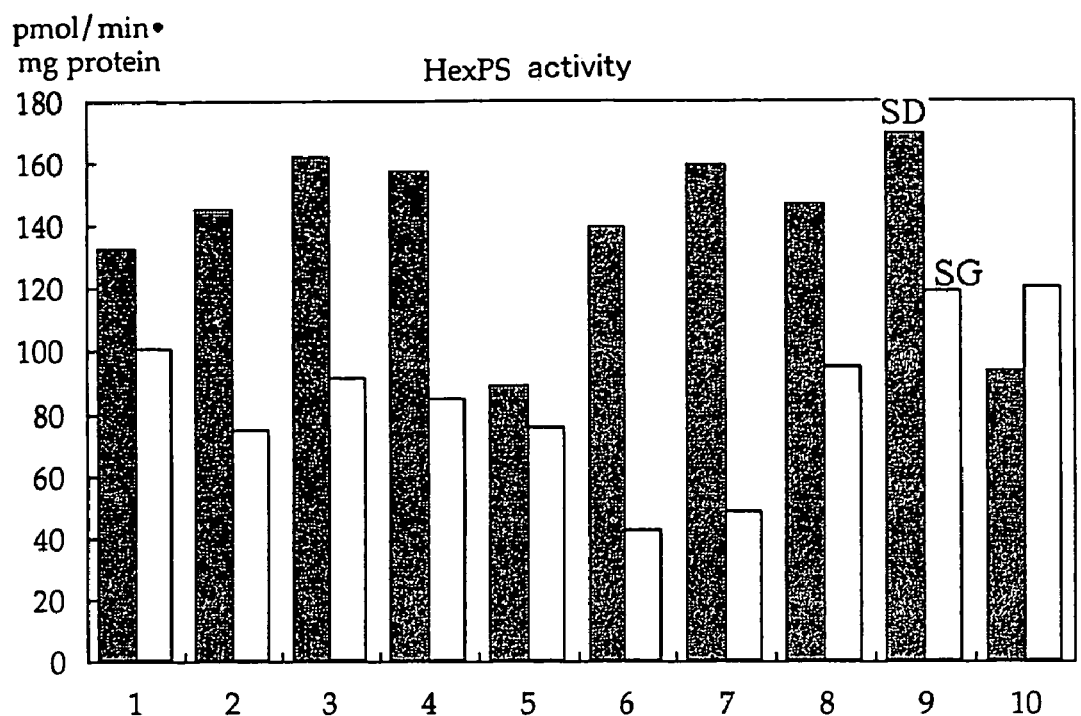
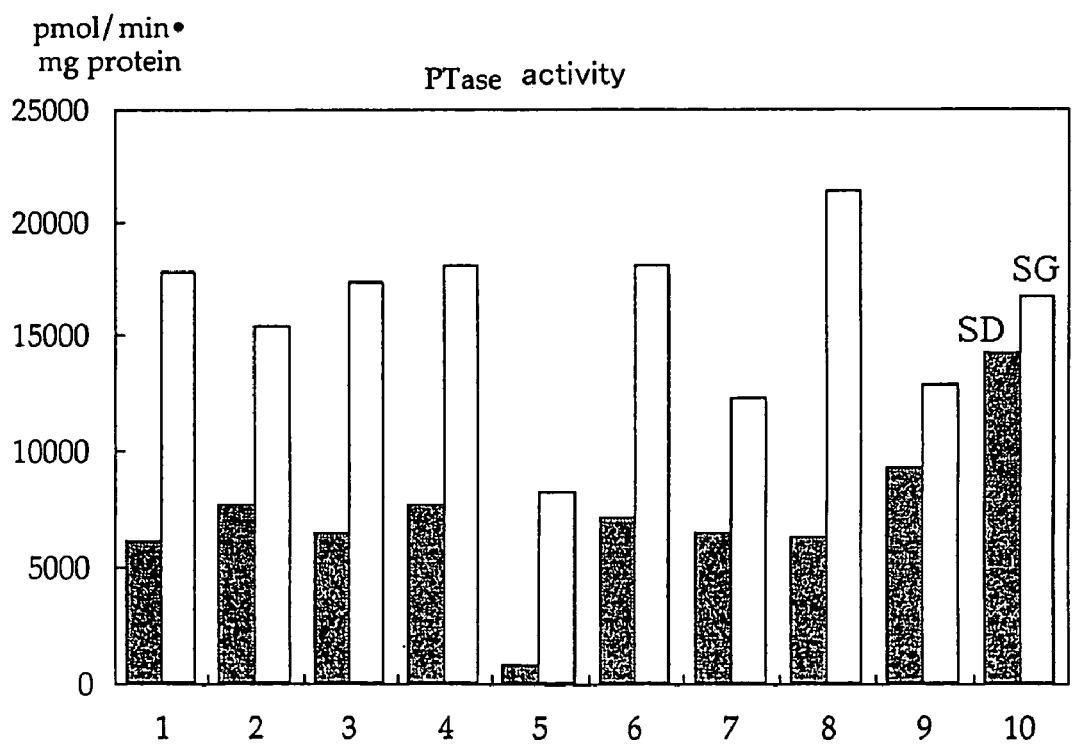

Fig.29A
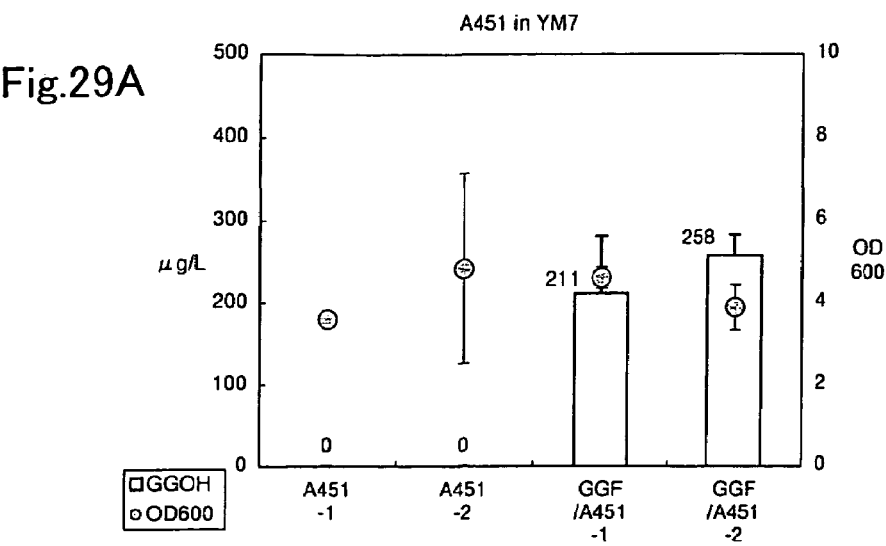
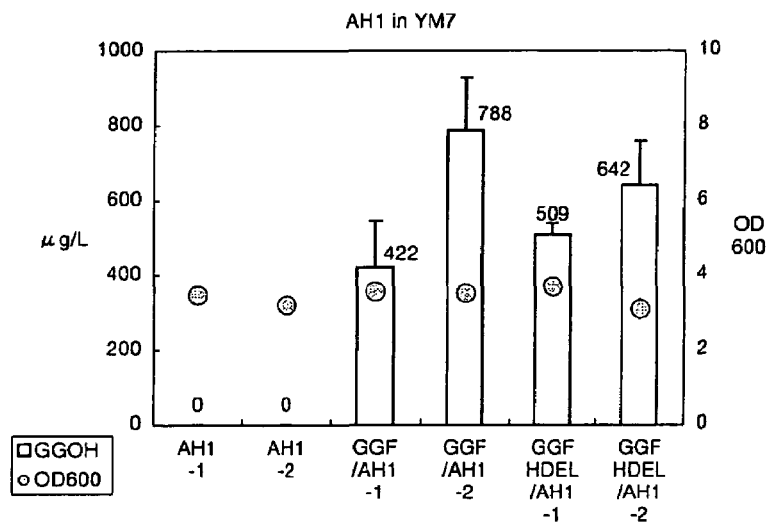
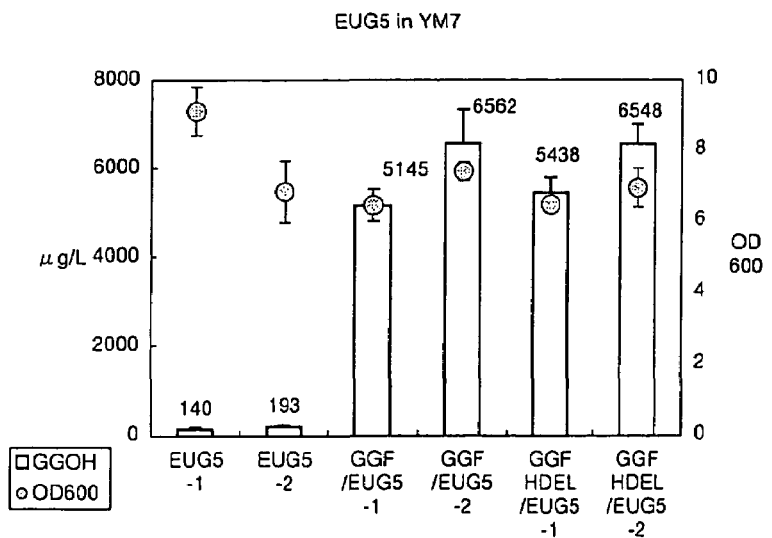

Fig.29B
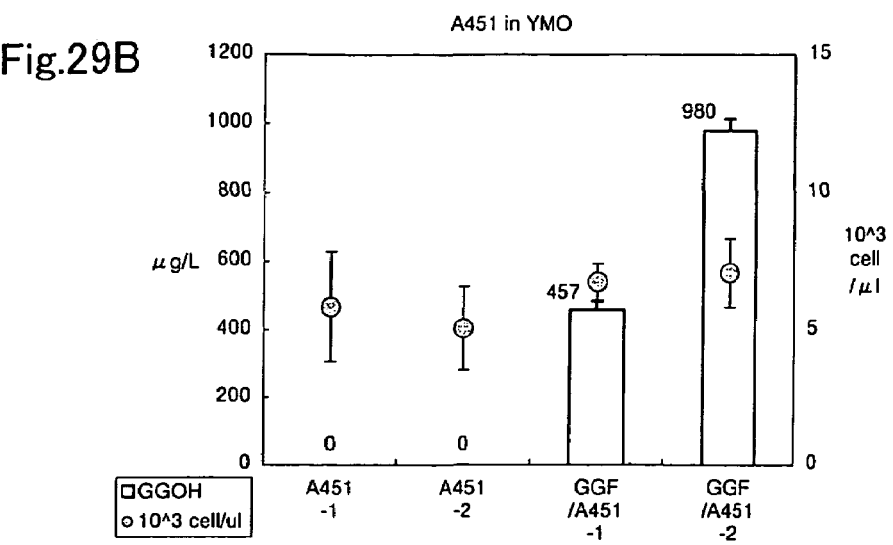
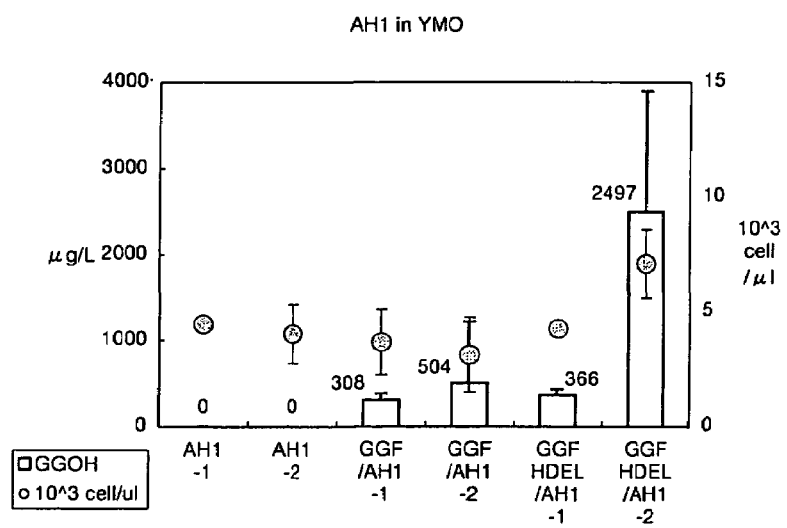
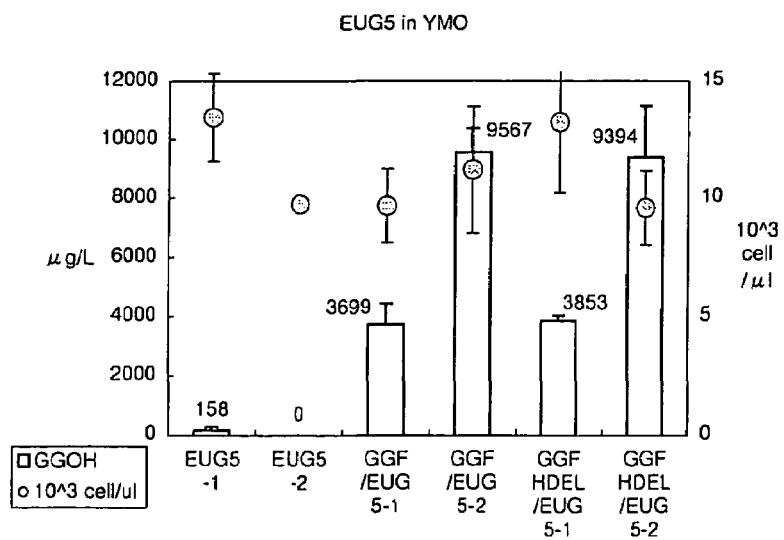

Fig.30A
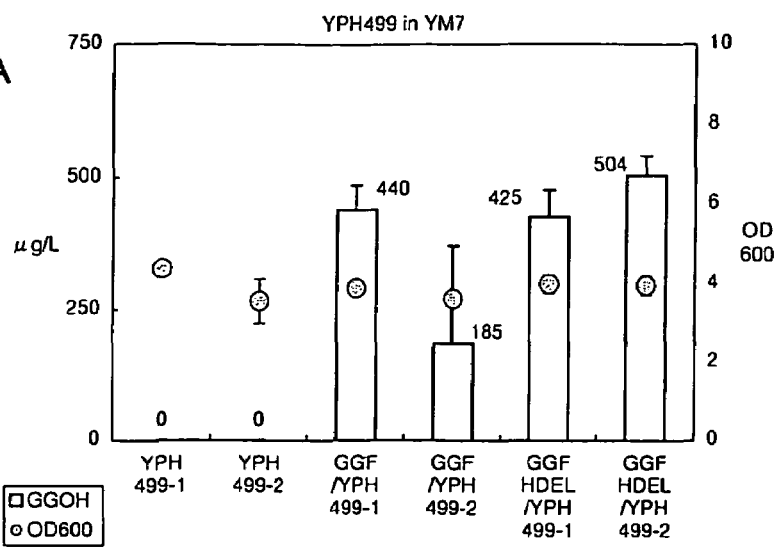
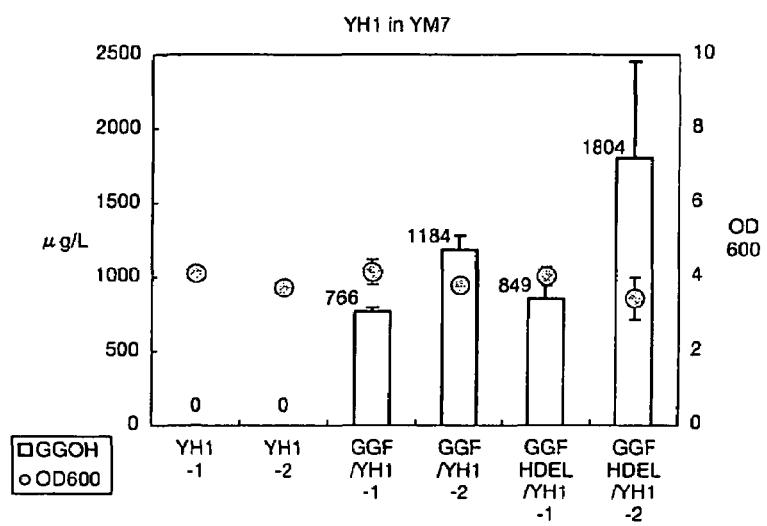
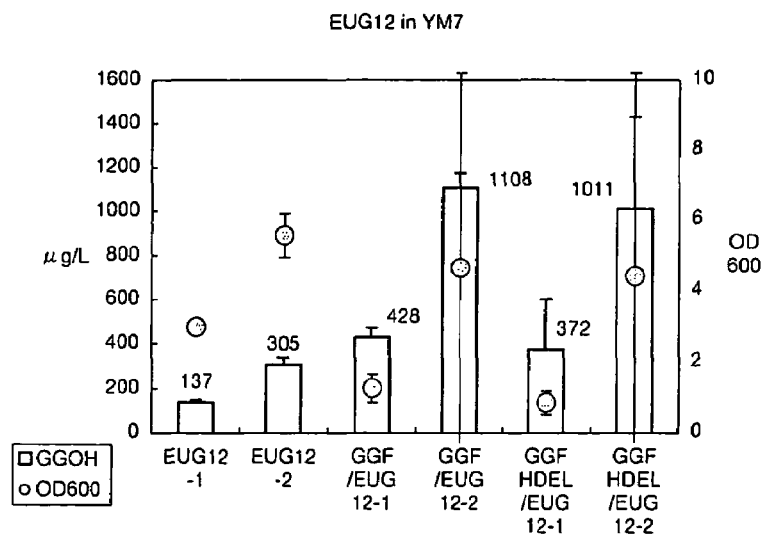

Fig.30B
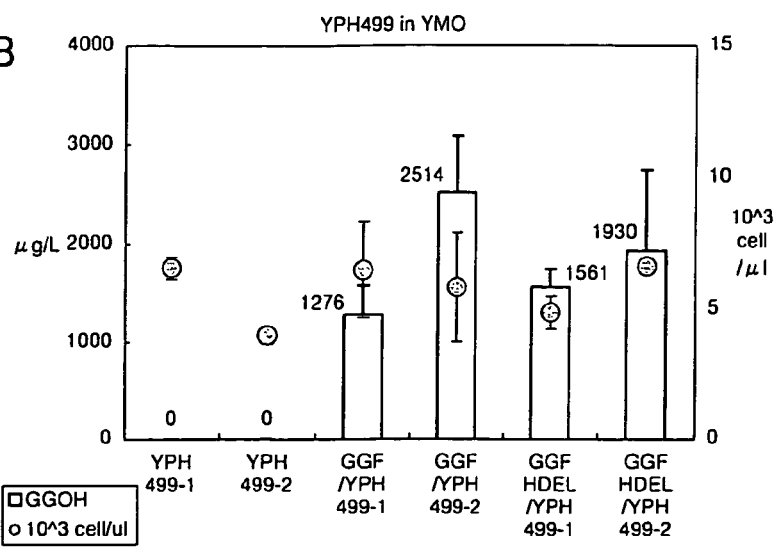
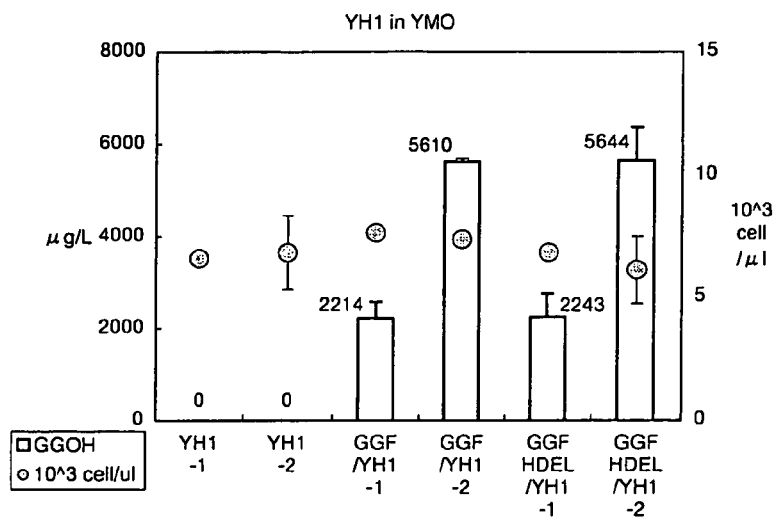
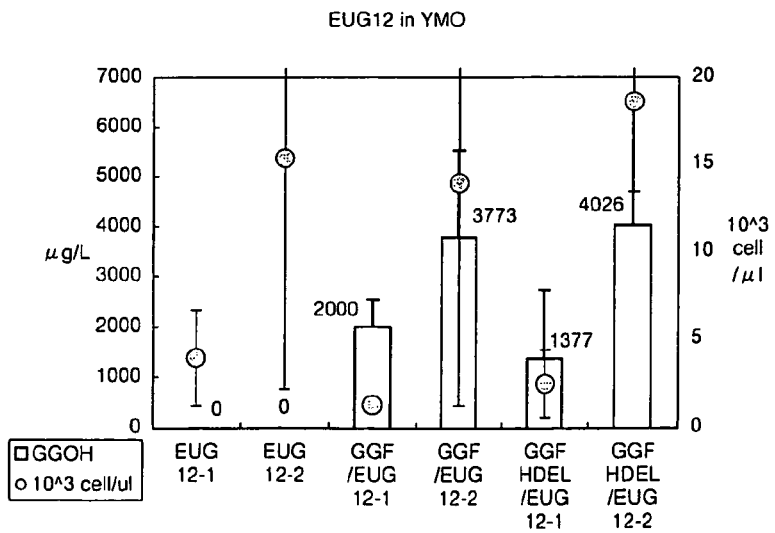

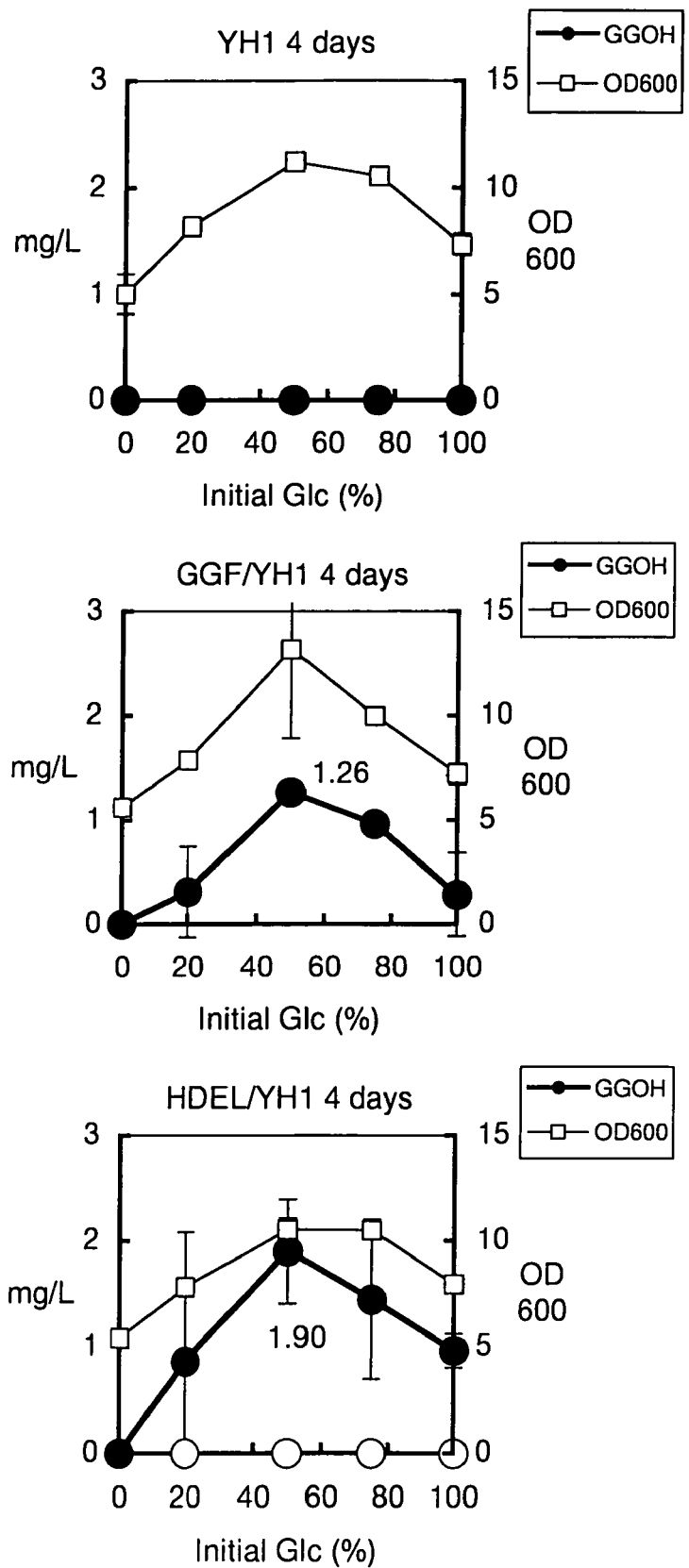

Fig.39
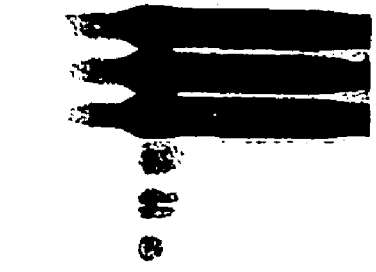
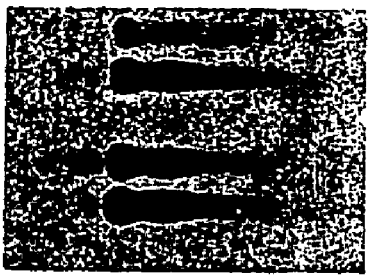
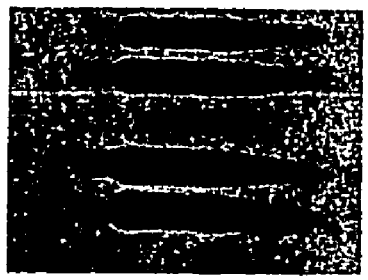
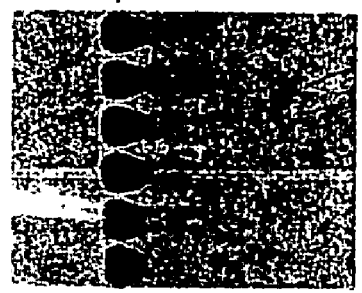

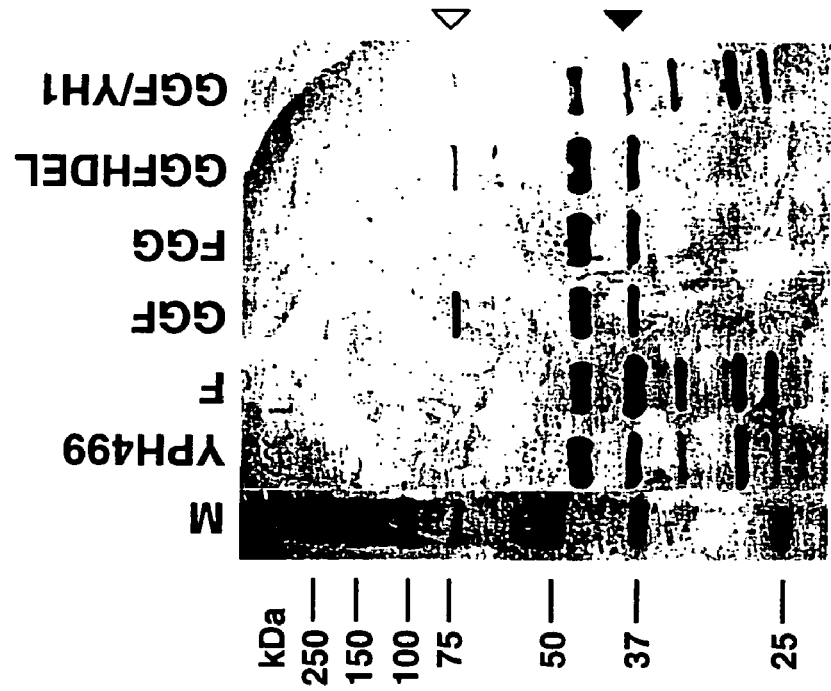
Fig. 40

SEQUENCE LISTING

```
<160> NUMBER OF SEQ ID NOS: 130

<210> SEQ ID NO 1
<211> LENGTH: 1059
<212> TYPE: DNA
<213> ORGANISM: Saccharomyces cerevisiae
<220> FEATURE:
<221> NAME/KEY: CDS
<222> LOCATION: (1)..(1056)

<400> SEQUENCE: 1 atg gct tca gaa aaa gaa att agg aga gag aga ttc ttg aac gtt ttc      48
Met Ala Ser Glu Lys Glu Ile Arg Arg Glu Arg Phe Leu Asn Val Phe
  1               5                  10                  15 cct aaa tta gta gag gaa ttg aac gca tcg ctt ttg gct tac ggt atg      96
Pro Lys Leu Val Glu Glu Leu Asn Ala Ser Leu Leu Ala Tyr Gly Met
                 20                  25                  30 cct aag gaa gca tgt gac tgg tat gcc cac tca ttg aac tac aac act     144
Pro Lys Glu Ala Cys Asp Trp Tyr Ala His Ser Leu Asn Tyr Asn Thr
             35                  40                  45 cca ggc ggt aag cta aat aga ggt ttg tcc gtt gtg gac acg tat gct     192
Pro Gly Gly Lys Leu Asn Arg Gly Leu Ser Val Val Asp Thr Tyr Ala
         50                  55                  60 att ctc tcc aac aag acc gtt gaa caa ttg ggg caa gaa gaa tac gaa     240
Ile Leu Ser Asn Lys Thr Val Glu Gln Leu Gly Gln Glu Glu Tyr Glu
```

```
                65                  70                  75                  80
aag gtt gcc att cta ggt tgg tgc att gag ttg ttg cag gct tac ttc       288
Lys Val Ala Ile Leu Gly Trp Cys Ile Glu Leu Leu Gln Ala Tyr Phe
                    85                  90                  95 ttg gtc gcc gat gat atg atg gac aag tcc att acc aga aga ggc caa       336
Leu Val Ala Asp Asp Met Met Asp Lys Ser Ile Thr Arg Arg Gly Gln
                100                 105                 110 cca tgt tgg tac aag gtt cct gaa gtt ggg gaa att gcc atc aat gac       384
Pro Cys Trp Tyr Lys Val Pro Glu Val Gly Glu Ile Ala Ile Asn Asp
            115                 120                 125 gca ttc atg tta gag gct gct atc tac aag ctt ttg aaa tct cac ttc       432
Ala Phe Met Leu Glu Ala Ala Ile Tyr Lys Leu Leu Lys Ser His Phe
        130                 135                 140 aga aac gaa aaa tac tac ata gat atc acc gaa ttg ttc cat gag gtc       480
Arg Asn Glu Lys Tyr Tyr Ile Asp Ile Thr Glu Leu Phe His Glu Val
145                 150                 155                 160 acc ttc caa acc gaa ttg ggc caa ttg atg gac tta atc act gca cct       528
Thr Phe Gln Thr Glu Leu Gly Gln Leu Met Asp Leu Ile Thr Ala Pro
                165                 170                 175 gaa gac aaa gtc gac ttg agt aag ttc tcc cta aag aag cac tcc ttc       576
Glu Asp Lys Val Asp Leu Ser Lys Phe Ser Leu Lys Lys His Ser Phe
            180                 185                 190 ata gtt act ttc aag act gct tac tat tct ttc tac ttg cct gtc gca       624
Ile Val Thr Phe Lys Thr Ala Tyr Tyr Ser Phe Tyr Leu Pro Val Ala
        195                 200                 205 ttg gcc atg tac gtt gcc ggt atc acg gat gaa aag gat ttg aaa caa       672
Leu Ala Met Tyr Val Ala Gly Ile Thr Asp Glu Lys Asp Leu Lys Gln
210                 215                 220 gcc aga gat gtc ttg att cca ttg ggt gaa tac ttc caa att caa gat       720
Ala Arg Asp Val Leu Ile Pro Leu Gly Glu Tyr Phe Gln Ile Gln Asp
225                 230                 235                 240 gac tac tta gac tgc ttc ggt acc cca gaa cag atc ggt aag atc ggt       768
Asp Tyr Leu Asp Cys Phe Gly Thr Pro Glu Gln Ile Gly Lys Ile Gly
                245                 250                 255 aca gat atc caa gat aac aaa tgt tct tgg gta atc aac aag gca ttg       816
Thr Asp Ile Gln Asp Asn Lys Cys Ser Trp Val Ile Asn Lys Ala Leu
            260                 265                 270 gaa ctt gct tcc gca gaa caa aga aag act tta gac gaa aat tac ggt       864
Glu Leu Ala Ser Ala Glu Gln Arg Lys Thr Leu Asp Glu Asn Tyr Gly
        275                 280                 285 aag aag gac tca gtc gca gaa gcc aaa tgc aaa aag att ttc aat gac       912
Lys Lys Asp Ser Val Ala Glu Ala Lys Cys Lys Lys Ile Phe Asn Asp
    290                 295                 300 ttg aaa att gaa cag cta tac cac gaa tat gaa gag tct att gcc aag       960
Leu Lys Ile Glu Gln Leu Tyr His Glu Tyr Glu Glu Ser Ile Ala Lys
305                 310                 315                 320 gat ttg aag gcc aaa att tct cag gtc gat gag tct cgt ggc ttc aaa      1008
Asp Leu Lys Ala Lys Ile Ser Gln Val Asp Glu Ser Arg Gly Phe Lys
                325                 330                 335 gct gat gtc tta act gcg ttc ttg aac aaa gtt tac aag aga agc aaa      1056
Ala Asp Val Leu Thr Ala Phe Leu Asn Lys Val Tyr Lys Arg Ser Lys
            340                 345                 350 tag                                                                  1059

<210> SEQ ID NO 2
<211> LENGTH: 352
<212> TYPE: PRT
<213> ORGANISM: Saccharomyces cerevisiae

<400> SEQUENCE: 2
```

```
Met Ala Ser Glu Lys Glu Ile Arg Arg Glu Arg Phe Leu Asn Val Phe
 1               5                  10                  15

Pro Lys Leu Val Glu Glu Leu Asn Ala Ser Leu Leu Ala Tyr Gly Met
             20                  25                  30

Pro Lys Glu Ala Cys Asp Trp Tyr Ala His Ser Leu Asn Tyr Asn Thr
         35                  40                  45

Pro Gly Gly Lys Leu Asn Arg Gly Leu Ser Val Asp Thr Tyr Ala
     50                  55                  60

Ile Leu Ser Asn Lys Thr Val Glu Gln Leu Gly Gln Glu Tyr Glu
 65                  70                  75                  80

Lys Val Ala Ile Leu Gly Trp Cys Ile Glu Leu Leu Gln Ala Tyr Phe
                 85                  90                  95

Leu Val Ala Asp Asp Met Met Asp Lys Ser Ile Thr Arg Arg Gly Gln
             100                 105                 110

Pro Cys Trp Tyr Lys Val Pro Glu Val Gly Glu Ile Ala Ile Asn Asp
         115                 120                 125

Ala Phe Met Leu Glu Ala Ala Ile Tyr Lys Leu Leu Lys Ser His Phe
     130                 135                 140

Arg Asn Glu Lys Tyr Tyr Ile Asp Ile Thr Glu Leu Phe His Glu Val
145                 150                 155                 160

Thr Phe Gln Thr Glu Leu Gly Gln Leu Met Asp Leu Ile Thr Ala Pro
                 165                 170                 175

Glu Asp Lys Val Asp Leu Ser Lys Phe Ser Leu Lys Lys His Ser Phe
             180                 185                 190

Ile Val Thr Phe Lys Thr Ala Tyr Tyr Ser Phe Tyr Leu Pro Val Ala
         195                 200                 205

Leu Ala Met Tyr Val Ala Gly Ile Thr Asp Glu Lys Asp Leu Lys Gln
     210                 215                 220

Ala Arg Asp Val Leu Ile Pro Leu Gly Glu Tyr Phe Gln Ile Gln Asp
225                 230                 235                 240

Asp Tyr Leu Asp Cys Phe Gly Thr Pro Glu Gln Ile Gly Lys Ile Gly
                 245                 250                 255

Thr Asp Ile Gln Asp Asn Lys Cys Ser Trp Val Ile Asn Lys Ala Leu
             260                 265                 270

Glu Leu Ala Ser Ala Glu Gln Arg Lys Thr Leu Asp Glu Asn Tyr Gly
         275                 280                 285

Lys Lys Asp Ser Val Ala Glu Ala Lys Cys Lys Lys Ile Phe Asn Asp
     290                 295                 300

Leu Lys Ile Glu Gln Leu Tyr His Glu Tyr Glu Glu Ser Ile Ala Lys
305                 310                 315                 320

Asp Leu Lys Ala Lys Ile Ser Gln Val Asp Glu Ser Arg Gly Phe Lys
                 325                 330                 335

Ala Asp Val Leu Thr Ala Phe Leu Asn Lys Val Tyr Lys Arg Ser Lys
             340                 345                 350

<210> SEQ ID NO 3
<211> LENGTH: 900
<212> TYPE: DNA
<213> ORGANISM: Escherichia coli
<220> FEATURE:
<221> NAME/KEY: CDS
<222> LOCATION: (1)..(897)

<400> SEQUENCE: 3 atg gac ttt ccg cag caa ctc gaa gcc tgc gtt aag cag gcc aac cag      48
```

```
            Met Asp Phe Pro Gln Gln Leu Glu Ala Cys Val Lys Gln Ala Asn Gln
              1               5                  10                  15 gcg ctg agc cgt ttt atc gcc cca ctg ccc ttt cag aac act ccc gtg        96
Ala Leu Ser Arg Phe Ile Ala Pro Leu Pro Phe Gln Asn Thr Pro Val
                 20                  25                  30 gtc gaa acc atg cag tat ggc gca tta tta ggt ggt aag cgc ctg cga       144
Val Glu Thr Met Gln Tyr Gly Ala Leu Leu Gly Gly Lys Arg Leu Arg
             35                  40                  45 cct ttc ctg gtt tat gcc acc ggt cat atg ttc ggc gtt agc aca aac       192
Pro Phe Leu Val Tyr Ala Thr Gly His Met Phe Gly Val Ser Thr Asn
         50                  55                  60 acg ctg gac gca ccc gct gcc gcc gtt gag tgt atc cac gct tac tca       240
Thr Leu Asp Ala Pro Ala Ala Ala Val Glu Cys Ile His Ala Tyr Ser
 65                  70                  75                  80 tta att cat gat gat tta ccg gca atg gat gat gac gat ctg cgt cgc       288
Leu Ile His Asp Asp Leu Pro Ala Met Asp Asp Asp Asp Leu Arg Arg
                 85                  90                  95 ggt ttg cca acc tgc cat gtg aag ttt ggc gaa gca aac gcg att ctc       336
Gly Leu Pro Thr Cys His Val Lys Phe Gly Glu Ala Asn Ala Ile Leu
            100                 105                 110 gct ggc gac gct tta caa acg ctg gcg ttc tcg att tta agc gat gcc       384
Ala Gly Asp Ala Leu Gln Thr Leu Ala Phe Ser Ile Leu Ser Asp Ala
        115                 120                 125 gat atg ccg gaa gtg tcg gac cgc gac aga att tcg atg att tct gaa       432
Asp Met Pro Glu Val Ser Asp Arg Asp Arg Ile Ser Met Ile Ser Glu
    130                 135                 140 ctg gcg agc gcc agt ggt att gcc gga atg tgc ggt ggt cag gca tta       480
Leu Ala Ser Ala Ser Gly Ile Ala Gly Met Cys Gly Gly Gln Ala Leu
145                 150                 155                 160 gat tta gac gcg gaa ggc aaa cac gta cct ctg gac gcg ctt gag cgt       528
Asp Leu Asp Ala Glu Gly Lys His Val Pro Leu Asp Ala Leu Glu Arg
                165                 170                 175 att cat cgt cat aaa acc ggc gca ttg att cgc gcc gcc gtt cgc ctt       576
Ile His Arg His Lys Thr Gly Ala Leu Ile Arg Ala Ala Val Arg Leu
            180                 185                 190 ggt gca tta agc gcc gga gat aaa gga cgt cgt gct ctg ccg gta ctc       624
Gly Ala Leu Ser Ala Gly Asp Lys Gly Arg Arg Ala Leu Pro Val Leu
        195                 200                 205 gac aag tat gca gag agc atc ggc ctt gcc ttc cag gtt cag gat gac       672
Asp Lys Tyr Ala Glu Ser Ile Gly Leu Ala Phe Gln Val Gln Asp Asp
    210                 215                 220 atc ctg gat gtg gtg gga gat act gca acg ttg gga aaa cgc cag ggt       720
Ile Leu Asp Val Val Gly Asp Thr Ala Thr Leu Gly Lys Arg Gln Gly
225                 230                 235                 240 gcc gac cag caa ctt ggt aaa agt acc tac cct gca ctt ctg ggt ctt       768
Ala Asp Gln Gln Leu Gly Lys Ser Thr Tyr Pro Ala Leu Leu Gly Leu
                245                 250                 255 gag caa gcc cgg aag aaa gcc cgg gat ctg atc gac gat gcc cgt cag       816
Glu Gln Ala Arg Lys Lys Ala Arg Asp Leu Ile Asp Asp Ala Arg Gln
            260                 265                 270 tcg ctg aaa caa ctg gct gaa cag tca ctc gat acc tcg gca ctg gaa       864
Ser Leu Lys Gln Leu Ala Glu Gln Ser Leu Asp Thr Ser Ala Leu Glu
        275                 280                 285 gcg cta gcg gac tac atc atc cag cgt aat aaa taa                       900
Ala Leu Ala Asp Tyr Ile Ile Gln Arg Asn Lys
    290                 295

<210> SEQ ID NO 4
<211> LENGTH: 299
<212> TYPE: PRT
```

<213> ORGANISM: Escherichia coli

<400> SEQUENCE: 4

```
Met Asp Phe Pro Gln Gln Leu Glu Ala Cys Val Lys Gln Ala Asn Gln
 1               5                  10                  15

Ala Leu Ser Arg Phe Ile Ala Pro Leu Pro Phe Gln Asn Thr Pro Val
             20                  25                  30

Val Glu Thr Met Gln Tyr Gly Ala Leu Leu Gly Gly Lys Arg Leu Arg
         35                  40                  45

Pro Phe Leu Val Tyr Ala Thr Gly His Met Phe Gly Val Ser Thr Asn
     50                  55                  60

Thr Leu Asp Ala Pro Ala Ala Val Glu Cys Ile His Ala Tyr Ser
 65                  70                  75                  80

Leu Ile His Asp Asp Leu Pro Ala Met Asp Asp Asp Leu Arg Arg
                 85                  90                  95

Gly Leu Pro Thr Cys His Val Lys Phe Gly Glu Ala Asn Ala Ile Leu
                100                 105                 110

Ala Gly Asp Ala Leu Gln Thr Leu Ala Phe Ser Ile Leu Ser Asp Ala
            115                 120                 125

Asp Met Pro Glu Val Ser Asp Arg Asp Arg Ile Ser Met Ile Ser Glu
        130                 135                 140

Leu Ala Ser Ala Ser Gly Ile Ala Gly Met Cys Gly Gly Gln Ala Leu
145                 150                 155                 160

Asp Leu Asp Ala Glu Gly Lys His Val Pro Leu Asp Ala Leu Glu Arg
                165                 170                 175

Ile His Arg His Lys Thr Gly Ala Leu Ile Arg Ala Ala Val Arg Leu
            180                 185                 190

Gly Ala Leu Ser Ala Gly Asp Lys Gly Arg Arg Ala Leu Pro Val Leu
        195                 200                 205

Asp Lys Tyr Ala Glu Ser Ile Gly Leu Ala Phe Gln Val Gln Asp Asp
    210                 215                 220

Ile Leu Asp Val Val Gly Asp Thr Ala Thr Leu Gly Lys Arg Gln Gly
225                 230                 235                 240

Ala Asp Gln Gln Leu Gly Lys Ser Thr Tyr Pro Ala Leu Leu Gly Leu
                245                 250                 255

Glu Gln Ala Arg Lys Lys Ala Arg Asp Leu Ile Asp Asp Ala Arg Gln
            260                 265                 270

Ser Leu Lys Gln Leu Ala Glu Gln Ser Leu Asp Thr Ser Ala Leu Glu
        275                 280                 285

Ala Leu Ala Asp Tyr Ile Ile Gln Arg Asn Lys
    290                 295
```

<210> SEQ ID NO 5
<211> LENGTH: 1008
<212> TYPE: DNA
<213> ORGANISM: Saccharomyces cerevisiae
<220> FEATURE:
<221> NAME/KEY: CDS
<222> LOCATION: (1)..(1005)

<400> SEQUENCE: 5

```
atg gag gcc aag ata gat gag ctg atc aat aat gat cct gtt tgg tcc     48
Met Glu Ala Lys Ile Asp Glu Leu Ile Asn Asn Asp Pro Val Trp Ser
 1               5                  10                  15 agc caa aat gaa agc ttg att tca aaa cct tat aat cac atc ctt ttg     96
Ser Gln Asn Glu Ser Leu Ile Ser Lys Pro Tyr Asn His Ile Leu Leu
             20                  25                  30
```

```
aaa cct ggc aag aac ttt aga cta aat tta ata gtt caa att aac aga      144
Lys Pro Gly Lys Asn Phe Arg Leu Asn Leu Ile Val Gln Ile Asn Arg
         35                  40                  45 gtt atg aat ttg ccc aaa gac cag ctg gcc ata gtt tcg caa att gtt      192
Val Met Asn Leu Pro Lys Asp Gln Leu Ala Ile Val Ser Gln Ile Val
 50                  55                  60 gag ctc ttg cat aat tcc agc ctt tta atc gac gat ata gaa gat aat      240
Glu Leu Leu His Asn Ser Ser Leu Leu Ile Asp Asp Ile Glu Asp Asn
 65                  70                  75                  80 gct ccc ttg aga agg gga cag acc act tct cac tta atc ttc ggt gta      288
Ala Pro Leu Arg Arg Gly Gln Thr Thr Ser His Leu Ile Phe Gly Val
                 85                  90                  95 ccc tcc act ata aac acc gca aat tat atg tat ttc aga gcc atg caa      336
Pro Ser Thr Ile Asn Thr Ala Asn Tyr Met Tyr Phe Arg Ala Met Gln
             100                 105                 110 ctt gta tcg cag cta acc aca aaa gag cct ttg tat cat aat ttg att      384
Leu Val Ser Gln Leu Thr Thr Lys Glu Pro Leu Tyr His Asn Leu Ile
         115                 120                 125 acg att ttc aac gaa gaa ttg atc aat cta cat agg gga caa ggc ttg      432
Thr Ile Phe Asn Glu Glu Leu Ile Asn Leu His Arg Gly Gln Gly Leu
 130                 135                 140 gat ata tac tgg aga gac ttt ctg cct gaa atc ata cct act cag gag      480
Asp Ile Tyr Trp Arg Asp Phe Leu Pro Glu Ile Ile Pro Thr Gln Glu
145                 150                 155                 160 atg tat ttg aat atg gtt atg aat aaa aca ggc ggc ctt ttc aga tta      528
Met Tyr Leu Asn Met Val Met Asn Lys Thr Gly Gly Leu Phe Arg Leu
                 165                 170                 175 acg ttg aga ctc atg gaa gcg ctg tct cct tcc tca cac cac ggc cat      576
Thr Leu Arg Leu Met Glu Ala Leu Ser Pro Ser Ser His His Gly His
             180                 185                 190 tcg ttg gtt cct ttc ata aat ctt ctg ggt att att tat cag att aga      624
Ser Leu Val Pro Phe Ile Asn Leu Leu Gly Ile Ile Tyr Gln Ile Arg
         195                 200                 205 gat gat tac ttg aat ttg aaa gat ttc caa atg tcc agc gaa aaa ggc      672
Asp Asp Tyr Leu Asn Leu Lys Asp Phe Gln Met Ser Ser Glu Lys Gly
 210                 215                 220 ttt gct gag gac att aca gag ggg aag tta tct ttt ccc atc gtc cac      720
Phe Ala Glu Asp Ile Thr Glu Gly Lys Leu Ser Phe Pro Ile Val His
225                 230                 235                 240 gcc ctt aac ttc act aaa acg aaa ggt caa act gag caa cac aat gaa      768
Ala Leu Asn Phe Thr Lys Thr Lys Gly Gln Thr Glu Gln His Asn Glu
                 245                 250                 255 att cta aga att ctc ctg ttg agg aca agt gat aaa gat ata aaa cta      816
Ile Leu Arg Ile Leu Leu Leu Arg Thr Ser Asp Lys Asp Ile Lys Leu
             260                 265                 270 aag ctg att caa ata ctg gaa ttc gac acc aat tca ttg gcc tac acc      864
Lys Leu Ile Gln Ile Leu Glu Phe Asp Thr Asn Ser Leu Ala Tyr Thr
         275                 280                 285 aaa aat ttt att aat caa tta gtg aat atg ata aaa aat gat aat gaa      912
Lys Asn Phe Ile Asn Gln Leu Val Asn Met Ile Lys Asn Asp Asn Glu
 290                 295                 300 aat aag tat tta cct gat ttg gct tcg cat tcc gac acc gcc acc aat      960
Asn Lys Tyr Leu Pro Asp Leu Ala Ser His Ser Asp Thr Ala Thr Asn
305                 310                 315                 320 tta cat gac gaa ttg tta tat ata ata gac cac tta tcc gaa ttg tga     1008
Leu His Asp Glu Leu Leu Tyr Ile Ile Asp His Leu Ser Glu Leu
                 325                 330                 335
```

<210> SEQ ID NO 6

<211> LENGTH: 335
<212> TYPE: PRT
<213> ORGANISM: Saccharomyces cerevisiae

<400> SEQUENCE: 6

Met Glu Ala Lys Ile Asp Glu Leu Ile Asn Asn Asp Pro Val Trp Ser
1               5                   10                  15

Ser Gln Asn Glu Ser Leu Ile Ser Lys Pro Tyr Asn His Ile Leu Leu
            20                  25                  30

Lys Pro Gly Lys Asn Phe Arg Leu Asn Leu Ile Val Gln Ile Asn Arg
        35                  40                  45

Val Met Asn Leu Pro Lys Asp Gln Leu Ala Ile Val Ser Gln Ile Val
    50                  55                  60

Glu Leu Leu His Asn Ser Ser Leu Leu Ile Asp Asp Ile Glu Asp Asn
65                  70                  75                  80

Ala Pro Leu Arg Arg Gly Gln Thr Thr Ser His Leu Ile Phe Gly Val
                85                  90                  95

Pro Ser Thr Ile Asn Thr Ala Asn Tyr Met Tyr Phe Arg Ala Met Gln
            100                 105                 110

Leu Val Ser Gln Leu Thr Thr Lys Glu Pro Leu Tyr His Asn Leu Ile
        115                 120                 125

Thr Ile Phe Asn Glu Glu Leu Ile Asn Leu His Arg Gly Gln Gly Leu
    130                 135                 140

Asp Ile Tyr Trp Arg Asp Phe Leu Pro Glu Ile Ile Pro Thr Gln Glu
145                 150                 155                 160

Met Tyr Leu Asn Met Val Met Asn Lys Thr Gly Gly Leu Phe Arg Leu
                165                 170                 175

Thr Leu Arg Leu Met Glu Ala Leu Ser Pro Ser Ser His His Gly His
            180                 185                 190

Ser Leu Val Pro Phe Ile Asn Leu Leu Gly Ile Ile Tyr Gln Ile Arg
        195                 200                 205

Asp Asp Tyr Leu Asn Leu Lys Asp Phe Gln Met Ser Ser Glu Lys Gly
    210                 215                 220

Phe Ala Glu Asp Ile Thr Glu Gly Lys Leu Ser Phe Pro Ile Val His
225                 230                 235                 240

Ala Leu Asn Phe Thr Lys Thr Lys Gly Gln Thr Glu Gln His Asn Glu
                245                 250                 255

Ile Leu Arg Ile Leu Leu Leu Arg Thr Ser Asp Lys Asp Ile Lys Leu
            260                 265                 270

Lys Leu Ile Gln Ile Leu Glu Phe Asp Thr Asn Ser Leu Ala Tyr Thr
        275                 280                 285

Lys Asn Phe Ile Asn Gln Leu Val Asn Met Ile Lys Asn Asp Asn Glu
    290                 295                 300

Asn Lys Tyr Leu Pro Asp Leu Ala Ser His Ser Asp Thr Ala Thr Asn
305                 310                 315                 320

Leu His Asp Glu Leu Leu Tyr Ile Ile Asp His Leu Ser Glu Leu
                325                 330                 335

<210> SEQ ID NO 7
<211> LENGTH: 3165
<212> TYPE: DNA
<213> ORGANISM: Saccharomyces cerevisiae
<220> FEATURE:
<221> NAME/KEY: CDS
<222> LOCATION: (1)..(3162)

<400> SEQUENCE: 7

```
atg ccg ccg cta ttc aag gga ctg aaa cag atg gca aag cca att gcc    48
Met Pro Pro Leu Phe Lys Gly Leu Lys Gln Met Ala Lys Pro Ile Ala
 1               5                  10                  15 tat gtt tca aga ttt tcg gcg aaa cga cca att cat ata ata ctt ttt    96
Tyr Val Ser Arg Phe Ser Ala Lys Arg Pro Ile His Ile Ile Leu Phe
             20                  25                  30 tct cta atc ata tcc gca ttc gct tat cta tcc gtc att cag tat tac   144
Ser Leu Ile Ile Ser Ala Phe Ala Tyr Leu Ser Val Ile Gln Tyr Tyr
                 35                  40                  45 ttc aat ggt tgg caa cta gat tca aat agt gtt ttt gaa act gct cca   192
Phe Asn Gly Trp Gln Leu Asp Ser Asn Ser Val Phe Glu Thr Ala Pro
 50                  55                  60 aat aaa gac tcc aac act cta ttt caa gaa tgt tcc cat tac tac aga   240
Asn Lys Asp Ser Asn Thr Leu Phe Gln Glu Cys Ser His Tyr Tyr Arg
 65                  70                  75                  80 gat tcc tct cta gat ggt tgg gta tca atc acc gcg cat gaa gct agt   288
Asp Ser Ser Leu Asp Gly Trp Val Ser Ile Thr Ala His Glu Ala Ser
                 85                  90                  95 gag tta cca gcc cca cac cat tac tat cta tta aac ctg aac ttc aat   336
Glu Leu Pro Ala Pro His His Tyr Tyr Leu Leu Asn Leu Asn Phe Asn
                100                 105                 110 agt cct aat gaa act gac tcc att cca gaa cta gct aac acg gtt ttt   384
Ser Pro Asn Glu Thr Asp Ser Ile Pro Glu Leu Ala Asn Thr Val Phe
            115                 120                 125 gag aaa gat aat aca aaa tat att ctg caa gaa gat ctc agt gtt tcc   432
Glu Lys Asp Asn Thr Lys Tyr Ile Leu Gln Glu Asp Leu Ser Val Ser
        130                 135                 140 aaa gaa att tct tct act gat gga acg aaa tgg agg tta aga agt gac   480
Lys Glu Ile Ser Ser Thr Asp Gly Thr Lys Trp Arg Leu Arg Ser Asp
145                 150                 155                 160 aga aaa agt ctt ttc gac gta aag acg tta gca tat tct ctc tac gat   528
Arg Lys Ser Leu Phe Asp Val Lys Thr Leu Ala Tyr Ser Leu Tyr Asp
                165                 170                 175 gta ttt tca gaa aat gta acc caa gca gac ccg ttt gac gtc ctt att   576
Val Phe Ser Glu Asn Val Thr Gln Ala Asp Pro Phe Asp Val Leu Ile
                180                 185                 190 atg gtt act gcc tac cta atg atg ttc tac acc ata ttc ggc ctc ttc   624
Met Val Thr Ala Tyr Leu Met Met Phe Tyr Thr Ile Phe Gly Leu Phe
            195                 200                 205 aat gac atg agg aag acc ggg tca aat ttt tgg ttg agc gcc tct aca   672
Asn Asp Met Arg Lys Thr Gly Ser Asn Phe Trp Leu Ser Ala Ser Thr
        210                 215                 220 gtg gtc aat tct gca tca tca ctt ttc tta gca ttg tat gtc acc caa   720
Val Val Asn Ser Ala Ser Ser Leu Phe Leu Ala Leu Tyr Val Thr Gln
225                 230                 235                 240 tgt att cta ggc aaa gaa gtt tcc gca tta act ctt ttt gaa ggt ttg   768
Cys Ile Leu Gly Lys Glu Val Ser Ala Leu Thr Leu Phe Glu Gly Leu
                245                 250                 255 cct ttc att gta gtt gtt ggt ttc aag cac aaa atc aag att gcc       816
Pro Phe Ile Val Val Val Gly Phe Lys His Lys Ile Lys Ile Ala
                260                 265                 270 cag tat gcc ctg gag aaa ttt gaa aga gtc ggt tta tct aaa agg att   864
Gln Tyr Ala Leu Glu Lys Phe Glu Arg Val Gly Leu Ser Lys Arg Ile
            275                 280                 285 act acc gat gaa atc gtt ttt gaa tcc gtg agc gaa gag ggt ggt cgt   912
Thr Thr Asp Glu Ile Val Phe Glu Ser Val Ser Glu Glu Gly Gly Arg
        290                 295                 300 ttg att caa gac cat ttg ctt tgt att ttt gcc ttt atc gga tgc tct   960
Leu Ile Gln Asp His Leu Leu Cys Ile Phe Ala Phe Ile Gly Cys Ser
```

-continued

```
                305                 310                 315                 320
atg tat gct cac caa ttg aag act ttg aca aac ttc tgc ata tta tca        1008
Met Tyr Ala His Gln Leu Lys Thr Leu Thr Asn Phe Cys Ile Leu Ser
                    325                 330                 335 gca ttt atc cta att ttt gaa ttg att tta act cct aca ttt tat tct        1056
Ala Phe Ile Leu Ile Phe Glu Leu Ile Leu Thr Pro Thr Phe Tyr Ser
                    340                 345                 350 gct atc tta gcg ctt aga ctg gaa atg aat gtt atc cac aga tct act        1104
Ala Ile Leu Ala Leu Arg Leu Glu Met Asn Val Ile His Arg Ser Thr
                    355                 360                 365 att atc aag caa aca tta gaa gaa gac ggt gtt gtt cca tct aca gca        1152
Ile Ile Lys Gln Thr Leu Glu Glu Asp Gly Val Val Pro Ser Thr Ala
                370                 375                 380 aga atc att tct aaa gca gaa aag aaa tcc gta tct tct ttc tta aat        1200
Arg Ile Ile Ser Lys Ala Glu Lys Lys Ser Val Ser Ser Phe Leu Asn
385                 390                 395                 400 ctc agt gtg gtt gtc att atc atg aaa ctc tct gtc ata ctg ttg ttt        1248
Leu Ser Val Val Val Ile Ile Met Lys Leu Ser Val Ile Leu Leu Phe
                    405                 410                 415 gtc ttc atc aac ttt tat aac ttt ggt gca aat tgg gtc aat gat gcc        1296
Val Phe Ile Asn Phe Tyr Asn Phe Gly Ala Asn Trp Val Asn Asp Ala
                    420                 425                 430 ttc aat tca ttg tac ttc gat aag gaa cgt gtt tct cta cca gat ttt        1344
Phe Asn Ser Leu Tyr Phe Asp Lys Glu Arg Val Ser Leu Pro Asp Phe
                    435                 440                 445 att acc tcg aat gcc tct gaa aac ttt aaa gag caa gct att gtt agt        1392
Ile Thr Ser Asn Ala Ser Glu Asn Phe Lys Glu Gln Ala Ile Val Ser
                450                 455                 460 gtc acc cca tta tta tat tac aaa ccc att aag tcc tac caa cgc att        1440
Val Thr Pro Leu Leu Tyr Tyr Lys Pro Ile Lys Ser Tyr Gln Arg Ile
465                 470                 475                 480 gag gat atg gtt ctt cta ttg ctt cgt aat gtc agt gtt gcc att cgt        1488
Glu Asp Met Val Leu Leu Leu Arg Asn Val Ser Val Ala Ile Arg
                    485                 490                 495 gat agg ttc gtc agt aaa tta gtt ctt tcc gcc tta gta tgc agt gct        1536
Asp Arg Phe Val Ser Lys Leu Val Leu Ser Ala Leu Val Cys Ser Ala
                    500                 505                 510 gtc atc aat gtg tat tta ttg aat gct gct aga att cat acc agt tat        1584
Val Ile Asn Val Tyr Leu Leu Asn Ala Ala Arg Ile His Thr Ser Tyr
                    515                 520                 525 act gca gac caa ttg gtg aaa act gaa gtc acc aag aag tct ttt act        1632
Thr Ala Asp Gln Leu Val Lys Thr Glu Val Thr Lys Lys Ser Phe Thr
                530                 535                 540 gct cct gta caa aag gct tct aca cca gtt tta acc aat aaa aca gtc        1680
Ala Pro Val Gln Lys Ala Ser Thr Pro Val Leu Thr Asn Lys Thr Val
545                 550                 555                 560 att tct gga tcg aaa gtc aaa agt tta tca tct gcg caa tcg agc tca        1728
Ile Ser Gly Ser Lys Val Lys Ser Leu Ser Ser Ala Gln Ser Ser Ser
                    565                 570                 575 tca gga cct tca tca tct agt gag gaa gat gat ccc gc gat att gaa        1776
Ser Gly Pro Ser Ser Ser Ser Glu Glu Asp Asp Ser Arg Asp Ile Glu
                580                 585                 590 agc ttg gat aag aaa ata cgt cct tta gaa gaa tta gaa gca tta tta        1824
Ser Leu Asp Lys Lys Ile Arg Pro Leu Glu Glu Leu Glu Ala Leu Leu
                    595                 600                 605 agt agt gga aat aca aaa caa ttg aag aac aaa gag gtc gct gcc ttg        1872
Ser Ser Gly Asn Thr Lys Gln Leu Lys Asn Lys Glu Val Ala Ala Leu
                610                 615                 620 gtt att cac ggt aag tta cct ttg tac gct ttg gag aaa aaa tta ggt        1920
Val Ile His Gly Lys Leu Pro Leu Tyr Ala Leu Glu Lys Lys Leu Gly
```

```
                Val Ile His Gly Lys Leu Pro Leu Tyr Ala Leu Glu Lys Lys Leu Gly
                625             630                 635                 640 gat act acg aga gcg gtt gcg gta cgt agg aag gct ctt tca att ttg        1968
Asp Thr Thr Arg Ala Val Ala Val Arg Arg Lys Ala Leu Ser Ile Leu
                645                 650                 655 gca gaa gct cct gta tta gca tct gat cgt tta cca tat aaa aat tat        2016
Ala Glu Ala Pro Val Leu Ala Ser Asp Arg Leu Pro Tyr Lys Asn Tyr
                660                 665                 670 gac tac gac cgc gta ttt ggc gct tgt tgt gaa aat gtt ata ggt tac        2064
Asp Tyr Asp Arg Val Phe Gly Ala Cys Cys Glu Asn Val Ile Gly Tyr
                675                 680                 685 atg cct ttg ccc gtt ggt gtt ata ggc ccc ttg gtt atc gat ggt aca        2112
Met Pro Leu Pro Val Gly Val Ile Gly Pro Leu Val Ile Asp Gly Thr
                690                 695                 700 tct tat cat ata cca atg gca act aca gag ggt tgt ttg gta gct tct        2160
Ser Tyr His Ile Pro Met Ala Thr Thr Glu Gly Cys Leu Val Ala Ser
705                 710                 715                 720 gcc atg cgt ggc tgt aag gca atc aat gct ggc ggt ggt gca aca act        2208
Ala Met Arg Gly Cys Lys Ala Ile Asn Ala Gly Gly Gly Ala Thr Thr
                725                 730                 735 gtt tta act aag gat ggt atg aca aga ggc cca gta gtc cgt ttc cca        2256
Val Leu Thr Lys Asp Gly Met Thr Arg Gly Pro Val Val Arg Phe Pro
                740                 745                 750 act ttg aaa aga tct ggt gcc tgt aag ata tgg tta gac tca gaa gag        2304
Thr Leu Lys Arg Ser Gly Ala Cys Lys Ile Trp Leu Asp Ser Glu Glu
                755                 760                 765 gga caa aac gca att aaa aaa gct ttt aac tct aca tca aga ttt gca        2352
Gly Gln Asn Ala Ile Lys Lys Ala Phe Asn Ser Thr Ser Arg Phe Ala
770                 775                 780 cgt ctg caa cat att caa act tgt cta gca gga gat tta ctc ttc atg        2400
Arg Leu Gln His Ile Gln Thr Cys Leu Ala Gly Asp Leu Leu Phe Met
785                 790                 795                 800 aga ttt aga aca act act ggt gac gca atg ggt atg aat atg att tct        2448
Arg Phe Arg Thr Thr Thr Gly Asp Ala Met Gly Met Asn Met Ile Ser
                805                 810                 815 aaa ggt gtc gaa tac tca tta aag caa atg gta gaa gag tat ggc tgg        2496
Lys Gly Val Glu Tyr Ser Leu Lys Gln Met Val Glu Glu Tyr Gly Trp
                820                 825                 830 gaa gat atg gag gtt gtc tcc gtt tct ggt aac tac tgt acc gac aaa        2544
Glu Asp Met Glu Val Val Ser Val Ser Gly Asn Tyr Cys Thr Asp Lys
                835                 840                 845 aaa cca gct gcc atc aac tgg atc gaa ggt cgt ggt aag agt gtc gtc        2592
Lys Pro Ala Ala Ile Asn Trp Ile Glu Gly Arg Gly Lys Ser Val Val
850                 855                 860 gca gaa gct act att cct ggt gat gtt gtc aga aaa gtg tta aaa agt        2640
Ala Glu Ala Thr Ile Pro Gly Asp Val Val Arg Lys Val Leu Lys Ser
865                 870                 875                 880 gat gtt tcc gca ttg gtt gag ttg aac att gct aag aat ttg gtt gga        2688
Asp Val Ser Ala Leu Val Glu Leu Asn Ile Ala Lys Asn Leu Val Gly
                885                 890                 895 tct gca atg gct ggg tct gtt ggt gga ttt aac gca cat gca gct aat        2736
Ser Ala Met Ala Gly Ser Val Gly Gly Phe Asn Ala His Ala Ala Asn
                900                 905                 910 tta gtg aca gct gtt ttc ttg gca tta gga caa gat cct gca caa aat        2784
Leu Val Thr Ala Val Phe Leu Ala Leu Gly Gln Asp Pro Ala Gln Asn
                915                 920                 925 gtt gaa agt tcc aac tgt ata aca ttg atg aaa gaa gtg gac ggt gat        2832
Val Glu Ser Ser Asn Cys Ile Thr Leu Met Lys Glu Val Asp Gly Asp
    930                 935                 940
```

```
ttg aga att tcc gta tcc atg cca tcc atc gaa gta ggt acc atc ggt    2880
Leu Arg Ile Ser Val Ser Met Pro Ser Ile Glu Val Gly Thr Ile Gly
945                 950                 955                 960 ggt ggt act gtt cta gaa cca caa ggt gcc atg ttg gac tta tta ggt    2928
Gly Gly Thr Val Leu Glu Pro Gln Gly Ala Met Leu Asp Leu Leu Gly
                965                 970                 975 gta aga ggc ccg cat gct acc gct cct ggt acc aac gca cgt caa tta    2976
Val Arg Gly Pro His Ala Thr Ala Pro Gly Thr Asn Ala Arg Gln Leu
            980                 985                 990 gca aga ata gtt gcc tgt gcc gtc ttg gca ggt gaa tta tcc tta tgt    3024
Ala Arg Ile Val Ala Cys Ala Val Leu Ala Gly Glu Leu Ser Leu Cys
        995                 1000                1005 gct gcc cta gca gcc ggc cat ttg gtt caa agt cat atg acc cac aac    3072
Ala Ala Leu Ala Ala Gly His Leu Val Gln Ser His Met Thr His Asn
    1010                1015                1020 agg aaa cct gct gaa cca aca aaa cct aac aat ttg gac gcc act gat    3120
Arg Lys Pro Ala Glu Pro Thr Lys Pro Asn Asn Leu Asp Ala Thr Asp
1025                1030                1035                1040 ata aat cgt ttg aaa gat ggg tcc gtc acc tgc att aaa tcc taa        3165
Ile Asn Arg Leu Lys Asp Gly Ser Val Thr Cys Ile Lys Ser
                1045                1050
```

<210> SEQ ID NO 8
<211> LENGTH: 1054
<212> TYPE: PRT
<213> ORGANISM: Saccharomyces cerevisiae

<400> SEQUENCE: 8

```
Met Pro Pro Leu Phe Lys Gly Leu Lys Gln Met Ala Lys Pro Ile Ala
 1               5                  10                  15

Tyr Val Ser Arg Phe Ser Ala Lys Arg Pro Ile His Ile Ile Leu Phe
                20                  25                  30

Ser Leu Ile Ile Ser Ala Phe Ala Tyr Leu Ser Val Ile Gln Tyr Tyr
            35                  40                  45

Phe Asn Gly Trp Gln Leu Asp Ser Asn Ser Val Phe Glu Thr Ala Pro
        50                  55                  60

Asn Lys Asp Ser Asn Thr Leu Phe Gln Glu Cys Ser His Tyr Tyr Arg
 65                  70                  75                  80

Asp Ser Ser Leu Asp Gly Trp Val Ser Ile Thr Ala His Glu Ala Ser
                85                  90                  95

Glu Leu Pro Ala Pro His His Tyr Leu Leu Asn Leu Asn Phe Asn
                100                 105                 110

Ser Pro Asn Glu Thr Asp Ser Ile Pro Glu Leu Ala Asn Thr Val Phe
            115                 120                 125

Glu Lys Asp Asn Thr Lys Tyr Ile Leu Gln Glu Asp Leu Ser Val Ser
        130                 135                 140

Lys Glu Ile Ser Ser Thr Asp Gly Thr Lys Trp Arg Leu Arg Ser Asp
145                 150                 155                 160

Arg Lys Ser Leu Phe Asp Val Lys Thr Leu Ala Tyr Ser Leu Tyr Asp
                165                 170                 175

Val Phe Ser Glu Asn Val Thr Gln Ala Asp Pro Phe Asp Val Leu Ile
            180                 185                 190

Met Val Thr Ala Tyr Leu Met Met Phe Tyr Thr Ile Phe Gly Leu Phe
        195                 200                 205

Asn Asp Met Arg Lys Thr Gly Ser Asn Phe Trp Leu Ser Ala Ser Thr
    210                 215                 220

Val Val Asn Ser Ala Ser Ser Leu Phe Leu Ala Leu Tyr Val Thr Gln
```

-continued

```
            225                 230                 235                 240
        Cys Ile Leu Gly Lys Glu Val Ser Ala Leu Thr Leu Phe Glu Gly Leu
                        245                 250                 255
        Pro Phe Ile Val Val Val Gly Phe Lys His Lys Ile Lys Ile Ala
                    260                 265                 270
        Gln Tyr Ala Leu Glu Lys Phe Glu Arg Val Gly Leu Ser Lys Arg Ile
                    275                 280                 285
        Thr Thr Asp Glu Ile Val Phe Glu Ser Val Ser Glu Glu Gly Gly Arg
                290                 295                 300
        Leu Ile Gln Asp His Leu Leu Cys Ile Phe Ala Phe Ile Gly Cys Ser
        305                 310                 315                 320
        Met Tyr Ala His Gln Leu Lys Thr Leu Thr Asn Phe Cys Ile Leu Ser
                        325                 330                 335
        Ala Phe Ile Leu Ile Phe Glu Leu Ile Leu Thr Pro Thr Phe Tyr Ser
                        340                 345                 350
        Ala Ile Leu Ala Leu Arg Leu Glu Met Asn Val Ile His Arg Ser Thr
                    355                 360                 365
        Ile Ile Lys Gln Thr Leu Glu Glu Asp Gly Val Val Pro Ser Thr Ala
                370                 375                 380
        Arg Ile Ile Ser Lys Ala Glu Lys Ser Val Ser Ser Phe Leu Asn
        385                 390                 395                 400
        Leu Ser Val Val Val Ile Ile Met Lys Leu Ser Val Ile Leu Leu Phe
                        405                 410                 415
        Val Phe Ile Asn Phe Tyr Asn Phe Gly Ala Asn Trp Val Asn Asp Ala
                        420                 425                 430
        Phe Asn Ser Leu Tyr Phe Asp Lys Glu Arg Val Ser Leu Pro Asp Phe
                        435                 440                 445
        Ile Thr Ser Asn Ala Ser Glu Asn Phe Lys Glu Gln Ala Ile Val Ser
                    450                 455                 460
        Val Thr Pro Leu Leu Tyr Tyr Lys Pro Ile Lys Ser Tyr Gln Arg Ile
        465                 470                 475                 480
        Glu Asp Met Val Leu Leu Leu Arg Asn Val Ser Val Ala Ile Arg
                        485                 490                 495
        Asp Arg Phe Val Ser Lys Leu Val Leu Ser Ala Leu Val Cys Ser Ala
                        500                 505                 510
        Val Ile Asn Val Tyr Leu Leu Asn Ala Ala Arg Ile His Thr Ser Tyr
                    515                 520                 525
        Thr Ala Asp Gln Leu Val Lys Thr Glu Val Thr Lys Lys Ser Phe Thr
                530                 535                 540
        Ala Pro Val Gln Lys Ala Ser Thr Pro Val Leu Thr Asn Lys Thr Val
        545                 550                 555                 560
        Ile Ser Gly Ser Lys Val Lys Ser Leu Ser Ser Ala Gln Ser Ser Ser
                        565                 570                 575
        Ser Gly Pro Ser Ser Ser Glu Glu Asp Ser Arg Asp Ile Glu
                    580                 585                 590
        Ser Leu Asp Lys Lys Ile Arg Pro Leu Glu Glu Leu Glu Ala Leu Leu
                    595                 600                 605
        Ser Ser Gly Asn Thr Lys Gln Leu Lys Asn Lys Glu Val Ala Ala Leu
                610                 615                 620
        Val Ile His Gly Lys Leu Pro Leu Tyr Ala Leu Glu Lys Lys Leu Gly
        625                 630                 635                 640
        Asp Thr Thr Arg Ala Val Ala Val Arg Arg Lys Ala Leu Ser Ile Leu
                        645                 650                 655
```

```
Ala Glu Ala Pro Val Leu Ala Ser Asp Arg Leu Pro Tyr Lys Asn Tyr
            660                 665                 670

Asp Tyr Asp Arg Val Phe Gly Ala Cys Cys Glu Asn Val Ile Gly Tyr
            675                 680                 685

Met Pro Leu Pro Val Gly Val Ile Gly Pro Leu Val Ile Asp Gly Thr
            690                 695                 700

Ser Tyr His Ile Pro Met Ala Thr Thr Glu Gly Cys Leu Val Ala Ser
705                 710                 715                 720

Ala Met Arg Gly Cys Lys Ala Ile Asn Ala Gly Gly Ala Thr Thr
                725                 730                 735

Val Leu Thr Lys Asp Gly Met Thr Arg Gly Pro Val Val Arg Phe Pro
            740                 745                 750

Thr Leu Lys Arg Ser Gly Ala Cys Lys Ile Trp Leu Asp Ser Glu Glu
            755                 760                 765

Gly Gln Asn Ala Ile Lys Lys Ala Phe Asn Ser Thr Ser Arg Phe Ala
            770                 775                 780

Arg Leu Gln His Ile Gln Thr Cys Leu Ala Gly Asp Leu Leu Phe Met
785                 790                 795                 800

Arg Phe Arg Thr Thr Thr Gly Asp Ala Met Gly Met Asn Met Ile Ser
                805                 810                 815

Lys Gly Val Glu Tyr Ser Leu Lys Gln Met Val Glu Glu Tyr Gly Trp
            820                 825                 830

Glu Asp Met Glu Val Val Ser Val Ser Gly Asn Tyr Cys Thr Asp Lys
            835                 840                 845

Lys Pro Ala Ala Ile Asn Trp Ile Glu Gly Arg Gly Lys Ser Val Val
850                 855                 860

Ala Glu Ala Thr Ile Pro Gly Asp Val Val Arg Lys Val Leu Lys Ser
865                 870                 875                 880

Asp Val Ser Ala Leu Val Glu Leu Asn Ile Ala Lys Asn Leu Val Gly
                885                 890                 895

Ser Ala Met Ala Gly Ser Val Gly Gly Phe Asn Ala His Ala Ala Asn
            900                 905                 910

Leu Val Thr Ala Val Phe Leu Ala Leu Gly Gln Asp Pro Ala Gln Asn
            915                 920                 925

Val Glu Ser Ser Asn Cys Ile Thr Leu Met Lys Glu Val Asp Gly Asp
            930                 935                 940

Leu Arg Ile Ser Val Ser Met Pro Ser Ile Glu Val Gly Thr Ile Gly
945                 950                 955                 960

Gly Gly Thr Val Leu Glu Pro Gln Gly Ala Met Leu Asp Leu Leu Gly
                965                 970                 975

Val Arg Gly Pro His Ala Thr Ala Pro Gly Thr Asn Ala Arg Gln Leu
            980                 985                 990

Ala Arg Ile Val Ala Cys Ala Val Leu Ala Gly Glu Leu Ser Leu Cys
            995                 1000                1005

Ala Ala Leu Ala Ala Gly His Leu Val Gln Ser His Met Thr His Asn
    1010                1015                1020

Arg Lys Pro Ala Glu Pro Thr Lys Pro Asn Asn Leu Asp Ala Thr Asp
1025                1030                1035                1040

Ile Asn Arg Leu Lys Asp Gly Ser Val Thr Cys Ile Lys Ser
                1045                1050
```

<210> SEQ ID NO 9
<211> LENGTH: 3165

```
<212> TYPE: DNA
<213> ORGANISM: Saccharomyces cerevisiae
<220> FEATURE:
<221> NAME/KEY: CDS
<222> LOCATION: (1)..(3162)

<400> SEQUENCE: 9 atg ccg ccg cta ttc aag gga ctg aaa cag atg gca aag cca att gcc    48
Met Pro Pro Leu Phe Lys Gly Leu Lys Gln Met Ala Lys Pro Ile Ala
1               5                  10                  15 tat gtt tca aga ttt tcg gcg aaa cga cca att cat ata ata ctt ttt    96
Tyr Val Ser Arg Phe Ser Ala Lys Arg Pro Ile His Ile Ile Leu Phe
            20                  25                  30 tct cta atc ata tcc gca ttc gct tat cta tcc gtc att cag tat tac   144
Ser Leu Ile Ile Ser Ala Phe Ala Tyr Leu Ser Val Ile Gln Tyr Tyr
        35                  40                  45 ttc aat ggt tgg caa cta gat tca aat agt gtt ttt gaa act gct cca   192
Phe Asn Gly Trp Gln Leu Asp Ser Asn Ser Val Phe Glu Thr Ala Pro
50                  55                  60 aat aaa gac ttc aac act cta ttt caa gaa tgt tcc cat tac tac aga   240
Asn Lys Asp Phe Asn Thr Leu Phe Gln Glu Cys Ser His Tyr Tyr Arg
65                  70                  75                  80 gat tcc tct cta gat ggt tgg gta tca atc acc gcg cat gaa gct agt   288
Asp Ser Ser Leu Asp Gly Trp Val Ser Ile Thr Ala His Glu Ala Ser
                85                  90                  95 gag tta cca gcc cca cac cat tac tat cta tta aac ctg aac ttc aat   336
Glu Leu Pro Ala Pro His His Tyr Tyr Leu Leu Asn Leu Asn Phe Asn
            100                 105                 110 agt cct aat gaa act gac tcc att cca gaa cta gct aac acg gtt ttt   384
Ser Pro Asn Glu Thr Asp Ser Ile Pro Glu Leu Ala Asn Thr Val Phe
        115                 120                 125 gag aaa gat aat aca aaa tat att ctg caa gaa gat ctc agc gtt tcc   432
Glu Lys Asp Asn Thr Lys Tyr Ile Leu Gln Glu Asp Leu Ser Val Ser
    130                 135                 140 aaa gaa att tct tct act gat gga acg aaa tgg agg tta aga agt gac   480
Lys Glu Ile Ser Ser Thr Asp Gly Thr Lys Trp Arg Leu Arg Ser Asp
145                 150                 155                 160 aga aaa agt ctt ttc gac gta aag acg tta gca tat tct ctc tac gat   528
Arg Lys Ser Leu Phe Asp Val Lys Thr Leu Ala Tyr Ser Leu Tyr Asp
                165                 170                 175 gta ttt tca gaa aat gta acc caa gca gac ccg ttt gac gtc ctt att   576
Val Phe Ser Glu Asn Val Thr Gln Ala Asp Pro Phe Asp Val Leu Ile
            180                 185                 190 atg gtt act gcc tac cta atg atg ttc tac acc ata ttc ggc ctc ttc   624
Met Val Thr Ala Tyr Leu Met Met Phe Tyr Thr Ile Phe Gly Leu Phe
        195                 200                 205 aat gac atg agg aag acc ggg tca aat ttt tgg ttg agc gcc tct aca   672
Asn Asp Met Arg Lys Thr Gly Ser Asn Phe Trp Leu Ser Ala Ser Thr
    210                 215                 220 gtg gtc aat tct gca tca tca ctt ttc tta gca ttg tat gtc acc caa   720
Val Val Asn Ser Ala Ser Ser Leu Phe Leu Ala Leu Tyr Val Thr Gln
225                 230                 235                 240 tgt att cta ggc aaa gaa gtt tcc gca tta act ctt ttt gaa ggt ttg   768
Cys Ile Leu Gly Lys Glu Val Ser Ala Leu Thr Leu Phe Glu Gly Leu
                245                 250                 255 cct ttc att gta gtt gtt gtt ggt ttc aag cac aaa atc aag att gcc   816
Pro Phe Ile Val Val Val Val Gly Phe Lys His Lys Ile Lys Ile Ala
            260                 265                 270 cag tat gcc ctg gag aaa ttt gaa aga gtc ggt tta tct aaa agg att   864
Gln Tyr Ala Leu Glu Lys Phe Glu Arg Val Gly Leu Ser Lys Arg Ile
        275                 280                 285
```

-continued

```
act acc gat gaa atc gtt ttt gaa tcc gtg agc gaa gag ggt ggt cgt      912
Thr Thr Asp Glu Ile Val Phe Glu Ser Val Ser Glu Glu Gly Gly Arg
290                 295                 300 ttg att caa gac cat ttg ctt tgt att ttt gcc ttt atc gga tgc tct      960
Leu Ile Gln Asp His Leu Leu Cys Ile Phe Ala Phe Ile Gly Cys Ser
305                 310                 315                 320 atg tat gct cac caa ttg aag act ttg aca aac ttc tgc ata tta tca     1008
Met Tyr Ala His Gln Leu Lys Thr Leu Thr Asn Phe Cys Ile Leu Ser
                325                 330                 335 gca ttt atc cta att ttc gaa ttg att tta act cct aca ttt tat tct     1056
Ala Phe Ile Leu Ile Phe Glu Leu Ile Leu Thr Pro Thr Phe Tyr Ser
340                 345                 350 gct atc tta gcg ctt aga ctg gaa atg aat gtt atc cac aga tct act     1104
Ala Ile Leu Ala Leu Arg Leu Glu Met Asn Val Ile His Arg Ser Thr
            355                 360                 365 att atc aag caa aca tta gaa gaa gac ggt gtt gtt cca tct aca gca     1152
Ile Ile Lys Gln Thr Leu Glu Glu Asp Gly Val Val Pro Ser Thr Ala
370                 375                 380 aga atc att tct aag gca gaa aag aaa tcc gta tct tct ttc tta aat     1200
Arg Ile Ile Ser Lys Ala Glu Lys Lys Ser Val Ser Ser Phe Leu Asn
385                 390                 395                 400 ctc agt gtg gtt gtc att atc atg aaa ctc tct gtc ata ctg ttg ttc     1248
Leu Ser Val Val Val Ile Ile Met Lys Leu Ser Val Ile Leu Leu Phe
                405                 410                 415 gtc ttc atc aac ttt tat aac ttt ggt gca aat tgg gtc aat gat gcc     1296
Val Phe Ile Asn Phe Tyr Asn Phe Gly Ala Asn Trp Val Asn Asp Ala
                420                 425                 430 ttc aat tca ttg tac ttc gat aag gaa cgt gtt tct cta cca gat ttt     1344
Phe Asn Ser Leu Tyr Phe Asp Lys Glu Arg Val Ser Leu Pro Asp Phe
            435                 440                 445 att acc tcg aat gcc tct gaa aac ttt aaa gag caa gct att gtt agt     1392
Ile Thr Ser Asn Ala Ser Glu Asn Phe Lys Glu Gln Ala Ile Val Ser
450                 455                 460 gtc acc cca tta tta tat tac aaa ccc att aag tcc tac caa cgc att     1440
Val Thr Pro Leu Leu Tyr Tyr Lys Pro Ile Lys Ser Tyr Gln Arg Ile
465                 470                 475                 480 gag gat atg gtt ctt cta ttg ctt cgt aat gtc agt gtt gcc att cgt     1488
Glu Asp Met Val Leu Leu Leu Arg Asn Val Ser Val Ala Ile Arg
                485                 490                 495 gat agg ttc gtc agt aaa tta gtt ctt tcc gcc tta gta tgc agt gct     1536
Asp Arg Phe Val Ser Lys Leu Val Leu Ser Ala Leu Val Cys Ser Ala
                500                 505                 510 gtc atc aat gtg tat tta tta aat gct gct aga att cat acc agt tat     1584
Val Ile Asn Val Tyr Leu Leu Asn Ala Ala Arg Ile His Thr Ser Tyr
            515                 520                 525 act gca gac caa ttg gtg aag act gaa gtc acc aag aag tct ttt act     1632
Thr Ala Asp Gln Leu Val Lys Thr Glu Val Thr Lys Lys Ser Phe Thr
530                 535                 540 gct cct gta caa aag gct tct aca cca gtt tta acc aat aaa aca gtc     1680
Ala Pro Val Gln Lys Ala Ser Thr Pro Val Leu Thr Asn Lys Thr Val
545                 550                 555                 560 att tct gga tcg aaa gtc aaa agt tta tca tct gcg caa tcg agc tca     1728
Ile Ser Gly Ser Lys Val Lys Ser Leu Ser Ser Ala Gln Ser Ser Ser
                565                 570                 575 tca gga cct tca tca tct agt gag gaa gat gat tcc cgc gat att gaa     1776
Ser Gly Pro Ser Ser Ser Ser Glu Glu Asp Asp Ser Arg Asp Ile Glu
            580                 585                 590 agc ttg gat aag aaa ata cgt cct tta gaa gaa tta gaa gca tca tta     1824
Ser Leu Asp Lys Lys Ile Arg Pro Leu Glu Glu Leu Glu Ala Ser Leu
```

```
                595                 600                 605
agt agt gga aat aca aaa caa ttg aag aac aaa gag gtc gct gcc ttg    1872
Ser Ser Gly Asn Thr Lys Gln Leu Lys Asn Lys Glu Val Ala Ala Leu
610                 615                 620 gtt att cac ggt aag tta cct ttg tac gct ttg gag aaa aaa tta ggt    1920
Val Ile His Gly Lys Leu Pro Leu Tyr Ala Leu Glu Lys Lys Leu Gly
625                 630                 635                 640 gat act acg aga gcg gtt gcg gta cgt agg aag gct ctt tca att ttg    1968
Asp Thr Thr Arg Ala Val Ala Val Arg Arg Lys Ala Leu Ser Ile Leu
            645                 650                 655 gca gaa gct cct gta tta gca tct gat cgt tta cca tat aaa aat tat    2016
Ala Glu Ala Pro Val Leu Ala Ser Asp Arg Leu Pro Tyr Lys Asn Tyr
        660                 665                 670 gac tac gac cgc gta ttt ggc gct tgt tgt gaa aat gtt ata ggt tac    2064
Asp Tyr Asp Arg Val Phe Gly Ala Cys Cys Glu Asn Val Ile Gly Tyr
            675                 680                 685 atg cct ttg ccc gtt ggt gtt ata ggc ccc ttg gtt atc gat ggt aca    2112
Met Pro Leu Pro Val Gly Val Ile Gly Pro Leu Val Ile Asp Gly Thr
690                 695                 700 tct tat cat ata cca atg gca act aca gag ggt tgt ttg gta gct tct    2160
Ser Tyr His Ile Pro Met Ala Thr Thr Glu Gly Cys Leu Val Ala Ser
705                 710                 715                 720 gcc atg cgt ggc tgt aag gca atc aat gct ggc ggt ggt gca aca act    2208
Ala Met Arg Gly Cys Lys Ala Ile Asn Ala Gly Gly Gly Ala Thr Thr
            725                 730                 735 gtt tta act aag gat ggt atg aca aga ggc cca gta gtc cgt ttc cca    2256
Val Leu Thr Lys Asp Gly Met Thr Arg Gly Pro Val Val Arg Phe Pro
        740                 745                 750 act ttg aaa aga tct ggt gcc tgt aag ata tgg tta gac tca gaa gag    2304
Thr Leu Lys Arg Ser Gly Ala Cys Lys Ile Trp Leu Asp Ser Glu Glu
            755                 760                 765 gga caa aac gca att aaa aaa gct ttt aac tct aca tca aga ttt gca    2352
Gly Gln Asn Ala Ile Lys Lys Ala Phe Asn Ser Thr Ser Arg Phe Ala
770                 775                 780 cgt ctg caa cat att caa act tgt cta gca gga gat tta ctc ttc atg    2400
Arg Leu Gln His Ile Gln Thr Cys Leu Ala Gly Asp Leu Leu Phe Met
785                 790                 795                 800 aga ttt aga aca act act ggt gac gca atg ggt atg aat atg att tct    2448
Arg Phe Arg Thr Thr Thr Gly Asp Ala Met Gly Met Asn Met Ile Ser
            805                 810                 815 aag ggt gtc gaa tac tca tta aag caa atg gta gaa gag tat ggc tgg    2496
Lys Gly Val Glu Tyr Ser Leu Lys Gln Met Val Glu Glu Tyr Gly Trp
        820                 825                 830 gaa gat atg gag gtt gtc tcc gtt tct ggt aac tac tgt acc gac aaa    2544
Glu Asp Met Glu Val Val Ser Val Ser Gly Asn Tyr Cys Thr Asp Lys
835                 840                 845 aaa cca gct gcc atc aac tgg atc gaa ggt cgt ggt aag agt gtc gtc    2592
Lys Pro Ala Ala Ile Asn Trp Ile Glu Gly Arg Gly Lys Ser Val Val
850                 855                 860 gca gaa gct act att cct ggt gat gtt gtc aga aaa gtg tta aaa agt    2640
Ala Glu Ala Thr Ile Pro Gly Asp Val Val Arg Lys Val Leu Lys Ser
865                 870                 875                 880 gat gtt tcc gca ttg gtt gag ttg aac att gct aag aat ttg gtt gga    2688
Asp Val Ser Ala Leu Val Glu Leu Asn Ile Ala Lys Asn Leu Val Gly
            885                 890                 895 tct gca atg gct ggg tct gtt ggt gga ttt aac gca cgt gca gct aat    2736
Ser Ala Met Ala Gly Ser Val Gly Gly Phe Asn Ala Arg Ala Ala Asn
        900                 905                 910 tta gtg aca gct gtt ttc ttg gca tta gga caa gat cct gca caa aat    2784
```

```
                Leu Val Thr Ala Val Phe Leu Ala Leu Gly Gln Asp Pro Ala Gln Asn
                    915                 920                 925 gtc gaa agt tcc aac tgt ata aca ttg atg aaa gaa gtg gac ggt gat           2832
Val Glu Ser Ser Asn Cys Ile Thr Leu Met Lys Glu Val Asp Gly Asp
        930                 935                 940 ttg aga att tcc gta tcc atg cca tcc atc gaa gta ggt acc atc ggt           2880
Leu Arg Ile Ser Val Ser Met Pro Ser Ile Glu Val Gly Thr Ile Gly
945                 950                 955                 960 ggt ggt act gtt cta gaa cca caa ggt gcc atg ttg gac tta tta ggt           2928
Gly Gly Thr Val Leu Glu Pro Gln Gly Ala Met Leu Asp Leu Leu Gly
                965                 970                 975 gta aga ggc cca cat gct acc gct cct ggt acc aac gca cgt caa tta           2976
Val Arg Gly Pro His Ala Thr Ala Pro Gly Thr Asn Ala Arg Gln Leu
            980                 985                 990 gca aga ata gtt gcc tgt gcc gtc ttg gca ggt gaa tta tcc tta tgt           3024
Ala Arg Ile Val Ala Cys Ala Val Leu Ala Gly Glu Leu Ser Leu Cys
        995                 1000                1005 gct gcc cta gca gcc ggc cat ttg gtt caa agt cat atg acc cac aac           3072
Ala Ala Leu Ala Ala Gly His Leu Val Gln Ser His Met Thr His Asn
    1010                1015                1020 agg aaa cct gct gaa cca aca aaa cct aac aat ttg gac gcc act gat           3120
Arg Lys Pro Ala Glu Pro Thr Lys Pro Asn Asn Leu Asp Ala Thr Asp
1025                1030                1035                1040 ata aat cgt ttg aaa gat ggg tcc gtc acc tgc att aaa tcc taa               3165
Ile Asn Arg Leu Lys Asp Gly Ser Val Thr Cys Ile Lys Ser
                1045                1050

<210> SEQ ID NO 10
<211> LENGTH: 1054
<212> TYPE: PRT
<213> ORGANISM: Saccharomyces cerevisiae

<400> SEQUENCE: 10

Met Pro Pro Leu Phe Lys Gly Leu Lys Gln Met Ala Lys Pro Ile Ala
 1               5                  10                  15

Tyr Val Ser Arg Phe Ser Ala Lys Arg Pro Ile His Ile Ile Leu Phe
             20                  25                  30

Ser Leu Ile Ile Ser Ala Phe Ala Tyr Leu Ser Val Ile Gln Tyr Tyr
         35                  40                  45

Phe Asn Gly Trp Gln Leu Asp Ser Asn Ser Val Phe Glu Thr Ala Pro
     50                  55                  60

Asn Lys Asp Phe Asn Thr Leu Phe Gln Glu Cys Ser His Tyr Tyr Arg
 65                  70                  75                  80

Asp Ser Ser Leu Asp Gly Trp Val Ser Ile Thr Ala His Glu Ala Ser
                 85                  90                  95

Glu Leu Pro Ala Pro His His Tyr Tyr Leu Leu Asn Leu Asn Phe Asn
            100                 105                 110

Ser Pro Asn Glu Thr Asp Ser Ile Pro Glu Leu Ala Asn Thr Val Phe
        115                 120                 125

Glu Lys Asp Asn Thr Lys Tyr Ile Leu Gln Glu Asp Leu Ser Val Ser
    130                 135                 140

Lys Glu Ile Ser Ser Thr Asp Gly Thr Lys Trp Arg Leu Arg Ser Asp
145                 150                 155                 160

Arg Lys Ser Leu Phe Asp Val Lys Thr Leu Ala Tyr Ser Leu Tyr Asp
                165                 170                 175

Val Phe Ser Glu Asn Val Thr Gln Ala Asp Pro Phe Asp Val Leu Ile
            180                 185                 190
```

-continued

```
Met Val Thr Ala Tyr Leu Met Met Phe Tyr Thr Ile Phe Gly Leu Phe
        195                 200                 205

Asn Asp Met Arg Lys Thr Gly Ser Asn Phe Trp Leu Ser Ala Ser Thr
        210                 215                 220

Val Val Asn Ser Ala Ser Ser Leu Phe Leu Ala Leu Tyr Val Thr Gln
225                 230                 235                 240

Cys Ile Leu Gly Lys Glu Val Ser Ala Leu Thr Leu Phe Glu Gly Leu
                245                 250                 255

Pro Phe Ile Val Val Val Gly Phe Lys His Lys Ile Lys Ile Ala
            260                 265                 270

Gln Tyr Ala Leu Glu Lys Phe Glu Arg Val Gly Leu Ser Lys Arg Ile
        275                 280                 285

Thr Thr Asp Glu Ile Val Phe Glu Ser Val Ser Glu Glu Gly Gly Arg
        290                 295                 300

Leu Ile Gln Asp His Leu Leu Cys Ile Phe Ala Phe Ile Gly Cys Ser
305                 310                 315                 320

Met Tyr Ala His Gln Leu Lys Thr Leu Thr Asn Phe Cys Ile Leu Ser
                325                 330                 335

Ala Phe Ile Leu Ile Phe Glu Leu Ile Leu Thr Pro Thr Phe Tyr Ser
            340                 345                 350

Ala Ile Leu Ala Leu Arg Leu Glu Met Asn Val Ile His Arg Ser Thr
        355                 360                 365

Ile Ile Lys Gln Thr Leu Glu Glu Asp Gly Val Val Pro Ser Thr Ala
        370                 375                 380

Arg Ile Ile Ser Lys Ala Glu Lys Lys Ser Val Ser Ser Phe Leu Asn
385                 390                 395                 400

Leu Ser Val Val Val Ile Ile Met Lys Leu Ser Val Ile Leu Leu Phe
                405                 410                 415

Val Phe Ile Asn Phe Tyr Asn Phe Gly Ala Asn Trp Val Asn Asp Ala
            420                 425                 430

Phe Asn Ser Leu Tyr Phe Asp Lys Glu Arg Val Ser Leu Pro Asp Phe
        435                 440                 445

Ile Thr Ser Asn Ala Ser Glu Asn Phe Lys Glu Gln Ala Ile Val Ser
        450                 455                 460

Val Thr Pro Leu Leu Tyr Tyr Lys Pro Ile Lys Ser Tyr Gln Arg Ile
465                 470                 475                 480

Glu Asp Met Val Leu Leu Leu Arg Asn Val Ser Val Ala Ile Arg
                485                 490                 495

Asp Arg Phe Val Ser Lys Leu Val Leu Ser Ala Leu Val Cys Ser Ala
            500                 505                 510

Val Ile Asn Val Tyr Leu Leu Asn Ala Ala Arg Ile His Thr Ser Tyr
        515                 520                 525

Thr Ala Asp Gln Leu Val Lys Thr Glu Val Thr Lys Lys Ser Phe Thr
        530                 535                 540

Ala Pro Val Gln Lys Ala Ser Thr Pro Val Leu Thr Asn Lys Thr Val
545                 550                 555                 560

Ile Ser Gly Ser Lys Val Lys Ser Leu Ser Ala Gln Ser Ser Ser
                565                 570                 575

Ser Gly Pro Ser Ser Ser Glu Glu Asp Asp Ser Arg Asp Ile Glu
            580                 585                 590

Ser Leu Asp Lys Lys Ile Arg Pro Leu Glu Glu Leu Glu Ala Ser Leu
        595                 600                 605

Ser Ser Gly Asn Thr Lys Gln Leu Lys Asn Lys Glu Val Ala Ala Leu
```

```
                610             615             620
Val Ile His Gly Lys Leu Pro Leu Tyr Ala Leu Glu Lys Lys Leu Gly
625                 630                 635                 640

Asp Thr Thr Arg Ala Val Ala Val Arg Arg Lys Ala Leu Ser Ile Leu
                645                 650                 655

Ala Glu Ala Pro Val Leu Ala Ser Asp Arg Leu Pro Tyr Lys Asn Tyr
                660                 665                 670

Asp Tyr Asp Arg Val Phe Gly Ala Cys Cys Glu Asn Val Ile Gly Tyr
                675                 680                 685

Met Pro Leu Pro Val Gly Val Ile Gly Pro Leu Val Ile Asp Gly Thr
690                 695                 700

Ser Tyr His Ile Pro Met Ala Thr Thr Glu Gly Cys Leu Val Ala Ser
705                 710                 715                 720

Ala Met Arg Gly Cys Lys Ala Ile Asn Ala Gly Gly Gly Ala Thr Thr
                725                 730                 735

Val Leu Thr Lys Asp Gly Met Thr Arg Gly Pro Val Val Arg Phe Pro
                740                 745                 750

Thr Leu Lys Arg Ser Gly Ala Cys Lys Ile Trp Leu Asp Ser Glu Glu
                755                 760                 765

Gly Gln Asn Ala Ile Lys Lys Ala Phe Asn Ser Thr Ser Arg Phe Ala
            770                 775                 780

Arg Leu Gln His Ile Gln Thr Cys Leu Ala Gly Asp Leu Leu Phe Met
785                 790                 795                 800

Arg Phe Arg Thr Thr Thr Gly Asp Ala Met Gly Met Asn Met Ile Ser
                805                 810                 815

Lys Gly Val Glu Tyr Ser Leu Lys Gln Met Val Glu Glu Tyr Gly Trp
                820                 825                 830

Glu Asp Met Glu Val Val Ser Val Ser Gly Asn Tyr Cys Thr Asp Lys
                835                 840                 845

Lys Pro Ala Ala Ile Asn Trp Ile Glu Gly Arg Gly Lys Ser Val Val
            850                 855                 860

Ala Glu Ala Thr Ile Pro Gly Asp Val Val Arg Lys Val Leu Lys Ser
865                 870                 875                 880

Asp Val Ser Ala Leu Val Glu Leu Asn Ile Ala Lys Asn Leu Val Gly
                885                 890                 895

Ser Ala Met Ala Gly Ser Val Gly Gly Phe Asn Ala Arg Ala Ala Asn
                900                 905                 910

Leu Val Thr Ala Val Phe Leu Ala Leu Gly Gln Asp Pro Ala Gln Asn
            915                 920                 925

Val Glu Ser Ser Asn Cys Ile Thr Leu Met Lys Glu Val Asp Gly Asp
            930                 935                 940

Leu Arg Ile Ser Val Ser Met Pro Ser Ile Glu Val Gly Thr Ile Gly
945                 950                 955                 960

Gly Gly Thr Val Leu Glu Pro Gln Gly Ala Met Leu Asp Leu Leu Gly
                965                 970                 975

Val Arg Gly Pro His Ala Thr Ala Pro Gly Thr Asn Ala Arg Gln Leu
                980                 985                 990

Ala Arg Ile Val Ala Cys Ala Val Leu Ala Gly Glu Leu Ser Leu Cys
            995                 1000                1005

Ala Ala Leu Ala Ala Gly His Leu Val Gln Ser His Met Thr His Asn
    1010                1015                1020

Arg Lys Pro Ala Glu Pro Thr Lys Pro Asn Asn Leu Asp Ala Thr Asp
1025                1030                1035                1040
```

```
Ile Asn Arg Leu Lys Asp Gly Ser Val Thr Cys Ile Lys Ser
              1045                1050

<210> SEQ ID NO 11
<211> LENGTH: 3165
<212> TYPE: DNA
<213> ORGANISM: Saccharomyces cerevisiae
<220> FEATURE:
<221> NAME/KEY: CDS
<222> LOCATION: (1)..(3162)

<400> SEQUENCE: 11 atg ccg ccg cta ttc aag gga ctg aaa cag atg gca aag cca att gcc      48
Met Pro Pro Leu Phe Lys Gly Leu Lys Gln Met Ala Lys Pro Ile Ala
  1               5                  10                  15 tat gtt tca aga ttt tcg gcg aaa cga cca att cat ata ata ctt ttt      96
Tyr Val Ser Arg Phe Ser Ala Lys Arg Pro Ile His Ile Ile Leu Phe
                 20                  25                  30 tct cta atc ata tcc gca ttc gct tat cta tcc gtc att cag tat tac     144
Ser Leu Ile Ile Ser Ala Phe Ala Tyr Leu Ser Val Ile Gln Tyr Tyr
             35                  40                  45 ttc aat ggt tgg caa cta gat tca aat agt gtt ttt gaa act gct cca     192
Phe Asn Gly Trp Gln Leu Asp Ser Asn Ser Val Phe Glu Thr Ala Pro
         50                  55                  60 aat aaa gac tcc aac act cta ttt caa gaa tgt tcc cat tac tac aga     240
Asn Lys Asp Ser Asn Thr Leu Phe Gln Glu Cys Ser His Tyr Tyr Arg
 65                  70                  75                  80 gat tcc tct cta gat ggt tgg gta tca atc acc gcg cat gaa gct agt     288
Asp Ser Ser Leu Asp Gly Trp Val Ser Ile Thr Ala His Glu Ala Ser
                 85                  90                  95 gag tta cca gcc cca cac cat tac tat cta tta aac ctg aac ttc aat     336
Glu Leu Pro Ala Pro His His Tyr Tyr Leu Leu Asn Leu Asn Phe Asn
                100                 105                 110 agt cct aat gaa act gac tcc att cca gaa cta gct aac acg gtt ttt     384
Ser Pro Asn Glu Thr Asp Ser Ile Pro Glu Leu Ala Asn Thr Val Phe
            115                 120                 125 gag aaa gat aat aca aaa tat att ctg caa gaa gat ctc agc gtt tcc     432
Glu Lys Asp Asn Thr Lys Tyr Ile Leu Gln Glu Asp Leu Ser Val Ser
        130                 135                 140 aaa gaa att tct tct act gat gga acg aaa tgg agg tta aga agt gac     480
Lys Glu Ile Ser Ser Thr Asp Gly Thr Lys Trp Arg Leu Arg Ser Asp
145                 150                 155                 160 aga aaa agt ctt ttc gac gta aag acg tta gca tat tct ctc tac gat     528
Arg Lys Ser Leu Phe Asp Val Lys Thr Leu Ala Tyr Ser Leu Tyr Asp
                165                 170                 175 gta ttt tca gaa aat gta acc caa gca gac ccg ttt gac gtc ctt att     576
Val Phe Ser Glu Asn Val Thr Gln Ala Asp Pro Phe Asp Val Leu Ile
                180                 185                 190 atg gtt act gcc tac cta atg atg ttc tac acc ata ttc ggc ctc ttc     624
Met Val Thr Ala Tyr Leu Met Met Phe Tyr Thr Ile Phe Gly Leu Phe
            195                 200                 205 aat gac atg agg aag acc ggg tca aat ttt tgg ttg agc gcc tct aca     672
Asn Asp Met Arg Lys Thr Gly Ser Asn Phe Trp Leu Ser Ala Ser Thr
        210                 215                 220 gtg gtc aat tct gca tca tca ctt ttc tta gca ttg tat gtc acc caa     720
Val Val Asn Ser Ala Ser Ser Leu Phe Leu Ala Leu Tyr Val Thr Gln
225                 230                 235                 240 tgt att cta ggc aaa gaa gtt tcc gca tta act ctt ttt gaa ggt ttg     768
Cys Ile Leu Gly Lys Glu Val Ser Ala Leu Thr Leu Phe Glu Gly Leu
                245                 250                 255
```

```
cct ttc att gta gtt gtt gtt ggt ttc aag cac aaa atc aag att gcc    816
Pro Phe Ile Val Val Val Val Gly Phe Lys His Lys Ile Lys Ile Ala
        260                 265                 270 cag tat gcc ctg gag aaa ttt gaa aga gtc ggt tta tct aaa agg att    864
Gln Tyr Ala Leu Glu Lys Phe Glu Arg Val Gly Leu Ser Lys Arg Ile
        275                 280                 285 act acc gat gaa atc gtt ttt gaa tcc gtg agc gaa gag ggt ggt cgt    912
Thr Thr Asp Glu Ile Val Phe Glu Ser Val Ser Glu Glu Gly Gly Arg
        290                 295                 300 ttg att caa gac cat ttg ctt tgt att ttt gcc ttt atc gga tgc tct    960
Leu Ile Gln Asp His Leu Leu Cys Ile Phe Ala Phe Ile Gly Cys Ser
305                 310                 315                 320 atg tat gct cac caa ttg aag act ttg aca aac ttc tgc ata tta tca   1008
Met Tyr Ala His Gln Leu Lys Thr Leu Thr Asn Phe Cys Ile Leu Ser
                325                 330                 335 gca ttt atc cta att ttc gaa ttg att tta act cct aca ttt tat tct   1056
Ala Phe Ile Leu Ile Phe Glu Leu Ile Leu Thr Pro Thr Phe Tyr Ser
                340                 345                 350 gct atc tta gcg ctt aga ctg gaa atg aat gtt atc cac aga tct act   1104
Ala Ile Leu Ala Leu Arg Leu Glu Met Asn Val Ile His Arg Ser Thr
                355                 360                 365 att atc aag caa aca tta gaa gaa gac ggt gtt gtt cca tct aca gca   1152
Ile Ile Lys Gln Thr Leu Glu Glu Asp Gly Val Val Pro Ser Thr Ala
        370                 375                 380 aga atc att tct aag gca gaa aag aaa tcc gta tct tct ttc tta aat   1200
Arg Ile Ile Ser Lys Ala Glu Lys Lys Ser Val Ser Ser Phe Leu Asn
385                 390                 395                 400 ctc agt gtg gtt gtc att atc atg aaa ctc tct gtc ata ctg ttg ttc   1248
Leu Ser Val Val Val Ile Ile Met Lys Leu Ser Val Ile Leu Leu Phe
                405                 410                 415 gtc ttc atc aac ttt tat aac ttt ggt gca aat tgg gtc aat gat gcc   1296
Val Phe Ile Asn Phe Tyr Asn Phe Gly Ala Asn Trp Val Asn Asp Ala
                420                 425                 430 ttc aat tca ttg tac ttc gat aag gaa cgt gtt tct cta cca gat ttt   1344
Phe Asn Ser Leu Tyr Phe Asp Lys Glu Arg Val Ser Leu Pro Asp Phe
                435                 440                 445 att acc tcg aat gcc tct gaa aac ttt aaa gag caa gct att gtt agt   1392
Ile Thr Ser Asn Ala Ser Glu Asn Phe Lys Glu Gln Ala Ile Val Ser
        450                 455                 460 gtc acc cca tta tta tat tac aaa ccc att aag tcc tac caa cgc att   1440
Val Thr Pro Leu Leu Tyr Tyr Lys Pro Ile Lys Ser Tyr Gln Arg Ile
465                 470                 475                 480 gag gat atg gtt ctt cta ttg ctt cgt aat gtc agt gtt gcc att cgt   1488
Glu Asp Met Val Leu Leu Leu Arg Asn Val Ser Val Ala Ile Arg
                485                 490                 495 gat agg ttc gtc agt aaa tta gtt ctt tcc gcc tta gta tgc agt gct   1536
Asp Arg Phe Val Ser Lys Leu Val Leu Ser Ala Leu Val Cys Ser Ala
                500                 505                 510 gtc atc aat gtg tat tta tta aat gct gct aga att cat acc agt tat   1584
Val Ile Asn Val Tyr Leu Leu Asn Ala Ala Arg Ile His Thr Ser Tyr
                515                 520                 525 act gca gac caa ttg gtg aag act gaa gtc acc aag aag tct ttt act   1632
Thr Ala Asp Gln Leu Val Lys Thr Glu Val Thr Lys Lys Ser Phe Thr
        530                 535                 540 gct cct gta caa aag gct tct aca cca gtt tta acc aat aaa aca gtc   1680
Ala Pro Val Gln Lys Ala Ser Thr Pro Val Leu Thr Asn Lys Thr Val
545                 550                 555                 560 att tct gga tcg aaa gtc aaa agt tta tca tct gcg caa tcg agc tca   1728
Ile Ser Gly Ser Lys Val Lys Ser Leu Ser Ser Ala Gln Ser Ser Ser
                565                 570                 575
```

-continued

| | | | | | | | | | | | | | | | | |
|---|---|---|---|---|---|---|---|---|---|---|---|---|---|---|---|---|
| tca | gga | cct | tca | tca | tct | agt | gag | gaa | gat | gat | tcc | cgc | gat | att | gaa | 1776 |
| Ser | Gly | Pro | Ser | Ser | Ser | Ser | Glu | Glu | Asp | Asp | Ser | Arg | Asp | Ile | Glu | |
| | | 580 | | | | | 585 | | | | | 590 | | | | |
| agc | ttg | gat | aag | aaa | ata | cgt | cct | tta | gaa | gaa | tta | gaa | gca | tta | tta | 1824 |
| Ser | Leu | Asp | Lys | Lys | Ile | Arg | Pro | Leu | Glu | Glu | Leu | Glu | Ala | Leu | Leu | |
| 595 | | | | | 600 | | | | | 605 | | | | | | |
| agt | agt | gga | aat | aca | aaa | caa | ttg | aag | aac | aaa | gag | gtc | gct | gcc | ttg | 1872 |
| Ser | Ser | Gly | Asn | Thr | Lys | Gln | Leu | Lys | Asn | Lys | Glu | Val | Ala | Ala | Leu | |
| 610 | | | | | 615 | | | | | 620 | | | | | | |
| gtt | att | cac | ggt | aag | tta | cct | ttg | tac | gct | ttg | gag | aaa | aaa | tta | ggt | 1920 |
| Val | Ile | His | Gly | Lys | Leu | Pro | Leu | Tyr | Ala | Leu | Glu | Lys | Lys | Leu | Gly | |
| 625 | | | | | 630 | | | | | 635 | | | | | 640 | |
| gat | act | acg | aga | gcg | gtt | gcg | gta | cgt | agg | aag | gct | ctt | tca | att | ttg | 1968 |
| Asp | Thr | Thr | Arg | Ala | Val | Ala | Val | Arg | Arg | Lys | Ala | Leu | Ser | Ile | Leu | |
| | | | | 645 | | | | | 650 | | | | | 655 | | |
| gca | gaa | gct | cct | gta | tta | gca | tct | gat | cgt | tta | cca | tat | aaa | aat | tat | 2016 |
| Ala | Glu | Ala | Pro | Val | Leu | Ala | Ser | Asp | Arg | Leu | Pro | Tyr | Lys | Asn | Tyr | |
| | | | 660 | | | | | 665 | | | | | 670 | | | |
| gac | tac | gac | cgc | gta | ttt | ggc | gct | tgt | tgt | gaa | aat | gtt | ata | ggt | tac | 2064 |
| Asp | Tyr | Asp | Arg | Val | Phe | Gly | Ala | Cys | Cys | Glu | Asn | Val | Ile | Gly | Tyr | |
| | | | 675 | | | | | 680 | | | | | 685 | | | |
| atg | cct | ttg | ccc | gtt | ggt | gtt | ata | ggc | ccc | ttg | gtt | atc | gat | ggt | aca | 2112 |
| Met | Pro | Leu | Pro | Val | Gly | Val | Ile | Gly | Pro | Leu | Val | Ile | Asp | Gly | Thr | |
| | | 690 | | | | | 695 | | | | | 700 | | | | |
| tct | tat | cat | ata | cca | atg | gca | act | aca | gag | ggt | tgt | ttg | gta | gct | tct | 2160 |
| Ser | Tyr | His | Ile | Pro | Met | Ala | Thr | Thr | Glu | Gly | Cys | Leu | Val | Ala | Ser | |
| 705 | | | | | 710 | | | | | 715 | | | | | 720 | |
| gcc | atg | cgt | ggc | tgt | aag | gca | atc | aat | gct | ggc | ggt | ggt | gca | aca | act | 2208 |
| Ala | Met | Arg | Gly | Cys | Lys | Ala | Ile | Asn | Ala | Gly | Gly | Gly | Ala | Thr | Thr | |
| | | | | 725 | | | | | 730 | | | | | 735 | | |
| gtt | tta | act | aag | gat | ggt | atg | aca | aga | ggc | cca | gta | gtc | cgt | ttc | cca | 2256 |
| Val | Leu | Thr | Lys | Asp | Gly | Met | Thr | Arg | Gly | Pro | Val | Val | Arg | Phe | Pro | |
| | | | 740 | | | | | 745 | | | | | 750 | | | |
| act | ttg | aaa | aga | tct | ggt | gcc | tgt | aag | ata | tgg | tta | gac | tca | gaa | gag | 2304 |
| Thr | Leu | Lys | Arg | Ser | Gly | Ala | Cys | Lys | Ile | Trp | Leu | Asp | Ser | Glu | Glu | |
| | | | 755 | | | | | 760 | | | | | 765 | | | |
| gga | caa | aac | gca | att | aaa | aaa | gct | ttt | aac | tct | aca | tca | aga | ttt | gca | 2352 |
| Gly | Gln | Asn | Ala | Ile | Lys | Lys | Ala | Phe | Asn | Ser | Thr | Ser | Arg | Phe | Ala | |
| | | 770 | | | | | 775 | | | | | 780 | | | | |
| cgt | ctg | caa | cat | att | caa | act | tgt | cta | gca | gga | gat | tta | ctc | ttc | atg | 2400 |
| Arg | Leu | Gln | His | Ile | Gln | Thr | Cys | Leu | Ala | Gly | Asp | Leu | Leu | Phe | Met | |
| 785 | | | | | 790 | | | | | 795 | | | | | 800 | |
| aga | ttt | aga | aca | act | act | ggt | gac | gca | atg | ggt | atg | aat | atg | att | tct | 2448 |
| Arg | Phe | Arg | Thr | Thr | Thr | Gly | Asp | Ala | Met | Gly | Met | Asn | Met | Ile | Ser | |
| | | | | 805 | | | | | 810 | | | | | 815 | | |
| aag | ggt | gtc | gaa | tac | tca | tta | aag | caa | atg | gta | gaa | gag | tat | ggc | tgg | 2496 |
| Lys | Gly | Val | Glu | Tyr | Ser | Leu | Lys | Gln | Met | Val | Glu | Glu | Tyr | Gly | Trp | |
| | | | 820 | | | | | 825 | | | | | 830 | | | |
| gaa | gat | atg | gag | gtt | gtc | tcc | gtt | tct | ggt | aac | tac | tgt | acc | gac | aaa | 2544 |
| Glu | Asp | Met | Glu | Val | Val | Ser | Val | Ser | Gly | Asn | Tyr | Cys | Thr | Asp | Lys | |
| | | 835 | | | | | 840 | | | | | 845 | | | | |
| aaa | cca | gct | gcc | atc | aac | tgg | atc | gaa | ggt | cgt | ggt | aag | agt | gtc | gtc | 2592 |
| Lys | Pro | Ala | Ala | Ile | Asn | Trp | Ile | Glu | Gly | Arg | Gly | Lys | Ser | Val | Val | |
| | | 850 | | | | | 855 | | | | | 860 | | | | |
| gca | gaa | gct | act | att | cct | ggt | gat | gtt | gtc | aga | aaa | gtg | tta | aaa | agt | 2640 |
| Ala | Glu | Ala | Thr | Ile | Pro | Gly | Asp | Val | Val | Arg | Lys | Val | Leu | Lys | Ser | |
| 865 | | | | | 870 | | | | | 875 | | | | | 880 | |
| gat | gtt | tcc | gca | ttg | gtt | gag | ttg | aac | att | gct | aag | aat | ttg | gtt | gga | 2688 |
| Asp | Val | Ser | Ala | Leu | Val | Glu | Leu | Asn | Ile | Ala | Lys | Asn | Leu | Val | Gly | |

-continued

```
                885                 890                 895
tct gca atg gct ggg tct gtt ggt gga ttt aac gca cat gca gct aat    2736
Ser Ala Met Ala Gly Ser Val Gly Gly Phe Asn Ala His Ala Ala Asn
        900                 905                 910 tta gtg aca gct gtt ttc ttg gca tta gga caa gat cct gca caa aat    2784
Leu Val Thr Ala Val Phe Leu Ala Leu Gly Gln Asp Pro Ala Gln Asn
            915                 920                 925 gtc gaa agt tcc aac tgt ata aca ttg atg aaa gaa gtg gac ggt gat    2832
Val Glu Ser Ser Asn Cys Ile Thr Leu Met Lys Glu Val Asp Gly Asp
        930                 935                 940 ttg aga att tcc gta tcc atg cca tcc atc gaa gta ggt acc atc ggt    2880
Leu Arg Ile Ser Val Ser Met Pro Ser Ile Glu Val Gly Thr Ile Gly
945                 950                 955                 960 ggt ggt act gtt cta gaa cca caa ggt gcc atg ttg gac tta tta ggt    2928
Gly Gly Thr Val Leu Glu Pro Gln Gly Ala Met Leu Asp Leu Leu Gly
                965                 970                 975 gta aga ggc cca cat gct acc gct cct ggt acc aac gca cgt caa tta    2976
Val Arg Gly Pro His Ala Thr Ala Pro Gly Thr Asn Ala Arg Gln Leu
            980                 985                 990 gca aga ata gtt gcc tgt gcc gtc ttg gca ggt gaa tta tcc tta tgt    3024
Ala Arg Ile Val Ala Cys Ala Val Leu Ala Gly Glu Leu Ser Leu Cys
        995                 1000                1005 gct gcc cta gca gcc ggc cat ttg gtt caa agt cat atg acc cac aac    3072
Ala Ala Leu Ala Ala Gly His Leu Val Gln Ser His Met Thr His Asn
    1010                1015                1020 agg aaa cct gct gaa cca aca aaa cct aac aat ttg gac gcc act gat    3120
Arg Lys Pro Ala Glu Pro Thr Lys Pro Asn Asn Leu Asp Ala Thr Asp
1025                1030                1035                1040 ata aat cgt ttg aaa gat ggg tcc gtc acc tgc att aaa tcc taa        3165
Ile Asn Arg Leu Lys Asp Gly Ser Val Thr Cys Ile Lys Ser
                1045                1050
```

<210> SEQ ID NO 12
<211> LENGTH: 1054
<212> TYPE: PRT
<213> ORGANISM: Saccharomyces cerevisiae

<400> SEQUENCE: 12

```
Met Pro Pro Leu Phe Lys Gly Leu Lys Gln Met Ala Lys Pro Ile Ala
1               5                   10                  15

Tyr Val Ser Arg Phe Ser Ala Lys Arg Pro Ile His Ile Ile Leu Phe
            20                  25                  30

Ser Leu Ile Ile Ser Ala Phe Ala Tyr Leu Ser Val Ile Gln Tyr Tyr
        35                  40                  45

Phe Asn Gly Trp Gln Leu Asp Ser Asn Ser Val Phe Glu Thr Ala Pro
    50                  55                  60

Asn Lys Asp Ser Asn Thr Leu Phe Gln Glu Cys Ser His Tyr Tyr Arg
65                  70                  75                  80

Asp Ser Ser Leu Asp Gly Trp Val Ser Ile Thr Ala His Glu Ala Ser
                85                  90                  95

Glu Leu Pro Ala Pro His His Tyr Tyr Leu Leu Asn Leu Asn Phe Asn
            100                 105                 110

Ser Pro Asn Glu Thr Asp Ser Ile Pro Glu Leu Ala Asn Thr Val Phe
        115                 120                 125

Glu Lys Asp Asn Thr Lys Tyr Ile Leu Gln Glu Asp Leu Ser Val Ser
    130                 135                 140

Lys Glu Ile Ser Ser Thr Asp Gly Thr Lys Trp Arg Leu Arg Ser Asp
145                 150                 155                 160
```

-continued

```
Arg Lys Ser Leu Phe Asp Val Lys Thr Leu Ala Tyr Ser Leu Tyr Asp
                165                 170                 175
Val Phe Ser Glu Asn Val Thr Gln Ala Asp Pro Phe Asp Val Leu Ile
            180                 185                 190
Met Val Thr Ala Tyr Leu Met Met Phe Tyr Thr Ile Phe Gly Leu Phe
        195                 200                 205
Asn Asp Met Arg Lys Thr Gly Ser Asn Phe Trp Leu Ser Ala Ser Thr
    210                 215                 220
Val Val Asn Ser Ala Ser Ser Leu Phe Leu Ala Leu Tyr Val Thr Gln
225                 230                 235                 240
Cys Ile Leu Gly Lys Glu Val Ser Ala Leu Thr Leu Phe Glu Gly Leu
                245                 250                 255
Pro Phe Ile Val Val Val Gly Phe Lys His Lys Ile Lys Ile Ala
            260                 265                 270
Gln Tyr Ala Leu Glu Lys Phe Glu Arg Val Gly Leu Ser Lys Arg Ile
        275                 280                 285
Thr Thr Asp Glu Ile Val Phe Glu Ser Val Ser Glu Glu Gly Gly Arg
    290                 295                 300
Leu Ile Gln Asp His Leu Leu Cys Ile Phe Ala Phe Ile Gly Cys Ser
305                 310                 315                 320
Met Tyr Ala His Gln Leu Lys Thr Leu Thr Asn Phe Cys Ile Leu Ser
                325                 330                 335
Ala Phe Ile Leu Ile Phe Glu Leu Ile Leu Thr Pro Thr Phe Tyr Ser
            340                 345                 350
Ala Ile Leu Ala Leu Arg Leu Glu Met Asn Val Ile His Arg Ser Thr
        355                 360                 365
Ile Ile Lys Gln Thr Leu Glu Glu Asp Gly Val Val Pro Ser Thr Ala
    370                 375                 380
Arg Ile Ile Ser Lys Ala Glu Lys Lys Ser Val Ser Ser Phe Leu Asn
385                 390                 395                 400
Leu Ser Val Val Ile Ile Met Lys Leu Ser Val Ile Leu Leu Phe
                405                 410                 415
Val Phe Ile Asn Phe Tyr Asn Phe Gly Ala Asn Trp Val Asn Asp Ala
            420                 425                 430
Phe Asn Ser Leu Tyr Phe Asp Lys Glu Arg Val Ser Leu Pro Asp Phe
        435                 440                 445
Ile Thr Ser Asn Ala Ser Glu Asn Phe Lys Glu Gln Ala Ile Val Ser
    450                 455                 460
Val Thr Pro Leu Leu Tyr Tyr Lys Pro Ile Lys Ser Tyr Gln Arg Ile
465                 470                 475                 480
Glu Asp Met Val Leu Leu Leu Arg Asn Val Ser Val Ala Ile Arg
                485                 490                 495
Asp Arg Phe Val Ser Lys Leu Val Leu Ser Ala Leu Val Cys Ser Ala
            500                 505                 510
Val Ile Asn Val Tyr Leu Leu Asn Ala Ala Arg Ile His Thr Ser Tyr
        515                 520                 525
Thr Ala Asp Gln Leu Val Lys Thr Glu Val Thr Lys Lys Ser Phe Thr
    530                 535                 540
Ala Pro Val Gln Lys Ala Ser Thr Pro Val Leu Thr Asn Lys Thr Val
545                 550                 555                 560
Ile Ser Gly Ser Lys Val Lys Ser Leu Ser Ser Ala Gln Ser Ser Ser
                565                 570                 575
```

-continued

```
Ser Gly Pro Ser Ser Ser Glu Glu Asp Asp Ser Arg Asp Ile Glu
        580             585             590
Ser Leu Asp Lys Lys Ile Arg Pro Leu Glu Glu Leu Glu Ala Leu Leu
    595             600             605
Ser Ser Gly Asn Thr Lys Gln Leu Lys Asn Lys Glu Val Ala Ala Leu
    610             615             620
Val Ile His Gly Lys Leu Pro Leu Tyr Ala Leu Glu Lys Lys Leu Gly
625             630             635             640
Asp Thr Thr Arg Ala Val Ala Val Arg Arg Lys Ala Leu Ser Ile Leu
            645             650             655
Ala Glu Ala Pro Val Leu Ala Ser Asp Arg Leu Pro Tyr Lys Asn Tyr
        660             665             670
Asp Tyr Asp Arg Val Phe Gly Ala Cys Cys Glu Asn Val Ile Gly Tyr
        675             680             685
Met Pro Leu Pro Val Gly Val Ile Gly Pro Leu Val Ile Asp Gly Thr
    690             695             700
Ser Tyr His Ile Pro Met Ala Thr Thr Glu Gly Cys Leu Val Ala Ser
705             710             715             720
Ala Met Arg Gly Cys Lys Ala Ile Asn Ala Gly Gly Gly Ala Thr Thr
            725             730             735
Val Leu Thr Lys Asp Gly Met Thr Arg Gly Pro Val Val Arg Phe Pro
        740             745             750
Thr Leu Lys Arg Ser Gly Ala Cys Lys Ile Trp Leu Asp Ser Glu Glu
        755             760             765
Gly Gln Asn Ala Ile Lys Lys Ala Phe Asn Ser Thr Ser Arg Phe Ala
    770             775             780
Arg Leu Gln His Ile Gln Thr Cys Leu Ala Gly Asp Leu Leu Phe Met
785             790             795             800
Arg Phe Arg Thr Thr Thr Gly Asp Ala Met Gly Met Asn Met Ile Ser
            805             810             815
Lys Gly Val Glu Tyr Ser Leu Lys Gln Met Val Glu Glu Tyr Gly Trp
            820             825             830
Glu Asp Met Glu Val Val Ser Val Ser Gly Asn Tyr Cys Thr Asp Lys
        835             840             845
Lys Pro Ala Ala Ile Asn Trp Ile Glu Gly Arg Gly Lys Ser Val Val
    850             855             860
Ala Glu Ala Thr Ile Pro Gly Asp Val Val Arg Lys Val Leu Lys Ser
865             870             875             880
Asp Val Ser Ala Leu Val Glu Leu Asn Ile Ala Lys Asn Leu Val Gly
            885             890             895
Ser Ala Met Ala Gly Ser Val Gly Gly Phe Asn Ala His Ala Ala Asn
            900             905             910
Leu Val Thr Ala Val Phe Leu Ala Leu Gly Gln Asp Pro Ala Gln Asn
        915             920             925
Val Glu Ser Ser Asn Cys Ile Thr Leu Met Lys Glu Val Asp Gly Asp
    930             935             940
Leu Arg Ile Ser Val Ser Met Pro Ser Ile Glu Val Gly Thr Ile Gly
945             950             955             960
Gly Gly Thr Val Leu Glu Pro Gln Gly Ala Met Leu Asp Leu Leu Gly
            965             970             975
Val Arg Gly Pro His Ala Thr Ala Pro Gly Thr Asn Ala Arg Gln Leu
        980             985             990
Ala Arg Ile Val Ala Cys Ala Val Leu Ala Gly Glu Leu Ser Leu Cys
```

```
                  995                1000               1005
Ala Ala Leu Ala Ala Gly His Leu Val Gln Ser His Met Thr His Asn
    1010               1015                1020
Arg Lys Pro Ala Glu Pro Thr Lys Pro Asn Asn Leu Asp Ala Thr Asp
1025               1030               1035               1040
Ile Asn Arg Leu Lys Asp Gly Ser Val Thr Cys Ile Lys Ser
            1045                1050

<210> SEQ ID NO 13
<211> LENGTH: 2925
<212> TYPE: DNA
<213> ORGANISM: Saccharomyces cerevisiae

<400> SEQUENCE: 13
atgccgccgc tattcaaggg actgaaacag atggcaaagc caattgccta tgtttcaaga      60
ttttcggcga acgaccaat  tcatataata cttttttctc taatcatatc cgcattcgct     120
tatctatccg tcattcagta ttacttcaat ggttggcaac tagattcaaa tagtgttttt     180
gaaactgctc caaataaaga cttcaacact ctatttcaag aatgttccca ttactacaga     240
gattcctctc tagatggttg ggtatcaatc accgcgcatg aagctagtga gttaccagcc     300
ccacaccatt actatctatt aaacctgaac ttcaatagtc ctaatgaaac tgactccatt     360
ccagaactag ctaacacggt ttttgagaaa gataatacaa aatatattct gcaagaagat     420
ctcagcgttt ccaaagaaat tcttctact  gatggaacga atggaggtt  aagaagtgac     480 agaaaaagtc ttttcgacgt aaagacgtta gcatattctc tctacgatgt attttcagaa     540
aatgtaaccc aagcagacca caaaatcaag attgcccagt atgccctgga gaaatttgaa     600
agagtcggtt tatctaaaag gattactacc gatgaaatcg ttttttgaatc cgtgagcgaa     660 gagggtggtc gtttgattca agaccatttg ctttgtattt ttgcctttat cggatgctct     720
atgtatgctc accaattgaa gactttgaca aacttctgca tattatcagc atttatccta     780
attttcgaat tgattttaac tcctacattt tattctgcta tcttagcgct tagactggaa     840
atgaatgtta tccacagatc tactattatc aagcaaacat agaagaaga  cggtgttgtt     900 ccatctacag caagaatcat ttctaaggca gaaagaaat  ccgtatcttc tttcttaaat     960
ctcagtgtgg ttgtcattat catgaaactc tctgtcatac tgttgttcgt cttcatcaac    1020
ttttataact tggtgcaaaa ttgggtcaat gatgccttca attcattgta cttcgataag    1080
gaacgtgttt ctctaccaga ttttattacc tcgaatgcct ctgaaaactt taagagcaa     1140 gctattgtta gtgtcacccc attattatat acaaaccca  ttaagtccta ccaacgcatt    1200
gaggatatgg ttcttctatt gcttcgtaat gtcagtgttg ccattcgtga taggttcgtc    1260
agtaaattag ttctttccgc cttagtatgc agtgctgtca tcaatgtgta tttattaaat    1320
gctgctagaa ttcataccag ttatactgca gaccaattgg tgaagactga agtcaccaag    1380
aagtctttta ctgctcctgt acaaaaggct tctacaccag ttttaaccaa taaaacagtc    1440
atttctggat cgaaagtcaa aagtttatca tctgcgcaat cgagctcatc aggaccttca    1500
tcatctagtg aggaagatga ttcccgcgat attgaaagct tggataagaa aatacgtcct    1560
ttagaagaat tagaagcatc attaagtagt ggaaatacaa aacaattgaa gaacaaagag    1620
gtcgctgcct tggttattca cggtaagtta ccttttgtacg ctttggagaa aaaattaggt    1680
gatactacga gagcggttgc ggtacgtagg aaggctcttt caattttggc agaagctcct    1740
gtattagcat ctgatcgttt accatataaa aattatgact acgaccgcgt atttggcgct    1800
```

```
tgttgtgaaa atgttatagg ttacatgcct ttgcccgttg gtgttatagg cccctttggtt    1860 atcgatggta catcttatca tataccaatg gcaactacag agggttgttt ggtagcttct    1920
gccatgcgtg gctgtaaggc aatcaatgct ggcggtggtg caacaactgt tttaactaag    1980
gatggtatga caagaggccc agtagtccgt ttcccaactt tgaaaagatc tggtgcctgt    2040
aagatatggt tagactcaga agagggacaa aacgcaatta aaaaagcttt taactctaca    2100
tcaagatttg cacgtctgca acatattcaa acttgtctag caggagattt actcttcatg    2160
agatttagaa caactactgg tgacgcaatg ggtatgaata tgatttctaa gggtgtcgaa    2220
tactcattaa agcaaatggt agaagagtat ggctgggaag atatggaggt tgtctccgtt    2280
tctggtaact actgtaccga caaaaaacca gctgccatca actggatcga aggtcgtggt    2340
aagagtgtcg tcgcagaagc tactattcct ggtgatgttg tcagaaaagt gttaaaaagt    2400
gatgtttccg cattggttga gttgaacatt gctaagaatt tggttggatc tgcaatggct    2460
gggtctgttg gtggatttaa cgcacgtgca gctaatttag tgacagctgt tttcttggca    2520
ttaggacaag atcctgcaca aaatgtcgaa agttccaact gtataacatt gatgaaagaa    2580
gtggacggtg atttgagaat ttccgtatcc atgccatcca tcgaagtagg taccatcggt    2640
ggtggtactg ttctagaacc acaaggtgcc atgttggact tattaggtgt aagaggccca    2700
catgctaccg ctcctggtac caacgcacgt caattagcaa gaatagttgc ctgtgccgtc    2760
ttggcaggtg aattatcctt atgtgctgcc ctagcagccg gccatttggt tcaaagtcat    2820
atgacccaca acaggaaacc tgctgaacca acaaaaaccta acaatttgga cgccactgat    2880
ataaatcgtt tgaaagatgg gtccgtcacc tgcattaaat cctaa                    2925
```

<210> SEQ ID NO 14  
<211> LENGTH: 3090  
<212> TYPE: DNA  
<213> ORGANISM: Saccharomyces cerevisiae

<400> SEQUENCE: 14

```
atgccgccgc tattcaaggg actgaaacag atggcaaagc caattgccta tgtttcaaga      60
ttttcggcga aacgaccaat tcatataata cttttttctc taatcatatc cgcattcgct    120
tatctatccg tcattcagta ttacttcaat ggttggcaac tagattcaaa tagtgttttt    180
gaaactgctc caaataaaga cttcaacact ctatttcaag aatgttccca ttactacaga    240
gattcctctc tagatggttg ggtatcaatc accgcgcatg aagctagtga gttaccagcc    300
ccacaccatt actatctatt aaacctgaac ttcaatagtc ctaatgaaac tgactccatt    360
ccagaactag ctaacacggt ttttgagaaa gataatacaa aatatattct gcaagaagat    420
ctcagcgttt ccaaagaaat tcttctact gatggaacga atggaggtt aagaagtgac    480 agaaaaagtc ttttcgacgt aaagacgtta gcatattctc tctacgatgt attttcagaa    540
aatgtaaccc aagcagaccc gtttgacgtc cttattatgg ttactgccta cctaatgatg    600
ttctacacca tattcggcct cttcaatgac atgaggaaga ccgggtcaaa tttttggttg    660
agcgcctcta cagtggtcaa ttctgcatca tcacttttct tagcattgta tgtcaccccaa    720 tgtattctag gcaaagaagt ttccgcatta actctttttg aaggtttgcc tttcattgta    780
gttgttgttg gtttcaagca caaaatcaag attgcccagt atgccctgga gaaatttgaa    840
agagtcggtt tatctaaaag gattactacc gatgaaatcg tttttgaatc cgtgagcgaa    900
gagggtggtc gtttgattca agaccatttg ctttgtattt ttgccttat cggatgctct    960 atgtatgctc accaattgaa gactttgaca aacttctgca tattatcagc atttatccta   1020
```

```
attttcgaat tgattttaac tcctacattt tattctgcta tcttagcgct tagactggaa      1080
atgaatgtta tccacagatc tactattatc aagcaaacat tagaagaaga cggtgttgtt      1140
ccatctacag caagaatcat ttctaaggca gaaaagaaat ccgtatcttc taactttggt      1200
gcaaattggg tcaatgatgc cttcaattca ttgtacttcg ataaggaacg tgtttctcta      1260
ccagatttta ttacctcgaa tgcctctgaa aactttaaag agcaagctat tgttagtgtc      1320
accccattat tatattacaa acccattaag tcctaccaac gcattgagga tatggttctt      1380
ctattgcttc gtaatgtcag tgttgccatt cgtgataggt tcgtcagtaa attagttctt      1440
tccgccttag tatgcagtgc tgtcatcaat gtgtatttat taaatgctgc tagaattcat      1500
accagttata ctgcagacca attggtgaag actgaagtca ccaagaagtc ttttactgct      1560
cctgtacaaa aggcttctac accagtttta accaataaaa cagtcatttc tggatcgaaa      1620
gtcaaaagtt tatcatctgc gcaatcgagc tcatcaggac cttcatcatc tagtgaggaa      1680
gatgattccc gcgatattga aagcttggat aagaaaatac gtcctttaga agaattagaa      1740
gcatcattaa gtagtggaaa tacaaaacaa ttgaagaaca aagaggtcgc tgccttggtt      1800
attcacggta agttaccttt gtacgctttg gagaaaaaat taggtgatac tacgagagcg      1860
gttgcggtac gtaggaaggc tctttcaatt ttggcagaag ctcctgtatt agcatctgat      1920
cgtttaccat ataaaaatta tgactacgac cgcgtatttg gcgcttgttg tgaaaatgtt      1980
ataggttaca tgcctttgcc cgttggtgtt ataggcccct tggttatcga tggtacatct      2040
tatcatatac caatggcaac tacagagggt tgtttggtag cttctgccat gcgtggctgt      2100
aaggcaatca atgctggcgg tggtgcaaca actgttttaa ctaaggatgg tatgacaaga      2160
ggcccagtag tccgtttccc aactttgaaa agatctggtg cctgtaagat atggttagac      2220
tcagaagagg gacaaaacgc aattaaaaaa gcttttaact ctacatcaag atttgcacgt      2280
ctgcaacata ttcaaacttg tctagcagga gatttactct tcatgagatt tagaacaact      2340
actggtgacg caatgggtat gaatatgatt tctaagggtg tcgaatactc attaaagcaa      2400
atggtagaag agtatggctg ggaagatatg gaggttgtct ccgtttctgg taactactgt      2460
accgacaaaa aaccagctgc catcaactgg atcgaaggtc gtggtaagag tgtcgtcgca      2520
gaagctacta ttcctggtga tgttgtcaga aaagtgttaa aaagtgatgt ttccgcattg      2580
gttgagttga acattgctaa gaatttggtt ggatctgcaa tggctgggtc tgttggtgga      2640
tttaacgcac gtgcagctaa tttagtgaca gctgtttctt tggcattagg acaagatcct      2700
gcacaaaatg tcgaaagttc caactgtata acattgatga agaagtggga cggtgatttg      2760
agaatttccg tatccatgcc atccatcgaa gtaggtacca tcggtggtgg tactgttcta      2820
gaaccacaag gtgccatgtt ggacttatta ggtgtaagag gcccacatgc taccgctcct      2880
ggtaccaacg cacgtcaatt agcaagaata gttgcctgtg ccgtcttggc aggtgaatta      2940
tccttatgtg ctgccctagc agccggccat ttggttcaaa gtcatatgac ccacaacagg      3000
aaacctgctg aaccaacaaa acctaacaat ttggacgcca ctgatataaa tcgtttgaaa      3060
gatgggtccg tcacctgcat taaatcctaa                                        3090
```

<210> SEQ ID NO 15
<211> LENGTH: 2973
<212> TYPE: DNA
<213> ORGANISM: Saccharomyces cerevisiae

<400> SEQUENCE: 15

```
atgccgccgc tattcaaggg actgaaacag atggcaaagc caattgccta tgtttcaaga    60
ttttcggcga aacgaccaat tcatataata cttttttctc taatcatatc cgcattcgct   120
tatctatccg tcattcagta ttacttcaat ggttggcaac tagattcaaa tagtgttttt   180
gaaactgctc caaataaaga cttcaacact ctatttcaag aatgttccca ttactacaga   240
gattcctctc tagatggttg ggtatcaatc accgcgcatg aagctagtga gttaccagcc   300
ccacaccatt actatctatt aaacctgaac ttcaatagtc ctaatgaaac tgactccatt   360
ccagaactag ctaacacggt ttttgagaaa gataatacaa aatatattct gcaagaagat   420
ctcagcgttt ccaaagaaat tcttctact gatggaacga aatggaggtt aagaagtgac   480
agaaaaagtc ttttcgacgt aaagacgtta gcatattctc tctacgatgt attttcagaa   540
aatgtaaccc aagcagaccc gtttgacgtc cttattatgg ttactgccta cctaatgatg   600
ttctacacca tattcggcct cttcaatgac atgaggaaga ccgggtcaaa ttttggttg    660
agcgcctcta cagtggtcaa ttctgcatca tcactttttct tagcattgta tgtcacccaa   720
tgtattctag caaagaagt ttccgcatta actcttttg aaggtttgcc tttcattgta    780
gttgttgttg gtttcaagca caaaatcaag attgcccagt atgccctgga gaaatttgaa   840
agagtcggtt tatctaaaag gattactacc gatgaaatcg ttttgaatc cgtgagcgaa    900
gagggtggtc gtttgattca agaccatttg ctttgtattt ttgcctttat cggatgctct   960
atgtatgctc accaattgaa gactttgaca aacttctgca tattatcagc atttatccta  1020
attttcgaat tgattttaac tcctacattt tattctgcta tcttagcgct tagactggaa  1080
atgaatgtta tccacagatc tactattatc aagcaaacat tagaagaaga cggtgttgtt  1140
ccatctacag caagaatcat ttctaaggca gaaaagaaat ccgtatcttc tttcttaaat  1200
ctcagtgtgg ttgtcattat catgaaactc tctgtcatac tgttgttcgt cttcatcaac  1260
ttttataact ttggtgcaaa tgggtcaat gatgccttca attcattgta cttcgataag   1320
gaacgtgttt ctctaccaga ttttattacc tcgaatgcct ctgaaaactt taaagagcaa  1380
cataccagtt atactgcaga ccaattggtg aagactgaag tcaccaagaa gtcttttact   1440
gctcctgtac aaaaggcttc tacaccagtt ttaaccaata aaacagtcat ttctggatcg  1500
aaagtcaaaa gttatcatc tgcgcaatcg agctcatcag gaccttcatc atctagtgag   1560
gaagatgatt cccgcgatat tgaaagcttg gataagaaaa tacgtccttt agaagaatta   1620
gaagcatcat taagtagtgg aaatacaaaa caattgaaga caaagaggt cgctgccttg   1680
gttattcacg gtaagttacc tttgtacgct ttggagaaaa aattaggtga tactacgaga   1740
gcggttgcgg tacgtaggaa ggctctttca attttggcag aagctcctgt attagcatct  1800
gatcgtttac catataaaaa ttatgactac gaccgcgtat ttggcgcttg ttgtgaaaat   1860
gttataggtt acatgccttt gcccgttggt gttataggcc ccttggttat cgatggtaca  1920
tcttatcata taccaatggc aactacgag ggttgtttgg tagcttctgc catgcgtggc   1980
tgtaaggcaa tcaatgctgg cggtggtgca acaactgttt taactaagga tggtatgaca  2040
agaggcccag tagtccgttt cccaactttg aaaagatctg gtgcctgtaa gatatggtta  2100
gactcagaag agggacaaaa cgcaattaaa aaagctttta actctacatc aagatttgca  2160
cgtctgcaac atattcaaac ttgtctagca ggagatttac tcttcatgag atttagaaca  2220
actactggtg acgcaatggg tatgaatatg atttctaagg gtgtcgaata ctcattaaag  2280
caaatggtag aagagtatgg ctgggaagat atggaggtt tctccgtttc tggtaactac   2340
tgtaccgaca aaaaccagc tgccatcaac tggatcgaag gtcgtggtaa gagtgtcgtc   2400
```

```
gcagaagcta ctattcctgg tgatgttgtc agaaaagtgt taaaaagtga tgtttccgca    2460
ttggttgagt tgaacattgc taagaatttg gttggatctg caatggctgg gtctgttggt    2520
ggatttaacg cacgtgcagc taatttagtg acagctgttt tcttggcatt aggacaagat    2580
cctgcacaaa atgtcgaaag ttccaactgt ataacattga tgaaagaagt ggacggtgat    2640
ttgagaattt ccgtatccat gccatccatc gaagtaggta ccatcggtgg tggtactgtt    2700
ctagaaccac aaggtgccat gttggactta ttaggtgtaa gaggcccaca tgctaccgct    2760
cctggtacca acgcacgtca attagcaaga atagttgcct gtgccgtctt ggcaggtgaa    2820
ttatccttat gtgctgccct agcagccggc catttggttc aaagtcatat gacccacaac    2880
aggaaacctg ctgaaccaac aaaacctaac aatttggacg ccactgatat aaatcgtttg    2940
aaagatgggt ccgtcacctg cattaaatcc taa                                 2973

<210> SEQ ID NO 16
<211> LENGTH: 2457
<212> TYPE: DNA
<213> ORGANISM: Saccharomyces cerevisiae

<400> SEQUENCE: 16
atgccgccgc tattcaaggg actgaaacag atggcaaagc caattgccta tgtttcaaga      60
ttttcggcga aacgaccaat tcatataata ctttttttctc taatcatatc cgcattcgct    120
tatctatccg tcattcagta ttacttcaat ggttggcaac tagattcaaa tagtgttttt    180
gaaactgctc caaataaaga cttcaacact ctatttcaag aatgttccca ttactacaga    240
gattcctctc tagatggttg ggtatcaatc accgcgcatg aagctagtga gttaccagcc    300
ccacaccatt actatctatt aaacctgaac ttcaatagtc ctaatgaaac tgactccatt    360
ccagaactag ctaacacggt ttttgagaaa gataatacaa aatatattct gcaagaagat    420
ctcagcgttt ccaaagaaat ttcttctact gatggaacga aatggaggtt aagaagtgac    480
agaaaaagtc ttttcgacgt aaagacgtta gcatattctc tctacgatgt attttcagaa    540
aatgtaaccc aagcagacaa ctttggtgca aattgggtca atgatgcctt caattcattg    600
tacttcgata aggaacgtgt ttctctacca gatttttatta cctcgaatgc ctctgaaaac    660
tttaaagagc aagctattgt tagtgtcacc ccattattat attacaaacc cattaagtcc    720
taccaacgca ttgaggatat ggttcttcta ttgcttcgta atgtcagtgt tgccattcgt    780
gataggttcg tcagtaaatt agttctttcc gccttagtat gcagtgctgt catcaatgtg    840
tatttattaa atgctgctag aattcatacc agttatactg cagaccaatt ggtgaagact    900
gaagtcacca agaagtcttt tactgctcct gtacaaaagg cttctacacc agttttaacc    960
aataaaacag tcatttctgg atcgaaagtc aaaagtttat catctgcgca atcgagctca   1020 tcaggaccctt catcatctag tgaggaagat gattcccgcg atattgaaag cttggataag   1080
aaaatacgtc ctttagaaga attagaagca tcattaagta gtggaaatac aaaacaattg   1140
aagaacaaag aggtcgctgc cttggttatt cacggtaagt tacctttgta cgctttggag   1200
aaaaaattag gtgatactac gagagcggtt gcggtacgta ggaaggctct ttcaattttg   1260
gcagaagctc ctgtattagc atctgatcgt ttaccatata aaaattatga ctacgaccgc   1320
gtatttggcg cttgttgtga aaatgttata ggttacatgc ctttgcccgt tggtgttata   1380 ggcccccttgg ttatcgatgg tacatcttat catataccaa tggcaactac agagggttgt   1440
ttggtagctt ctgccatgcg tggctgtaag gcaatcaatg ctggcggtgg tgcaacaact   1500
```

```
gttttaacta aggatggtat gacaagaggc ccagtagtcc gtttcccaac tttgaaaaga    1560
tctggtgcct gtaagatatg gttagactca gaagagggac aaaacgcaat taaaaaagct    1620
tttaactcta catcaagatt tgcacgtctg caacatattc aaacttgtct agcaggagat    1680
ttactcttca tgagatttag aacaactact ggtgacgcaa tgggtatgaa tatgatttct    1740
aagggtgtcg aatactcatt aaagcaaatg gtagaagagt atggctggga agatatggag    1800
gttgtctccg tttctggtaa ctactgtacc gacaaaaaac cagctgccat caactggatc    1860
gaaggtcgtg gtaagagtgt cgtcgcagaa gctactattc ctggtgatgt tgtcagaaaa    1920
gtgttaaaaa gtgatgtttc cgcattggtt gagttgaaca ttgctaagaa tttggttgga    1980
tctgcaatgg ctgggtctgt tggtggattt aacgcacgtg cagctaattt agtgacagct    2040
gttttcttgg cattaggaca agatcctgca caaaatgtcg aaagttccaa ctgtataaca    2100
ttgatgaaag aagtggacgg tgatttgaga atttccgtat ccatgccatc catcgaagta    2160
ggtaccatcg gtggtggtac tgttctagaa ccacaaggtg ccatgttgga cttattaggt    2220
gtaagaggcc cacatgctac cgctcctggt accaacgcac gtcaattagc aagaatagtt    2280
gcctgtgccg tcttggcagg tgaattatcc ttatgtgctg ccctagcagc cggccatttg    2340
gttcaaagtc atatgaccca caacaggaaa cctgctgaac caacaaaacc taacaatttg    2400
gacgccactg atataaatcg tttgaaagat gggtccgtca cctgcattaa atcctaa      2457

<210> SEQ ID NO 17
<211> LENGTH: 2151
<212> TYPE: DNA
<213> ORGANISM: Saccharomyces cerevisiae

<400> SEQUENCE: 17
atgccgccgc tattcaaggg actgaaacag atggcaaagc caattgccta tgtttcaaga      60
ttttcggcga aacgaccaat tcatataata ctttttttctc taatcatatc cgcattcgct    120
tatctatccg tcattcagta ttacttcaat ggttggcaac tagattcaaa tagtgttttt    180
gaaactgctc caaataaaga cttcaacact ctatttcaag aatgttccca ttactacaga    240
gattcctctc tagatggttg ggtatcaatc accgcgcatg aagctagtga gttaccagcc    300
ccacaccatt actatctatt aaacctgaac ttcaatagtc ctaatgaaac tgactccatt    360
ccagaactag ctaacacggt ttttgagaaa gataatacaa aatatattct gcaagaagat    420
ctcagcgttt ccaaagaaat ttcttctact gatggaacga atggaggtt aagaagtgac    480 agaaaaagtc ttttcgacgt aaagacgtta gcatattctc tctacgatgt attttcagaa    540
aatgtaaccc aagcagacca taccagttat actgcagacc aattggtgaa gactgaagtc    600
accaagaagt cttttactgc tcctgtacaa aaggcttcta caccagtttt aaccaataaa    660
acagtcattt ctggatcgaa agtcaaaagt ttatcatctg cgcaatcgag ctcatcagga    720
ccttcatcat ctagtgagga agatgattcc cgcgatattg aaagcttgga taagaaaata    780
cgtcctttag aagaattaga agcatcatta agtagtggaa atacaaaaca attgaagaac    840
aaagaggtcg ctgccttggt tattcacggt aagttacctt tgtacgcttt ggagaaaaaa    900
ttaggtgata ctacgagagc ggttgcggta cgtaggaagg ctctttcaat tttggcagaa    960
gctcctgtat agcatctga tcgtttacca tataaaaatt atgactacga ccgcgtattt   1020
ggcgcttgtt gtgaaaatgt tataggttac atgcctttgc ccgttggtgt tataggcccc   1080
ttggttatcg atggtacatc ttatcatata ccaatggcaa ctacagaggg ttgtttggta   1140
gcttctgcca tgcgtggctg taaggcaatc aatgctggcg gtggtgcaac aactgttta    1200
```

```
actaaggatg gtatgacaag aggcccagta gtccgtttcc caactttgaa aagatctggt    1260
gcctgtaaga tatggttaga ctcagaagag ggacaaaacg caattaaaaa agcttttaac    1320
tctacatcaa gatttgcacg tctgcaacat attcaaactt gtctagcagg agatttactc    1380
ttcatgagat ttagaacaac tactggtgac gcaatgggta tgaatatgat ttctaagggt    1440
gtcgaatact cattaaagca aatggtagaa gagtatggct gggaagatat ggaggttgtc    1500
tccgtttctg gtaactactg taccgacaaa aaaccagctg ccatcaactg gatcgaaggt    1560
cgtggtaaga gtgtcgtcgc agaagctact attcctggtg atgttgtcag aaaagtgtta    1620
aaaagtgatg tttccgcatt ggttgagttg aacattgcta agaatttggt tggatctgca    1680
atggctgggt ctgttggtgg atttaacgca cgtgcagcta atttagtgac agctgttttc    1740
ttggcattag acaagatcc tgcacaaaat gtcgaaagtt ccaactgtat aacattgatg    1800
aaagaagtgg acggtgattt gagaatttcc gtatccatgc catccatcga agtaggtacc    1860
atcggtggtg gtactgttct agaaccacaa ggtgccatgt tggacttatt aggtgtaaga    1920
ggcccacatg ctaccgctcc tggtaccaac gcacgtcaat tagcaagaat agttgcctgt    1980
gccgtcttgg caggtgaatt atccttatgt gctgccctag cagccggcca tttggttcaa    2040
agtcatatga cccacaacag gaaacctgct gaaccaacaa aacctaacaa tttggacgcc    2100
actgatataa atcgtttgaa agatgggtcc gtcacctgca ttaaatccta a            2151
```

<210> SEQ ID NO 18
<211> LENGTH: 1620
<212> TYPE: DNA
<213> ORGANISM: Saccharomyces cerevisiae

<400> SEQUENCE: 18

```
atgccgccgc tattcaaggg actgaaacat accagttata ctgcagacca attggtgaag      60
actgaagtca ccaagaagtc ttttactgct cctgtacaaa aggcttctac accagtttta     120
accaataaaa cagtcatttc tggatcgaaa gtcaaaagtt tatcatctgc gcaatcgagc     180
tcatcaggac cttcatcatc tagtgaggaa gatgattccc gcgatattga aagcttggat     240
aagaaaatac gtcctttaga gaattagaa gcatcattaa gtagtggaaa tacaaaacaa     300
ttgaagaaca aagaggtcgc tgccttggtt attcacggta agttaccttt gtacgctttg     360
gagaaaaaat taggtgatac tacgagagcg gttgcggtac gtaggaaggc tctttcaatt     420
ttggcagaag ctcctgtatt agcatctgat cgtttaccat ataaaaatta tgactacgac     480
cgcgtatttg gcgcttgttg tgaaaatgtt ataggttaca tgcctttgcc cgttggtgtt     540
ataggcccct tggttatcga tggtacatct tatcatatac caatggcaac tacagagggt     600
tgtttggtag cttctgccat gcgtggctgt aaggcaatca atgctggcgg tggtgcaaca     660
actgttttaa ctaaggatgg tatgacaaga ggcccagtag tccgtttccc aactttgaaa     720
agatctggtg cctgtaagat atggttagac tcagaagagg gacaaaacgc aattaaaaaa     780
gcttttaact ctacatcaag atttgcacgt ctgcaacata ttcaaacttg tctagcagga     840
gatttactct tcatgagatt tagaacaact actggtgacg caatgggtat gaatatgatt     900
tctaagggtg tcgaatactc attaaagcaa atggtagaag agtatggctg ggaagatatg     960
gaggttgtct ccgtttctgg taactactgt accgacaaaa aaccagctgc catcaactgg    1020
atcgaaggtc gtggtaagag tgtcgtcgca gaagctacta ttcctggtga tgttgtcaga    1080
aaagtgttaa aaagtgatgt ttccgcattg gttgagttga acattgctaa gaatttggtt    1140
```

```
ggatctgcaa tggctgggtc tgttggtgga tttaacgcac gtgcagctaa tttagtgaca    1200
gctgttttct tggcattagg acaagatcct gcacaaaatg tcgaaagttc caactgtata    1260
acattgatga agaagtggac ggtgatttg  agaatttccg tatccatgcc atccatcgaa    1320
gtaggtacca tcggtggtgg tactgttcta gaaccacaag gtgccatgtt ggacttatta    1380
ggtgtaagag gcccacatgc taccgctcct ggtaccaacg cacgtcaatt agcaagaata    1440
gttgcctgtg ccgtcttggc aggtgaatta tccttatgtg ctgccctagc agccggccat    1500
ttggttcaaa gtcatatgac ccacaacagg aaacctgctg aaccaacaaa acctaacaat    1560
ttggacgcca ctgatataaa tcgtttgaaa gatgggtccg tcacctgcat aaatcctaa     1620

<210> SEQ ID NO 19
<211> LENGTH: 1377
<212> TYPE: DNA
<213> ORGANISM: Saccharomyces cerevisiae

<400> SEQUENCE: 19
atgccgccgc tattcaaggg actgaaagca tcattaagta gtggaaatac aaaacaattg      60
aagaacaaag aggtcgctgc cttggttatt cacggtaagt tacctttgta cgctttggag    120
aaaaaattag gtgatactac gagagcggtt gcggtacgta ggaaggctct ttcaattttg    180
gcagaagctc ctgtattagc atctgatcgt ttaccatata aaaattatga ctacgaccgc    240
gtatttggcg cttgttgtga aaatgttata ggttacatgc cttgcccgt  tggtgttata    300 ggccccttgg ttatcgatgg tacatcttat catataccaa tggcaactac agagggttgt    360
ttggtagctt ctgccatgcg tggctgtaag gcaatcaatg ctggcggtgg tgcaacaact    420
gttttaacta aggatggtat gacaagaggc ccagtagtcc gtttcccaac tttgaaaaga    480
tctggtgcct gtaagatatg gttagactca gaagagggac aaaacgcaat taaaaaagct    540
tttaactcta catcaagatt tgcacgtctg caacatattc aaacttgtct agcaggagat    600
ttactcttca tgagatttag aacaactact ggtgacgcaa tgggtatgaa tatgatttct    660
aagggtgtcg aatactcatt aaagcaaatg gtagaagagt atggctggga agatatggag    720
gttgtctccg tttctggtaa ctactgtacc gacaaaaaac cagctgccat caactggatc    780
gaaggtcgtg gtaagagtgt cgtcgcagaa gctactattc ctggtgatgt tgtcagaaaa    840
gtgttaaaaa gtgatgtttc cgcattggtt gagttgaaca ttgctaagaa tttggttgga    900
tctgcaatgg ctgggtctgt tggtggattt aacgcacgtg cagctaattt agtgacagct    960
gttttcttgg cattaggaca agatcctgca caaaatgtcg aaagttccaa ctgtataaca   1020
ttgatgaaag aagtggacgg tgatttgaga atttccgtat ccatgccatc catcgaagta   1080
ggtaccatcg gtggtggtac tgttctagaa ccacaaggtg ccatgttgga cttattaggt   1140
gtaagaggcc acatgctac  cgctcctggt accaacgcac gtcaattagc aagaatagtt   1200
gcctgtgccg tcttggcagg tgaattatcc ttatgtctg  ccctagcagc cggccatttg   1260
gttcaaagtc atatgaccca acaggaaacc ctgctgaac  caacaaaacc taacaatttg   1320
gacgccactg atataaatcg tttgaaagat gggtccgtca cctgcattaa atcctaa      1377

<210> SEQ ID NO 20
<211> LENGTH: 1302
<212> TYPE: DNA
<213> ORGANISM: Saccharomyces cerevisiae

<400> SEQUENCE: 20
atgccgccgc tattcaaggg actgaaacct ttgtacgctt tggagaaaaa attaggtgat      60
```

-continued

```
actacgagag cggttgcggt acgtaggaag gctctttcaa ttttggcaga agctcctgta      120
ttagcatctg atcgtttacc atataaaaat tatgactacg accgcgtatt tggcgcttgt      180
tgtgaaaatg ttataggtta catgcctttg cccgttggtg ttataggccc cttggttatc      240
gatggtacat cttatcatat accaatggca actacagagg gttgtttggt agcttctgcc      300
atgcgtggct gtaaggcaat caatgctggc ggtggtgcaa caactgtttt aactaaggat      360
ggtatgacaa gaggcccagt agtccgtttc ccaactttga aaagatctgg tgcctgtaag      420
atatggttag actcagaaga gggacaaaac gcaattaaaa aagcttttaa ctctacatca      480
agatttgcac gtctgcaaca tattcaaact tgtctagcag gagatttact cttcatgaga      540
tttagaacaa ctactggtga cgcaatgggt atgaatatga tttctaaggg tgtcgaatac      600
tcattaaagc aaatggtaga agagtatggc tgggaagata tggaggttgt ctccgtttct      660
ggtaactact gtaccgacaa aaaaccagct gccatcaact ggatcgaagg tcgtggtaag      720
agtgtcgtcg cagaagctac tattcctggt gatgttgtca gaaaagtgtt aaaaagtgat      780
gtttccgcat tggttgagtt gaacattgct aagaatttgg ttggatctgc aatggctggg      840
tctgttggtg gatttaacgc acgtgcagct aatttagtga cagctgtttt cttggcatta      900
ggacaagatc ctgcacaaaa tgtcgaaagt tccaactgta taacattgat gaaagaagtg      960
gacggtgatt tgagaatttc cgtatccatg ccatccatcg aagtaggtac catcggtggt     1020
ggtactgttc tagaaccaca aggtgccatg ttggacttat taggtgtaag aggcccacat     1080
gctaccgctc ctggtaccaa cgcacgtcaa ttagcaagaa tagttgcctg tgccgtcttg     1140
gcaggtgaat tatccttatg tgctgcccta gcagccggcc atttggttca aagtcatatg     1200
acccacaaca ggaaacctgc tgaaccaaca aaacctaaca atttggacgc cactgatata     1260
aatcgtttga agatgggtc cgtcacctgc attaaatcct aa                         1302
```

<210> SEQ ID NO 21
<211> LENGTH: 1203
<212> TYPE: DNA
<213> ORGANISM: Saccharomyces cerevisiae

<400> SEQUENCE: 21

```
atgccgccgc tattcaaggg actgaaatct gatcgtttac catataaaaa ttatgactac       60
gaccgcgtat tggcgcttg ttgtgaaaat gttataggtt acatgccttt gcccgttggt      120
gttataggcc ccttggttat cgatggtaca tcttatcata taccaatggc aactacagag      180
ggttgtttgg tagcttctgc catgcgtggc tgtaaggcaa tcaatgctgg cggtggtgca      240
acaactgttt taactaagga tggtatgaca agaggcccag tagtccgttt cccaactttg      300
aaaagatctg gtgcctgtaa gatatggtta gactcagaag agggacaaaa cgcaattaaa      360 aaagcttta actctacatc aagatttgca cgtctgcaac atattcaaac ttgtctagca      420
ggagatttac tcttcatgag atttagaaca actactggtg acgcaatggg tatgaatatg      480
atttctaagg gtgtcgaata ctcattaaag caaatggtag aagagtatgg ctgggaagat      540
atggaggttg tctccgtttc tggtaactac tgtaccgaca aaaaaccagc tgccatcaac      600
tggatcgaag gtcgtggtaa gagtgtcgtc gcagaagcta ctattcctgg tgatgttgtc      660
agaaaagtgt taaaaagtga tgtttccgca ttggttgagt tgaacattgc taagaatttg      720
gttggatctg caatggctgg gtctgttggt ggatttaacg cacgtgcagc taatttagtg      780
acagctgttt tcttggcatt aggacaagat cctgcacaaa atgtcgaaag ttccaactgt      840
```

```
ataacattga tgaaagaagt ggacggtgat tgagaatttt ccgtatccat gccatccatc    900
gaagtaggta ccatcggtgg tggtactgtt ctagaaccac aaggtgccat gttggactta    960
ttaggtgtaa gaggcccaca tgctaccgct cctggtacca acgcacgtca attagcaaga   1020
atagttgcct gtgccgtctt ggcaggtgaa ttatccttat gtgctgccct agcagccggc   1080
catttggttc aaagtcatat gacccacaac aggaaacctg ctgaaccaac aaaacctaac   1140
aatttggacg ccactgatat aaatcgtttg aagatgggt ccgtcacctg cattaaatcc    1200
taa                                                                  1203
```

<210> SEQ ID NO 22
<211> LENGTH: 975
<212> TYPE: DNA
<213> ORGANISM: Saccharomyces cerevisiae

<400> SEQUENCE: 22

```
atgccgccgc tattcaaggg actgaaaaag gatggtatga caagaggccc agtagtccgt     60
ttcccaactt tgaaaagatc tggtgcctgt aagatatggt tagactcaga agagggacaa    120
aacgcaatta aaaaagcttt taactctaca tcaagatttg cacgtctgca acatattcaa    180
acttgtctag caggagattt actcttcatg agatttagaa caactactgg tgacgcaatg    240
ggtatgaata tgatttctaa gggtgtcgaa tactcattaa agcaaatggt agaagagtat    300
ggctgggaag atatggaggt tgtctccgtt tctggtaact actgtaccga caaaaaacca    360
gctgccatca actggatcga aggtcgtggt aagagtgtcg tcgcagaagc tactattcct    420
ggtgatgttg tcagaaaagt gttaaaaagt gatgtttccg cattggttga gttgaacatt    480
gctaagaatt tggttggatc tgcaatggct gggtctgttg gtggatttaa cgcacgtgca    540
gctaatttag tgacagctgt tttcttggca ttaggacaag atcctgcaca aaatgtcgaa    600
agttccaact gtataacatt gatgaaagaa gtggacggtg atttgagaat ttccgtatcc    660
atgccatcca tcgaagtagg taccatcggt ggtggtactg ttctagaacc acaaggtgcc    720
atgttggact tattaggtgt aagaggccca catgctaccg ctcctggtac caacgcacgt    780
caattagcaa gaatagttgc ctgtgccgtc ttggcaggtg aattatcctt atgtgctgcc    840
ctagcagccg gccatttggt tcaaagtcat atgacccaca acaggaaacc tgctgaacca    900
acaaaaccta caatttgga cgccactgat ataaatcgtt tgaagatggg gtccgtcacc    960
tgcattaaat cctaa                                                     975
```

<210> SEQ ID NO 23
<211> LENGTH: 992
<212> TYPE: DNA
<213> ORGANISM: Saccharomyces cerevisiae

<400> SEQUENCE: 23

```
ggatcctcta gctccctaac atgtaggtgg cggaggggag atatacaata gaacagatac     60
cagacaagac ataatgggct aaacaagact acaccaatta cactgcctca ttgatggtgg    120
tacataacga actaatactg tagccctaga cttgatagcc atcatcatat cgaagtttca    180
ctaccctttt tccatttgcc atctattgaa gtaataatag gcgcatgcaa cttctttttct   240 tttttttttct tttctctctc cccgttgtt gtctcaccat atccgcaatg acaaaaaaat    300
gatggaagac actaaaggaa aaaattaacg acaaagacag caccaacaga tgtcgttgtt    360
ccagagctga tgaggggtat ctcgaagcac acgaaacttt ttccttcctt cattcacgca    420
cactactctc taatgagcaa cggtatacgg ccttccttcc agttacttga atttgaaata    480
```

```
aaaaaagttt gctgtcttgc tatcaagtat aaatagacct gcaattatta atcttttgtt      540
tcctcgtcat tgttctcgtt cccttcttc cttgtttctt tttctgcaca atatttcaag      600
ctataccaag catacaatca actggtaccc gggtcgactc gagctctaga ggttaactaa      660
gcgaatttct tatgatttat gattttatt attaaataag ttataaaaaa aataagtgta      720
tacaaatttt aaagtgactc ttaggtttta aaacgaaaat tcttattctt gagtaactct      780
ttcctgtagg tcaggttgct ttctcaggta tagcatgagg tcgctcttat tgaccacatc      840
tctaccggca tgccgagcaa atgcctgcaa atcgctcccc atttcaccca attgtagata      900
tgctaactcc agcaatgagt tgatgaatct cggtgtgtat tttatgtcct cagaggacaa      960
cacctgttgt aatcgttctt ccacacggat cc                                   992

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence:Synthetic
      peptide

<400> SEQUENCE: 24

His Asp Glu Leu
  1

<210> SEQ ID NO 25
<211> LENGTH: 894
<212> TYPE: DNA
<213> ORGANISM: Bacillus stearothermophilus

<400> SEQUENCE: 25
gtggcgcagc tttcagttga acagtttctc aacgagcaaa acaggcggt ggaaacagcg       60 ctctcccgtt atatagagcg cttagaaggg ccggcgaagc tgaaaaaggc gatgcgtac     120 tcattggagg ccggcggcaa acgaatccgt ccgttgctgc ttctgtccac cgttcgggcg     180
ctcggcaaag acccggcggt cggattgccc gtcgcctgcg cgattgaaat gatccatacg     240
tactctttga tccatgatga tttgccgagc atggacaacg atgatttgcg gcgcggcaag     300
ccgacgaacc ataaagtgtt cggcgaggcg atggccatct ggcgggggga cgggttgttg     360
acgtacgcgt ttcaattgat caccgaaatc gacgatgagc gcatccctcc ttccgtccgg     420
cttcggctca tcgaacggct ggcgaaagcg gccggtccgg aagggatggt cgccggtcag     480
gcagccgata tggaaggaga ggggaaaacg ctgacgcttt cggagctcga atacattcat     540
cggcataaaa ccgggaaaat gctgcaatac agcgtgcacg ccggcgcctt gatcggcggc     600
gctgatgccc ggcaaacgcg ggagcttgac gaattcgccg cccatctagg ccttgccttt     660
caaattcgcg atgatattct cgatattgaa ggggcagaag aaaaaatcgg caagccggtc     720
ggcagcgacc aaagcaacaa caaagcgacg tatccagcgt tgctgtcgct tgccggcgcg     780
aaggaaaagt tggcgttcca tatcgaggcg gcgcagcgcc atttacggaa cgccgacgtt     840
gacggcgccg cgctcgccta tatttgcgaa ctggtcgccg cccgcgacca ttaa           894

<210> SEQ ID NO 26
<211> LENGTH: 1197
<212> TYPE: DNA
<213> ORGANISM: Saccharomyces cerevisiae

<400> SEQUENCE: 26
```

```
atgtctcaga acgtttacat tgtatcgact gccagaaccc caattggttc attccagggt      60
tctctatcct ccaagacagc agtggaattg ggtgctgttg ctttaaaagg cgccttggct     120
aaggttccag aattggatgc atccaaggat tttgacgaaa ttattttggg taacgttctt     180
tctgccaatt tgggccaagc tccggccaga caagttgctt ggctgccgg tttgagtaat     240 catatcgttg caagcacagt taacaaggtc tgtgcatccg ctatgaaggc aatcattttg     300
ggtgctcaat ccatcaaatg tggtaatgct gatgttgtcg tagctggtgg ttgtgaatct     360
atgactaacg caccatacta catgccagca gcccgtgcgg gtgccaaatt tggccaaact     420
gttcttgttg atggtgtcga aagagatggg ttgaacgatg cgtacgatgg tctagccatg     480
ggtgtacacg cagaaaagtg tgcccgtgat tgggatatta ctagagaaca acaagacaat     540
tttgccatcg aatcctacca aaaatctcaa aaatctcaaa aggaaggtaa attcgacaat     600
gaaattgtac ctgttaccat taagggattt agaggtaagc ctgatactca agtcacgaag     660
gacgaggaac ctgctagatt acacgttgaa aaattgagat ctgcaaggac tgttttccaa     720
aaagaaaacg gtactgttac tgccgctaac gcttctccaa tcaacgatgg tgctgcagcc     780
gtcatcttgg tttccgaaaa agttttgaag gaaaagaatt tgaagccttt ggctattatc     840
aaaggttggg gtgaggccgc tcatcaacca gctgatttta catgggctcc atctcttgca     900
gttccaaagg ctttgaaaca tgctggcatc gaagacatca attctgttga ttactttgaa     960
ttcaatgaag ccttttcggt tgtcggtttg gtgaacacta agattttgaa gctagaccca    1020
tctaaggtta atgtatatgg tggtgctgtt gctctaggtc acccattggg ttgttctggt    1080
gctagagtgg ttgttacact gctatccatc ttacagcaag aaggaggtaa gatcggtgtt    1140
gccgccattt gtaatggtgg tggtggtgct tcctctattg tcattgaaaa gatatga      1197
```

```
<210> SEQ ID NO 27
<211> LENGTH: 1476
<212> TYPE: DNA
<213> ORGANISM: Saccharomyces cerevisiae

<400> SEQUENCE: 27
```

```
atgaaactct caactaaact ttgttggtgt ggtattaaag gaagacttag gccgcaaaag      60
caacaacaat tacacaatac aaacttgcaa atgactgaac taaaaaaaca aaagaccgct     120
gaacaaaaaa ccagacctca aaatgtcggt attaaaggta tccaaattta catcccaact     180
caatgtgtca accaatctga gctagagaaa tttgatggcg tttctcaagg taaatacaca     240
attggtctgg gccaaaccaa catgtctttt gtcaatgaca gagaagatat ctactcgatg     300
tccctaactg ttttgtctaa gttgatcaag agttacaaca tcgacaccaa caaaattggt     360
agattagaag tcggtactga aactctgatt gacaagtcca gtctgtcaa gtctgtcttg     420 atgcaattgt ttggtgaaaa cactgacgtc gaaggtattg acacgcttaa tgcctgttac     480
ggtggtacca acgcgttgtt caactctttg aactggatta atctaacgc atgggatggt     540 agagacgcca ttgtagtttg cggtgatatt gccatctacg ataagggtgc cgcaagacca     600
accggtggtg ccggtactgt tgctatgtgg atcggtcctg atgctccaat tgtatttgac     660
tctgtaagag cttcttacat ggaacacgcc tacgattttt acaagccaga tttcaccagc     720
gaatatcctt acgtcgatgg tcatttttca ttaacttgtt acgtcaaggc tcttgatcaa     780
gtttacaaga gttattccaa gaaggctatt tctaaagggt tggttagcga tcccgctggt     840
tcggatgctt tgaacgtttt gaatatttc gactacaacg ttttccatgt tccaacctgt     900
aaattggtca caaaatcata cggtagatta ctatataacg atttcagagc caatcctcaa     960
```

```
ttgttcccag aagttgacgc cgaattagct actcgcgatt atgacgaatc tttaaccgat    1020
aagaacattg aaaaaacttt tgttaatgtt gctaagccat tccacaaaga gagagttgcc    1080
caatctttga ttgttccaac aaacacaggt aacatgtaca ccgcatctgt ttatgccgcc    1140
tttgcatctc tattaaacta tgttggatct gacgacttac aaggcaagcg tgttggttta    1200
ttttcttacg gttccggttt agctgcatct ctatattctt gcaaaattgt tggtgacgtc    1260
caacatatta tcaaggaatt agatattact aacaaattag ccaagagaat caccgaaact    1320
ccaaaggatt acgaagctgc catcgaattg agagaaaatg cccatttgaa gaagaacttc    1380
aaacctcaag gttccattga gcatttgcaa agtggtgttt actacttgac caacatcgat    1440
gacaaattta aagatctta cgatgttaaa aataa                                1476
```

<210> SEQ ID NO 28
<211> LENGTH: 1332
<212> TYPE: DNA
<213> ORGANISM: Saccharomyces cerevisiae

<400> SEQUENCE: 28

```
atgtcattac cgttcttaac ttctgcaccg ggaaaggtta ttattttgg tgaacactct     60 gctgtgtaca acaagcctgc cgtcgctgct agtgtgtctg cgttgagaac ctacctgcta    120
ataagcgagt catctgcacc agatactatt gaattggact cccggacat tagctttaat     180 cataagtggt ccatcaatga tttcaatgcc atcaccgagg atcaagtaaa ctcccaaaaa    240
ttggccaagg ctcaacaagc caccgatggc ttgtctcagg aactcgttag tcttttggat    300
ccgttgttag ctcaactatc cgaatccttc cactaccatg cagcgttttg tttcctgtat    360
atgtttgttt gcctatgccc ccatgccaag aatattaagt tttctttaaa gtctacttta    420
cccatcggtg ctgggttggg ctcaagcgcc tctatttctg tatcactggc cttagctatg    480
gcctacttgg gggggttaat aggatctaat gacttggaaa agctgtcaga aaacgataag    540
catatagtga atcaatgggc cttcataggt gaaaagtgta ttcacggtac cccttcagga    600
atagataacg ctgtggccac ttatggtaat gccctgctat tgaaaaaga ctcacataat    660 ggaacaataa acacaaacaa ttttaagttc ttagatgatt cccagccat tccaatgatc    720 ctaacctata ctagaattcc aaggtctaca aaagatcttg ttgctcgcgt tcgtgtgttg    780
gtcaccgaga aatttcctga agttatgaag ccaattctag atgccatggg tgaatgtgcc    840
ctacaaggct tagagatcat gactaagtta agtaaatgta aagcaccga tgacgaggct    900 gtagaaacta ataatgaact gtatgaacaa ctattggaat tgataagaat aaatcatgga    960
ctgcttgtct caatcggtgt ttctcatcct ggattagaac ttattaaaaa tctgagcgat    1020
gatttgagaa ttggctccac aaaacttacc ggtgctggtg gcggcggttg ctctttgact    1080
ttgttacgaa gagacattac tcaagagcaa attgacagct tcaaaagaa attgcaagat    1140 gattttagtt acgagacatt tgaaacagac ttgggtggga ctggctgctg tttgttaagc    1200
gcaaaaaatt tgaataaaga tcttaaaatc aaatccctag tattccaatt atttgaaaat    1260
aaaactacca caaagcaaca aattgacgat ctattattgc caggaaacac gaatttacca    1320
tggacttcat aa                                                        1332
```

<210> SEQ ID NO 29
<211> LENGTH: 1356
<212> TYPE: DNA
<213> ORGANISM: Saccharomyces cerevisiae

<400> SEQUENCE: 29

```
atgtcagagt tgagagcctt cagtgcccca gggaaagcgt tactagctgg tggatattta      60
gttttagata caaatatga agcatttgta gtcggattat cggcaagaat gcatgctgta     120
gcccatcctt acggttcatt gcaagggtct gataagtttg aagtgcgtgt gaaaagtaaa     180
caatttaaag atggggagtg gctgtaccat ataagtccta aaagtggctt cattcctgtt     240
tcgataggcg gatctaagaa ccctttcatt gaaaagtta tcgctaacgt atttagctac     300
tttaaaccta acatggacga ctactgcaat agaaacttgt tcgttattga tattttctct     360
gatgatgcct accattctca ggaggatagc gttaccgaac atcgtggcaa cagaagattg     420
agttttcatt cgcacagaat tgaagaagtt cccaaaacag gctgggctc ctcggcaggt     480
ttagtcacag ttttaactac agctttggcc tcctttttg tatcggacct ggaaaataat     540
gtagacaaat atagagaagt tattcataat ttagcacaag ttgctcattg tcaagctcag     600
ggtaaaattg gaagcgggtt tgatgtagcg gcggcagcat atggatctat cagatataga     660
agattcccac ccgcattaat ctctaatttg ccagatattg gaagtgctac ttacggcagt     720
aaactggcgc atttggttga tgaagaagac tggaatatta cgattaaaag taaccattta     780
ccttcgggat taactttatg gatgggcgat attaagaatg gttcagaaac agtaaaactg     840
gtccagaagg taaaaaattg gtatgattcg catatgccag aaagcttgaa aatatataca     900
gaactcgatc atgcaaattc tagatttatg gatggactat ctaaactaga tcgcttacac     960
gagactcatg acgattacag cgatcagata tttgagtctc ttgagaggaa tgactgtacc    1020
tgtcaaaagt atcctgaaat cacagaagtt agagatgcag ttgccacaat tagacgttcc    1080
tttagaaaaa taactaaaga atctggtgcc gatatcgaac ctcccgtaca aactagctta    1140
ttggatgatt gccagacctt aaaaggagtt cttacttgct aatacctgg tgctggtggt    1200
tatgacgcca ttcagtgat tactaagcaa gatgttgatc ttagggctca aaccgctaat    1260
gacaaaagat tttctaaggt tcaatggctg gatgtaactc aggctgactg gggtgttagg    1320
aaagaaaaag atccggaaac ttatcttgat aaataa                             1356
```

<210> SEQ ID NO 30
<211> LENGTH: 1191
<212> TYPE: DNA
<213> ORGANISM: Saccharomyces cerevisiae

<400> SEQUENCE: 30

```
atgaccgttt acacagcatc cgttaccgca cccgtcaaca tcgcaaccct taagtattgg      60
gggaaagggg acacgaagtt gaatctgccc accaattcgt ccatatcagt gactttatcg     120
caagatgacc tcagaacgtt gacctctgcg gctactgcac ctgagtttga acgcgacact     180
ttgtggttaa atgagaacc acacagcatc gacaatgaaa gaactcaaaa ttgtctgcgc     240
gacctacgcc aattaagaaa ggaaatggaa tcgaaggacg cctcattgcc cacattatct     300
caatggaaac tccacattgt ctccgaaaat aactttccta cagcagctgg tttagcttcc     360
tccgctgctg gctttgctgc attggtctct gcaattgcta agttatacca attaccacag     420
tcaacttcag aaatatctag aatagcaaga aaggggtctg gttcagcttg tagatcgttg     480
tttggcggat acgtggcctg ggaaatggga aaagctgaag atggtcatga ttccatggca     540
gtacaaatcg cagacagctc tgactggcct cagatgaaag cttgtgtcct agttgtcagc     600
gatattaaaa aggatgtgag ttccactcag ggtatgcaat tgaccgtggc aacctccgaa     660
ctatttaaag aaagaattga acatgtcgta ccaaagagat ttgaagtcat gcgtaaagcc     720
```

| | |
|---|---|
| attgttgaaa aagatttcgc caccttttgca aaggaaacaa tgatggattc caactctttc | 780 |
| catgccacat gtttggactc tttccctcca atattctaca tgaatgacac ttccaagcgt | 840 |
| atcatcagtt ggtgccacac cattaatcag ttttacggag aaacaatcgt tgcatacacg | 900 |
| tttgatgcag gtccaaatgc tgtgttgtac tacttagctg aaaatgagtc gaaactcttt | 960 |
| gcatttatct ataaattgtt tggctctgtt cctggatggg acaagaaatt tactactgag | 1020 |
| cagcttgagg ctttcaacca tcaatttgaa tcatctaact ttactgcacg tgaattggat | 1080 |
| cttgagttgc aaaaggatgt tgccagagtg attttaactc aagtcggttc aggcccacaa | 1140 |
| gaaacaaacg aatctttgat tgacgcaaag actggtctac caaaggaata a | 1191 |

<210> SEQ ID NO 31
<211> LENGTH: 867
<212> TYPE: DNA
<213> ORGANISM: Saccharomyces cerevisiae

<400> SEQUENCE: 31

| | |
|---|---|
| atgactgccg acaacaatag tatgccccat ggtgcagtat ctagttacgc caaattagtg | 60 |
| caaaaccaaa cacctgaaga cattttggaa gagtttcctg aaattattcc attacaacaa | 120 |
| agacctaata cccgatctag tgagacgtca aatgacgaaa gcggagaaac atgttttttct | 180 |
| ggtcatgatg aggagcaaat taagttaatg aatgaaaatt gtattgtttt ggattgggac | 240 |
| gataatgcta ttggtgccgg taccaagaaa gtttgtcatt taatgaaaaa tattgaaaag | 300 |
| ggtttactac atcgtgcatt ctccgtcttt attttcaatg aacaaggtga attacttta | 360 |
| caacaaagag ccactgaaaa aataactttc cctgatcttt ggactaaacac atgctgctct | 420 |
| catccactat gtattgatga cgaattaggt ttgaagggta agctagacga taagattaag | 480 |
| ggcgctatta ctgcggcggt gagaaaacta gatcatgaat taggtattcc agaagatgaa | 540 |
| actaagacaa ggggtaagtt tcacttttta aacagaatcc attacatggc accaagcaat | 600 |
| gaaccatggg gtgaacatga aattgattac atcctatttt ataagatcaa cgctaaagaa | 660 |
| aacttgactg tcaacccaaa cgtcaatgaa gttagagact tcaaatgggt ttcaccaaat | 720 |
| gatttgaaaa ctatgtttgc tgacccaagt tacaagttta cgccttggtt taagattatt | 780 |
| tgcgagaatt acttattcaa ctggtgggag caattagatg accttttctga agtggaaaat | 840 |
| gacaggcaaa ttcatagaat gctataa | 867 |

<210> SEQ ID NO 32
<211> LENGTH: 549
<212> TYPE: DNA
<213> ORGANISM: Escherichia coli

<400> SEQUENCE: 32

| | |
|---|---|
| atgcaaacgg aacacgtcat tttattgaat gcacagggag ttcccacggg tacgctggaa | 60 |
| aagtatgccg cacacacggc agacacccgc ttacatctcg cgttctccag ttggctgttt | 120 |
| aatgccaaag acaattatt agttaccgc cgcgcactga gcaaaaaagc atggcctggc | 180 |
| gtgtggacta actcggtttg tgggcaccca caactgggag aaagcaacga agacgcagtg | 240 |
| atccgccgtt gccgttatga gcttggcgtg gaaattacgc ctcctgaatc tatctatcct | 300 |
| gactttcgct accgcgccac cgatccgagt ggcattgtgg aaaatgaagt gtgtccggta | 360 |
| tttgccgcac gcaccactag tgcgttacag atcaatgatg atgaagtgat ggattatcaa | 420 |
| tggtgtgatt tagcagatgt attacacggt attgatgcca cgccgtgggc gttcagtccg | 480 |

```
tggatggtga tgcaggcgac aaatcgcgaa gccagaaaac gattatctgc atttacccag    540
cttaaataa                                                            549
```

<210> SEQ ID NO 33
<211> LENGTH: 900
<212> TYPE: DNA
<213> ORGANISM: Escherichia coli
<220> FEATURE:
<221> NAME/KEY: CDS
<222> LOCATION: (1)..(897)

<400> SEQUENCE: 33

```
atg gac ttt ccg cag caa ctc gaa gcc tgc gtt aag cag gcc aac cag    48
Met Asp Phe Pro Gln Gln Leu Glu Ala Cys Val Lys Gln Ala Asn Gln
  1               5                  10                  15 gcg ctg agc cgt ttt atc gcc cca ctg ccc ttt cag aac act ccc gtg    96
Ala Leu Ser Arg Phe Ile Ala Pro Leu Pro Phe Gln Asn Thr Pro Val
             20                  25                  30 gtc gaa acc atg cag tat ggc gca tta tta ggt ggt aag cgc ctg cga    144
Val Glu Thr Met Gln Tyr Gly Ala Leu Leu Gly Gly Lys Arg Leu Arg
         35                  40                  45 cct ttc ctg gtt tat gcc acc ggt cat atg ttc ggc gtt agc aca aac    192
Pro Phe Leu Val Tyr Ala Thr Gly His Met Phe Gly Val Ser Thr Asn
 50                  55                  60 acg ctg gac gca ccc gct gcc gcc gtt gaa tgc atc cac gct gac tca    240
Thr Leu Asp Ala Pro Ala Ala Ala Val Glu Cys Ile His Ala Asp Ser
 65                  70                  75                  80 tta att cat gat gat tta ccg gca atg gat gat gac gat ctg cgt cgc    288
Leu Ile His Asp Asp Leu Pro Ala Met Asp Asp Asp Asp Leu Arg Arg
                 85                  90                  95 ggt ttg cca acc tgc cat gtg aag ttt ggc gaa gca aac gcg att ctc    336
Gly Leu Pro Thr Cys His Val Lys Phe Gly Glu Ala Asn Ala Ile Leu
            100                 105                 110 gct ggc gac gct tta caa acg ctg gcg ttc tcg att tta agc gat gcc    384
Ala Gly Asp Ala Leu Gln Thr Leu Ala Phe Ser Ile Leu Ser Asp Ala
        115                 120                 125 gat atg ccg gaa gtg tcg gac cgc gac aga att tcg atg att tct gaa    432
Asp Met Pro Glu Val Ser Asp Arg Asp Arg Ile Ser Met Ile Ser Glu
    130                 135                 140 ctg gcg agc gcc agt ggt att gcc gga atg tgc ggt ggt cag gca tta    480
Leu Ala Ser Ala Ser Gly Ile Ala Gly Met Cys Gly Gly Gln Ala Leu
145                 150                 155                 160 gat tta gac gcg gaa ggc aaa cac gta cct ctg gac gcg ctt gag cgt    528
Asp Leu Asp Ala Glu Gly Lys His Val Pro Leu Asp Ala Leu Glu Arg
                165                 170                 175 att cat cgt cat aaa acc ggc gca ttg att cgc gcc gcc gtt cgc ctt    576
Ile His Arg His Lys Thr Gly Ala Leu Ile Arg Ala Ala Val Arg Leu
            180                 185                 190 ggt gca tta agc gcc gga gat aaa gga cgt cgt gct ctg ccg gta ctc    624
Gly Ala Leu Ser Ala Gly Asp Lys Gly Arg Arg Ala Leu Pro Val Leu
        195                 200                 205 gac aag tat gca gag agc atc ggc ctt gcc ttc cag gtt cag gat gac    672
Asp Lys Tyr Ala Glu Ser Ile Gly Leu Ala Phe Gln Val Gln Asp Asp
    210                 215                 220 atc ctg gat gtg gtg gga gat act gca acg ttg gga aaa cgc cag ggt    720
Ile Leu Asp Val Val Gly Asp Thr Ala Thr Leu Gly Lys Arg Gln Gly
225                 230                 235                 240 gcc gac cag caa ctt ggt aaa agt acc tac cct gca ctt ctg ggt ctt    768
Ala Asp Gln Gln Leu Gly Lys Ser Thr Tyr Pro Ala Leu Leu Gly Leu
                245                 250                 255
```

```
gag caa gcc cgg aag aaa gcc cgg gat ctg atc gac gat gcc cgt cag       816
Glu Gln Ala Arg Lys Lys Ala Arg Asp Leu Ile Asp Asp Ala Arg Gln
        260                 265                 270 tcg ctg aaa caa ctg gct gaa cag tca ctc gat acc tcg gca ctg gaa       864
Ser Leu Lys Gln Leu Ala Glu Gln Ser Leu Asp Thr Ser Ala Leu Glu
    275                 280                 285 gcg cta gcg gac tac atc atc cag cgt aat aaa taa                       900
Ala Leu Ala Asp Tyr Ile Ile Gln Arg Asn Lys
        290                 295

<210> SEQ ID NO 34
<211> LENGTH: 299
<212> TYPE: PRT
<213> ORGANISM: Escherichia coli

<400> SEQUENCE: 34

Met Asp Phe Pro Gln Gln Leu Glu Ala Cys Val Lys Gln Ala Asn Gln
  1               5                  10                  15

Ala Leu Ser Arg Phe Ile Ala Pro Leu Pro Phe Gln Asn Thr Pro Val
                 20                  25                  30

Val Glu Thr Met Gln Tyr Gly Ala Leu Leu Gly Gly Lys Arg Leu Arg
             35                  40                  45

Pro Phe Leu Val Tyr Ala Thr Gly His Met Phe Gly Val Ser Thr Asn
         50                  55                  60

Thr Leu Asp Ala Pro Ala Ala Val Glu Cys Ile His Ala Asp Ser
 65                  70                  75                  80

Leu Ile His Asp Asp Leu Pro Ala Met Asp Asp Asp Leu Arg Arg
                 85                  90                  95

Gly Leu Pro Thr Cys His Val Lys Phe Gly Glu Ala Asn Ala Ile Leu
            100                 105                 110

Ala Gly Asp Ala Leu Gln Thr Leu Ala Phe Ser Ile Leu Ser Asp Ala
        115                 120                 125

Asp Met Pro Glu Val Ser Asp Arg Asp Arg Ile Ser Met Ile Ser Glu
    130                 135                 140

Leu Ala Ser Ala Ser Gly Ile Ala Gly Met Cys Gly Gly Gln Ala Leu
145                 150                 155                 160

Asp Leu Asp Ala Glu Gly Lys His Val Pro Leu Asp Ala Leu Glu Arg
                165                 170                 175

Ile His Arg His Lys Thr Gly Ala Leu Ile Arg Ala Ala Val Arg Leu
            180                 185                 190

Gly Ala Leu Ser Ala Gly Asp Lys Gly Arg Arg Ala Leu Pro Val Leu
        195                 200                 205

Asp Lys Tyr Ala Glu Ser Ile Gly Leu Ala Phe Gln Val Gln Asp Asp
    210                 215                 220

Ile Leu Asp Val Val Gly Asp Thr Ala Thr Leu Gly Lys Arg Gln Gly
225                 230                 235                 240

Ala Asp Gln Gln Leu Gly Lys Ser Thr Tyr Pro Ala Leu Leu Gly Leu
                245                 250                 255

Glu Gln Ala Arg Lys Lys Ala Arg Asp Leu Ile Asp Asp Ala Arg Gln
            260                 265                 270

Ser Leu Lys Gln Leu Ala Glu Gln Ser Leu Asp Thr Ser Ala Leu Glu
        275                 280                 285

Ala Leu Ala Asp Tyr Ile Ile Gln Arg Asn Lys
    290                 295

<210> SEQ ID NO 35
```

-continued

```
<211> LENGTH: 900
<212> TYPE: DNA
<213> ORGANISM: Escherichia coli
<220> FEATURE:
<221> NAME/KEY: CDS
<222> LOCATION: (1)..(897)

<400> SEQUENCE: 35 atg gac ttt ccg cag caa ctc gaa gcc tgc gtt aag cag gcc aac cag      48
Met Asp Phe Pro Gln Gln Leu Glu Ala Cys Val Lys Gln Ala Asn Gln
 1               5                  10                  15 gcg ctg agc cgt ttt atc gcc cca ctg ccc ttt cag aac act ccc gtg      96
Ala Leu Ser Arg Phe Ile Ala Pro Leu Pro Phe Gln Asn Thr Pro Val
            20                  25                  30 gtc gaa acc atg cag tat ggc gca tta tta ggt ggt aag cgc ctg cga     144
Val Glu Thr Met Gln Tyr Gly Ala Leu Leu Gly Gly Lys Arg Leu Arg
        35                  40                  45 cct ttc ctg gtt tat gcc acc ggt cat atg ttc ggc gtt agc aca aac     192
Pro Phe Leu Val Tyr Ala Thr Gly His Met Phe Gly Val Ser Thr Asn
    50                  55                  60 acg ctg gac gca ccc gct gcc gcc gtt gaa tgc atc cac gct gaa tca     240
Thr Leu Asp Ala Pro Ala Ala Ala Val Glu Cys Ile His Ala Glu Ser
65                  70                  75                  80 tta att cat gat gat tta ccg gca atg gat gat gac gat ctg cgt cgc     288
Leu Ile His Asp Asp Leu Pro Ala Met Asp Asp Asp Asp Leu Arg Arg
                85                  90                  95 ggt ttg cca acc tgc cat gtg aag ttt ggc gaa gca aac gcg att ctc     336
Gly Leu Pro Thr Cys His Val Lys Phe Gly Glu Ala Asn Ala Ile Leu
            100                 105                 110 gct ggc gac gct tta caa acg ctg gcg ttc tcg att tta agc gat gcc     384
Ala Gly Asp Ala Leu Gln Thr Leu Ala Phe Ser Ile Leu Ser Asp Ala
        115                 120                 125 gat atg ccg gaa gtg tcg gac cgc gac aga att tcg atg att tct gaa     432
Asp Met Pro Glu Val Ser Asp Arg Asp Arg Ile Ser Met Ile Ser Glu
    130                 135                 140 ctg gcg agc gcc agt ggt att gcc gga atg tgc ggt ggt cag gca tta     480
Leu Ala Ser Ala Ser Gly Ile Ala Gly Met Cys Gly Gly Gln Ala Leu
145                 150                 155                 160 gat tta gac gcg gaa ggc aaa cac gta cct ctg gac gcg ctt gag cgt     528
Asp Leu Asp Ala Glu Gly Lys His Val Pro Leu Asp Ala Leu Glu Arg
                165                 170                 175 att cat cgt cat aaa acc ggc gca ttg att cgc gcc gcc gtt cgc ctt     576
Ile His Arg His Lys Thr Gly Ala Leu Ile Arg Ala Ala Val Arg Leu
            180                 185                 190 ggt gca tta agc gcc gga gat aaa gga cgt cgt gct ctg ccg gta ctc     624
Gly Ala Leu Ser Ala Gly Asp Lys Gly Arg Arg Ala Leu Pro Val Leu
        195                 200                 205 gac aag tat gca gag agc atc ggc ctt gcc ttc cag gtt cag gat gac     672
Asp Lys Tyr Ala Glu Ser Ile Gly Leu Ala Phe Gln Val Gln Asp Asp
    210                 215                 220 atc ctg gat gtg gtg gga gat act gca acg ttg gga aaa cgc cag ggt     720
Ile Leu Asp Val Val Gly Asp Thr Ala Thr Leu Gly Lys Arg Gln Gly
225                 230                 235                 240 gcc gac cag caa ctt ggt aaa agt acc tac cct gca ctt ctg ggt ctt     768
Ala Asp Gln Gln Leu Gly Lys Ser Thr Tyr Pro Ala Leu Leu Gly Leu
                245                 250                 255 gag caa gcc cgg aag aaa gcc cgg gat ctg atc gac gat gcc gtc cag     816
Glu Gln Ala Arg Lys Lys Ala Arg Asp Leu Ile Asp Asp Ala Arg Gln
            260                 265                 270 tcg ctg aaa caa ctg gct gaa cag tca ctc gat acc tcg gca ctg gaa     864
Ser Leu Lys Gln Leu Ala Glu Gln Ser Leu Asp Thr Ser Ala Leu Glu
```

```
                275                 280                 285
gcg cta gcg gac tac atc atc cag cgt aat aaa taa                       900
Ala Leu Ala Asp Tyr Ile Ile Gln Arg Asn Lys
    290                 295
```

<210> SEQ ID NO 36
<211> LENGTH: 299
<212> TYPE: PRT
<213> ORGANISM: Escherichia coli

<400> SEQUENCE: 36

```
Met Asp Phe Pro Gln Gln Leu Glu Ala Cys Val Lys Gln Ala Asn Gln
  1               5                  10                  15

Ala Leu Ser Arg Phe Ile Ala Pro Leu Pro Phe Gln Asn Thr Pro Val
             20                  25                  30

Val Glu Thr Met Gln Tyr Gly Ala Leu Leu Gly Gly Lys Arg Leu Arg
         35                  40                  45

Pro Phe Leu Val Tyr Ala Thr Gly His Met Phe Gly Val Ser Thr Asn
     50                  55                  60

Thr Leu Asp Ala Pro Ala Ala Val Glu Cys Ile His Ala Glu Ser
 65                  70                  75                  80

Leu Ile His Asp Asp Leu Pro Ala Met Asp Asp Asp Leu Arg Arg
                 85                  90                  95

Gly Leu Pro Thr Cys His Val Lys Phe Gly Glu Ala Asn Ala Ile Leu
            100                 105                 110

Ala Gly Asp Ala Leu Gln Thr Leu Ala Phe Ser Ile Leu Ser Asp Ala
        115                 120                 125

Asp Met Pro Glu Val Ser Asp Arg Asp Arg Ile Ser Met Ile Ser Glu
    130                 135                 140

Leu Ala Ser Ala Ser Gly Ile Ala Gly Met Cys Gly Gly Gln Ala Leu
145                 150                 155                 160

Asp Leu Asp Ala Glu Gly Lys His Val Pro Leu Asp Ala Leu Glu Arg
                165                 170                 175

Ile His Arg His Lys Thr Gly Ala Leu Ile Arg Ala Ala Val Arg Leu
            180                 185                 190

Gly Ala Leu Ser Ala Gly Asp Lys Gly Arg Arg Ala Leu Pro Val Leu
        195                 200                 205

Asp Lys Tyr Ala Glu Ser Ile Gly Leu Ala Phe Gln Val Gln Asp Asp
    210                 215                 220

Ile Leu Asp Val Val Gly Asp Thr Ala Thr Leu Gly Lys Arg Gln Gly
225                 230                 235                 240

Ala Asp Gln Gln Leu Gly Lys Ser Thr Tyr Pro Ala Leu Leu Gly Leu
                245                 250                 255

Glu Gln Ala Arg Lys Lys Ala Arg Asp Leu Ile Asp Asp Ala Arg Gln
            260                 265                 270

Ser Leu Lys Gln Leu Ala Glu Gln Ser Leu Asp Thr Ser Ala Leu Glu
        275                 280                 285

Ala Leu Ala Asp Tyr Ile Ile Gln Arg Asn Lys
    290                 295
```

<210> SEQ ID NO 37
<211> LENGTH: 900
<212> TYPE: DNA
<213> ORGANISM: Escherichia coli
<220> FEATURE:
<221> NAME/KEY: CDS
<222> LOCATION: (1)..(897)

<400> SEQUENCE: 37

```
atg gac ttt ccg cag caa ctc gaa gcc tgc gtt aag cag gcc aac cag      48
Met Asp Phe Pro Gln Gln Leu Glu Ala Cys Val Lys Gln Ala Asn Gln
1               5                   10                  15 gcg ctg agc cgt ttt atc gcc cca ctg ccc ttt cag aac act ccc gtg      96
Ala Leu Ser Arg Phe Ile Ala Pro Leu Pro Phe Gln Asn Thr Pro Val
            20                  25                  30 gtc gaa acc atg cag tat ggc gca tta tta ggt ggt aag cgc ctg cga     144
Val Glu Thr Met Gln Tyr Gly Ala Leu Leu Gly Gly Lys Arg Leu Arg
        35                  40                  45 cct ttc ctg gtt tat gcc acc ggt cat atg ttc ggc gtt agc aca aac     192
Pro Phe Leu Val Tyr Ala Thr Gly His Met Phe Gly Val Ser Thr Asn
    50                  55                  60 acg ctg gac gca ccc gct gcc gcc gtt gaa tgc atc cac gct atg tca     240
Thr Leu Asp Ala Pro Ala Ala Ala Val Glu Cys Ile His Ala Met Ser
65                  70                  75                  80 tta att cat gat gat tta ccg gca atg gat gat gac gat ctg cgt cgc     288
Leu Ile His Asp Asp Leu Pro Ala Met Asp Asp Asp Asp Leu Arg Arg
                85                  90                  95 ggt ttg cca acc tgc cat gtg aag ttt ggc gaa gca aac gcg att ctc     336
Gly Leu Pro Thr Cys His Val Lys Phe Gly Glu Ala Asn Ala Ile Leu
            100                 105                 110 gct ggc gac gct tta caa acg ctg gcg ttc tcg att tta agc gat gcc     384
Ala Gly Asp Ala Leu Gln Thr Leu Ala Phe Ser Ile Leu Ser Asp Ala
        115                 120                 125 gat atg ccg gaa gtg tcg gac cgc gac aga att tcg atg att tct gaa     432
Asp Met Pro Glu Val Ser Asp Arg Asp Arg Ile Ser Met Ile Ser Glu
    130                 135                 140 ctg gcg agc gcc agt ggt att gcc gga atg tgc ggt ggt cag gca tta     480
Leu Ala Ser Ala Ser Gly Ile Ala Gly Met Cys Gly Gly Gln Ala Leu
145                 150                 155                 160 gat tta gac gcg gaa ggc aaa cac gta cct ctg gac gcg ctt gag cgt     528
Asp Leu Asp Ala Glu Gly Lys His Val Pro Leu Asp Ala Leu Glu Arg
                165                 170                 175 att cat cgt cat aaa acc ggc gca ttg att cgc gcc gcc gtt cgc ctt     576
Ile His Arg His Lys Thr Gly Ala Leu Ile Arg Ala Ala Val Arg Leu
            180                 185                 190 ggt gca tta agc gcc gga gat aaa gga cgt cgt gct ctg ccg gta ctc     624
Gly Ala Leu Ser Ala Gly Asp Lys Gly Arg Arg Ala Leu Pro Val Leu
        195                 200                 205 gac aag tat gca gag agc atc ggc ctt gcc ttc cag gtt cag gat gac     672
Asp Lys Tyr Ala Glu Ser Ile Gly Leu Ala Phe Gln Val Gln Asp Asp
    210                 215                 220 atc ctg gat gtg gtg gga gat act gca acg ttg gga aaa cgc cag ggt     720
Ile Leu Asp Val Val Gly Asp Thr Ala Thr Leu Gly Lys Arg Gln Gly
225                 230                 235                 240 gcc gac cag caa ctt ggt aaa agt acc tac cct gca ctt ctg ggt ctt     768
Ala Asp Gln Gln Leu Gly Lys Ser Thr Tyr Pro Ala Leu Leu Gly Leu
                245                 250                 255 gag caa gcc cgg aag aaa gcc cgg gat ctg atc gac gat gcc cgt cag     816
Glu Gln Ala Arg Lys Lys Ala Arg Asp Leu Ile Asp Asp Ala Arg Gln
            260                 265                 270 tcg ctg aaa caa ctg gct gaa cag tca ctc gat acc tcg gca ctg gaa     864
Ser Leu Lys Gln Leu Ala Glu Gln Ser Leu Asp Thr Ser Ala Leu Glu
        275                 280                 285 gcg cta gcg gac tac atc atc cag cgt aat aaa taa                     900
Ala Leu Ala Asp Tyr Ile Ile Gln Arg Asn Lys
    290                 295
```

<210> SEQ ID NO 38
<211> LENGTH: 299
<212> TYPE: PRT
<213> ORGANISM: Escherichia coli

<400> SEQUENCE: 38

```
Met Asp Phe Pro Gln Gln Leu Glu Ala Cys Val Lys Gln Ala Asn Gln
 1               5                  10                  15
Ala Leu Ser Arg Phe Ile Ala Pro Leu Pro Phe Gln Asn Thr Pro Val
            20                  25                  30
Val Glu Thr Met Gln Tyr Gly Ala Leu Leu Gly Gly Lys Arg Leu Arg
        35                  40                  45
Pro Phe Leu Val Tyr Ala Thr Gly His Met Phe Gly Val Ser Thr Asn
    50                  55                  60
Thr Leu Asp Ala Pro Ala Ala Val Glu Cys Ile His Ala Met Ser
65                  70                  75                  80
Leu Ile His Asp Asp Leu Pro Ala Met Asp Asp Asp Leu Arg Arg
                85                  90                  95
Gly Leu Pro Thr Cys His Val Lys Phe Gly Glu Ala Asn Ala Ile Leu
            100                 105                 110
Ala Gly Asp Ala Leu Gln Thr Leu Ala Phe Ser Ile Leu Ser Asp Ala
        115                 120                 125
Asp Met Pro Glu Val Ser Asp Arg Asp Arg Ile Ser Met Ile Ser Glu
    130                 135                 140
Leu Ala Ser Ala Ser Gly Ile Ala Gly Met Cys Gly Gly Gln Ala Leu
145                 150                 155                 160
Asp Leu Asp Ala Glu Gly Lys His Val Pro Leu Asp Ala Leu Glu Arg
                165                 170                 175
Ile His Arg His Lys Thr Gly Ala Leu Ile Arg Ala Ala Val Arg Leu
            180                 185                 190
Gly Ala Leu Ser Ala Gly Asp Lys Gly Arg Arg Ala Leu Pro Val Leu
        195                 200                 205
Asp Lys Tyr Ala Glu Ser Ile Gly Leu Ala Phe Gln Val Gln Asp Asp
    210                 215                 220
Ile Leu Asp Val Val Gly Asp Thr Ala Thr Leu Gly Lys Arg Gln Gly
225                 230                 235                 240
Ala Asp Gln Gln Leu Gly Lys Ser Thr Tyr Pro Ala Leu Leu Gly Leu
                245                 250                 255
Glu Gln Ala Arg Lys Lys Ala Arg Asp Leu Ile Asp Asp Ala Arg Gln
            260                 265                 270
Ser Leu Lys Gln Leu Ala Glu Gln Ser Leu Asp Thr Ser Ala Leu Glu
        275                 280                 285
Ala Leu Ala Asp Tyr Ile Ile Gln Arg Asn Lys
    290                 295
```

<210> SEQ ID NO 39
<211> LENGTH: 894
<212> TYPE: DNA
<213> ORGANISM: Bacillus stearothermophilus

<400> SEQUENCE: 39

```
gtggcgcagc tttcagttga acagtttctc aacgagcaaa acaggcggt ggaaacagcg      60 ctctcccgtt atatagagcg cttagaaggg ccggcgaagc tgaaaaaggc gatggcgtac     120
tcattggagg ccggcggcaa acgaatccgt ccgttgctgc ttctgtccac cgttcgggcg     180
```

```
ctcggcaaag acccggcggt cggattgccc gtcgcctgcg cgattgaaat gatccatacg    240
atgtctttga ttcatgatga tttgccgagc atggacaacg atgatttgcg gcgcggcaag    300
ccgacgaacc ataaagtgtt cggcgaggcg atggccatct ggcgggggga cgggttgttg    360
acgtacgcgt ttcaattgat caccgaaatc gacgatgagc gcatccctcc ttccgtccgg    420
cttcggctca tcgaacggct ggcgaaagcg gccggtccgg aagggatggt cgccggtcag    480
gcagccgata tggaaggaga ggggaaaacg ctgacgcttt cggagctcga atacattcat    540
cggcataaaa ccgggaaaat gctgcaatac agcgtgcacg ccggcgcctt gatcggcggc    600
gctgatgccc ggcaaacgcg ggagcttgac gaattcgccg cccatctagg ccttgccttt    660
caaattcgcg atgatattct cgatattgaa ggggcagaag aaaaaatcgg caagccggtc    720
ggcagcgacc aaagcaacaa caaagcgacg tatccagcgt tgctgtcgct tgccggcgcg    780
aaggaaaagt tggcgttcca tatcgaggcg gcgcagcgcc atttacggaa cgccgacgtt    840
gacggcgccg cgctcgccta tatttgcgaa ctggtcgccg cccgcgacca ttaa          894
```

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 40
tgcatctcga gggccgcatc atgtaattag                                      30

<210> SEQ ID NO 41
<211> LENGTH: 32
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 41
cattagggcc cggccgcaaa ttaaagcctt cg                                   32

<210> SEQ ID NO 42
<211> LENGTH: 33
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 42
cacggagctc cagttcgagt ttatcattat caa                                  33

<210> SEQ ID NO 43
<211> LENGTH: 35
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 43
ctctccgcgg tttgtttgtt tatgtgtgtt tattc                                35

<210> SEQ ID NO 44
<211> LENGTH: 34

-continued

```
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 44
ccgcgagctc ttacccataa ggttgtttgt gacg                                    34

<210> SEQ ID NO 45
<211> LENGTH: 36
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 45
ctttccgcgg gtttagttaa ttatagttcg ttgacc                                  36

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 46
atggcttcag aaaagaaat tag                                                 23

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 47
ctatttgctt ctcttgtaaa ctt                                                23

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 48
tgaggcatgc aatttccgca gcaactcg                                           28

<210> SEQ ID NO 49
<211> LENGTH: 28
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 49
tcagaattca tcagggggcct attaatac                                          28

<210> SEQ ID NO 50
<211> LENGTH: 23
<212> TYPE: DNA
```

```
<213> ORGANISM: Artificial Sequence
<220> FEATURE:
<223> OTHER INFORMATION: Description of Artificial Sequence:Synthetic
      DNA

<400> SEQUENCE: 50
atggaggcca agatagatga gct                                               23

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 51
tcacaattcg gataagtggt cta                                               23

<210> SEQ ID NO 52
<211> LENGTH: 32
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 52
tccccgcgga tgtctcagaa cgtttacatt gt                                     32

<210> SEQ ID NO 53
<211> LENGTH: 33
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 53
tgctctagat catatctttt caatgacaat gga                                    33

<210> SEQ ID NO 54
<211> LENGTH: 25
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 54
atgaaactct caactaaact ttgtt                                             25

<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 55
gttcagcaag atgcaatcga tgggg                                             25

<210> SEQ ID NO 56
<211> LENGTH: 23
<212> TYPE: DNA
<213> ORGANISM: Artificial Sequence
```

```
<220> FEATURE:
<223> OTHER INFORMATION: Description of Artificial Sequence:Synthetic
      DNA

<400> SEQUENCE: 56
atgccgccgc tattcaaggg act                                            23

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 57
ttaggattta atgcaggtga cgg                                            23

<210> SEQ ID NO 58
<211> LENGTH: 27
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 58
ccaaataaag actccaacac tctattt                                        27

<210> SEQ ID NO 59
<211> LENGTH: 27
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 59
gaattagaag cattattaag tagtgga                                        27

<210> SEQ ID NO 60
<211> LENGTH: 27
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 60
ggatttaacg cacatgcagc taattta                                        27

<210> SEQ ID NO 61
<211> LENGTH: 27
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 61
gtctgcttgg gttacatttt ctgaaaa                                        27

<210> SEQ ID NO 62
<211> LENGTH: 27
<212> TYPE: DNA
<213> ORGANISM: Artificial Sequence
<220> FEATURE:
```

-continued

<223> OTHER INFORMATION: Description of Artificial Sequence:Synthetic
     DNA

<400> SEQUENCE: 62
cataccagtt atactgcaga ccaattg                                     27

<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence:Synthetic
     DNA

<400> SEQUENCE: 63
gaatactcat taaagcaaat ggtagaa                                     27

<210> SEQ ID NO 64
<211> LENGTH: 31
<212> TYPE: DNA
<213> ORGANISM: Artificial Sequence
<220> FEATURE:
<223> OTHER INFORMATION: Description of Artificial Sequence:Synthetic
     DNA

<400> SEQUENCE: 64
aactgcagat gtcattaccg ttcttaactt c                                31

<210> SEQ ID NO 65
<211> LENGTH: 31
<212> TYPE: DNA
<213> ORGANISM: Artificial Sequence
<220> FEATURE:
<223> OTHER INFORMATION: Description of Artificial Sequence:Synthetic
     DNA

<400> SEQUENCE: 65
ccgagctctt atgaagtcca tggtaaattc g                                31

<210> SEQ ID NO 66
<211> LENGTH: 31
<212> TYPE: DNA
<213> ORGANISM: Artificial Sequence
<220> FEATURE:
<223> OTHER INFORMATION: Description of Artificial Sequence:Synthetic
     DNA

<400> SEQUENCE: 66
aactgcagat gtcattaccg ttcttaactt c                                31

<210> SEQ ID NO 67
<211> LENGTH: 31
<212> TYPE: DNA
<213> ORGANISM: Artificial Sequence
<220> FEATURE:
<223> OTHER INFORMATION: Description of Artificial Sequence:Synthetic
     DNA

<400> SEQUENCE: 67
ccgagctctt atgaagtcca tggtaaattc g                                31

<210> SEQ ID NO 68
<211> LENGTH: 31
<212> TYPE: DNA
<213> ORGANISM: Artificial Sequence
<220> FEATURE:
<223> OTHER INFORMATION: Description of Artificial Sequence:Synthetic

DNA

<400> SEQUENCE: 68
aactgcagat gaccgtttac acagcatccg t    31

<210> SEQ ID NO 69
<211> LENGTH: 31
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 69
cggaattctt attcctttgg tagaccagtc t    31

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 70
atgactgccg acaacaatag tat    23

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 71
ttatagcatt ctatgaattt gcc    23

<210> SEQ ID NO 72
<211> LENGTH: 32
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 72
tccccgcgga tgcaaacgga acacgtcatt tt    32

<210> SEQ ID NO 73
<211> LENGTH: 33
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 73
tgctctagat tatttaagct gggtaaatgc aga    33

<210> SEQ ID NO 74
<211> LENGTH: 45
<212> TYPE: DNA
<213> ORGANISM: Artificial Sequence
<220> FEATURE:
<223> OTHER INFORMATION: Description of Artificial Sequence:Synthetic
      DNA

```
<400> SEQUENCE: 74
atcatgaatt aatgagtcag cgtggatgca ttcaacggcg gcagc                45

<210> SEQ ID NO 75
<211> LENGTH: 45
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 75
atcatgaatt aatgattcag cgtggatgca ttcaacggcg gcagc                45

<210> SEQ ID NO 76
<211> LENGTH: 45
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 76
atcatgaatt aatgacatag cgtggatgca ttcaacggcg gcagc                45

<210> SEQ ID NO 77
<211> LENGTH: 27
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 77
tttcagtccc ttgaatagcg gcggcat                                    27

<210> SEQ ID NO 78
<211> LENGTH: 27
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 78
cacaaaatca agattgccca gtatgcc                                    27

<210> SEQ ID NO 79
<211> LENGTH: 27
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 79
agaagatacg gatttctttt ctgcttt                                    27

<210> SEQ ID NO 80
<211> LENGTH: 27
<212> TYPE: DNA
<213> ORGANISM: Artificial Sequence
<220> FEATURE:
<223> OTHER INFORMATION: Description of Artificial Sequence:Synthetic
      DNA
```

```
<400> SEQUENCE: 80
aactttggtg caaattgggt caatgat                                    27

<210> SEQ ID NO 81
<211> LENGTH: 27
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 81 ttgctctttta aagttttcag aggcatt                                   27

<210> SEQ ID NO 82
<211> LENGTH: 27
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 82
gcattattaa gtagtggaaa tacaaaa                                    27

<210> SEQ ID NO 83
<211> LENGTH: 27
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 83
cctttgtacg ctttggagaa aaaatta                                    27

<210> SEQ ID NO 84
<211> LENGTH: 27
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 84
tctgatcgtt taccatataa aaattat                                    27

<210> SEQ ID NO 85
<211> LENGTH: 27
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 85
aaggatggta tgacaagagg cccagta                                    27

<210> SEQ ID NO 86
<211> LENGTH: 16
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 86
```

```
tttccgcgga aacatg                                              16
```

<210> SEQ ID NO 87
<211> LENGTH: 14
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 87

```
aattgacggc cgtc                                                14
```

<210> SEQ ID NO 88
<211> LENGTH: 27
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 88

```
ggccgcaaat taaagccttc gagcgtc                                  27
```

<210> SEQ ID NO 89
<211> LENGTH: 27
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 89

```
acggattaga agccgccgag cgggtga                                  27
```

<210> SEQ ID NO 90
<211> LENGTH: 33
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 90

```
gccgttgaca gagggtccga gctcggtacc aag                           33
```

<210> SEQ ID NO 91
<211> LENGTH: 34
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 91

```
catactgacc cattgtcaat gggtaataac tgat                          34
```

<210> SEQ ID NO 92
<211> LENGTH: 18
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 92

-continued tgtccggtaa atggagac                                                    18

<210> SEQ ID NO 93
<211> LENGTH: 18
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 93
tgttctcgct gctcgttt                                                    18

<210> SEQ ID NO 94
<211> LENGTH: 19
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 94
atgggaaagc tattacaat                                                   19

<210> SEQ ID NO 95
<211> LENGTH: 18
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 95
caaggttgca atggccat                                                    18

<210> SEQ ID NO 96
<211> LENGTH: 19
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 96
caatgtaggg ctatatatg                                                   19

<210> SEQ ID NO 97
<211> LENGTH: 18
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 97
aacttgggga atggcaca                                                    18

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 98
tctcgaaaaa gggtttgcca t                                                21

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 99
tcactaggtg taaagagggc t                                        21

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 100
tgttgaagct tgcatgcctg c                                        21

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 101
ttgtaaaacg acggccagtg a                                        21

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 102
atggaggcca agatagatga g                                        21

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 103
tcacaattcg gataagtggt c                                        21

<210> SEQ ID NO 104
<211> LENGTH: 27
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 104
tcctaatgcc aagaaaacag ctgtcac                                  27

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 105
atggcaaacc cttttcgag a                                              21

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 106
agccctcttt acacctagtg a                                             21

<210> SEQ ID NO 107
<211> LENGTH: 27
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 107
tccccgcgga tggaggccaa gatagat                                       27

<210> SEQ ID NO 108
<211> LENGTH: 27
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 108
caactcgagt cacaattcgg ataagtg                                       27

<210> SEQ ID NO 109
<211> LENGTH: 38
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 109
gctctagagt tcgtcgtgtt tgcttctctt gtaaactt                           38

<210> SEQ ID NO 110
<211> LENGTH: 32
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 110
tatctcgagt cacaattcgt catgtaaatt gg                                 32

<210> SEQ ID NO 111
<211> LENGTH: 28
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 111
gcagggaccc caattcggat aagtggtc                                       28

<210> SEQ ID NO 112
<211> LENGTH: 28
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 112
gtagggtccc tggaggccaa gatagatg                                       28

<210> SEQ ID NO 113
<211> LENGTH: 29
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 113
gcagggaccc tttgcttctc ttgtaaact                                      29

<210> SEQ ID NO 114
<211> LENGTH: 29
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 114
gtagggtcct cagaaaaaga aattaggag                                      29

<210> SEQ ID NO 115
<211> LENGTH: 18
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 115
tgtaaaacga cggccagt                                                  18

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 116
taatacgact cactataggg                                                20

<210> SEQ ID NO 117

```
<211> LENGTH: 38
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 117
gctctagagt tcgtcgtgtt tgcttctctt gtaaactt                          38

<210> SEQ ID NO 118
<211> LENGTH: 32
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 118
tatctcgagt cacaattcgt catgtaaatt gg                                32

<210> SEQ ID NO 119
<211> LENGTH: 18
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 119
acggtaagaa atccaagc                                                18

<210> SEQ ID NO 120
<211> LENGTH: 18
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 120
tatgagtcgg cacccact                                                18

<210> SEQ ID NO 121
<211> LENGTH: 10
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 121

Cys Tyr Ile Ile Asp His Leu Ser Glu Leu
  1               5                  10

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 122

Cys Leu Asn Lys Val Tyr Lys Arg Ser Lys
  1               5                  10
```

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 123
ttttaagagc ttggtgagcg c                                          21

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 124
tcgagttcaa gagaaaaaaa a                                          21

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 125
ttcaattcat cattttttt t                                           21

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 126
gggtaataac tgatataatt a                                          21

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 127
atggattcta gaacagttgg t                                          21

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 128
ttacttgttt tctagataag c                                          21

<210> SEQ ID NO 129

```
<211> LENGTH: 21
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 129
atgactaacg aaaaggtctg g                                              21

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 130
ttaagctgct gcggagcttc c                                              21
```

METHODS OF PRODUCING PRENYL ALCOHOLS

This application is a 371 national phase application of PCT/JP01/11214 filed on 20 Dec. 2001, claiming priority to JP 2000-403067, filed on 28 Dec. 2000, the content of which is incorporated herein by reference in its entirety.

TECHNICAL FIELD

The present invention relates to methods of producing prenyl alcohols.

BACKGROUND ART

The biosynthesis of terpenoids (isoprenoids) begins with the synthesis of geranyl diphosphate (GPP; $C_{10}$), farnesyl diphosphate (FPP; $C_{15}$) and geranylgeranyl diphosphate (GGPP; $C_{20}$), which are straight chain prenyl diphosphates, through the condensation reaction of isopentenyl diphosphate (IPP; $C_5$) with an allylic diphosphate substrate in succession (FIG. 1). In FIG. 1, the abbreviations and words in boxes represent enzymes. Specifically, hmgR represents hydroxymethylglutaryl-CoA (HMG-CoA) reductase; GGPS represents GGPP synthase; and FPS represents FPP synthase.

Among prenyl diphosphates, FPP is the most important intermediate for the biosynthesis, and is a precursor for the synthesis of numerous kinds of terpenoids, e.g., steroids including ergosterol (provitamin $D_2$), the side chains of quinone (vitamin K; VK), sesquiterpenes, squalene (SQ), the anchor molecules of farnesylated proteins, natural rubber, etc.

GGPP is also an important intermediate for the terpenoid biosynthesis, and is essential for the biosynthesis of such compounds as retinol (vitamin A; VA), β-carotene (provitamin A), phylloquinone (vitamin $K_1$; $VK_1$), the anchor molecules of geranylgeranylated proteins, the side chains of chlorophyll, gibberellins, and the ether lipid of archaea.

Farnesol (FOH; $C_{15}$) and geranylgeraniol (GGOH; $C_{20}$), which are alcohol derivatives of FPP and GGPP, respectively, and their isomers such as nerolidol (NOH; $C_{15}$) are known as fragrant substances in essential oils used in perfumes. They are also important as starting materials for the synthesis of various compounds including the above-mentioned vitamins useful as pharmacological agents (FIG. 1).

Thus, it is desired to establish a system in which a pure product of the so-called active-type prenyl alcohol, not a mixture of cis- and trans- ((Z)- and (E)-) isomers, can be produced in a large quantity.

Although it had been believed that all the biosynthesis of IPP is performed via the mevalonate pathway (the pathway in which IPP is synthesized from acetyl-CoA through mevalonate), M. Rohmer et al. elucidated a novel pathway for IPP synthesis using bacteria at the end of 1980's. This is called the non-mevalonate pathway or DXP (1-deoxyxylulose 5-phosphate) pathway, in which IPP is synthesized from glyceraldehyde-3-phosphate and pyruvate through 1-deoxyxylulose 5-phosphate.

GGOH is currently produced by chemical synthesis (see, for example, Japanese Unexamined Patent Publication No. 8-133999). However, the chemical synthesis of GGOH requires more steps than that of FOH or NOH with shorter carbon chains, and thus requires a higher cost. Besides, though chemically synthesized GGOH has the same carbon skeleton as that of naturally occurring GGOH, it is obtained as a mixture of (E)-type (trans type) and (Z)-type (cis type) in double bond pattern. (E, E, E)-GGOH (hereinafter, abbreviated to (all-E)-GGOH) is the form synthesized in metabolic pathways in organisms and is industrially valuable. In order to obtain (all-E)-GGOH in a pure form, refining by column chromatography, high precision distillation, etc. is necessary. However, it is difficult to carry out high precision distillation of GGOH that is a thermally unstable allyl alcohol. Also, refining by column chromatography is not suitable for industrial practice since it requires large quantities of solvents and column packings, as well as complicated operations of analyzing and recovering serially eluting fractions and removing the solvent; thus, this method is complicated and requires a high cost. Under circumstances, it is desired to establish a method of biosynthesis of (all-E)-GGOH by controlling the generation of (E)- and (Z)-geometrical isomers or by utilizing characteristics such as the repeat structures of reaction products. However, such a method has not been established yet. The substrates for GGOH synthesis are provided via the mevalonate pathway in cells of, for example, budding yeast *Saccharomyces cerevisiae*. However, even when HMG-CoA reductase that is believed to be a key enzyme for GGOH synthesis was used, the use only increased the ability of squalene synthesis through FPP synthesis (Japanese Unexamined Patent Publication No. 5-192184; Donald et al., (1997) *Appl. Environ. Microbiol.* 63, 3341-3344). Further, even when a squalene synthase gene-deficient strain of a special budding yeast that had acquired sterol intake ability was cultured, accumulation of 1.3 mg of FOH per liter of culture broth was only revealed (Chambon et al., (1990) *Curr. Genet.* 18, 41-46); no method of biosynthesis of NOH has been known. With respect to the biosynthesis of GGOH, production of 0.66-3.25 mg per liter of culture broth is achieved by culturing plant cells in Japanese Unexamined Patent Publication No. 9-238692. However, this method needs an expensive plant cell culture medium inappropriate for industrial application and also requires light for culturing cells. Thus, this method is less practical even compared to the conventional GGOH preparation from natural products such as essential oils. There is known no method of biosynthesis of GGOH suitable for industrialization, e.g., biosynthesis by culturing microorganisms.

SUMMARY OF THE INVENTION

It is an object of the invention to provide a method of producing a prenyl alcohol by culturing a recombinant that has been transformed with a recombinant DNA for expression comprising a prenyl diphosphate synthase gene.

As a result of intensive and extensive researches toward solution of the above problem, the present inventors attempted to develop prenyl alcohol production systems by introducing genes of enzymes involved in prenyl diphosphate synthesis into hosts. As such hosts, those microorganisms which have been widely used in the fermentation industry from old times, which carry out the synthesis of prenyl diphosphate via the mevalonate pathway or DXP pathway, and which can be subjected to various genetic engineering techniques, e.g., unicellular eucaryotes (in particular yeast) or procaryotes (such as bacteria, in particular *E. coli*), were used. In order to construct systems with which genes of enzymes involved in prenyl diphosphate synthesis in yeast (e.g., genes of mevalonate pathway-related enzymes represented by HMG-CoA reductase gene, IPP Δ-isomerase gene, various prenyl diphosphate synthase genes, or mutants or fusion genes thereof) are expressed artificially in host cells, expression shuttle vectors were created which comprise a constitutive (permanent expression type) or inducible expression promoter and various auxotrophic markers. Then, a gene of interest or a mutant thereof was incorporated into the vector, which was then introduced into a host cell. The inventors have succeeded in obtaining prenyl alcohols (in particular geranylgeraniol) from the culture of the resultant recombinant, achieving the above-mentioned object. Thus, the present invention has been completed. When bacteria, in particular *E. coli*, were used as a host, a gene of an enzyme involved in prenyl diphosphate synthesis (e.g., a mutant of FPP synthase gene, or IPPΔ-isomerase gene) was introduced into the host cell using a conventional vector. The recombinant was cultured, and geranylgeraniol was obtained from the resultant culture after dephosphorylation. Thus, the above-mentioned object has been achieved, and the present invention has been completed.

The present invention is summarized as follows.

(1) A method of producing a prenyl alcohol (e.g., geranylgeraniol), comprising creating a recombinant by transferring into a host a recombinant DNA for expression or a DNA for genomic integration each comprising a prenyl diphosphate synthase gene or a mutant thereof, culturing the resultant recombinant, and recovering the prenyl alcohol from the resultant culture.

(2) A method of producing a prenyl alcohol, comprising creating a recombinant by transferring into a host a recombinant DNA for expression or a DNA for genomic integration each comprising a prenyl diphosphate synthase gene or a mutant thereof and a recombinant DNA for expression or a DNA for genomic integration each comprising a hydroxymethylglutaryl-CoA reductase gene or a mutant thereof, culturing the resultant recombinant, and recovering the prenyl alcohol from the resultant culture.

(3) A method of producing geranylgeraniol, comprising creating a recombinant by transferring into a host a recombinant DNA for expression or a DNA for genomic integration each comprising a prenyl diphosphate synthase gene or a mutant thereof and a recombinant DNA for expression or a DNA for genomic integration each comprising an isopentenyl diphosphate Δ-isomerase gene, culturing the resultant recombinant, and recovering geranylgeraniol from the resultant culture.

(4) The prenyl diphosphate synthase gene may be selected from the group consisting of the following genes (a) and (b) and fusion genes (c) and (d):
  (a) farnesyl diphosphate synthase gene or a mutant thereof
  (b) geranylgeranyl diphosphate synthase gene or a mutant thereof
  (c) a fusion gene composed of farnesyl diphosphate synthase gene or a mutant thereof and geranylgeranyl diphosphate synthase gene or a mutant thereof
  (d) the above gene (a) or (b) or the fusion gene (c) to which a nucleotide sequence encoding an amino acid sequence of His Asp Glu Leu is added.

Specific examples of farnesyl diphosphate synthase gene include a gene encoding the amino acid sequence as shown in SEQ ID NO: 2 or 4, and specific examples of geranylgeranyl diphosphate synthase gene include a gene encoding the amino acid sequence as shown in SEQ ID NO: 6.

(5) A method of producing geranylgeraniol, comprising creating a recombinant by transferring into a host a recombinant DNA for expression or a DNA for genomic integration each comprising a hydroxymethylglutaryl-CoA reductase gene or a mutant thereof, culturing the resultant recombinant, and recovering geranylgeraniol from the resultant culture.

(6) A method of producing geranylgeraniol, comprising creating a recombinant by transferring into a host a recombinant DNA for expression or a DNA for genomic integration each comprising a hydroxymethylglutaryl-CoA reductase gene or a mutant thereof and a recombinant DNA for expression or a DNA for genomic integration comprising a gene selected from the group consisting of the following (e) through (j):
  (e) isopentenyl diphosphate Δ-isomerase gene
  (f) mevalonate kinase gene
  (g) acetyl-CoA acetyltransferase gene
  (h) hydroxymethylglutaryl-CoA synthase gene
  (i) phosphomevalonate kinase gene
  (j) diphosphomevalonate decarboxylase gene;
culturing the resultant recombinant, and recovering geranylgeraniol from the resultant culture.

(7) According to the above-described methods, geranylgeraniol can be produced at a concentration of at least 0.05 mg/L. Specific examples of hosts useful in these methods include yeast (e.g., *Saccharomyces cerevisiae*) and *Escherichia coli*. Preferable *S. cerevisiae* strains useful in these methods include A451 strain, YPH499 strain, YPH500 strain, W303-1A strain and W303-1B strain, or strains derived from any one of these strains.

(8) A recombinant DNA for expression comprising any gene selected from the above-described group consisting of genes (a) and (b) and fusion genes (c) and (d), as well as a transcription promoter and a transcription terminator.

(9) The transcription promoter may be any one selected from the group consisting of ADH1 promoter, TDH3 (GAP) promoter, TEF2 promoter, GAL1 promoter and tac promoter; and the transcription terminator may be CYC1 terminator.

(10) A recombinant obtained by transferring the above-described recombinant DNA into a host. Specific examples of the host are as described above.

(11) A method of producing a prenyl alcohol, comprising culturing a microorganism having an ability to produce the prenyl alcohol using a medium comprising any one of the following components (i) through (vi):
  (i) sugar
  (ii) alcohol
  (iii) ammonia gas, aqueous ammonia and/or an ammonium salt
  (iv) a mixture of sodium hydroxide and sulfuric acid
  (v) a mixture of $KH_2PO_4$, magnesium sulfate, ammonium sulfate, corn steep liquor, calcium chloride and a surfactant
  (vi) a mixture of two or more of the above components (i) through (v);
and recovering the prenyl alcohol from the resultant culture.

In the method described in (11) above, the microorganism may be cultured using a feed solution comprising the following component (i), (ii) or (iii) or a mixture of two or more of these components:
  (i) sugar
  (ii) alcohol
  (iii) ammonia gas, aqueous ammonia and/or an ammonium salt.

The feed solution may have the component as described below and may be added to the medium in the following manner, for example.

Briefly, the carbon source component of the feed solution consists of glucose alone up to 12-24 hours after the start of cultivation, and then the carbon source component is shifted to a component containing ethanol. This shifting may be made in such a manner that the ratio of ethanol to the total carbon source component of the feed solution is 50% or more after 12-24 hours after the start of cultivation. Alternatively, the carbon source component of the feed solution may consist of ethanol alone after 12-24 hours after the start of cultivation.

The term "feed" means that a specific solution or components are supplied or added to a culture broth by any arbitrary method during cultivation. A cultivation method in which a specific component(s) is/are supplied or added to a fermenter is called "fed-batch culture".

The concentration of the prenyl alcohol accumulated in the culture is at least 0.1 g/L or more, preferably 1 g/L or more. As a specific example of the prenyl alcohol, geranylgeraniol may be given, and specific examples of the microorganism include yeast such as *Saccharomyces cerevisiae*. In the present invention, *Saccharomyces cerevisiae* A451 strain, YPH499 strain, YPH500 strain, W303-1A strain or W303-1B strain, or a strain derived from any one of these strains may be used.

Further, in the method described in (11) above, the microorganism is preferably a recombinant. As a specific example of such a recombinant, the following a) or b) may be given:

a) a recombinant created by transferring into a host a recombinant DNA for expression or a DNA for genomic integration each comprising a mevalonate pathway-related gene or a mutant thereof or a prenyl diphosphate synthase gene or a mutant thereof b) a recombinant created by transferring into a host a recombinant DNA for expression or a DNA for genomic integration each comprising a prenyl-phosphate synthase gene or a mutant thereof and a recombinant DNA for expression or a DNA for genomic integration each comprising a mevalonate pathway-related gene or a mutant thereof.

Specific examples of the host include *Saccharomyces cerevisiae*. More specifically, *Saccharomyces cerevisiae* A451 strain, YPH499 strain, YPH500 strain, W303-1A strain or W303-1B strain, or a strain derived from any one of these strains may be used.

As a specific example of the mevalonate pathway-related gene, hydroxymethylglutaryl-CoA reductase gene (e.g., HMG1 gene) may be given.

Specific examples of the prenyl diphosphate synthase gene include any gene selected from the group consisting of the following genes (a) and (b) and fusion genes (c) and (d):

(a) farnesyl diphosphate synthase gene or a mutant thereof (b) geranylgeranyl diphosphate synthase gene or a mutant thereof (c) a fusion gene composed of farnesyl diphosphate synthase gene or a mutant thereof and geranylgeranyl diphosphate synthase gene or a mutant thereof (d) the above gene (a) or (b) or the fusion gene (c) to which a nucleotide sequence encoding an amino acid sequence of His Asp Glu Leu is added.

Further, the microorganism useful in the present invention is a prototroph, a diploid cell, or a prototroph and, at the same time, a diploid cell.

Further, the present invention is characterized by controlling the pH of the medium. The pH control is carried out using, e.g., ammonium gas, an ammonium salt solution, a sodium hydroxide solution or sulfuric acid.

Hereinbelow, the present invention will be described in more detail. The present specification encompasses the contents disclosed in the specification and/or drawings of Japanese Patent Application No. 2000-403067 based on which the present application claims priority.

Using metabolic engineering techniques, the present inventors attempted to establish a system in which an active prenyl alcohol, in particular (all-E)-geranylgeraniol (hereinafter, referred to as "GGOH") is produced.

It is believed that GGOH is synthesized from geranylgeranyl diphosphate (GGPP) as a precursor. Generally, simply increasing GGPP synthase activity will only results in acceleration of the synthesis of GGPP from isopentenyl diphosphate (IPP) and 3,3-dimethylallyl pyrophosphate (DMAPP), and it is unpredictable that such increasing would result in production of GGOH (FIG. 1). Besides, GGPP in vivo is known only as a precursor for the synthesis of various final products such as carotenoids and prenylated proteins (FIG. 1). Thus, even when GGPP synthesis rate is increased, the level of those final products are expected to increase, but whether an industrially valuable GGPP synthesis system can be established or not is unpredictable. Even when the expression level of HMG-CoA reductase (a key enzyme in the mevalonate pathway) is increased by enhancing the enzyme activity of HMG-CoA reductase or the activities of the enzymes mentioned in (e) through (j) above, it is unpredictable which synthesis (i.e., FPP synthesis or GGPP synthesis) would be increased; thus, the increasing of the above expression level could not be expected to be effective for GGPP synthesis. Further, according to the information accumulated so far, it cannot be expected also that the expression of the gene of FPP synthase (which catalyzes the synthesis of farnesyl diphosphate (FPP), a precursor of FOH) would be effective for GGOH production (FIG. 1).

In the present invention, the inventors have developed mass production systems for prenyl alcohols, in particular GGOH, by constructing recombinant DNAs to introduce prenyl diphosphate synthase genes, HMG-CoA reductase gene and/or IPPΔ-isomerase gene into host cells, and creating recombinants with the DNAs.

1. Preparation of Recombinant DNAs for Expression or DNA Fragments for Genomic Integration In the present invention, one example of the recombinant DNA for expression that is used in the transformation of hosts may be obtained by ligating or inserting a transcription promoter DNA and a transcription terminator DNA into a gene prenyl diphosphate synthase gene. It is also possible to prepare in advance a gene expression cassette comprising a prenyl diphosphate synthase gene to which a transcription promoter and a transcription terminator have been ligated, and to incorporate the cassette into a vector. The ligation or insertion of the promoter and terminator may be performed in any arbitrary order, but it is preferable to ligate the promoter upstream of the prenyl diphosphate synthase gene and he terminator downstream of the gene. Alternatively, in the present invention, a prenyl diphosphate synthase gene, a transcription promoter and a transcription terminator may be incorporated successively into an appropriate DNA, e.g., a vector. If the direction of transcription is properly considered, the incorporation may be performed in any arbitrary order.

Specific examples of prenyl diphosphate synthase gene include farnesyl diphosphate synthase gene (called "FPP synthase gene") and geranylgeranyl diphosphate synthase gene (called "GGPP synthase gene"). Specific examples of FPP synthase gene include *Saccharomyces cerevisiae* ERG20 (SEQ ID NO: 1), *Escherichia coli* ispA (SEQ ID NO: 3) and *Bacillus stearothermophilus*-derived FPP synthase genes (Japanese Unexamined Patent Publication No. 5-219961; U.S. Pat. No. 5,786,192). Specific examples of GGPP synthase gene include *Saccharomyces cerevisiae* BTS1 (SEQ ID NO: 5), *Sulfolobus acidocaldarius* crtE (Japanese Unexamined Patent Publication No. 7-308913; U.S. Pat. No. 5,773, 273) and *Thermus thermophilus* Tth (Japanese Unexamined Patent Publication No. 9-107974; U.S. Pat. No. 6,107,072). These genes can be obtained by conventional gene isolation methods or by using commercial kits. In the present invention, it is also possible to use a mutant of FPP synthase gene or a mutant of GGPP synthase gene.

Further, in the present invention, a vector comprising a fusion gene composed of GGPP synthase gene or a mutant thereof and FPP synthase gene or a mutant thereof may be constructed so that the polypeptides produced by the expression of the GGPP synthase gene and the FPP synthase gene take a form of a fusion protein. In the present invention, such a gene constructed from two or more genes so that a fusion protein is produced as an expression product is called a "fusion gene". In order to prepare a fusion gene, such a method may be used in which one DNA is digested with an appropriate restriction enzyme, and then the other DNA pre-digested with the same restriction enzyme is ligated thereto in such a manner that the reading frame of the amino acid sequence of the protein encoded by the latter DNA is not shifted.

Further, in the present invention, for the purpose of adding an endoplasmic reticulum (ER) transition signal (an amino acid sequence represented by His Asp Glu Leu (SEQ ID NO: 24); hereinafter, referred to as "HDEL sequence") to the C-terminal of the protein produced by the expression of a prenyl diphosphate synthase gene or a mutant thereof or the above-described fusion gene, a nucleotide sequence encoding the amino acid sequence may be added to the prenyl diphosphate synthase gene or the fusion gene to thereby create a modified gene.

Further, in the present invention, it is also possible to produce prenyl alcohols (in particular GGOH) by transferring into a host a hydroxymethylglutaryl-CoA (HMG-CoA) reductase gene (SEQ ID NO: 7) or a mutant thereof alone or as a fusion gene with the above-mentioned prenyl diphosphate synthase gene (including a mutant thereof) and expressing the gene. Alternatively, it is also possible to transfer into a host both the prenyl diphosphate synthase gene or mutant thereof and the HMG-CoA reductase gene or mutant thereof and to co-express the two genes. Specific examples of HMG-CoA reductase gene include *Saccharomyces cerevisiae* HMG1 and HMG2.

The above-described mutants of prenyl diphosphate synthase genes and HMG-CoA reductase gene may be deletion mutant genes having a deletion of one part of region (e.g., deletion of 2217 nucleotides at the maximum for HMG-CoA reductase gene), or mutant genes having a deletion, substitution or addition of one or several to ten nucleotides in the nucleotide sequences of wild type genes or the above-mentioned deletion mutant genes. Accordingly, the amino acid sequence encoded by such a mutant gene may have a mutation(s). Specifically, the amino acid sequences of wild-type prenyl diphosphate synthases (FPP synthase: SEQ ID NO:2 or 4; GGPP synthase: SEQ ID NO: 6) or the amino acid sequence of wild-type MMG-CoA reductase (SEQ ID NO: 8) may have a mutation(s), such as deletion, substitution or addition of one or several (e.g., one to ten, preferably, one to three) amino acids. The amino acid sequence of wild-type HMG-CoA reductase (SEQ ID NO: 8) may have a deletion of 739 amino acids at the maximum, and such a deletion mutant type enzyme may further have a mutation(s), such as deletion, addition, substitution or insertion of one or several (e.g., one to ten, preferably, one to three) amino acids. Specifically, wild-type HMG-CoA reductase gene or its deletion mutants as illustrated in FIG. 2B may be used in the invention, and the amino acid sequences encoded by them may have one to ten site-specific substitutions as a result of nucleotide substitutions, such as shown in FIG. 2A. Further, when a wild-type prenyl diphosphate synthase gene (e.g., SEQ ID NO: 1, 3 or 5) or wild-type HMG-CoA reductase gene (SEQ ID NO: 7) is amplified by PCR (polymerase chain reaction), substitution mutations of nucleotides that occur in the resultant DNA fragments due to the low fidelity of a DNA polymerase, such as Taq DNA polymerase, are called "PCR errors". In the present invention, for example, an HMG-CoA reductase gene may also be used in which encoded polypeptide has substitution mutations attributable to nucleotide substitutions resulted from PCR errors when wild-type HMG-CoA reductase gene (SEQ ID NO: 7) was used as a template; this HMG-CoA reductase gene is designated "HMG1'". Embodiments of nucleotide substitutions resulted from PCR errors when wild-type HMG-CoA reductase gene (SEQ ID NO: 7) was used as a template are shown in FIG. 2A. HMG1' has the nucleotide sequence as shown in SEQ ID NO: 9, and the amino acid sequence encoded thereby is shown in SEQ ID NO: 10. In FIG. 2A, the mutations of nucleotides are expressed in the following order: the relevant nucleotide before substitution (in one letter code), the position of this nucleotide counted taking the first nucleotide in the initiation codon of the wild-type HMG-CoA reductase gene as 1, and the nucleotide after substitution (in one letter code). The mutations of amino acids contained in the amino acid sequence of the PCR error-type HMG-CoA reductase are expressed in the following order: the relevant amino acid before substitution (in one letter code), the position of this amino acid in the HMG-CoA reductase, and the amino acid after substitution (in one letter code). Further, the PCR error-type nucleotide sequence described above may be modified partially by techniques such as site-directed mutagenesis. Such a modified HMG-CoA reductase gene may also be used in the invention. Embodiments of nucleotide substitutions resulted from PCR errors are shown in FIG. 2A. Further, the above-described PCR error-type nucleotide sequence may be modified partially by techniques such as site-directed mutagenesis. A gene (SEQ ID NO: 11) encoding such a modified-type HMG-CoA reductase (SEQ ID NO: 12) may also be used in the invention.

Further, as examples of HMG-CoA reductase genes (including PCR error-type) encoding deletion mutants in which predicted transmembrane domains are deleted, HMG1Δ genes that are deletion mutants of the PCR error-type HMG-CoA reductase gene HMG1' are shown (FIG. 2B). The upper most row in this Figure represents HMG1' gene without deletion. The portion indicated with thin solid line (-) represents the deleted region. Table 1 below shows which region of HMG1' gene (SEQ ID NO: 9) has been deleted in each deletion mutant gene. HMG1' deletion mutant genes are expressed as "HMG1Δxxy" according to the deletion pattern, in which "xx" represents the deletion pattern and "y" a working number (any arbitrary number). In FIG. 2B, "Δ026" is shown as one example of HMG1Δ02y. (Examples of other deletion patterns are also shown in a similar manner.)

TABLE 1

Embodiments of Deletion

| Designation of Deletion Mutant | Primer 1 | Primer 2 | Plasmid | Deletion of Predicted Transmembrane Domain(s) | Deleted Regions | Sequence after Deletion |
|---|---|---|---|---|---|---|
| HMG1Δ02y | HMG1(558-532) | HMG1(799-825) | pYHMG02X | #2-#3 | Nucleotide Positions 559-798 | SEQ ID NO:13 |
| HMG1Δ04y | HMG1(1191-1165) | HMG1(1267-1293) | pYHMG04X | #6 | Nucleotide Positions 1192-1266 | SEQ ID NO:14 |
| HMG1Δ05y | HMG1(1380-1354) | HMG1(1573-1599) | pYHMG05X | #7 | Nucleotide Positions 1381-1572 | SEQ ID NO:15 |
| HMG1Δ06y | HMG1(558-532) | HMG1(1267-1293) | pYHMG06X | #2-#6 | Nucleotide Positions 559-1266 | SEQ ID NO:16 |
| HMG1Δ07y | HMG1(558-532) | HMG1(1573-1599) | pYHMG07X | #2-#7 | Nucleotide Positions 559-1572 | SEQ ID NO:17 |
| HMG1Δ08y | HMG1(27-1) | HMG1(1573-1599) | pYHMG08X | #1-#7 | Nucleotide Positions 27-1572 | SEQ ID NO:18 |
| HMG1Δ10y | HMG1(27-1) | HMG1(1816-1842) | pYHMG10X | #1-#7 (-605 aa) | Nucleotide Positions 27-1815 | SEQ ID NO:19 |
| HMG1Δ11y | HMG1(27-1) | HMG1(1891-1917) | pYHMG11X | #1-#7 (-631 aa) | Nucleotide Positions 27-1890 | SEQ ID NO:20 |
| HMG1Δ12y | HMG1(27-1) | HMG1(1990-2016) | pYHMG12X | #1-#7 (-663 aa) | Nucleotide Positions 27-1989 | SEQ ID NO:21 |
| HMG1Δ13y | HMG1(27-1) | HMG1(2218-2244) | pYHMG13X | #1-#7 (-739 aa) | Nucleotide Positions 27-2217 | SEQ ID NO:22 |

| | Primer Sequence | |
|---|---|---|
| HMG1(27-1) | 5' TTT CAG TCC CTT GAA TAG CGG CGG CAT 3' | SEQ ID NO:77 |
| HMG1(558-532) | 5' GTC TGC TTG GGT TAC ATT TTC TGA AAA 3' | SEQ ID NO:61 |
| HMG1(799-825) | 5' CAC AAA ATC AAG ATT GCC CAG TAT GCC 3' | SEQ ID NO:78 |
| HMG1(1191-1165) | 5' AGA AGA TAC GGA TTT CTT TTC TGC TTT 3' | SEQ ID NO:79 |
| HMG1(1267-1293) | 5' AAC TTT GGT GCA AAT TGG GTC AAT GAT 3' | SEQ ID NO:80 |
| HMG1(1380-1354) | 5' TTG CTC TTT AAA GTT TTC AGA GGC ATT 3' | SEQ ID NO:81 |
| HMG1(1573-1599) | 5' CAT ACC AGT TAT ACT GCA GAC CAA TTG 3' | SEQ ID NO:62 |
| HMG1(1816-1842) | 5' GCA TTA TTA AGT AGT GGA AAT ACA AAA 3' | SEQ ID NO:82 |
| HMG1(1891-1917) | 5' CCT TTG TAC GCT TTG GAG AAA AAA TTA 3' | SEQ ID NO:83 |
| HMG1(1990-2016) | 5' TCT GAT CGT TTA CCA TAT AAA AAT TAT 3' | SEQ ID NO:84 |
| HMG1(2218-2244) | 5' AAG GAT GGT ATG ACA AGA GGC CCA GTA 3' | SEQ ID NO:85 |

Further, in the present invention, it is also possible to produce prenyl alcohols, in particular GGOH, by transferring into a host an isopentenyl diphosphate Δ-isomerase (IPP Δ-isomerase) gene together with the above-described prenyl diphosphate synthase gene or mutant thereof. Specific examples of IPP Δ-isomerase gene include *E coli*-derived idi (SEQ ID NO: 32). Specific examples of prenyl diphosphate synthase genes include *E coli*-derived ispAm mutant genes (Y79M: SEQ ID NO: 37; Y79E: SEQ ID NO: 35; Y79D: SEQ ID NO: 33) and *Bacillus stearothermophilus*-derived fpsm (Y81M: SEQ ID NO: 39). Mutant genes derived from this ispA encode mutant enzymes in which the amino acid residue Tyr at position 79 of wild-type FPP synthase (SEQ ID NO: 4) is changed to Asp (SEQ ID NO: 34), Glu (SEQ ID NO: 36) or Met (SEQ ID NO: 38) by substitution mutation.

The DNA used in the invention is not particularly limited as long as it may be retained in host cells hereditarily. Specific examples of DNA that may be used include plasmid DNA, bacteriophage, retrotransposon DNA, yeast artificial chromosomal DNA (YAC: yeast artificial chromosome), etc. With respect to DNA fragments for genomic integration, these fragments do not need replication ability. Thus, DNA fragments prepared by PCR or chemical synthesis may be used.

Specific examples of useful plasmid DNA include YCp-type *E. coli*-yeast shuttle vectors such as pRS413, pRS414, pRS415, pRS416, YCp50, pAUR112 or pAUR123; YEp-type *E. coli*-yeast shuttle vectors such as pYES2 or YEp13; YIp-type *E. coli*-yeast shuttle vectors such as pRS403, pRS404, pRS405, pRS406, pAUR101 or pAUR135; *E. coli*-derived plasmids (e.g., ColE plasmids such as pBR322, pBR325, pUC18, pUC19, pUC118, pUC119, pTV118N, pTV119N, pBluescript, pHSG298, pHSG396 or pTrc99A; p15A plasmids such as pACYC177 or pACYC184; and pSC101 plasmids such as pMW118, pMW119, pMW218 or pMW219) and *Bacillus subtilis*-derived plasmids (e.g., pUB110, pTP5). Specific examples of useful phage DNA include λ phage (Charon4A, Charon21A, EMBL3, EMBL4, λgt10, λgt11, λZAP), φX174, M13mp18 and M13mp19. Specific examples of useful retrotransposon include Ty factor. Specific examples of YAC vectors include pYACC2.

When recombinant DNAs are transferred into hosts, selectable marker genes are used in many cases. However, the use of marker genes are not necessarily required if there is an appropriate assay method.

As the transcription promoter, a constitutive (permanent expression type) promoter or an inducible promoter may be used. The term "constitutive promoter" means a transcription promoter of a gene involved in a major metabolic pathway. Such a promoter has transcription activity under any growth conditions. The "inducible promoter" means a promoter that has transcription activity only under specific growth conditions and whose activity is repressed under other growth conditions.

Any transcription promoter may be used as long as it has activity in hosts such as yeast. For example, GAL1 promoter, GAL10 promoter, TDH3 (GAP) promoter, ADH1 promoter, TEF2 promoter or the like may be used for expression in yeast. For expression in *E. coli*, trp promoter, lac promoter, trc promoter, tac promoter or the like may be used.

Further, the recombinant DNA may comprise cis-elements such as an enhancer, a splicing signal, a poly A addition signal, selectable markers, etc., if desired. Specific examples of useful selectable markers include marker genes such as URA3, LEU2, TRP1 and HIS3 whose indicators are non-auxotrophic phenotypes, and antibiotic resistance genes such as Amp$^r$, Tet$^r$, Cm$^r$, Km$^r$ and AUR1-C.

A transcription terminator derived from any gene may be used as long as it has activity in hosts such as yeast. For expression in yeast, ADH1 terminator, CYC1 terminator or the like may be used. For expression in *E. coli*, rrnB terminator may be used, for example. In order to express a gene of interest in bacterial cells, an SD sequence (typically, 5'-AGGAGG-3') may also be incorporated upstream of the initiation codon of the gene as a ribosome binding site for effective translation.

The expression vectors prepared in the present invention as recombinant DNAs for gene transfer may be designated and identified by indicating the name of the relevant gene after the name of the plasmid used. Table 2 shows relations between the designations of expression vectors and their constitutions when pRS435GAP was used as a plasmid. When pRS434, pRS444 and pRS445 plasmids were used in combination with the above-mentioned promoters, such relations may be described in the same manner as used for pRS435GAP.

TABLE 2

| Designation of Expression Vector | Constitution |
| --- | --- |
| pRS435GG | Plasmid pRS435GAP to which GGPP synthase gene BTS1 is ligated |
| pRS435F | Plasmid pRS435GAP to which FPP synthase gene ERG20 is ligated |
| pRS435GGF | Plasmid pRS435GAP to which a fusion gene where GGPP synthase gene BTS1 and FPP synthase gene ERG20 were ligated in this order is ligated |
| pRS435FGG | Plasmid pRS435GAP to which a fusion gene where FPP synthase gene ERG20 and GGPP synthase gene BTS1 were ligated in this order is ligated |
| pRS435GGHDEL | pRS435GG to which a nucleotide sequence encoding HDEL sequence is ligated |
| pRS435FHDEL | pRS435F to which a nucleotide sequence encoding HDEL sequence is ligated |
| pRS435FGGHDEL | pRS435FGG to which a nucleotide sequence encoding HDEL sequence is ligated |
| pRS435GGFHDEL | pRS435GGF to which a nucleotide sequence encoding HDEL sequence is ligated |

When HMG1 gene is ligated to plasmid pRS434GAP, the resultant vector is expressed as "pRS434GAP-HMG1". Table 3 shows relations between the designations of expression vectors and their constitutions when pRS434GAP was used as a plasmid. When the plasmid was pRS435GAP, pRS445GAP or the like, such relations may be described in the same manner as used for pRS434GAP.

TABLE 3

| Designation of Expression Vector | Constitution |
| --- | --- |
| pRS434GAP-HMG1 | Plasmid pRS434GAP to which HMG-CoA reductase gene HMG1 is ligated |
| pRS434GAP-HMG1Δ | Plasmid pRS434GAP to which deletion mutant gene HMG1Δ of HMG-CoA reductase gene HMG1 is ligated |

2. Preparation of Recombinants

The recombinants of the invention can be obtained by transferring into hosts the recombinant DNAs of the invention in such a manner that various prenyl diphosphate synthase genes or fusion genes thereof, and/or HMG-CoA reductase gene (including mutants of these genes; the same applies to the rest of the present specification unless otherwise noted), or IPP Δ-isomerase gene can be expressed. The host used in the invention is not particularly limited. Any host may be used as long as it can produce a prenyl alcohol(s). Preferably, yeast or *E. coli* is used.

In the present invention, the recombinant DNA comprising a transcription promoter and a transcription terminator, as well as a prenyl diphosphate synthase gene, HMG-CoA reductase gene, IPP A-isomerase gene or one of the genes listed in (e) through (j) above may be introduced into fungi including unicellular eucaryotes such as yeast; procaryotes; animal cells; plant cells; etc. to obtain recombinants.

Fungi useful in the invention include Myxomycota, Phycomycetes, Ascomycota, Basidiomycota, and Fungi Imperfecti. Among fungi, some unicellular eucaryotes are well known as yeast that is important in industrial applicability. For example, yeast belonging to Ascomycota, yeast belonging to Basidiomycota, or yeast belonging to Fungi Imperfecti may be enumerated. Specific examples of yeast useful in the invention include yeast belonging to Ascomycota, in particular, budding yeast such as *Saccharomyces cerevisiae* (known as Baker's yeast), *Candida utilis* or *Pichia pastris*; and fission yeast such as *Shizosaccharomyces pombe*. The yeast strain useful in the invention is not particularly limited as long as it can produce a prenyl alcohol(s). In the case of *S. cerevisiae*, specific examples of useful strains include A451, EUG5, EUG8, EUG12, EUG27, YPH499, YPH500, W303-1A, W303-1B, ATCC28382, AURGG101, AURGG102, AH1 and YH1 as shown below. As a method for transferring the recombinant DNA into yeast, such method as electroporation, the spheroplast method, or the lithium acetate method may be employed.

A451 (ATCC200589, MATα can1 leu2 trp1 ura3 aro7)

YPH499 (ATCC76625, MATa ura3-52 lys2-801 ade2-101 trp1-Δ63 his3-Δ200 leu2-Δ1, Stratagene, La Jolla, Calif.)

YPH500 (ATCC76626, MATα ura3-52 lys2-801 ade2-101 trp1-Δ63 his3-Δ200 leu2-Δ1, Stratagene)

W303-1A (MATa leu2-3 leu2-112 his3-11 ade2-1 ura3-1 trp1 can1-100)

W303-1B (MATα leu2-3 leu2-112 his3-11 ade2-1 ura3-1 trp1-1 can1-100)

AURGG101 (A451, aur1::AUR1-C): A451-derived strain established in the invention; integrating AUR1-C gene.

AURGG102 (A451, aur1::GAL1p-BTS1&AUR1-C): A451-derived strain established in the present invention; comprising GAL1 promoter, BTS1 and CYC1 terminator together with AUR1-C gene in AUR1 locus.

EUG5, EUG8 (A451, ERG9p::URA3-GAL1p): A451-derived strains established in the present invention; comprising squalene synthase gene ERG9, transformant selection marker gene URA3 and transcription promoter GAL1p.

EUG12 (YPH499, ERG9p::URA3-GAL1p): YPH499-derived strain established in the present invention; comprising ERG9, URA3 and GAL1p.

EUG27 (YPH500, ERG9p::URA3-GAL1p): YPH500-derived strain established in the present invention; comprising ERG9, URA3 and GAL1p.

AH1 strain (pRS434GAP-HMG1/A451): A451-derived strain established in the present invention; pRS434GAP-HMG1 is transferred into A451.

YH1 strain (pRS434GAP-HMG1/YPH499): YPH499-derived strain established in the present invention; pRS434GAP-HMG1 is transferred into YPH499.

Procaryotes useful in the invention include archaea and bacteria. As archaea, methane producing microorganisms such as *Metanobacterium*; halophilic microorganisms such as *Halobacterium*, and thermophilic acidophilic microorganisms such as *Sulfolobus* may be enumerated. As bacteria, various Gram-negative or Gram-positive bacteria that are highly valuable in industrial or scientific applicability may be enumerated, e.g., *Escherichia* such as *E. coli*, *Bacillus* such as *B. subtilis* or *B. brevis*, *Pseudomonas* such as *P. putida*, *Agrobacterium* such as *A. tumefaciens* or *A. rhizogenes*, *Corynebacterium* such as *C. glutamicum*, *Lactobacillus* such as *L. plantarum*, and *Actinomycetes* such as *Actinomyces* or *Streptmyces*.

When a bacterium such as *E. coli* is used as a host, preferably, the recombinant DNA of the invention is not only capable of autonomous replication in the host but also composed of a transcription promoter, an SD sequence as ribosome RNA binding site, and the gene of the invention. A transcription terminator may also be inserted appropriately into the recombinant DNA. The DNA may also contain a gene that controls the promoter. Specific examples of *E. coli* strains useful in the invention include, but are not limited to, BL21, DH5α, HB101, JM101, JM109, MV1184, TH2, XL1-Blue and Y-1088. As the transcription promoter, any promoter may be used as long as it can direct the expression of the gene of the invention in a host such as *E. coli*. For example, an *E. coli*- or phage-derived promoter such as trp promoter, lac promoter, $P_L$ promoter or $P_R$ promoter may be used. A promoter whose design is artificially altered may also be used. As a method for introducing the recombinant vector into a bacterium, any method of DNA transfer into bacteria may be used. For example, a method using calcium ions, electroporation, etc. may be used.

Whether the gene of the invention has been introduced into the host cell or not can be confirmed by such methods as PCR (polymerase chain reaction) or Southern blot hybridization. For example, DNA is prepared from the resultant recombinant and subjected to PCR using a pair of primers specific to the transferred DNA. Subsequently, the amplified product is subjected to agarose gel electrophoresis, polyacrylamide gel electrophoresis or capillary electrophoresis, followed by staining with ethidium bromide, SYBR Green solution or the like, or detection of DNA with a UV detector. By detecting the amplified product as a single band or peak, the transferred DNA can be confirmed. Alternatively, PCR may be performed using primers labeled with a fluorescent dye or the like to thereby detect the amplified product.

3. Production of Prenyl Alcohols

In the present invention, a prenyl alcohol(s) can be obtained by culturing the above-described recombinant comprising a prenyl diphosphate synthase gene or a mutant thereof (including a fusion gene), and/or an HMG-CoA reductase gene or a mutant thereof, or a mevalonate pathway-related enzyme gene selected from the above-described (e) through (j) transferred thereinto, and recovering the prenyl alcohol(s) from the resultant culture. The term "culture" used herein means any of the following materials: culture supernatant, cultured cells or microorganisms per se, or disrupted products from cultured cells or microorganisms. The recombinant of the invention is cultured by conventional methods used in the cultivation of its host. As a specific example of the prenyl alcohol, GGOH may be given. These prenyl alcohols are accumulated in culture independently or as a mixture.

As a medium to culture the recombinant obtained from a microorganism host, either a natural or synthetic medium may be used as long as it contains carbon sources, nitrogen sources and inorganic salts assimilable by the microorganism and is capable of effective cultivation of the recombinant. As carbon sources, carbohydrates such as glucose, galactose, fructose, sucrose, raffinose, starch; organic acids such as acetic acid, propionic acid; and alcohols such as ethanol and propanol may be enumerated. As nitrogen sources, ammonia;

ammonium salts of inorganic or organic acids such as ammonium chloride, ammonium sulfate, ammonium acetate, ammonium phosphate; other nitrogen-containing compounds; Peptone; meat extract; corn steep liquor, various amino acids, etc. may be enumerated. As inorganic substances, potassium dihydrogen phosphate, dipotassium hydrogen phosphate, magnesium phosphate, magnesium sulfate, sodium chloride, iron(II) sulfate, manganese sulfate, copper sulfate, calcium carbonate, etc. may be enumerated. Usually, the recombinant is cultured under aerobic conditions (such as shaking culture or aeration agitation culture) at 26 to 42° C. Preferably, when the host is *S. cerevisiae*, the recombinant is cultured at 30° C. for 2 to 7 days; when the host is *E. coli*, the recombinant is cultured at 37° C. for 12 to 18 hours. The adjustment of pH is carried out using an inorganic or organic acid, an alkali solution, etc.

When a recombinant integrating an expression vector containing an inducible transcription promoter is cultured, an inducer may be added to the medium if necessary. For example, when GAL1 promoter was used in the vector, galactose may be used as a carbon source. When a microorganism (*E. coli*) transformed with an expression vector containing a promoter inducible by isopropyl-β-D-thiogalactopyranoside (IPTG) is cultured, IPTG may be added to the medium.

When cultured under the above-described conditions, the host can produce a prenyl alcohol(s) at a high yield(s). For mass-production of prenyl alcohols, a jar fermenter culture apparatus may be employed. In particular, when the host is *S. cerevisiae* YPH499 and the transferred plasmid DNA is pRS435GGF or pRS434GAP-HMG1, the recombinant can produce 1.5 mg or more of a prenyl alcohol per liter of the medium; depending on culture conditions, the recombinant can produce 128 mg or even more.

In the present invention, it is possible to increase the production efficiency of prenyl alcohols by adding to the above-described medium such substances as terpenoids, oils, or surfactants. Specific examples of these additives include the following.

Terpenoids: squalene, tocopherol, IPP, DMAPP

Oils: soybean oil, fish oil, almond oil, olive oil

Surfactants: Tergitol, Triton X-305, Span 85, ADEKANOL LG109 (Asahi Denka), ADEKANOL LG294 (Asahi Denka), ADEKANOL LG295S (Asahi Denka), ADEKANOL LG297 (Asahi Denka), ADEKANOL B-3009A (Asahi Denka), ADEKA PLURONIC L-61 (Asahi Denka)

The concentration of oils is 0.01% or more, preferably 1-3%. The concentration of surfactants is 0.005-1%, preferably 0.05-0.5%. The concentration of terpenoids is 0.01% or more, preferably 1-3%.

Further, in the present invention, it is also possible to culture a microorganism having an ability to produce a prenyl alcohol using a medium comprising any one of the components (i) through (vi) described below and recovering the prenyl alcohol from the resultant culture. Further, fed-batch culture may be conducted using a feed solution comprising any one of the components (i) through (v) described below.

(i) sugar (ii) alcohol (iii) ammonia gas, aqueous ammonia and/or an ammonium salt (iv) a mixture of sodium hydroxide and sulfuric acid (v) a mixture of $KH_2PO_4$, magnesium sulfate, ammonium sulfate, corn steep liquor, calcium chloride and a surfactant (vi) a mixture of two or more of the above components (i) through (v).

Specific examples of the above sugar include glucose, sucrose, galactose and lactose. Specific examples of the above alcohol include methanol, ethanol, propanol, isopropanol and butanol.

As carbon source components in the feed solution, a combination of glucose and ethanol is preferable, and it is more preferable to add to the medium ammonia gas or an ammonium salt (e.g., ammonium acetate) for pH control. As a method of adding a feed solution, it is preferable to use a feed solution whose carbon source is glucose alone up to 12-24 hours after the start of the cultivation and then to shift to another feed solution containing ethanol in its carbon source component. Alternatively, glucose may remain the sole carbon source throughout the cultivation. The ratio of ethanol to the total carbon source of the feed solution may be any ratio. The ratio may be 50% or more, or even 100%.

Strains that are able to propagate without supplementation of specific nutrients to the medium are called prototrophs. Generally, a prototroph is a strain that has the same phenotype as that of its corresponding wild-type strain in nutritional requirements. On the other hand, auxotrophs (auxotrophic mutant strains) are frequently used as host strains for creating recombinants. The phenotype of such an auxotroph may be changed to the same phenotype as that of the corresponding prototroph by complementing the auxotrophic mutation. Briefly, a wild-type gene corresponding to the mutant gene causing the auxotrophic mutation is transferred into the auxotroph. When the wild-type gene is dominant to the mutant gene causing the auxotrophic mutation, it is also possible to complement the mutation by mating or conjugating the auxotroph with a strain having the wild-type gene. In the present invention, a prototroph can be obtained, for example, by replacing some of the mutant genes causing nutritional requirements in the genome of a GGOH producing clone (YH1 strain comprising a fusion gene composed of GGPP synthase gene and FPP synthase gene) with corresponding wild-type genes, and then mating the resultant clone with a YPH500-derived clone that has dominant wild-type genes to the remaining mutant genes. In the present invention, it is preferable to use a microorganism that is a diploid cell and, at the same time, a prototroph.

After the cultivation, the prenyl alcohol of interest is recovered by disrupting microorganisms or cells by, e.g., homogenizer treatment, if the alcohol is produced within the microorganisms or cells. Alternatively, the alcohol may be extracted directly using organic solvents without disrupting the cells. If the prenyl alcohol of the invention is produced outside the microorganisms or cells, the culture broth is used as it is or subjected to centrifugation, etc. to remove the microorganisms or cells. Thereafter, the prenyl alcohol of interest is extracted from the culture by, e.g., extraction with an organic solvent. If necessary, the prenyl alcohol may be further isolated and purified by various types of chromatography or the like.

In the present invention, preferable combinations of host strains and vectors, as well as relationships between these combinations and yields of prenyl alcohols are as illustrated in Table 4 below.

TABLE 4

|  | Promoter | Gene | Host | Reagent added | GGOH Yield (mg/l) 1 | GGOH Yield (mg/l) 2 | GGOH Yield (mg/l) 3 |
| --- | --- | --- | --- | --- | --- | --- | --- |
| hosts | — | — | Sc A451 | — | (0.00-0.02) |  |  |
|  | — | — | AURGG101 | — | (0.00-0.02) |  |  |
|  | — | — | Sc YPH499 | — | (0.00) |  |  |
|  | — | — | Ec JM109 | — | (0.00) |  |  |
| HMG1 | GAP | HMG1 | Sc A451 | — | 0.07 | 0.07-0.35 | — |
|  | ADH1 | HMG1 | Sc A451 | — | 0.05 | 0.05-0.14 | — |
|  | GAL1 | HMG1 | Sc A451 | — | 0.05 | 0.05-0.1 | — |
|  | GAL1 | HMG1 | Sc AURGG101 | — | 0.05 | 0.05-2.2 | — |
|  | GAP | HMG1 | Sc EUG8 | — | 0.05 | 0.05-0.16 | — |
|  | GAP | HMG1 | Sc EUG12 | — | 0.05 | 0.05-1.03 | — |
|  | GAP | HMG1 | Sc EUG27 | — | 0.05 | 0.05-0.63 | — |
| HMG1Δ | GAL1 | HMG1Δ044 | Sc A451 | — | 0.05 | — | — |
|  | GAL1 | HMG1Δ056 | Sc A451 | — | 0.05 | 0.05-0.07 | — |
|  | GAL1 | HMG1Δ062 | Sc A451 | — | 0.05 | 0.05-0.07 | — |
|  | GAL1 | HMG1Δ078 | Sc A451 | — | 0.05 | — | — |
|  | GAL1 | HMG1Δ081 | Sc A451 | — | 0.05 | — | — |
|  | GAL1 | HMG1Δ112 | Sc A451 | — | 0.05 | 0.05-0.06 | — |
|  | GAL1 | HMG1Δ122 | Sc A451 | — | 0.05 | 0.05-0.06 | — |
|  | GAL1 | HMG1Δ044 | Sc AURGG101 | — | 0.05 | 0.05-2.2 | 2.2-7.9 |
|  | GAL1 | HMG1Δ062 | Sc AURGG101 | — | 0.05 | 0.05-0.06 | — |
|  | GAL1 | HMG1Δ075 | Sc AURGG101 | — | 0.05 | 0.05-0.06 | — |
|  | GAL1 | HMG1Δ081 | Sc AURGG101 | — | 0.05 | — | — |
|  | GAP | HMGΔ044 | Sc EUG5 | — | 0.05 | 0.05-0.09 | — |
|  | GAP | HMGΔ056 | Sc EUG5 | — | 0.05 | 0.05-0.11 | — |
|  | GAP | HMGΔ062 | Sc EUG5 | — | 0.05 | 0.05-0.13 | — |
|  | GAP | HMGΔ076 | Sc EUG5 | — | 0.05 | 0.05-0.15 | — |
|  | GAP | HMGΔ081 | Sc EUG5 | — | 0.05 | 0.05-0.14 | — |
|  | GAP | HMGΔ100 | Sc EUG5 | — | 0.05 | 0.05-0.18 | — |
|  | GAP | HMGΔ112 | Sc EUG5 | — | 0.05 | 0.05-0.34 | — |
|  | GAP | HMGΔ122 | Sc EUG5 | — | 0.05 | 0.05-0.13 | — |
|  | GAP | HMGΔ133 | Sc EUG5 | — | 0.05 | 0.05-0.71 | — |
|  | GAP | HMGΔ026 | Sc EUG12 | — | 0.05 | 0.05-0.63 | — |
|  | GAP | HMGΔ044 | Sc EUG12 | — | 0.05 | 0.05-0.44 | — |
|  | GAP | HMGΔ056 | Sc EUG12 | — | 0.05 | 0.05-0.40 | — |
|  | GAP | HMGΔ062 | Sc EUG12 | — | 0.05 | 0.05-0.45 | — |
|  | GAP | HMGΔ076 | Sc EUG12 | — | 0.05 | 0.05-0.55 | — |
|  | GAP | HMGΔ081 | Sc EUG12 | — | 0.05 | 0.05-0.49 | — |
|  | GAP | HMGΔ100 | Sc EUG12 | — | 0.05 | 0.05-0.44 | — |
|  | GAP | HMGΔ112 | Sc EUG12 | — | 0.05 | 0.05-0.53 | — |
|  | GAP | HMGΔ122 | Sc EUG12 | — | 0.05 | 0.05-0.50 | — |
|  | GAP | HMGΔ133 | Sc EUG12 | — | 0.05 | 0.05-0.44 | — |
| HMG1 + HMG1Δ | GAL1, GAP | HMG1Δ044, HMG1 | Sc AURGG101 | — | 0.27 | 0.27-0.93 | — |
| FPS gene | GAP | ERG20 | Sc A451 | — | 0.05 | 0.05-0.07 | — |
|  | lac | fpsm | Ec JM109 | IPP&DMAPP | 6.9 | 6.9-16 | — |
|  | tac | ispAm(Y79D) | Ec JM109 | IPP&DMAPP | 0.06 | 0.06-0.12 | — |
|  | tac | ispAm(Y79E) | Ec JM109 | IPP&DMAPP | 0.14 | 0.14-0.26 | — |
|  | tac | ispAm | Ec JM109 | IPP&DMAPP | 6.0 | 6.0-22 | — |
| BTS1 (YIp) | GAL1 | BTS1 integrated | Sc A451 (AURGG102) | — | 0.05 | 0.05-0.07 | — |
|  | GAL1 | BTS1 integrated | Sc YPH499 (AURGG703) | — | 0.05 | 0.05-0.07 | — |
| BTS1 (YEp) | GAP | BTS1 | Sc A451 | — | 0.10 | 0.10-0.58 | — |
|  | GAP | BTS1 | Sc YPH499 | — | 0.05 | 0.05-0.15 | — |
|  | GAP | BTS1 | Sc EUG8 | — | 0.05 | 0.05-1.4 | — |
|  | GAP | BTS1 | Sc EUG12 | — | 0.05 | 0.05-1.6 | — |
|  | GAP | BTS1 | Sc EUG27 | — | 0.05 | 0.05-1.5 | — |
| HMG1Δ + FPS gene | GAL1, GAP | HMG1Δ044, ERG20 | Sc AURGG101 | — | 0.38 | 0.38-11.3 | — |
|  | GAL1, GAP | HMG1Δ044, ispA | Sc AURGG101 | — | 0.11 | 0.11-1.64 | — |
| HMG1 + BTS1 (YEp) | GAP, GAP | HMG1, BTS1 | Sc A451 | — | 0.14 | 0.14-0.58 | — |
|  | TEF, GAP | HMG1, BTS1 | Sc YPH499 | — | 0.13 | 0.13-0.63 | — |
| HMG1 + BTS1 (YIp) | GAP, GAL1 | HMG1, BTS1 | Sc AURGG102 | — | 0.05 | 0.05-1.3 | — |
|  | GAP, GAL1 | HMG1, BTS1 | Sc AURGG703 | — | 0.05 | 0.05-0.46 | — |
| HMG1Δ + BTS1 (YEp) | GAL1, GAP | HMG1Δ044, BTS1 | Sc AURGG101 | — | 0.46 | 0.46-9.8 | — |
|  | GAP, GAL1 | HMG1Δ027, BTS1 integrated | Sc AURGG102 | — | 0.05 | 0.05-0.08 | — |
|  | GAP, GAL1 | HMG1Δ044, BTS1 integrated | Sc AURGG102 | — | 0.05 | 0.05-0.42 | — |
|  | GAP, GAL1 | HMG1Δ045, BTS1 integrated | Sc AURGG102 | — | 0.05 | 0.05-0.61 | — |
|  | GAP, GAL1 | HMG1Δ059, BTS1 integrated | Sc AURGG102 | — | 0.05 | 0.05-0.10 | — |
|  | GAP, GAL1 | HMG1Δ062, BTS1 integrated | Sc AURGG102 | — | 0.05 | 0.05-0.42 | — |
|  | GAP, GAL1 | HMG1Δ063, BTS1 integrated | Sc AURGG102 | — | 0.05 | 0.05-0.11 | — |
|  | GAP, GAL1 | HMG1Δ075, BTS1 integrated | Sc AURGG102 | — | 0.05 | 0.05-0.40 | — |
|  | GAP, GAL1 | HMG1Δ083, BTS1 integrated | Sc AURGG102 | — | 0.05 | 0.05-0.21 | — |
|  | GAP, GAL1 | HMG1Δ094, BTS1 integrated | Sc AURGG102 | — | 0.05 | 0.05-0.14 | — |
|  | GAP, GAL1 | HMG1Δ106, BTS1 integrated | Sc AURGG102 | — | 0.05 | 0.05-0.12 | — |
|  | GAP, GAL1 | HMG1Δ122, BTS1 integrated | Sc AURGG102 | — | 0.05 | 0.05-0.16 | — |
|  | GAP, GAL1 | HMG1Δ123, BTS1 integrated | Sc AURGG102 | — | 0.05 | 0.05-0.09 | — |

TABLE 4-continued

| | Promoter | Gene | Host | Reagent added | GGOH Yield (mg/l) 1 | GGOH Yield (mg/l) 2 | GGOH Yield (mg/l) 3 |
|---|---|---|---|---|---|---|---|
| | GAP, GAL1 | HMG1Δ134, BTS1 integrated | Sc AURGG102 | — | 0.05 | 0.05-0.11 | — |
| | GAP, GAL1 | HMG1Δ044, BTS1 integrated | Sc AURGG703 | — | 0.12 | 0.12-0.20 | — |
| | GAP, GAL1 | HMG1Δ062, BTS1 integrated | Sc AURGG703 | — | 0.16 | 0.16-0.24 | — |
| HMG1Δ + MVN genes | GAL1, GAP | HMG1Δ044, HMGS | Sc AURGG101 | — | 0.20 | 0.20-1.3 | — |
| | GAL1, GAP | HMG1Δ044, ERG12 | Sc AURGG101 | — | 0.21 | 0.21-1.0 | — |
| | GAL1, GAP | HMG1Δ044, ERG8 | Sc AURGG101 | — | 0.12 | 0.12-2.7 | — |
| | GAL1, GAP | HMG1Δ044, ERG10 | Sc AURGG101 | — | 0.17 | 0.17-1.22 | — |
| | GAL1, GAP | HMG1Δ044, ERG19 | Sc AURGG101 | — | 0.05 | 0.05-1.89 | — |
| | GAL1, GAP | HMG1Δ044, IDI1 | Sc AURGG101 | — | 0.05 | 0.05-0.79 | — |
| | GAL1, GAP | HMG1Δ044, idi | Sc AURGG101 | — | 0.43 | 0.43-1.2 | — |
| FPS gene + idi | tac, idi | ispAm, idi | Ec JM109 | — | 0.07 | — | — |
| FGG fusion | GAP | ERG20-BTS1 | Sc YPH499 | — | 0.06 | 0.06-0.27 | — |
| | GAP | ERG20-BTS1-HDEL | Sc YPH499 | — | 0.05 | 0.05-0.12 | — |
| GGF fusion | GAP | BTS1-ERG20 | Sc A451 | — | 0.05 | 0.05-0.35 | 0.46-0.98 |
| | GAP | BTS1-ERG20 | Sc YPH499 | — | 0.17 | 0.17-0.46 | 1.3-2.5 |
| | GAP | BTS1-ERG20 | Sc EUG5 | — | 0.05 | 0.05-2.9 | 5.1-6.6 |
| | GAP | BTS1-ERG20 | Sc EUG12 | — | 0.07 | 0.07-5.4 | 2.0-3.8 |
| | GAP | BTS1-ERG20-HDEL | Sc A451 | — | 0.05 | 0.05-0.07 | 0.07-0.56 |
| | GAP | BTS1-ERG20-HDEL | Sc YPH499 | — | 0.44 | 0.44-0.80 | 1.6-1.9 |
| | GAP | BTS1-ERG20-HDEL | Sc EUG5 | — | 0.21 | 0.21-0.35 | 5.5-6.5 |
| | GAP | BTS1-ERG20-HDEL | Sc EUG12 | — | 1.3 | 1.3-5.6 | — |
| HMG1 + BTSHDEL | GAP, GAP | HMG1, BTS1-HDEL | Sc YPH499 | — | 0.14 | 0.14-0.23 | — |
| HMG1 + FGG fusion | GAP, GAP | HMG1, ERG20-BTS | Sc YPH499 | — | 0.20 | 0.20-0.46 | — |
| | GAP, GAP | HMG1, ERG20-BTS1-HDEL | Sc YPH499 | — | 0.11 | 0.11-0.29 | — |
| HMG1 + GGF fusion | GAP, GAP | HMG1, BTS1-ERG20 | Sc A451 | — | 0.05 | 0.05-4.1 | — |
| | GAP, GAP | HMG1, BTS1-ERG20 | Sc YPH499 | — | 0.46 | 0.46-2.1 | 2.1-128 |
| | GAP, GAP | HMG1, BTS1-ERG20-HDEL | Sc A451 | — | 0.05 | 0.05-5.1 | — |
| | GAP, GAP | HMG1, BTS1-ERG20-HDEL | Sc YPH499 | — | 1.0 | 1.0-1.9 | 2.2-5.6 |

In "GGOH Yield" columns, the column marked with "1" shows the lower limit; the column marked with "2" shows a preferable range; and the column marked with "3" shows a more preferable range.
In the "Host" column, "Sc" represents *S. cerevisiae*; "Ec" represents *E. coli*.
"fps" represents *B. stearothermophilus* FPS gene.
"fpsm" represents *B. stearothermophilus* FPSm (Y81M) gene.
"idi" represents *E. coli* IPP isomerase gene. /Plasmid is p3-47-13.
"ispAm" represents *E. coli* ispAm (Y79M) gene. /Plasmid is pALispA16m.

(i) When plasmid pRS445GG is prepared by integrating GGPP synthase gene BTS1 into pRS445GAP and transferred into A451 or YPH499 strain as a host, GGOH yield increases (about 0.4 mg/L on the average).

(ii) When plasmid pRS435FGG, pRS445FGG, pRS435GGF or pRS445GGF is prepared by integrating a fusion gene composed of GGPP synthase gene BTS1 and FPP synthase gene ERG20 into plasmid pRS435GAP or pRS445GAP and transferred into A451 or YPH499 strain as a host; or when plasmid pRS435FGGHDEL, pRS445FGGHDEL or pRS435GGFHDEL comprising a nucleotide sequence encoding an HDEL sequence ligated to one end of the above fusion gene (i.e., plasmid comprising a gene modified so that an HDEL sequence is added to the C-terminal of the polypeptide to be produced by the expression of the fusion gene) is prepared and transferred into A451 or YPH499 strain; 0.20 mg/L of GGOH is produced on the average with ERG20-BTS1 fusion; 0.39 mg/L of GGOH is produced on the average with BTS1-ERG20 fusion, and 0.62 mg/L of GGOH is produced on the average with BTS1-ERG20-HDEL fusion.

(iii) When plasmid pRS434GAP-HMG1 (pRS434GAP integrating HMG-CoA reductase gene HMG1) and plasmid pRS435GGF comprising the above-described fusion gene are transferred into YPH499 as a host and co-expressed therein, the recombinant produces 1.55 mg/L of GGOH on the average. When this recombinant is cultured in YMO medium (YM medium supplemented with soybean oil, etc.) at 30° C. for 7 days, it produces 5.61 mg/L of GGOH.

(iv) When both pRS435GGFHDEL and pRS434GAP-HMG1 are transferred into YPH499 as a host and co-expressed therein, the recombinant produces 1.50 mg/L of GGOH on the average. When this recombinant is cultured in YMO medium at 30° C. for 7 days, it produces 5.64 mg/L of GGOH.

(v) When both pRS435GGF and pRS434GAP-HMG1 are transferred into YPH499 as a host and the resultant recombinant is cultured in a jar fermenter for 109 hours, the recombinant produces 128 mg/L of GGOH.

(vi) When HMG-CoA reductase gene and GGF fusion gene are co-expressed, most of the recombinant clones produce 100 mg/L or more of GGOH, and produce 189 mg/L of GGOH at the maximum.

(vii) When pRS435GGF/YH3 clone obtained by converting a clone co-expressing HMG-CoA reductase gene and GGF fusion gene into a prototroph and then diploidizing is subjected to fed-batch culture, the clone produces 0.47 g/L of GGOH when 500 g/L glucose solution is used as a feed solution after 20 hours after the start of cultivation; and produces 1.16 g/L of GGOH when 400 g/L ethanol solution is used as the feed solution.

(viii) When pRS435GGF/YH3 clone is subjected to fed-batch culture, the clone produces 2.5 g/L of GGOH under the following conditions: the ratio of ethanol to the total carbon source of the feed solution after 21 hours after the start of cultivation is 71%, and ammonium acetate is added to the feed solution.

BRIEF DESCRIPTION OF THE DRAWINGS

FIG. 5 shows the sequences of ADH1 promoter and terminator.

FIG. 11 is a diagram showing expression vectors for B. stearothermophilus FPP synthase mutant gene (Y81M). The ampicillin resistance marker gene (Amp) in each vector is shown crossed out to indicate its insertional inactivation by a DNA fragment bearing the Y81M mutant gene.

FIG. 15A presents graphs showing the specific activities of prenyl diphosphate synthases in crude enzyme solution.

FIG. 15B presents graphs showing the specific activities of prenyl diphosphate synthases in crude enzyme solution.

FIG. 29A is a graph showing the results of determination of GGOH yields in A451-derived clones.

FIG. 29B is a graph showing the results of determination of GGOH yields in A451-derived clones.

FIG. 30A is a graph showing the results of determination of GGOH yields in YPH499-derived clones.

FIG. 30B is a graph showing the results of determination of GGOH yields in YPH499-derived clones.

FIG. 35B is a graph showing the GGOH yields of pRS435GGF- or pRS435GGFHDEL-transferred YH1 strain when cultured for 4 days with indicated sugar compositions.

FIG. 39 presents photographs showing the results of Northern blot hybridization conducted in order to confirm the expression of fusion genes.

FIG. 40 presents photographs showing the results of Western blotting.

DETAILED DESCRIPTION

Hereinbelow, the present invention will be described more specifically with reference to the following Examples. However, the technical scope of the present invention is not limited to these Examples.

The Examples encompass the following contents.
(1) Expression vectors, such as pRS435GAP, are prepared using pRS vectors (Stratagene), pYES vector (Invitrogen), *Saccharomyces cerevisiae* YPH499-derived genomic DNA, etc.
(2) Cloning of Mevalonate Pathway-Related Enzyme Genes
Acetyl-CoA acetyltransferase gene, HMG-CoA reductase gene or mutants thereof, mevalonate kinase gene, phosphomevalonate kinase gene, diphosphomevalonate decarboxylase gene, isopentenyl diphosphate Δ-isomerase gene, farnesyl diphosphate synthase gene or substitution-mutants thereof, and geranylgeranyl diphosphate synthase gene are cloned, and then their expression vectors are prepared.
(3) Plasmids comprising mevalonate pathway-related enzyme genes are transferred into hosts such as A451, YPH499, etc. Also, mutant strains (EUG strains) were created by replacing the ERG9 transcription promoter in the genomic DNA of A451 or YPH499 with pYES2-derived GAL1 transcription promoter, and used as hosts for transferring prenyl diphosphate synthase genes thereinto.
(4) AURGG101, which is an A451-derived strain integrating AUR1-C gene, and AURGG102, which is an A451-derived strain comprising GAL1 promoter, BTS1 and CYC1 terminator together with AUR1-C gene in its AUR1 locus, are created and used as hosts for gene transfer.
(5) Prenyl diphosphate synthase gene expression vectors are transferred into hosts, which are then cultured in YM7 medium (YM medium whose pH is adjusted to 7 with NaOH), YMO medium, IPP and DMAPP-containing medium, etc. Each culture broth is subjected to extraction to isolate and quantitatively determine prenyl alcohols (in particular GGOH). Recombinants that have shown favorable results are cultured in a jar fermenter for a long period to obtain prenyl alcohols in large quantities. Further, effects upon GGOH production when recombinants are converted into prototrophs and then diploidized are examined. Also, effects of compounds (such as ethanol or ammonia) added to the medium upon GGOH production are examined.

EXAMPLE 1

Construction of Expression Vectors (1) *E. coli-S. cerevisiae* Shuttle Vectors

Figure 3:
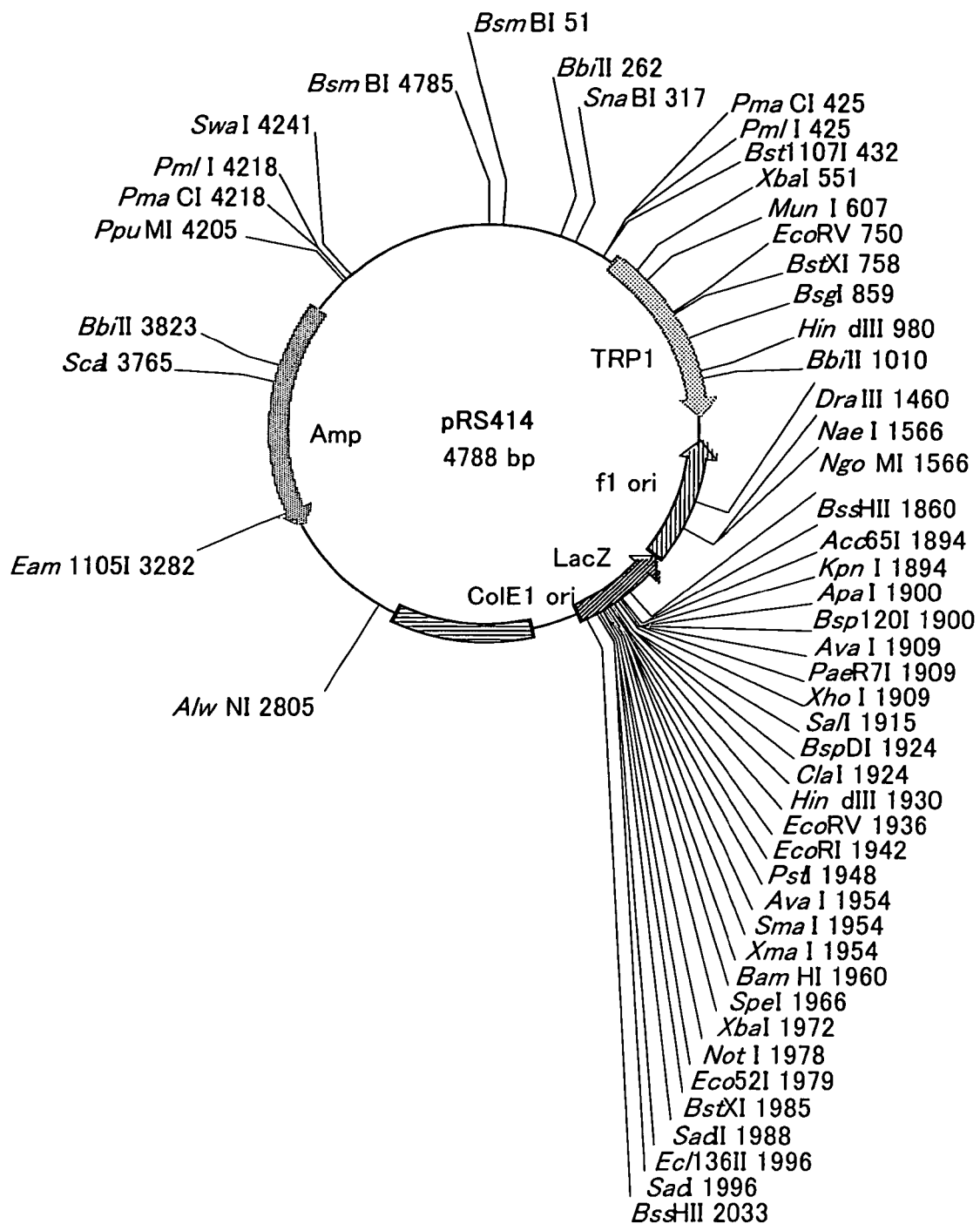
FIG. 3 is a diagram showing plasmid pRS414.

Plasmids pRS404, pRS404 and pRS414 (FIG. 3) were purchased from Stratagene. Plasmid pAUR123 was purchased from Takara, and plasmid pYES2 (FIG. 4) was purchased from Invitrogen (Carlsbad, Calif.).

(2) Genomic DNA

*S. cerevisiae* genomic DNA was prepared from *S. cerevisiae* YPH499 using Dr. GenTLE™ (a genomic DNA preparation kit for yeast) purchased from Takara and according to the protocol attached to the kit.

*E. coli* genomic DNA was prepared from *E. coli* JM109 (Takara) by the following procedures. Briefly, JM109 cells were cultured in 1.5 ml of 2×YT medium and harvested by centrifugation. To these cells, 567μl of TE (pH 8.0), 3μl of 20 mg/ml proteinase K (Boehringer Mannheim, Mannheim, Germany) and 30μl of 10% SDS were added. The resultant mixture was kept at 37° C. for 1 hr, and then 100μl of 5M NaCl was added thereto and mixed. Eighty μl of CTAB/NaCl solution (10% CTAB, 0.7 M NaCl) was added thereto, and the resultant mixture was heated at 65° C. for 10 min. This mixture was extracted with 700μl of chloroform/isoamyl alcohol (24:1), and the aqueous layer was further extracted with 600μl of phenol/chloroform/isoamyl alcohol (25:24:1). After the extraction, 0.6 volumes of isopropanol was added to the aqueous layer, which was then centrifuged. The precipitate fraction was washed with 70% ethanol, dried, and then dissolved in 100μl of TE (pH 8.0) to thereby obtain an *E. coli* genomic DNA solution. $OD_{260}$ of the DNA was measured, and the DNA was quantitatively determined. Then, TE was added to the solution to give a DNA concentration of 1 μg/μl.

Plasmid DNA from *E. coli* was prepared using Wizard PureFection Plasmid DNA Purification System (Promega, Madison, Wis.).

(3) Insertion of ADH1p-ADH1t Fragment into pRS414

Plasmid pRS414 (FIG. 3) was digested with NaeI and PvuII to obtain a 4.1 kbp fragment without fl ori and LacZ moieties. This fragment was purified by agarose gel electrophoresis. Plasmid pAUR123 was digested with BamHI and blunt-ended with Klenow enzyme. Then, a 1.0 kbp fragment containing ADH1 transcription promoter (ADH1p) and ADH1 transcription terminator (ADH1t) (FIG. 5; SEQ ID NO: 23) was purified by agarose gel electrophoresis. The 4.1 kbp fragment from pRS414 still retained the replication origins for *E. coli* and yeast, a transformation marker Amp$^r$ for *E. coli*, and an auxotrophic marker TRP1 for yeast. On the other hand, the 1.0 kbp fragment from pAUR123 contained ADH1p, ADH1t, and a cloning site flanked by them. These two fragments were ligated to each other with a DNA ligation kit (Takara) and transformed into *E. coli* SURE2 supercompetent cells (Stratagene, La Jolla, Calif.).

Figure 6A:
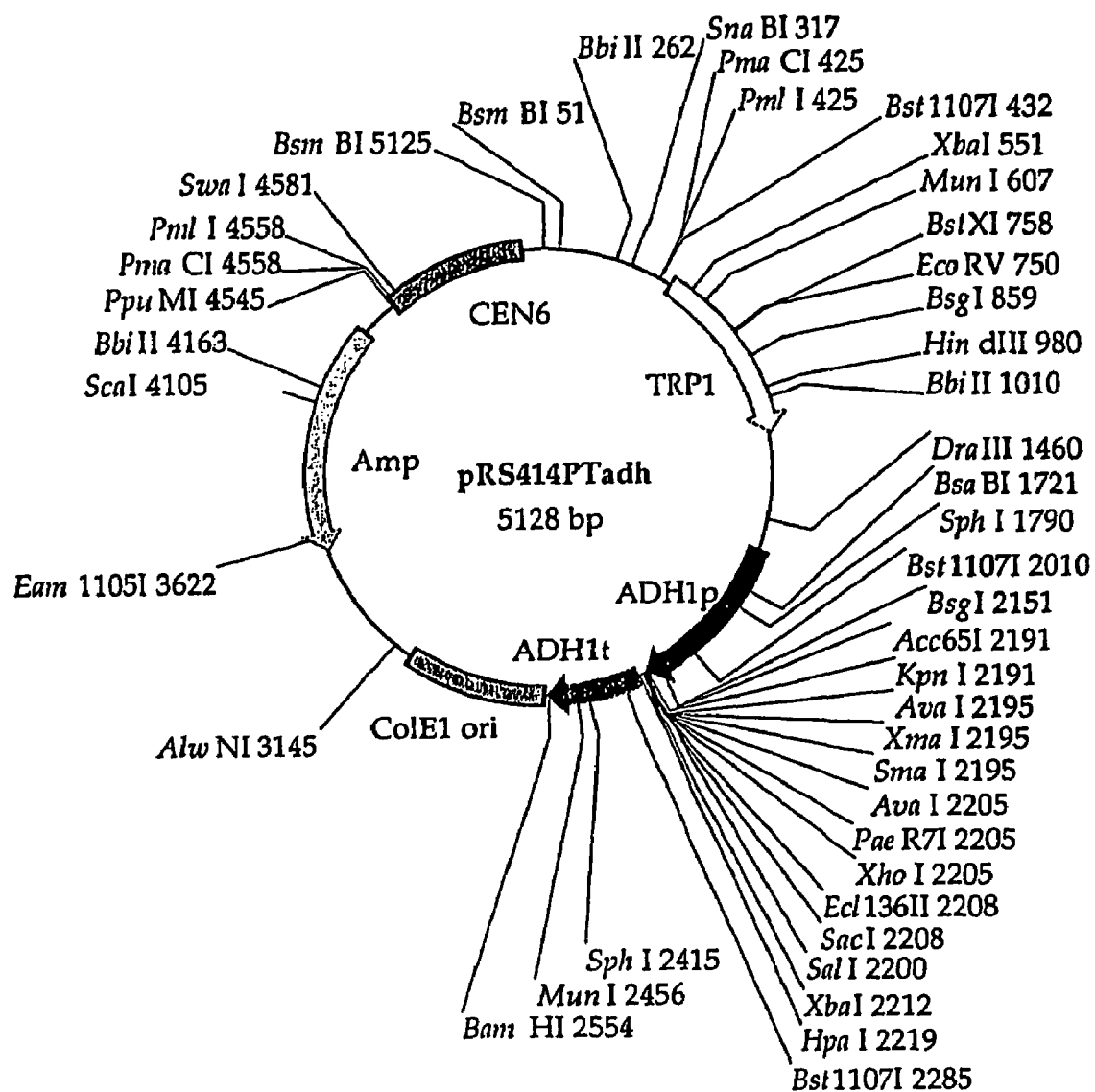
FIG. 6A is a diagram showing plasmid pRS414PTadh.
Figure 6B:
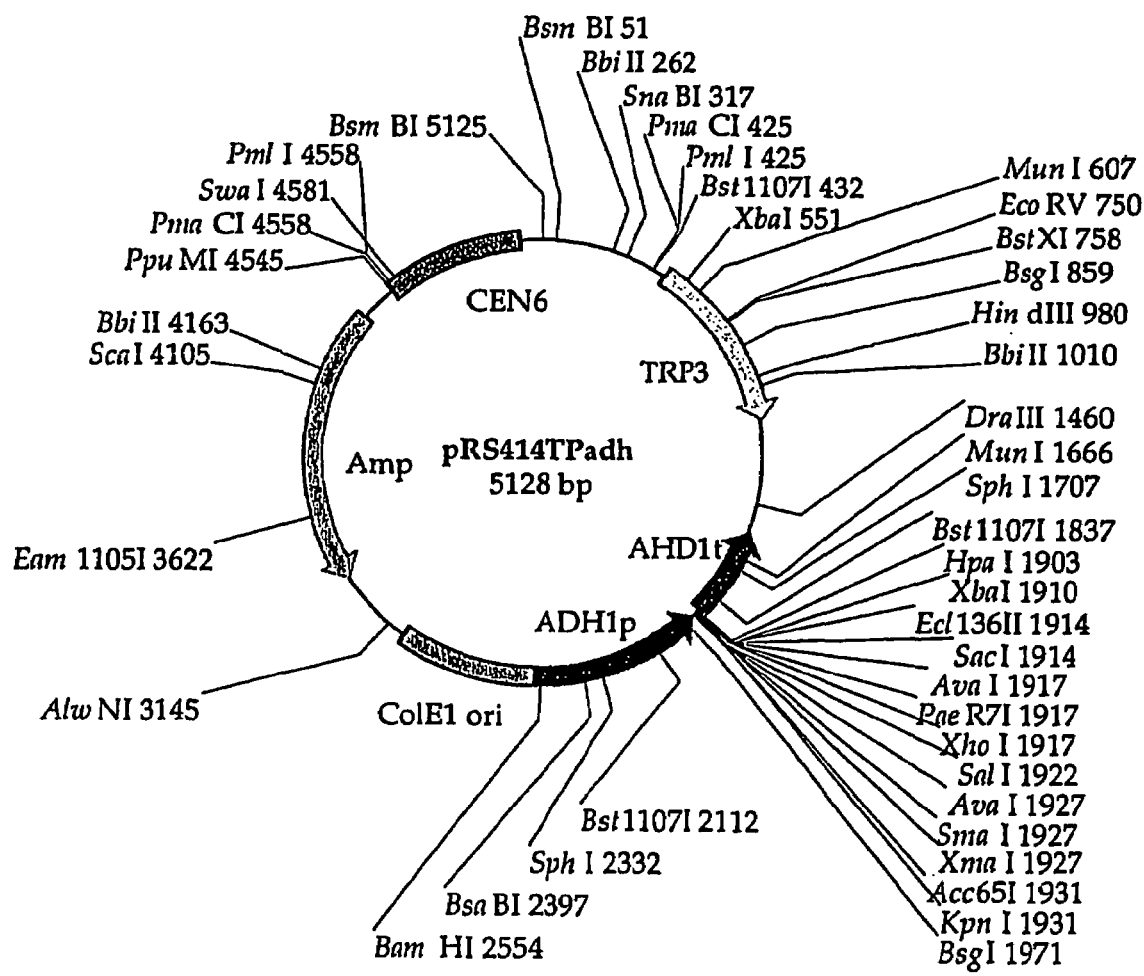
FIG. 6B is a diagram showing plasmid pRS414TPadh.
Figure 7A:
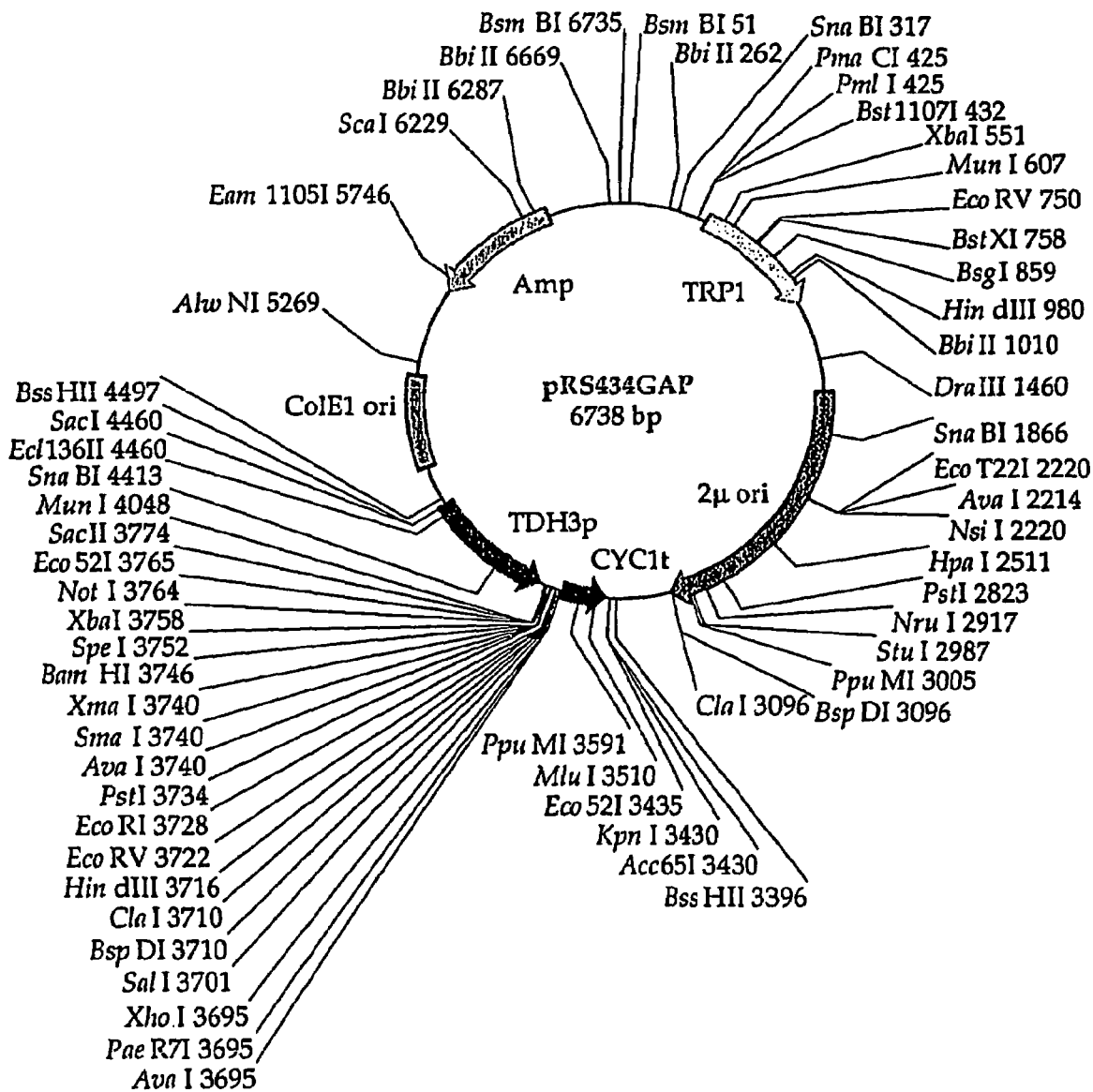
FIG. 7A is a diagram showing plasmid pRS434GAP.
Figure 7B:
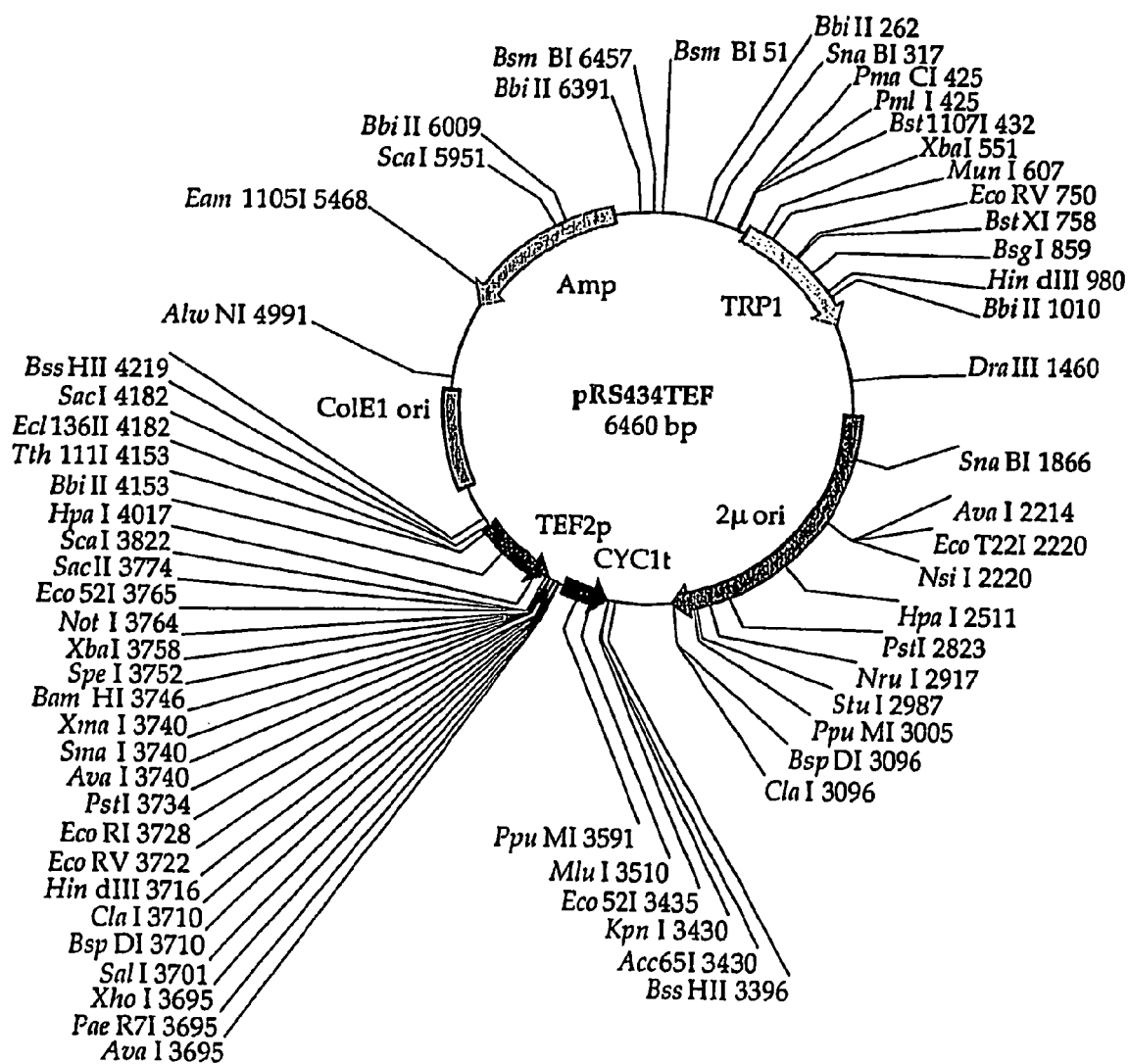
FIG. 7B is a diagram showing plasmid pRS434TEF.
Figure 7C:
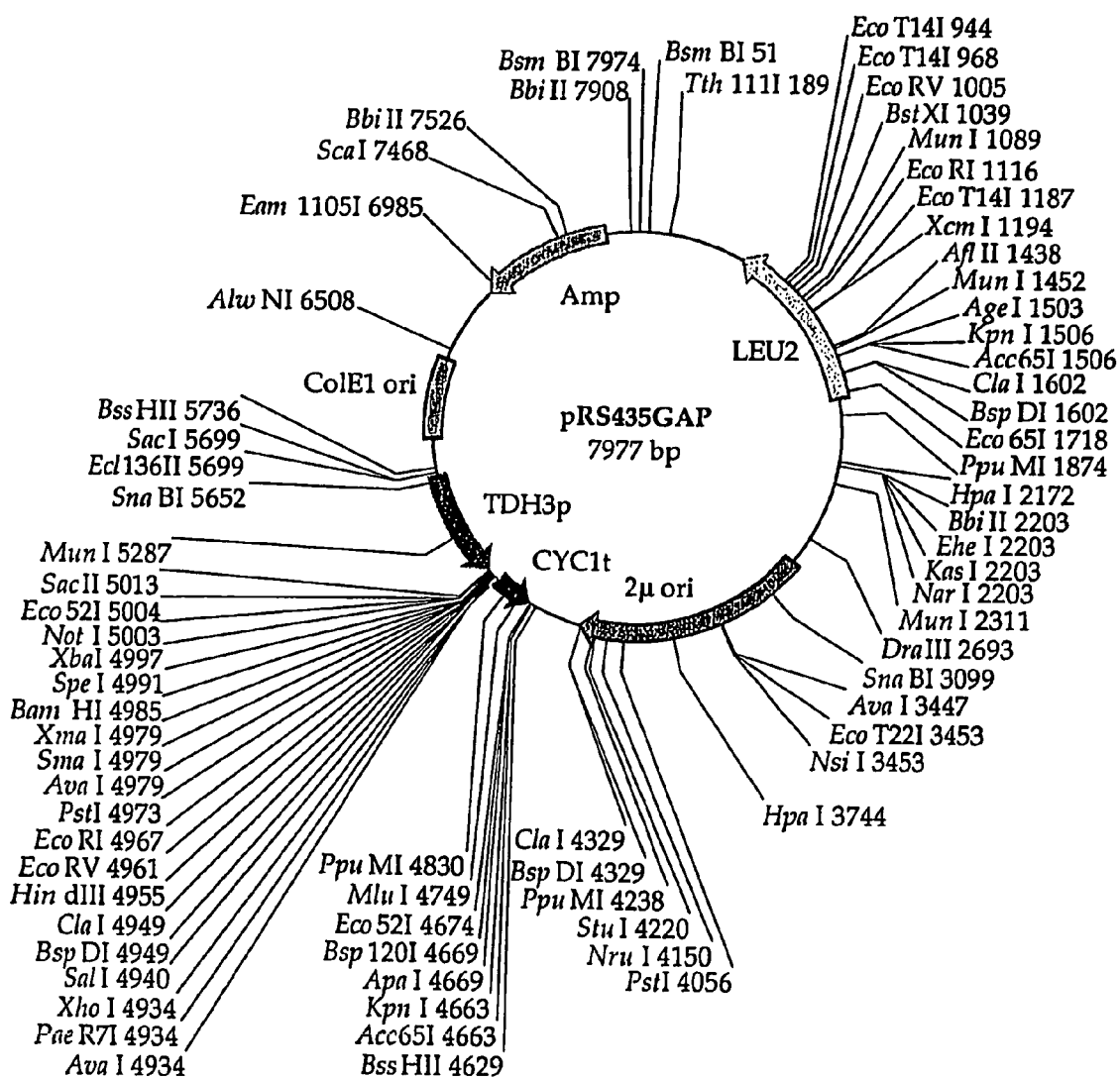
FIG. 7C is a diagram showing plasmid pRS435GAP.
Figure 7D:
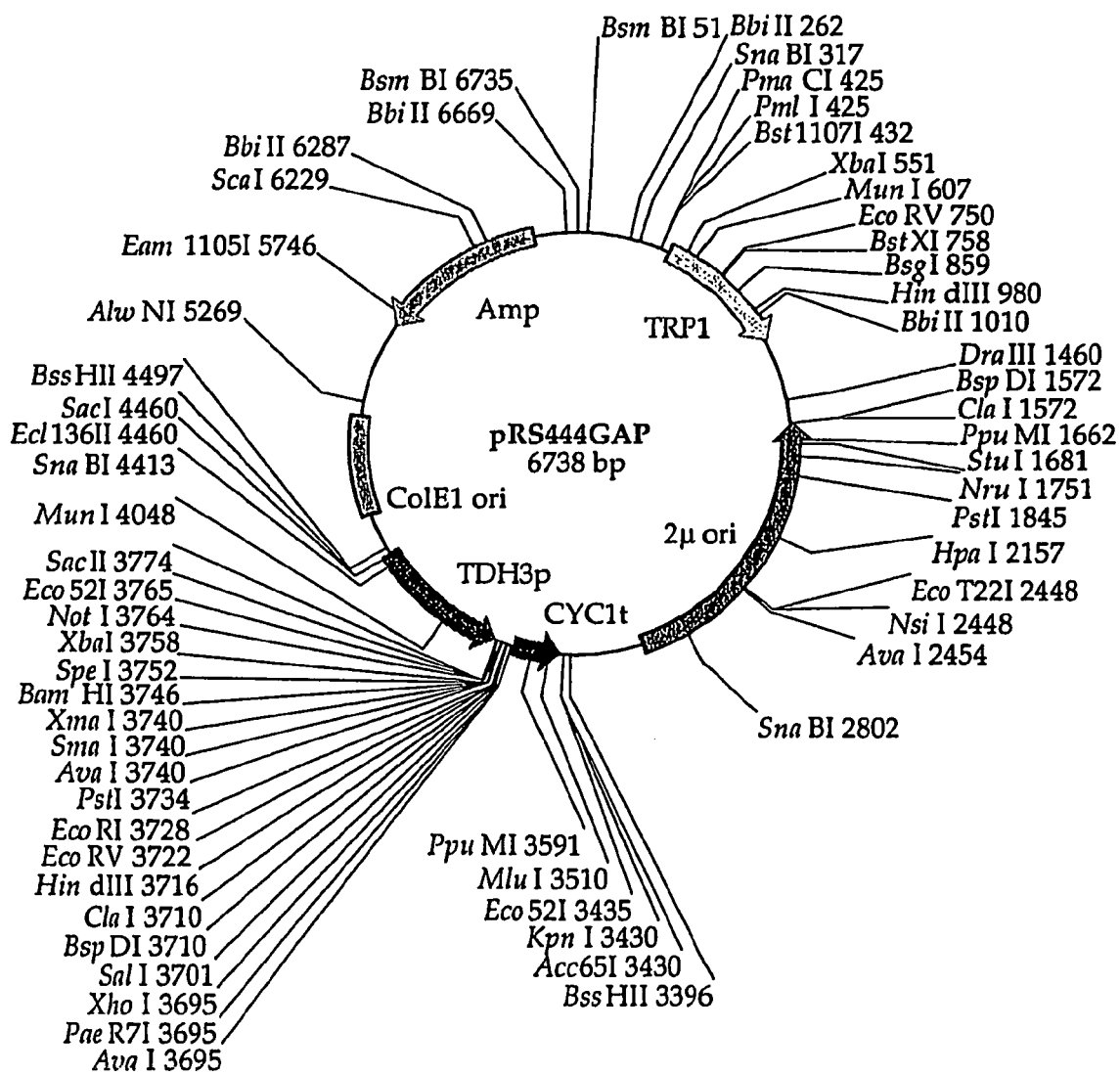
FIG. 7D is a diagram showing plasmid pRS444GAP.
Figure 7E:
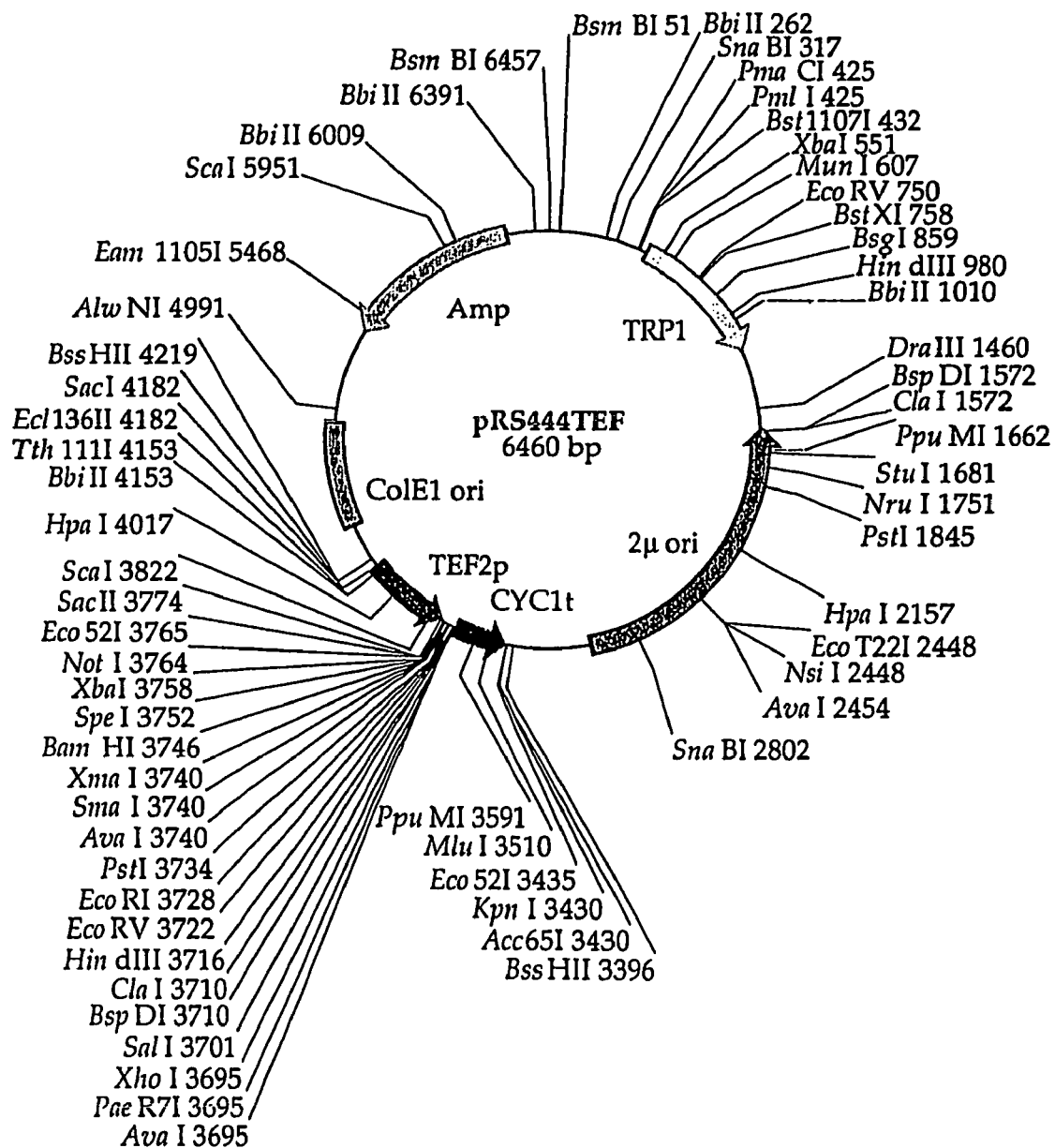
FIG. 7E is a diagram showing plasmid pRS444TEF.
Figure 7F:
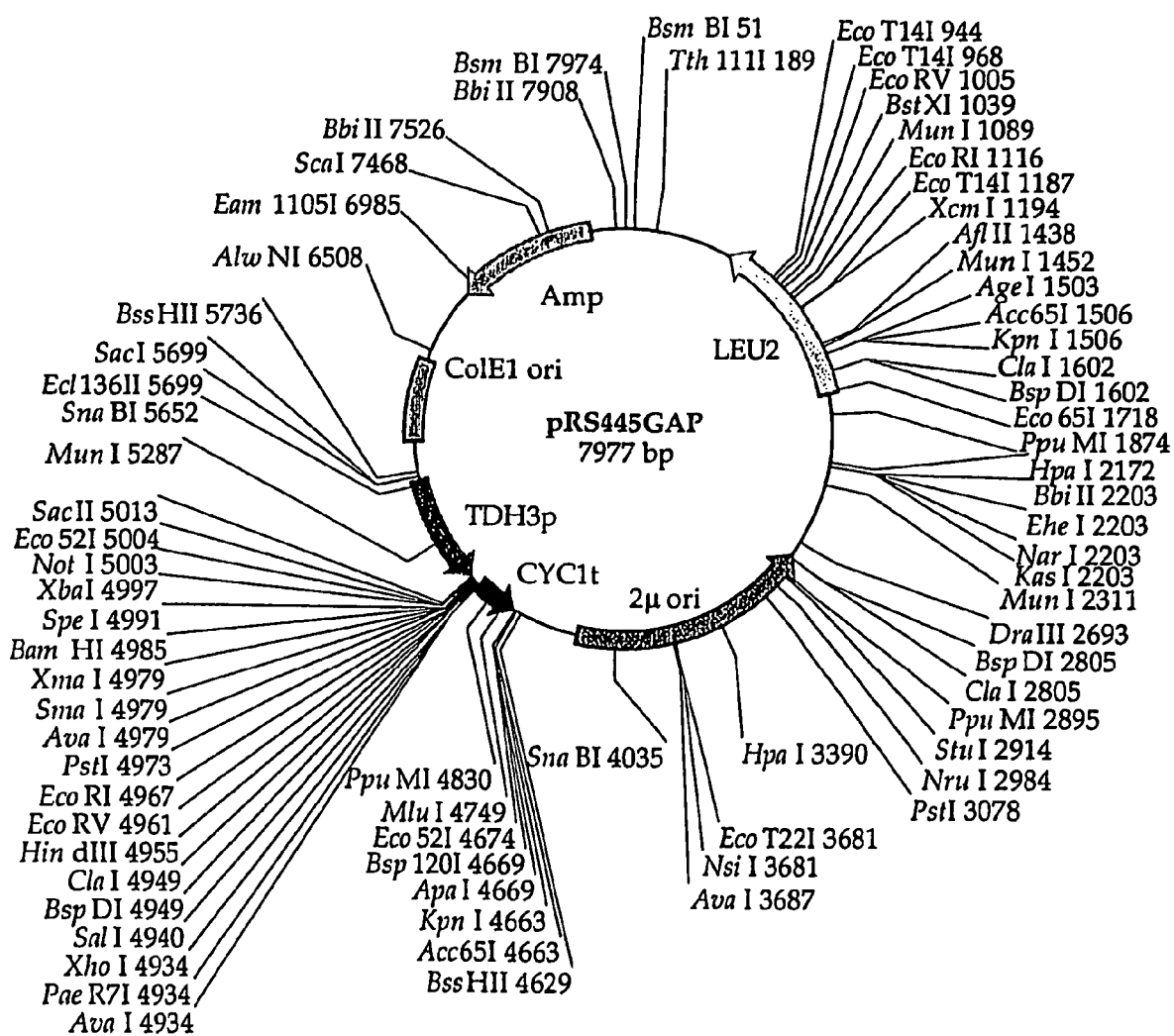
FIG. 7F is a diagram showing plasmid pRS445GAP.

Plasmid DNA was prepared from the resultant recombinant. Mapping of the DNA with SalI and ScaI revealed that the ADH1p-ADHt fragment has been inserted into pRS414 in two directions to thereby yield two plasmids pRS414PTadh (FIG. 6A) and pRS414TPadh (FIG. 6B).

(4) Insertion of CYC1t Fragment into pRS Vectors

CYC1t (CYC1 transcription terminator) fragment was prepared by PCR. The following oligo-DNAs, XhoI-Tcyc1FW and ApaI-Tcyc1RV, were used as PCR primers. As a template, pYES2 was used.

XhoI-Tcyc1FW:
(SEQ ID NO: 40)
5'-TGC ATC TCG AGG GCC GCA TCA TGT AAT TAG-3'

ApaI-Tcyc1RV:
(SEQ ID NO: 41)
5'-CAT TAG GGC CCG GCC GCA AAT TAA AGC CTT CG-3'

Briefly, 50µl of a reaction solution containing 0.1 µg of pYES2, 50 pmol of each primer DNA, 1× Pfu buffer containing MgSO$_4$ (Promega, Madison, Wis.), 10 nmol dNTPs, 1.5 units of Pfu DNA polymerase (Promega) and 1µl of Perfect Match polymerase enhancer (Stratagene) was prepared. The reaction conditions were as follows: first denaturation at 95° C. for 2 min; 30 cycles of denaturation at 95° C. for 45 sec, annealing at 60° C. for 30 sec, and extension at 72° C. for 1 min; and final extension at 72° C. for 5 min. After completion of the reaction, the solution was stored at 4° C. The amplified DNA was digested with XhoI and ApaI, and the resultant 260 bp DNA fragment was purified by agarose gel electrophoresis to obtain CYC1t-XA.

CYC1t-XA was inserted into the XhoI-ApaI site of pRS404 and pRS406 to thereby obtain pRS404Tcyc and pRS406Tcyc, respectively.

(5) Preparation of Transcription Promoters

DNA fragments comprising transcription promoters were prepared by PCR using pAUR123 or yeast genomic DNA as a template. The DNA primers used are as follows.

SacI-Ptdh3FW:
(SEQ ID NO: 42)
5'-CAC GGA GCT CCA GTT CGA GTT TAT CAT TAT CAA-3'

SacII-Ptdh3RV:
(SEQ ID NO: 43)
5'-CTC TCC GCG GTT TGT TTG TTT ATG TGT GTT TAT TC-3'

SacI-Ptef2FW:
(SEQ ID NO: 44)
5'-CCG CGA GCT CTT ACC CAT AAG GTT GTT TGT GAC G-3'

SacII-Ptef2RV:
(SEQ ID NO: 45)
5'-CTT TCC GCG GGT TTA GTT AAT TAT AGT TCG TTG ACC-3'

For the amplification of ADH1 transcription promoter (ADH1p), SacI-Padh1FW and SacII-Padh1RV were used as PCR primers and pAUR123 as a template. For the amplification of TDH3 (GAP) transcription promoter (TDH3p (GAPp)), SacI-Ptdh3FW and SacII-Ptdh3RV were used as PCR primers; and for the amplification of TEF2 transcription promoter (TEF2p), SacI-Ptef2FW and SacII-Ptef2RV were used as PCR primers. For these promoters, yeast genomic DNA was used as a template. As a reaction solution, a 100 µl solution containing 0.1 µg of pAUR123 or 0.46 µg of yeast genomic DNA, 100 pmol of each primer DNA, 1× ExTaq buffer (Takara), 20 nmol dNTPs, 0.5 U of ExTaq DNA polymerase (Takara) and 1µl of Perfect Match polymerase enhancer was prepared. The reaction conditions were as follows: first denaturation at 95° C. for 2 min, then 30 cycles each consisting of 45 sec at 95° C., 1 min at 60° C. and 2 min at 72° C., and final extension at 72° C. for 4 min. After completion of the reaction, the solution was stored at 4° C. The amplified 4 types of DNAs were digested with SacI and SacII, and the resultant 620 bp, 680 bp, 710 bp and 400 bp DNA fragments were purified separately by agarose gel electrophoresis to thereby obtain TDH3p and TEF2p, respectively.

(6) Preparation of 2 µDNA Replication Origin Region pYES2, which is a YEp vector, was digested with SspI and NheI. The resultant 1.5 kbp fragment containing 2 µDNA replication origin (2 µori) was purified by agarose gel electrophoresis and then blunt-ended. This DNA fragment was designated 2 µOriSN.

(7) Preparation of YEp Type Expression Vectors

2 µOriSN was inserted into the NaeI site of pRS404Tcyc and pRS406Tcyc pretreated with BAP (bacterial alkaline phosphatase: Takara). The resultant plasmids were transformed into *E. coli* SURE2, and then plasmid DNA was prepared. The plasmid DNA was digested with DraIII; and EcoRI, HpaI or PstI; and PvuII, followed by agarose gel electrophoresis to examine the insertion and the direction of 2µ ori. The resultant pRS404Tcyc and pRS405Tcyc into which 2µ ori had been inserted in the same direction as in pYES2 were designated pRS434Tcyc2µOri and pRS435Tcyc2µOri, respectively. The resultant pRS404Tcyc and pRS405Tcyc into which 2µ ori had been inserted in the opposite direction to that in pYES2 were designated pRS444Tcyc2µOri and pRS445Tcyc2µOri, respectively.

A transcription promoter-containing fragment, i.e., ADH1p, TDH3p (GAPp), PGK1p or TEF2p, was inserted into the SacI-SacII site of the above-described four plasmids pRS434Tcyc2µOri, pRS435Tcyc2µOri, pRS444Tcyc2µOri and pRS445Tcyc2µOri to clone the DNA. As a result, the following plasmids were obtained: (i) pRS434GAP and pRS434TEF from pRS434Tcyc2μOri; (ii) pRS435GAP from pRS435Tcyc2μOri; (iii) pRS444GAP and pRS444TEF from pRS444Tcyc2μOri; (iv) pRS445GAP from pRS445Tcyc2μOri (FIGS. 7A-7F).

The expression vectors prepared in the present invention are summarized in Table 5 below.

TABLE 5

| Vector | Type | Marker and Direction* | | Promoter, Terminator and Direction* | | | ori and Direction* | |
|---|---|---|---|---|---|---|---|---|
| pRS414PTadh | YCp | TRP1 | + | ADH1 | ADH1 | + | ARS4 & CEN6 | + |
| pRS414TPadh | YCp | TRP1 | + | ADH1 | ADH1 | − | ARS4 & CEN6 | + |
| pRS434GAP | YEp | TRP1 | + | TDH3 | CYC1 | − | 2μ | + |
| pRS434TEF | YEp | TRP1 | + | TEF2 | CYC1 | − | 2μ | + |
| pRS435GAP | YEp | LEU2 | + | TDH3 | CYC1 | − | 2μ | + |
| pRS444GAP | YEp | TRP1 | + | TDH3 | CYC1 | − | 2μ | − |
| pRS444TEF | YEp | TRP1 | + | TEF2 | CYC1 | − | 2μ | − |
| pRS445GAP | YEp | LEU2 | + | TDH3 | CYC1 | − | 2μ | − |

*The "+" and "−" marks appearing after markers and gene expression transcription units indicate downstream and direction upstream direction, respectively.

The "+" mark appearing after ori indicates that the ori is inserted in the same direction as that in pRS (for YCp vectors) or pYES (for YEp vectors); the "−" mark indicates that the ori is inserted in the direction opposite to that in pRS (for YCp vectors) or pYES (for YEp vectors).

(8) Introduction of YEp Type Expression Vectors into Yeast

In order to examine whether the DNA replication region of the prepared YEp type expression vectors functions or not, about 40 ng of each YEp type expression vector was introduced into YPH499 strain using Frozen-EZ Yeast Transformation II (Zymo Research, Orange, Calif.). (The procedures followed the protocol attached to the kit.) Then, colonies growing on SD-W (DOB+CMS (−Trp); BIO101, Vista, Calif.) agar plate at 30° C. were examined. The results are shown in Table 6 below.

TABLE 6

| | GAP | TEF |
|---|---|---|
| pRS 434 | >1000 | >1000 |
| 435 | >1000 | — |
| 444 | >1000 | >1000 |
| 445 | >1000 | — |

The results shown in Table 6 revealed that each of the YEp type vectors prepared in the invention is retained normally as a vector.

EXAMPLE 2

Cloning of Mevalonate Pathway-Releted Enzyme Genes

In the cloning of genes from yeast cDNA, an *S. cerevisiae* DBY746-derived cDNA library "Quick-Clone cDNA" purchased from Clontech (Palo Alto, Calif.) was used.

(1) Cloning of Farnesyl Diphosphate Synthase Genes (1-1) *Saccharomyces cerevisiae*-Derived FPP Synthase Gene ERG20:

An approximately 0.9 kbp DNA fragment encoding *S. cerevisiae* FPP synthase gene ERG20 (SEQ ID NO: 1) was amplified by PCR (polymerase chain reaction) using the above cDNA as a template. The PCR primers used are as follows.

Primer 1 (SCFPS1):
(SEQ ID NO: 46)
5'-ATG GCT TCA GAA AAA GAA ATT AG-3'

Primer 2 (SCFPS2):
(SEQ ID NO: 47)
5'-CTA TTT GCT TCT CTT GTA AAC TT-3'

| 10x ExTaq buffer (Takara) | 5 μl |
|---|---|
| 2.5 mM dNTP mix | 4 μl |
| 5 U/μl ExTaq (Takara) | 1 μl |
| 10 pmol Primer 1 | |
| 10 pmol Primer 2 | |
| 0.5 ng cDNA | |
| | 50 μl in total |

The PCR was carried out in the reaction solution described above for 30 cycles each consisting of 45 sec at 94° C., 1 min at 55° C. and 2 min at 72° C.

Unless otherwise indicated, PCR reactions in the following Examples were carried out under the same conditions as described above.

Figure 8:
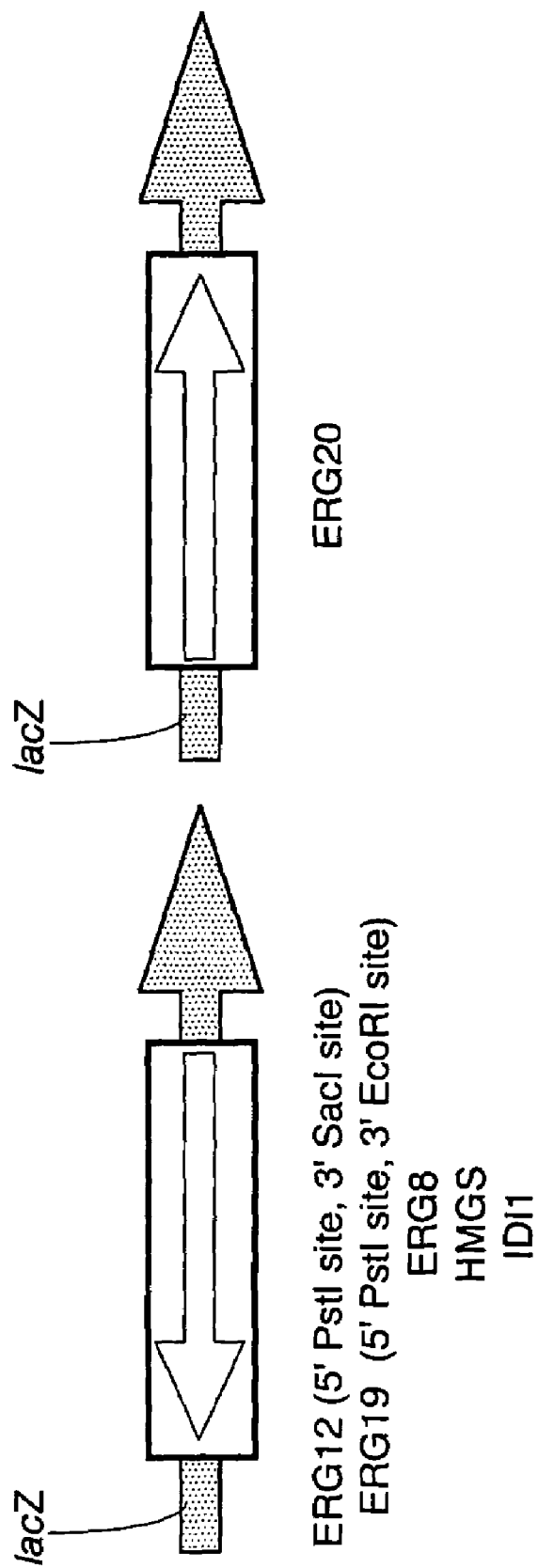
FIG. 8 is a diagram showing the direction of each of the mevalonate pathway-related enzymes inserted into pT7 vector.

The amplified fragment was purified by agarose gel electrophoresis and then cloned into pT7Blue-T (Novagen, Madison, Wis.) by T/A ligation. It was found that ERG20 was inserted into pT7Blue-T in the same direction as that of lacZ in this plasmid (FIG. 8). The nucleotide sequence of the cloned fragment was determined and compared to the corresponding nucleotide sequence registered in SGD (*Saccharo-*

*myces* Genome Database, Stanford University ). As a result, no PCR errors were found in nucleotide positions 1-300 and 610-1059.

The plasmid DNA prepared was designated pT7ERG20.

(1-2) *Escherichia coli*-Derived FPP Synthase Gene ispA:

*E. coli*-derived FPP synthase gene ispA (SEQ ID NO: 3) was cloned by PCR using *E. coli* genomic DNA as a template and the following synthetic oligo DNAs as primers.

```
                                      (SEQ ID NO: 48)
ISPA1: 5'-TGA GGC ATG CAA TTT CCG CAG CAA CTC G-3'

(SEQ ID NO: 49)
ISPA2: 5'-TC AGA ATT CAT CAG GGG CCT ATT AAT AC-3'
```

The PCR was carried out in 100μl of a reaction solution containing 1× EXTaq buffer, 0.5 mM dNTPs 100 pmol ISPA1, 100 pmol ISPA2, 0.2 μg of *E. coli* genomic DNA and 5 units of ExTaq for 30 cycles each consisting of 1 min at 94° C., 1 min at 55° C. and 1.5 min at 72° C. The PCR product was digested with EcoRI and SphI, and subjected to agarose gel electrophoresis to purify a 1.0 kbp DNA fragment. This fragment was inserted into the EcoRI-SphI site of pALTER-Ex2 (Promega), which was then transferred into *E. coli* JM109 for cloning the gene. As a result, plasmids pALispA4, pAL-ispA8, pALispA15, pALispA16 and pALispA18 were obtained; restriction enzyme mapping with EcoRI, SphI, NdeI, SmaI and BamHI confirmed that ispA gene was transferred correctly into these plasmids.

(1-3) *Bacillus stearothermophilus*-derived FPP Synthase Gene pFE15 disclosed in Japanese Unexamined Patent Publication No. 5-219961 was digested with NotI and SmaI, followed by purification of an FPP synthase gene fragment containing a 2.9 kbp transcription unit. This gene fragment was inserted into the ScaI site of pACYC177 (Nippon Gene) to thereby prepare an expression vector comprising *B. stearothermophilus*-derived FPP synthase gene fps (SEQ ID NO: 25).

(2) Cloning of Geranylgeranyl Diphosphate Synthase Gene

*S. cerevisiae*-derived GGPP synthase gene BTS1 (SEQ ID NO: 5) was cloned as described below.

Briefly, based on information about the *S. cerevisiae*-derived GGPP synthase gene available in the GenBanik database (National Center for Biotechnology Information; NCBI) (A.N.U31632)(Y Jiang, et al., *J. Biol. Chem.* 270 (37), 21793-21799 (1995)), a pair of primers matching the N-terminal and C-terminal of the protein encoded by the gene were designed. Using these primers and a yeast cDNA library (Clontech; No. CL7220-1) as a template, PCR was carried out.

```
N-terminal primer:
                                      (SEQ ID NO: 50)
5'-ATG GAG GCC AAG ATA GAT GAG CT-3'

C-terminal primer:
                                      (SEQ ID NO: 51)
5'-TCA CAA TTC GGA TAA GTG GTC TA-3'
```

The PCR was performed using Perfect Match Polymerase Enhancer (Stratagene) for 30 cycles each consisting of denaturation for 45 sec at 94° C., annealing for 1 min at 55° C. and extension for 2 min at 72° C.

A fragment of interest (approx. 1.0 kbp) was confirmed. This BTS1 fragment was cloned into pT7Blue T vector capable of TA cloning, followed by sequencing of the entire region of BTS1. The results revealed that the nucleotide sequence of this gene was completely identical with the corresponding nucleotide sequence registered at the GenBank (SEQ ID NO: 5). Thus, it was confirmed that this gene is the *S. cerevisiae*-derived GGPP synthase gene.

(3) Cloning of Acetyl-CoA Acetyltransferase Gene

An approximately 1.2 kbp genomic DNA fragment encoding *S. cerevisiae* acetyl-CoA acetyltransferase gene ERG10 (SEQ ID NO: 26) was amplified by PCR using ExTaq DNA polymerase. The resultant fragment was cloned into the SacII-XbaI site of pRS435GAP and pRS445GAP. The PCR primers used are as follows.

```
Primer 1 (SacII-ERG10):
                                      (SEQ ID NO: 52)
5'-TCC CCG CGG ATG TCT CAG AAC GTT TAC ATT GT-3'

Primer 2 (XbaI-ERG10):
                                      (SEQ ID NO: 53)
5'-TGC TCT AGA TCA TAT CTT TTC AAT GAC AAT GGA-3'
(Underlined portions indicate restriction enzyme
recognition sites.)
```

The PCR was performed in the co-presence of Perfect Match Polymerase Enhancer for 30 cycles each consisting of 45 sec at 95° C., 1 min at 60° C. and 2 min at 72° C. The resultant plasmids were subjected to SmaI, ScaI, NcoI and BamHI recognition site mapping to examine whether they were prepared as designed. The successfully prepared plasmids were designated pRS435GAP-ERG10 and pRS445GAP-ERG10, respectively.

(4) Cloning of HMG-CoA Synthase Gene

An approximately 1.5 kbp fragment encoding *S. cerevisiae* HMG-CoA synthase gene HMGS (SEQ ID NO: 27) was amplified by PCR using cDNA as a template. For the annealing temperature, 50° C. was employed. The PCR primers used are as follows.

```
Primer 1 (HMGS-1-2):
                                      (SEQ ID NO: 54)
5'-ATG AAA CTC TCA ACT AAA CTT TGT T-3'

Primer 2 (scHMGS-15):
                                      (SEQ ID NO: 55)
5'-GTT CAG CAA GAT GCA ATC GAT GGG G-3'
```

The PCR fragment was purified by agarose gel electrophoresis and then cloned into pT7Blue-T by T/A ligation. It was found that HMGS was inserted into pT7Blue in the opposite direction to that of lacZ in this plasmid (FIG. 8). The nucleotide sequence of the cloned fragment was determined. Comparison of this sequence with the corresponding sequence in SGD revealed that the nucleotide A at position 39 (counted taking the first nucleotide A of the initiation codon ATG as position 1) was changed to G as a result of PCR error (A39G; hereinafter, PCR errors are expressed in the same manner).

Further, 5 additional errors of T144C, T223C, T1038C, C1122T and A1370G were also found. Of these PCR errors, T223C and A1370G caused changes in the encoded amino acids. T223C changed Ser at position 75 to Pro (S75P; hereinafter, amino acid sequence errors are expressed in the same manner), and A1370G caused another amino acid sequence error K457R.

The resultant plasmid was designated pT7HMGS.

(5) Cloning of HMG-CoA Reductase Gene

S. cerevisiae-derived HMG-CoA reductase gene HMG1 was cloned as described below.

Briefly, based on information about S. cerevisiae-derived HMG-CoA reductase gene HMG1 (A.N. M22002) (M. E. Basson, et al., *Mol. Cell. Biol.* 8, 3797-3808 (1988): SEQ ID NO: 7) registered at the GenBank, a pair of primers matching the N-terminal and the C-terminal of the protein encoded by this gene were designed. Using these primers and the yeast cDNA library (Clontech) as a template, PCR was carried out.

```
N-terminal primer:
                                    (SEQ ID NO: 56)
5'-ATG CCG CCG CTA TTC AAG GGA CT-3'

C-terminal primer:
                                    (SEQ ID NO: 57)
5'-TTA GGA TTT AAT GCA GGT GAC GG-3'
```

The PCR was performed using Perfect Match Polymerase Enhancer for 30 cycles each consisting of denaturation for 45 sec at 94° C., annealing for 1 min at 55° C. and extension for 2 min at 72° C.

Figure 1:
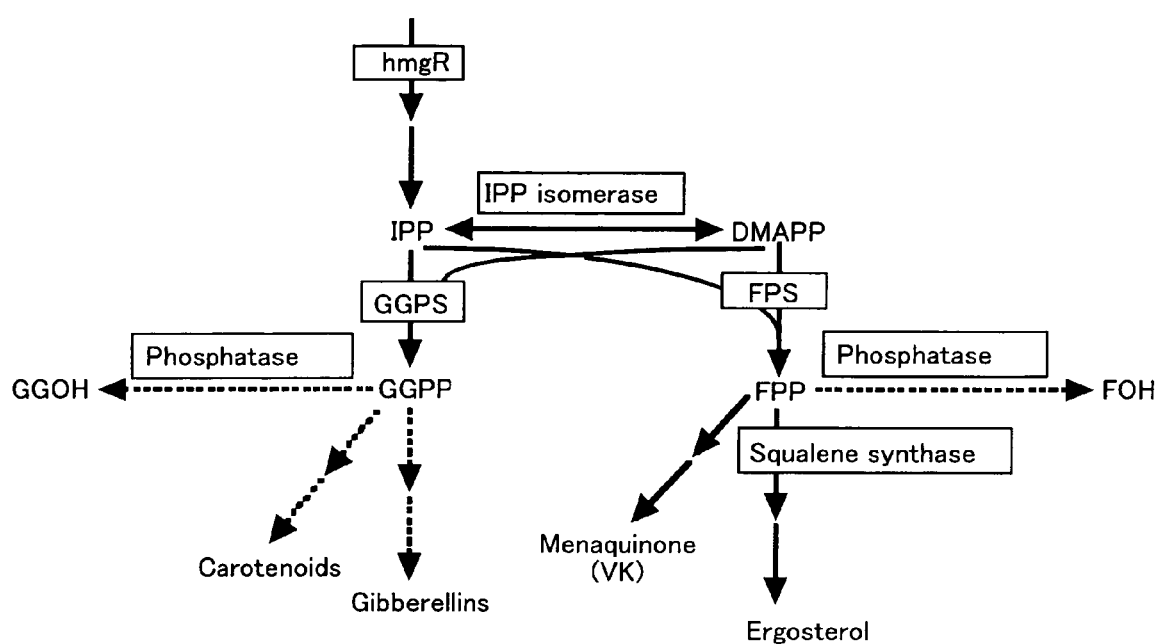
FIG. 1 is a chart showing metabolic pathways of mevalonate pathway-related enzymes.
Figures 2A, 2B:
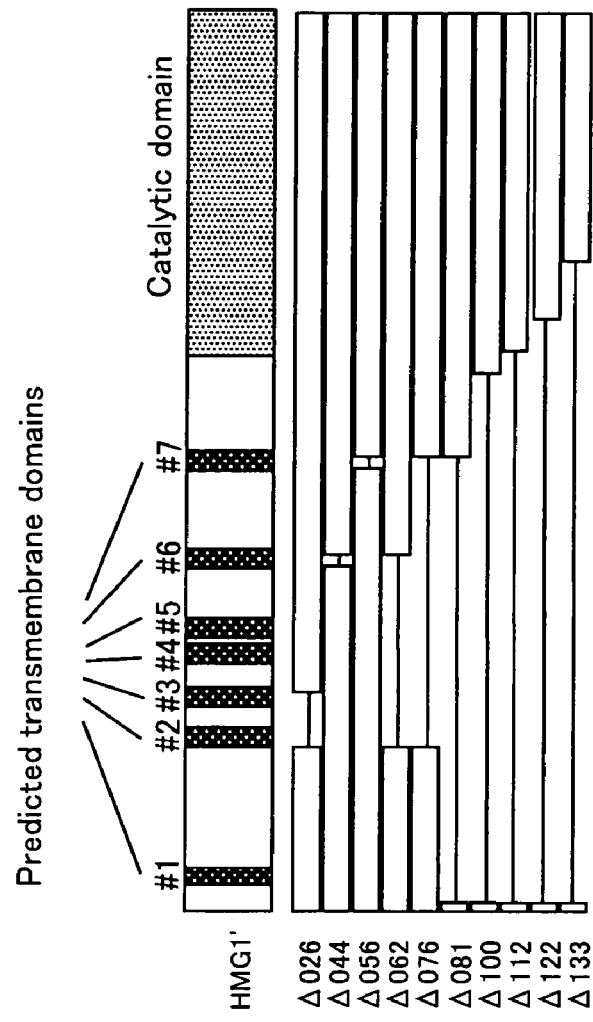
FIG. 2A is a table showing a pattern of substitution mutations.
FIG. 2B is a construction diagram for deletion type HMG1 genes.

A fragment of interest (3.2 kbp) was confirmed. This fragment (HMG1) was cloned into pT7Blue T vector capable of TA cloning to thereby obtain pT7-HMG1. The nucleotide sequence of the thus cloned HMG1 was determined. As a result, the nucleotide sequence as shown in SEQ ID NO: 9 and the amino acid sequence as shown in SEQ ID NO: 10 were obtained. The thus determined nucleotide sequence was partially different from the corresponding nucleotide sequence registered at the GenBank due to PCR errors (FIG. 2A). This mutant type HMG-CoA reductase gene containing PCR errors is designated HMG1'.

(6) Correction of PCR Errors in HMG-CoA Reductase Gene

PCR errors were corrected by subcloning the HMG1 fragment from pT7HMG1 and correcting those errors in the HMG1 region that would cause amino acid substitution mutations.

Briefly, an HMG1' gene fragment was subcloned from plasmid pT7HMG1 comprising HMG1', a PCR error type DNA of HMG-CoA reductase gene HMG1. Then, the PCR errors in the HMG1 region that would cause amino acid substitution mutations were corrected by site-directed mutagenesis to thereby prepare pALHMG106. The details of this preparation are as described below.

Plasmid pT7HMG1 was used as cloned HMG1. As a vector for introducing site-directed mutations, pALTER-1 (Promega) was purchased.

Site-directed mutagenesis was carried out according to the procedures described in "Protocols and Application Guide, 3rd edition, 1996 Promega, ISBN 1-882274-57-1" published by Promega. As oligos for introducing mutations, the following three oligos were synthesized chemically.

```
HMG1 (190-216):
5'-CCAAATAAAGACTCCAACACTCTATTT-3'   (SEQ ID NO: 58)

HMG1 (1807-1833):
5'-GAATTAGAAGCATTATTAAGTAGTGGA-3'   (SEQ ID NO: 59)

HMG1(2713-2739):
5'-GGATTTAACGCACATGCAGCTAATTTA-3'   (SEQ ID NO: 60)
```

First, pT7HMG1 was digested with SmaI, ApaLI and SalI, followed by preparation of a 3.2 kbp HMG1 fragment by agarose gel electrophoresis. This fragment was inserted into the SmaI-SalI site of pALTER-1 to prepare pALHMG1. After denaturation of this plasmid with alkali, the above-described oligos for introducing mutations, Amp repair oligo (Promega) as repair oligo, and Tet knockout oligo (Promega) as knockout oligo were annealed thereto. The resultant plasmid was introduced into *E. coli* ES1301 (Promega). Then, transformants retaining the plasmid into which site-directed mutations had been introduced was subjected to enrichment culture using 125µg/ml of ampicillin, followed by preparation of plasmid DNA. The nucleotide sequence of the resultant plasmid DNA was examined with primers having the sequences as shown below. The results revealed that all the sequences corresponding to HMG1 (190-216), HMG1 (1807-1833) and HMG1 (2713-2739) were corrected to the intended sequences (SEQ ID NO: 11). The amino acid sequence encoded by the corrected nucleotide sequence (SEQ ID NO: 12) was consistent with the amino acid sequence encoded by HMG1' (SEQ ID NO: 10) (silent mutations).

```
HMG1 (558-532)
5'-GTCTGCTTGGGTTACATTTTCTGAAAA-3'   (SEQ ID NO: 61)

HMG1 (1573-1599)
5'-CATACCAGTTATACTGCAGACCAATTG-3'   (SEQ ID NO: 62)

HMG1 (2458-2484)
5'-GAATACTCATTAAAGCAAATGGTAGAA-3'   (SEQ ID NO: 63)
```

Figure 9:
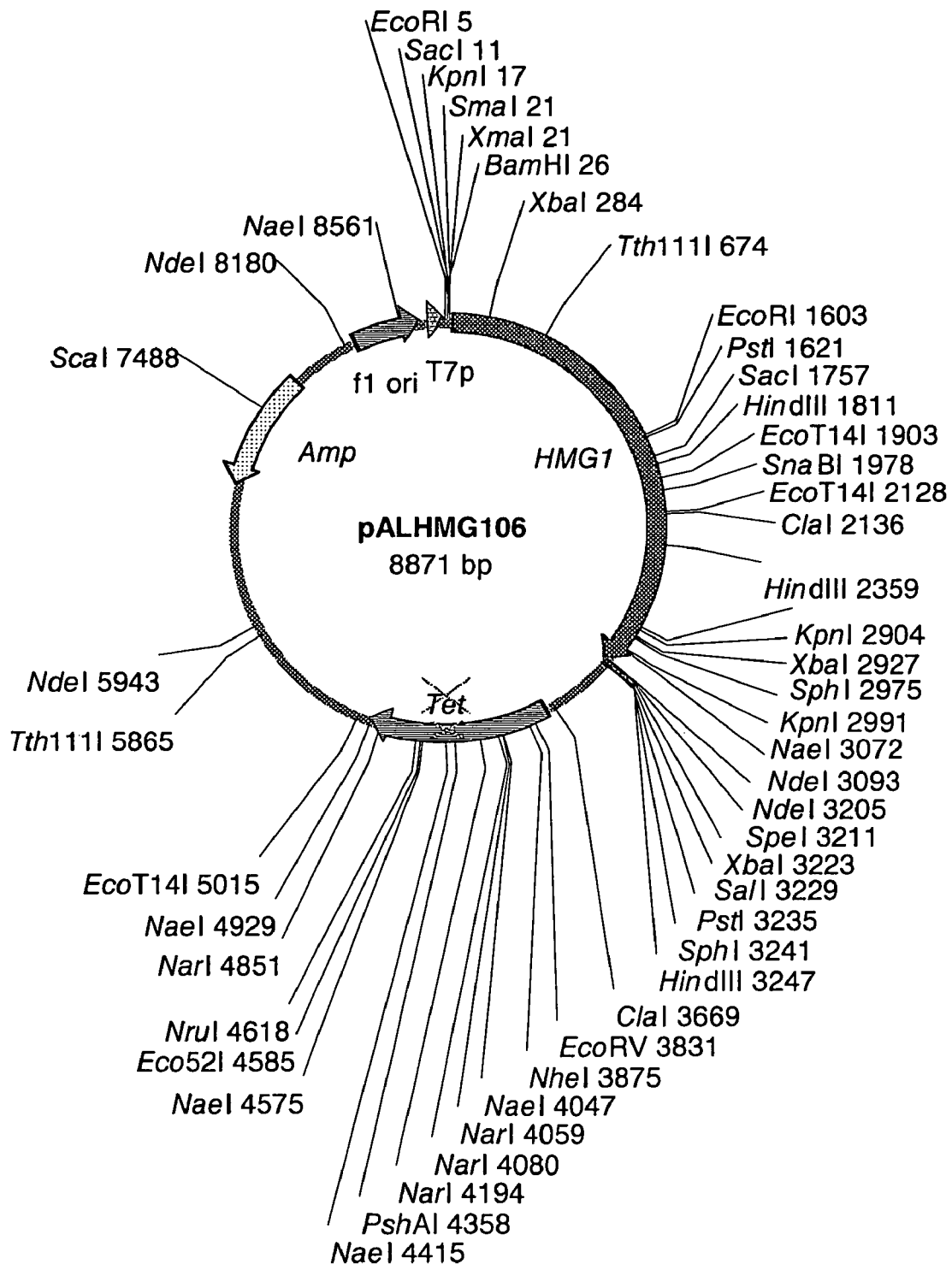
FIG. 9 is a physical map of plasmid pALHMG106. The tetracycline resistance marker gene (Tet) is shown crossed out to indicate its inactivation during construction of the plasimid.

The plasmid where the sequence within the HMG1 region had been corrected was designated pALHMG106 (FIG. 9).

(7) Cloning of Mevalonate Kinase Gene

An approximately 1.3 kbp fragment encoding *S. cerevisiae* mevalonate kinase gene ERG12 (SEQ ID NO: 28) was amplified by PCR using cDNA as a template. The PCR primers used are as follows.

```
Primer 1 (ATM-1):
                                    (SEQ ID NO: 64)
5'-AAC TGC AGA TGT CAT TAC CGT TCT TAA CTT C-3'

Primer 2 (ATM-2):
                                    (SEQ ID NO: 65)
5'-CCG AGC TCT TAT GAA GTC CAT GGT AAA TTC G-3'
(Underlined portions indicate restriction enzyme
recognition sites.)
```

The resultant fragment was digested with PstI and SacI, purified by agarose gel electrophoresis, and then cloned into the PstI-SacI site of pT7Blue. By these procedures, ERG12 was inserted into pT7Blue in the opposite direction to that of lacZ in this plasmid (FIG. 8). The nucleotide sequence of the cloned fragment was sequenced and compared with the corresponding sequence registered at SGD. As a result, no PCR error was found.

The plasmid DNA prepared was designated pT7ERG12.

(8) Cloning of Phosphomevalonate Kinase Gene

An approximately 1.3 kbp fragment encoding *S. cerevisiae* ERG8 (SEQ ID NO: 29) was amplified by PCR using cDNA as a template. The PCR primers used are as follows.

```
Primer 1 (YSCE-1):
                                    (SEQ ID NO: 66)
5'-AAC TGC AGA TGT CAT TAC CGT TCT TAA CTT C-3'

Primer 2 (YSCE-2):
                                    (SEQ ID NO: 67)
5'-CCG AGC TCT TAT GAA GTC CAT GGT AAA TTC G-3'
```

The PCR fragment was purified by agarose gel electrophoresis and then cloned into pT7Blue-T by T/A ligation. By these procedures, ERG8 was inserted into pT7Blue-T in the opposite direction to that of lacZ in this plasmid (FIG. 8). The nucleotide sequence of the cloned fragment was determined and compared with the corresponding sequence registered at SGD. As a result, the following PCR errors were found: A70C, A72G, G146A, C171G, G224C, A306G, T387C, G574T, C637G, C638C, G729A, G739A, T759A, A879C and A1222G. Of these errors, A70C and A72G caused an amino acid error of T24P; G146A caused an amino acid error of G49E; G224C caused an amino acid error of S75T; G574T caused an amino acid error of A192S; C637G and G638C caused an amino acid error of R213A; G739A caused an amino acid error of D247N; and A1222G caused an amino acid error of T408A.

The plasmid DNA prepared was designated pT7ERG8.

(9) Cloning of Diphosphomevalonate Decarboxylase Gene

An approximately 1.2 kbp fragment encoding *S. cerevisiae* diphosphomevalonate decarboxylase gene ERG19 (MVD1) (SEQ ID NO: 30) was amplified by PCR using cDNA as a template. The PCR primers used are as follows.

```
Primer 1 (SCU-1):
                                    (SEQ ID NO: 68)
5'-AAC TGC AGA TGA CCG TTT ACA CAG CAT CCG T-3'

Primer 2 (SCU-2):
                                    (SEQ ID NO: 69)
5'-CGG AAT TCT TAT TCC TTT GGT AGA CCA GTC T-3'
(Restriction enzyme recognition sites are under-
lined.)
```

The amplified fragment was digested with PstI and EcoRI, purified by agarose gel electrophoresis, and cloned into the PstI-EcoRI site of pT7Blue. By these procedures, ERG19 (MVD1) was inserted into pT7Blue in the direction opposite to that of lacZ in this plasmid (FIG. 8). The nucleotide sequence of the cloned fragment was determined and compared with the corresponding sequence registered in SGD. As a result, no PCR error was found.

The plasmid DNA prepared was designated pT7ERG19.

(10) Cloning of Isopentenyl Diphosphate Δ-Isomerase Gene (10-1) *S. cerevisiae*-Derived IPP Δ-Isomerase Gene IDI1

An approximately 0.9 kbp fragment encoding *S. cerevisiae* IDI1 gene (SEQ ID NO: 31) was amplified by PCR using cDNA as a template. As PCR primers, Primer 1 (SCIPP-1) and Primer 2 (SCIPP-2) were used.

```
Primer 1 (SCIPP-1):
                                    (SEQ ID NO: 70)
5'-ATG ACT GCC GAC AAC AAT AGT AT-3'

Primer 2 (SCIPP-2):
                                    (SEQ ID NO: 71)
5'-TTA TAG CAT TCT ATG AAT TTG CC-3'
```

The PCR fragment was purified by agarose gel electrophoresis and then cloned into pT7Blue-T by T/A ligation. By these procedures, IDI1 was inserted into pT7Blue-T in the opposite direction to that of lacZ in this plasmid (FIG. 8). The nucleotide sequence of the cloned fragment was determined and compared with the corresponding sequence registered at SGD. As a result, no PCR error was found.

The plasmid DNA prepared was designated pT7ID1.

(10-2) *E. coli*-Derived IPP Δ-Isomerase Gene idi

Using, as a template, plasmid p3-47-13 (Hemmi et al., (1998) *J. Biochem.* 123, 1088-1096) in which a genomic DNA comprising *E. coli* ORF182 (an open reading frame expected to encode a polypeptide homologous to IPP Δ-isomerase; gene name: idi) is cloned, an ORF182 fragment of approx. 0.55 kbp was amplified by PCR. The PCR was performed in the co-presence of Perfect Match Polymerase Enhancer for 30 cycles each consisting of 45 sec at 95° C., 1 min at 60° C. and 2 min at 72° C. The PCR primers used are as follows.

```
Primer 1 (SacII-ORF182(1-23)):
                                    (SEQ ID NO: 72)
5'-TCC CCG CGG ATG CAA ACG GAA CAC GTC ATT TT-3'

Primer 2 (XbaI-ORF182(549-525)):
                                    (SEQ ID NO: 73)
5'-TGC TCT AGA TTA TTT AAG CTG GGT AAA TGC AGA-3'
(Underlined portion indicates a restriction enzyme
recognition site.)
```

Figure 10:
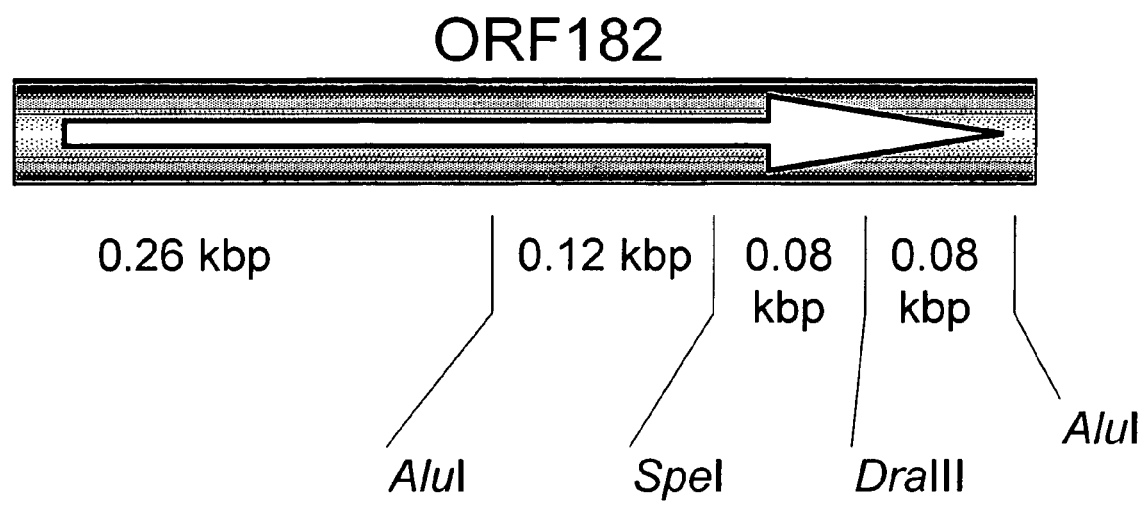
FIG. 10 is a diagram showing the restriction enzyme recognition sites on ORF182 fragment.

The PCR product was digested with SpeI, DraIII and AluI, and then cut by agarose gel electrophoresis. As a result, the physical map as shown in FIG. 10 was obtained, which was consistent with the nucleotide sequence data (SEQ ID NO: 32) of the ORF182 fragment (idi) in the EcoGene Database of *Escherichia coli* Sequence and Function, University of Miami. Then, the amplified 0.55 kbp fragment was digested with SacII and XbaI, purified by agarose gel electrophoresis and cloned into the SacII-XbaI site of pRS435GAP and pRS445GAP. The resultant plasmids were designated pRS435GAP-ORF182 and pRS445GAP-ORF182, respectively.

The *E. coli* IPPΔ-isomerase gene (SEQ ID NO: 32) was previously called ORF182 (according to NCBI BLAST search; GenBank Accession No. AE000372), but Hahn et al., (1999) *J. Bacteriol.*, 181: 4499-4504 designated this gene idi. As plasmids in which idi is cloned, p3-47-11 and p3-47-13 described in Hemmi et al., (1998) *J. Biochem.*, 123: 1088-1096 were used in the invention.

EXAMPLE 3

Cloning of Mutant Genes (1) Conversion of *Escherichia coli* FPP Synthase Gene into GGPP Synthase Gene (Cloning of Mutants of FPP Synthase Gene)

The codon encoding the amino acid residue Tyr at position 79 of the polypeptide encoded by *E. coli* ispA was modified by substitution mutation using pALispA4, pALispA8, pAL-ispA15, pALispA16 and pALispA18 obtained in section (1-2) in Example 2 and according to the protocol described in the "Protocols and Applications Guide, 3rd edition, 1996 Promega, ISBN 1-882274-57-1" published by Promega. The following oligonucleotides for introducing mutations (sometimes referred to as "mutation oligo(s)") were prepared by chemical synthesis.

```
ISPA-D:
                                    (SEQ ID NO: 74)
5'-ATC ATG AAT TAA TGA GTC AGC GTG GAT GCA TTC AAC
GGC GGC AGC-3'

ISPA-E:
                                    (SEQ ID NO: 75)
5'-ATC ATG AAT TAA TGA TTC AGC GTG GAT GCA TTC AAC
GGC GGC AGC-3'
```

-continued

ISPA-M:
(SEQ ID NO: 76)
5'-ATC ATG AAT TAA TGA CAT AGC GTG GAT GCA TTC AAC GGC GGC AGC-3'

In the above mutation oligo ISPA-M, nucleotides at positions 16-18 (the underlined 3 nucleotides) correspond to the codon encoding the amino acid residue Tyr at position 79 of the wild-type FPP synthase; these three nucleotides are designed so that this codon encodes Met. Similarly, mutation oligos ISPA-D and IDPA-E are designed so that this codon encodes Asp and Glu, respectively. The nucleotides at positions 26-31 (the underlined 6 nucleotides) in the above mutation oligos are designed so that an EcoT22I (NsiI) site is newly formed as a result of the substitution mutation. With this site, mutant genes can be easily discriminated by restriction enzyme mapping. These mutation oligos are phosphorylated at 5' end with T4 polynucleotide kinase (Promega) and purified by gel filtration with Nick Column (Pharmacia Biotech, Uppsala, Sweden) before use. In the introduction of mutations, Cm repair oligo (Promega) was used as repair oligo and Tet knockout oligo (Promega) as knockout oligo. Cm repair oligo, Tet knockout oligo and the mutation oligo were annealed to alkali-denatured pALispA16, which was then transformed into *E. coli* ES1301 mutS (Promega). Plasmid DNA was prepared from *E. coli* colonies growing in the presence of 20 µg/ml of Cm (chloramphenicol) and transformed into *E. coli* JM109. Then, plasmid DNA was prepared from colonies growing on agar plates containing 20 µg/ml of Cm. Those plasmids comprising the substitution mutant type ispA (called "ispAm") created by using pALispA4 as a template and ISPA-D, ISPA-E or ISPA-M as a mutation oligo are designated p4D, p4E and p4M, respectively. Likewise, those plasmids prepared by using pALisp8 as a template were designated p8D, p8E and p8M, respectively; those plasmids prepared by using pALisp15 as a template were designated p15D, p15E and p15M, respectively; those plasmids prepared by using pALisp16 as a template were designated p16D, p16E and p16M, respectively; and those plasmids prepared by using pALisp18 as a template were designated p18D, p18E and p18M, respectively.

The gene encoding the Y79D mutant type amino acid sequence (SEQ ID NO: 34) is shown in SEQ ID NO: 33; the gene encoding the Y79E mutant type amino acid sequence (SEQ ID NO: 36) is shown in SEQ ID NO: 35; and the gene encoding the Y79M mutant type amino acid sequence (SEQ ID NO: 38) is shown in SEQ ID NO: 37. The thus obtained plasmids were appropriately selected and used.

(2) Cloning of a Mutant of *Bacillus stearothermophilus* FPP Synthase Gene

Expression vectors comprising a substitution mutant of *B. stearothermophilus* FPP synthase gene (fps: SEQ ID NO: 39) was prepared from pFPS(Y81M) disclosed in Ohnuma et al., (1996) *J. Biol. Chem.*, 271, 30748-30754.

pFPS is a plasmid integrating fps downstream of lac promoter in pTV118N (Takara), and this plasmid expresses *B. stearothermophilus* FPP synthase gene in *E. coli* in the presence of IPTG First, Y81M mutation (i.e., substitution mutation that changes Tyr at position 81 of the amino acid sequence encoded by the FPP synthase gene to Met) was introduced into the FPP synthase gene by site-directed mutagenesis [to thereby obtain pFPS(Y81M)]. As a result of the introduction of Y81M mutation, the reaction product specificity of the enzyme encoded in pEPS(Y81M) was changed; here, the FPP synthase gene was modified to a GGPP synthase gene without decrease of the specific activity of the encoded enzyme. Subsequently, pFPS(Y81M) was digested with PshBI and blunt-ended with Klenow enzyme. Then, a 2.7 Kbp fragment containing the transcription unit was purified and inserted into the HincII site of Amp$^r$ gene in pACYC177. The resultant plasmid in which the mutant fps gene fragment was inserted in the same direction as that of Amp$^r$ gene was designated pFPS21m, and the plasmid in which the mutant fps gene fragment was inserted in the opposite direction to that of Amp$^r$ gene was designated pFPS31m (FIG. 11).

(3) Cloning of Deletion Mutants of HMG-CoA Reductase Gene

Figure 4:
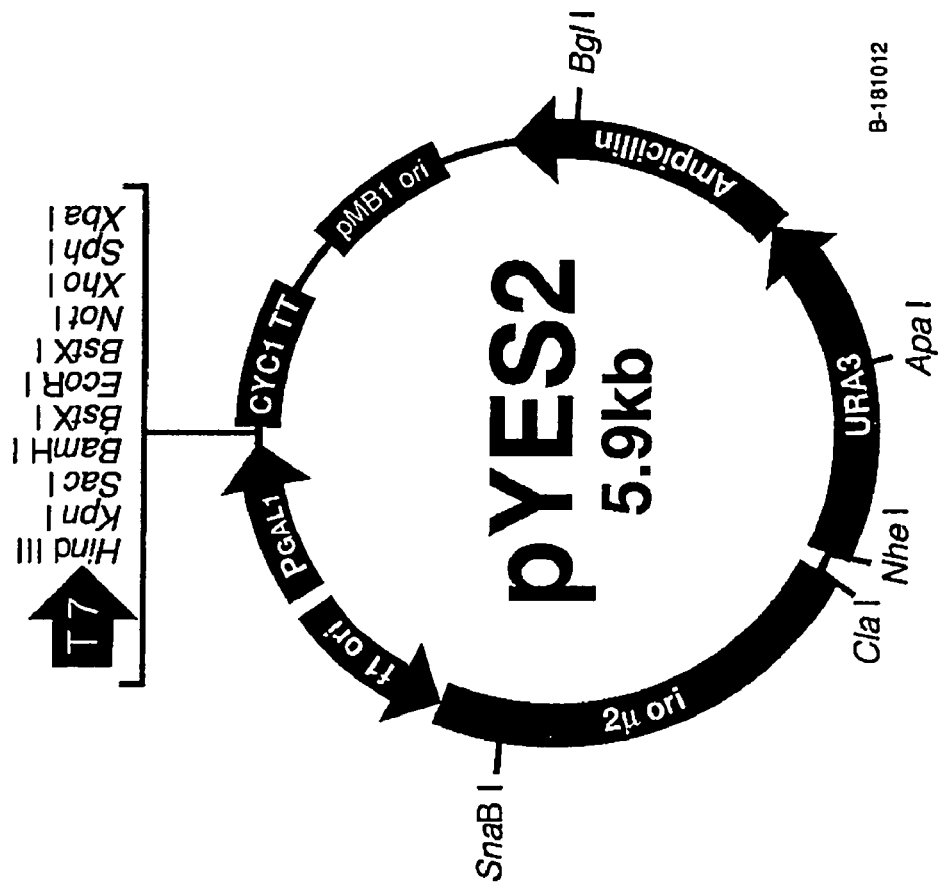
FIG. 4 is a diagram showing plasmid pYES2.

Vectors pRS414PTadh and pRS414TPadh, each comprising a constitutive promoter ADH1p, were digested with restriction enzymes, followed by insertion of HMG1 to thereby prepare plasmids pRS414PTadh-HMG1 and pRS414TPadh-HMG1.

pT7-HMG1 prepared in (5) in Example 2 was digested with BamHI, SalI and ScaI to obtain HMG1' gene having PCR errors. This gene was transferred into the BamHI-XhoI site of pYES2 (Invitrogen, Carlsbad, Calif.) to thereby obtain a recombinant vector pYES-HMG1. The nucleotide sequence within the vector was confirmed to be the nucleotide sequence of SEQ ID NO: 3. pYES is a shuttle vector for expression in yeast having the ori of yeast 2 µmDNA as a replication origin and GAL1 promoter inducible by galactose (FIG. 4).

In order to prepare expression vectors for deletion mutants of HMG-CoA reductase gene having deletion of regions corresponding to transmembrane domains of HMG-CoA reductase, PCR was carried out using pYES-HMG1 prepared above as a template to thereby generate DNA fragments (including the vector moiety) in which a part of the HMG1 coding region is deleted. The resultant fragments were blunt-ended with Klenow enzyme, circularized by self-ligation, and transformed into *E. coli* JM109. Then, plasmid DNA was prepared. Synthetic DNA sequences used as primers and their combinations are shown in Table 1 above.

For each of the plasmid DNA obtained, it was confirmed with 373A DNA sequencer (Perkin Elmer, Foster City, Calif.) that there was no shift in the reading frame of amino acids between the upstream and downstream of the deleted region in HMG1, and that there was no amino acid substitution resulting from PCR errors around the junction site. As a result, the following plasmids were obtained which had no amino acid substitution resulting from PCR errors around the junction site and in which a part of the gene could be deleted without any shift in the reading frame. Deletion mutants of HMG1 gene are expressed as, e.g., "Δ02y" according to the deletion pattern (where y represents any working number), and a pYES2 vector comprising Δ02y is expressed as, e.g., pYHMG026. (This expression method is also applied to other deletion mutants.)

HMG1Δ026: SEQ ID NO: 13
HMG1Δ044: SEQ ID NO: 14
HMG1Δ056: SEQ ID NO: 15
HMG1Δ062: SEQ ID NO: 16
HMG1Δ076: SEQ ID NO: 17
HMG1Δ081: SEQ ID NO: 18
HMG1Δ100: SEQ ID NO: 19
HMG1Δ112: SEQ ID NO: 20
HMG1Δ122: SEQ ID NO: 21
HMG1Δ133: SEQ ID NO: 22

Plasmids:
pYHMG026, pYHMG027, pYHMG044, pYHMG045, pYHMG059, pYHMG062,
pYHMG063, pYHMG065, pYHMG076, pYHMG081, pYHMG083, pYHMG085,
pYHMG094, pYHMG100, pYHMG106, pYHMG107, pYHMG108, pYHMG109,
pYHMG112, pYHMG122, pYHMG123, pYHMG125, pYHMG133 and pYHMG134.

EXAMPLE 4

Subcloning of Genes into Vectors

As *E. coli-S. cerevisiae* YEp shuttle vectors having a constitutive transcription promoter, pRS vectors prepared in Example 1 were used.

(1) Subcloning of FPP Synthase Gene (1-1) *S. cerevisiae*-Derived FPP Synthase Gene ERG20:

pT7ERG20 described in section (1-1) in Example 2 was digested with XbaI and BamHI, and subjected to agarose gel electrophoresis to thereby purify an ERG20 gene fragment of 1.1 kbp. This fragment was inserted into the XbaI-BamHI site of pRS435GAP and pRS445GAP to obtain pRS435GAP-ERG20 and pRS445GAP-ERG20, respectively.

(1-2) *E. coli*-Derived FPP Synthase Gene ispA:

pALispA4 described in section (1-2) in Example 2 was digested with SphI and EcoRI, and subjected to agarose gel electrophoresis to thereby purify an ispA gene fragment of 1.0 kbp. To this fragment, SphI-SacII linker DNA (5'-pTTT CCG CGG AAA CAT G-3'; SEQ ID NO: 86) and EcoRI-Eco52I linker DNA (5'-pAAT TGA CGG CCG TC -3'; SEQ ID NO: 87) were ligated. Then, the fragment was digested with SacII and Eco52I. The resultant SacII-Eco52I fragment of 1.0 kbp was inserted into the SacII-Eco52I site of pRS435GAP and pRS445GAP for subcloning. For each of the subcloned plasmids, recognition sites of SacI, SacII, NdeI, NsiI (EcoT22I) Aor51HI, XbaI, SmaI, BamHI, PstI, NdeI, PvuII and EcoT14I were mapped, followed by selection of plasmids that were constructed as designed. The selected plasmids were designated pRS435GAP-ispA and pRS445GAP-ispA, respectively.

(1-3) *B. stearothermophilus*-Derived FPP Synthase Gene

*B. stearothermophilus*-derived FPP synthase gene was cloned into a vector directly from a genomic PCR fragment.

(2) Subcloning of GGPP Synthase Gene or Mutants Thereof (2-1) *S. cerevisiae*-Derived GGPP Synthase Gene BTS1:

The pT7Blue-T vector described in section (2) in Example 2 was digested with BamHI and SalI to obtain a fragment encoding BTS1, which was then introduced into the BamHI-XhoI site of pYES2 (Invitrogen). The resultant recombinant vector was designated pYESGGPS.

pYESGGPS was digested with BamHI and MluI, and subjected to agarose gel electrophoresis to purify a 1.3 kbp fragment. This fragment was inserted into the BamHI-MluI site of pRS435GAP and pRS445GAP to obtain pRS435GAP-BTS1 and pRS445GAP-BTS1, respectively.

(2-2) *E. coli*-Derived GGPP Synthase Gene (Substitution Mutant Type FPP Synthase Gene) ispAm:

p16M described in section (1) in Example 3 was digested with SphI and EcoRI, and subjected to agarose gel electrophoresis to purify an 1.0 kbp fragment encoding ispAm gene. To this fragment, SphI-SacII linker DNA and EcoRI-Eco52I linker DNA described in section (1-2) in this Example were ligated, followed by digestion with SacII and Eco52I. The resultant SacII-Eco52I fragment (1.0 kbp) was inserted into the SacII-Eco52I site of pRS435GAP and pRS445GAP for subcloning. For each of the subcloned plasmids, recognition sites of SacI, SacII, NdeI, NsiI (EcoT22I) Aor51HI, XbaI, SmaI, BamHI, PstI, PvuII and EcoT14I were mapped, followed by selection of plasmids that were constructed as designed. Of these recognition sites, NsiI (EcoT22I) recognition site is a site that was newly introduced when a substitution mutation was introduced into ispA. If the plasmid can be cut with this restriction enzyme, it is confirmed that the gene in the plasmid is the ispA mutant gene ispAm. The selected plasmids were designated pRS435GAP-ispAm and pRS445GAP-ispAm, respectively.

(3) Subcloning of Acetyl-CoA Acetyltransferase Gene

Acetyl-CoA acetyltransferase gene ERG10 was cloned into pRS vector directly from a genomic PCR fragment.

(4) Subcloning of HMG-CoA Synthase Gene

A 1.5 kbp BamHI-SalI fragment encoding HMGS gene was prepared from pT7HMGS described in section (4) in Example 2, and inserted into the BamHI-SalI site of pRS435GAP and pRS445GAP. The HMGS-subcloned plasmids were examined by KpnI restriction site mapping, followed by selection of plasmids that were constructed as designed. The selected plasmids were designated pRS435GAP-HMGS and pRS445GAP-HMGS, respectively.

(5) Subcloning of HMG-CoA Reductase Gene or Mutants Thereof

The pT7Blue-T vector described in section (5) in Example 2 was digested with BamHI, SalI and ScaI to thereby cut out HMG1' gene encoding a PCR error-type mutant HMG-CoA reductase. This gene was inserted into the BamHI-XhoI site of pYES2 (Invitrogen). The resultant plasmid was designated pYES-HMG1.

Vectors pRS414PTadh and pRS414TPadh, each comprising a constitutive promoter ADH1p, were digested with SmaI and SalI. Then, HMG1 gene was inserted thereinto to prepare pRS414PTadh-HMG1 and pRS414TPadh-HMG1.

Further, pALHMG106 (FIG. 9) described in section (6) in Example 2 was digested with SmaI and SalI, and subjected to agarose gel electrophoresis to purify a 3.2 kbp fragment encoding the PCR error-corrected HMG1 gene. This fragment was inserted into the SmaI-SalI site of pRS434GAP, pRS444GAP, pRS434TEF, pRS444TEF, pRS434PGK and pRS444PGK. Physical maps of the HMG1-subcloned plasmids were examined by restriction enzyme mapping using XhoI, SpeI, NaeI and SphI, and by confirming the nucleotide sequences of the border regions of the inserted 3.2 kbp HMG1 gene. Then, those plasmids constructed exactly as designed were selected and designated pRS434GAP-HMG1, pRS444GAP-HMG1, pRS434TEF-HMG1, pRS444TEF-HMG1, pRS434PGK-HMG1 and pRS444PGK-HMG1, respectively.

Deletion mutants of HMG-CoA reductase gene were obtained from pYES2-derived plasmids incorporating corresponding deletion mutants of HMG1 described in Example 3 and cloned into pRS434GAP in a manner similar to that described in the preceding paragraph.

(6) Subcloning of Mevalonate Kinase Gene

A SmaI-SalI 1.3 kbp fragment encoding ERG12 gene was prepared from pT7ERG12 described in section (7) in Example 2, and inserted into the SmaI-SalI site of pRS435GAP and pRS445GAP. The ERG12-subcloned plasmids were examined by KpnI recognition site mapping, followed by selection of those plasmids constructed exactly as designed. The selected plasmids were designated pRS435GAP-ERG12 and pRS445GAP-ERG12, respectively.

(7) Subcloning of Phosphomevalonate Kinase Gene

A BamI-SalI 1.3 kbp fragment encoding ERG8 gene was prepared from pT7ERG8 described in section (8) in Example 2, and inserted into the SmaI-SalI site of pRS435GAP and pRS445GAP. The ERG8-subcloned plasmids were examined by XbaI recognition site mapping, followed by selection of those plasmids constructed exactly as designed. The selected plasmids were designated pRS435GAP-ERG8 and pRS445GAP-ERG8, respectively.

(8) Subcloning of Diphosphomevalonate Decarboxylase Gene pT7ERG19 described in section (9) in Example 2 was digested with BamHI and SalI, and subjected to agarose gel electrophoresis to purify a BamHI-SalI 1.5 kbp fragment encoding ERG19 gene. This fragment was inserted into the BamHI-SalI site of pRS435GAP and pRS445GAP. The ERG19-subcloned plasmids were examined by XbaI recognition site mapping, followed by selection of those plasmids constructed exactly as designed. The selected plasmids were designated pRS435GAP-ERG19 and pRS445GAP-ERG19, respectively.

(9) Subcloning of Isopentenyl Diphosphate Δ-Isomerase Gene (9-1) *S. cerevisiae*-Derived IPP Δ-Isomerase Gene IDI1:

A BamHI-SalI 0.9 kbp fragment was prepared from pT7IDI1 described in section (10-1) in Example 2 and inserted into the BamHI-SalI site of pRS435GAP and pRS445GAP. The subcloned plasmids were examined by recognition site mapping using NcoI and BamHI, followed by selection of those plasmids constructed exactly as designed. The selected plasmids were designated pRS435GAP-IDI1 and pRS445GAP-IDI1, respectively.

(9-2) *E. coli*-Derived IPP Δ-Isomerase Gene ORF182 (idi):

ORF 182 (idi) was cloned into pRS vector directly from a genomic PCR fragment as described in section (10-2) in Example 2.

EXAMPLE 5

Preparation of AURGG101, AURGG102and AURG703

A 1.9 kbp SalI fragment having a primary structure of GAL1 promoter=BTS1=CYC1 terminator (GAL1p-BTS1-CYC1t) was prepared by PCR using pYESGGPS described in section (2-1) in Example 4 as a template and the following primers PYES2 (1-27) and PYES2 (861-835).

```
PYES2 (1-27):
                                (SEQ ID NO: 88)
5'-GGC CGC AAA TTA AAG CCT TCG AGC GTC-3'

PYES2 (861-835):
                                (SEQ ID NO: 89)
5'-ACG GAT TAG AAG CCG CCG AGC GGG TGA-3'
```

This fragment was inserted into the SalI site of pAUR101 (Takara) to obtain pAURGG115. It was confirmed by DNA sequencing that the BTS1 gene in pAURGG115 had no PCR error.

pAURGG115 was linearized with Eco065I and introduced into A451 strain and YPH499 strain by the lithium acetate method. Then, colonies growing on YPD agar plates (1% yeast extract, 2% peptone, 2% dextrose, 2% agar) containing 1 μg/ml aureobasidin at 30° C. were selected as transformants.

The resultant transformants were cultured again on aureobasidin selection plates for single colony selection.

As a result, two strains AURGG101 and AURGG102 were obtained as A451-derived recombinants. Also, AURGG703 was obtained as a YPH499-derived recombinant. Southern blot hybridization (FIG. 12) and PCR mapping (FIG. 13) described later revealed that BTS1 gene is not integrated in AURGG101 and that AUR1 has been replaced with AUR1-C, a marker gene, in this strain. On the other hand, it was found that GAL1 promoter=BTS1=CYC1 terminator is integrated in the AUR1 locus of AURGG102.

EXAMPLE 6

Creation of EUG Strains

A gene map around squalene synthase gene ERG9 was obtained from SGD. Based on this map, PCR primer DNAs for amplifying DNA fragments for replacing ERG9 transcription promoter (ERG9p) were designed. On the other hand, a 1.8 kbp DNA fragment comprising a transformant selection marker gene URA3 and a transcription promoter GAL1p was prepared by PCR amplification using, as a template, pYES2Δ obtained by digesting pYES2 with NaeI and NheI, blunt-ending with Klenow enzyme and deleting 2 μori by self-ligation.

The primers used in the PCR are as follows.

```
E-MCSf:
                                (SEQ ID NO: 90)
5'-GCC GTT GAC AGA GGG TCC GAG CTC GGT ACC AAG-3'

E-URA3r:
                                (SEQ ID NO: 91)
5'-CAT ACT GAC CCA TTG TCA ATG GGT AAT AAC TGA
T-3'
```

In each of the above primers, an Eam1105I recognition site (the underlined portion) was added so that a 0.7 kbp DNA fragment comprising a downstream portion of YHR189W and a 0.9 kbp DNA fragment comprising an upstream portion of ERG9 can be ligated to the 1.8 kbp fragment by T/A ligation. The YHR189W fragment was prepared by PCR using the following primers YHR189Wf and YHR189Wr, and YPH499 genomic DNA as a template. The ERG9 fragment was prepared by PCR using the following primers ERG9f and ERG9r, and YPH499 genomic DNA as a template. YPH499 genomic DNA was prepared with a yeast genomic DNA preparation kit "Dr. GenTLE™" (Takara).

```
YHR189Wf:
5'-TGT CCG GTA AAT GGA GAC-3'    (SEQ ID NO: 92)

YHR189Wr:
5'-TGT TCT CGC TGC TCG TTT-3'    (SEQ ID NO: 93)

ERG9f:
5'-ATG GGA AAG CTA TTA CAA T-3'  (SEQ ID NO: 94)

ERG9r:
5'-CAA GGT TGC AAT GGC CAT-3'    (SEQ ID NO: 95)
```

Briefly, the 1.8 kbp DNA fragment was digested with Eam1105I and then ligated to the 0.7 kbp DNA fragment. With the resultant fragment as a template, 2nd PCR was carried out using the above-described primers YHR189Wf and E-MCSf. The amplified 2.5 kbp DNA fragment was digested with Eam1105I and then ligated to the 0.9 kbp fragment. With the resultant fragment as a template, 3rd PCR was carried out using the following primers YHR189W-3f and ERG9-2r. As a result, a 3.4 kbp DNA fragment was amplified. This was used as a DNA fragment for transformation.

```
YHR189W-3f:
5'-CAA TGT AGG GCT ATA TAT G-3'    (SEQ ID NO: 96)

ERG9-2r:
5'-AAC TTG GGG AAT GGC ACA-3'      (SEQ ID NO: 97)
```

The vector was introduced into yeast strains using Frozen EZ Yeast Transformation II kit purchased from Zymo Research (Orange, Calif.). The resultant recombinants were cultured on an agar medium (called SGR(-URA) medium) that had been obtained by adding CSM(-URA) (purchased from BIO 101, Vista, Calif.) and adenine sulfate (final concentration 40 mg/L) to SGR medium, at 30° C. Colonies grown on the medium were spread on the same medium again, and single colony isolation was conducted.

The resultant recombinants were designated EUG (ERG9p::URA3-GAL1p) clones. Of these clones, those derived from A451 were designated EUG1 through EUG10; those derived from YPH499 were designated EUG11 through EUG20; those derived from YPH500 were designated EUG21 through EUG30; those derived from W303-1A were designated EUG31 through EUG50; and those derived from W303-1B were designated EUG51 through EUG70.

Those clones that exhibit a decrease in growth rate as a result of repression of ERG9 expression by the glucose repression in SD medium were selected. As a result, EUG5 and EUG8 were obtained from A451; EUG12 was obtained from YPH499; and EUG27 was obtained from YPH500.

Genomic DNA was prepared from EUG5, EUG8, EUG12 and EUG27 using Dr. GenTLE™, and PCR was carried out using the genomic DNA as a template. The results confirmed that the 1.8 kbp PCR fragment comprising URA3 and GAL1p is integrated upstream of the ERG9 coding region in each genome.

EXAMPLE 7

Analysis of Genes and Enzyme Activities

In this Example, the expression of genes in various recombinant yeast clones prepared (for the preparation thereof, see Examples 8-13 describing prenyl alcohol production) was analyzed by various techniques including determination of the enzyme activities of prenyl diphosphate synthases, Northern blot hybridization, Southern blot hybridization, PCR mapping and determination of prenyl alcohol yields.

(1) Southern Blotting

Yeast DNA was prepared using the yeast DNA purification kit Dr. GenTLE™ according to the protocol attached to the kit.

The DNA thus prepared from yeast was digested with NdeI and StuI, followed by 0.8% agarose gel electrophoresis using 3 µg of the DNA per lane. As molecular weight markers, 0.5 µg each of 1 kb ladder and λ/HindIII (both from Promega, Madison, Wis.) were used. After the electrophoresis, the DNA was denatured with alkali, neutralized and transferred onto Hybond N nylon membrane (Amersham, Buckinghamshire, England) by capillary blotting with 20×SSC according to conventional methods. The resultant membrane was subjected to UV irradiation with a UV cross-linker (Stratagene) under conditions of optimal cross-linking, to thereby fix the DNA on the membrane.

(2) Northern Blotting

RNA was prepared according to the method described in *Current Protocols in Molecular Biology*, John Wiley & Sons, pp. 13.12.2-13.12.3 with a modification. The modification was that once prepared RNA samples were further treated with DNase I.

After separation of RNA by formaldehyde-denatured agarose gel electrophoresis, the RNA was transferred onto Hybond N nylon membrane by capillary blotting with 20×SSC according to conventional methods. Five micrograms of total RNA was electrophoresed per lane. As a molecular marker, 20 ng of DIG-RNA Marker I was used. The resultant membrane was subjected to UV irradiation with a UV cross-linker (Stratagene) under conditions of optimal cross-linking, to thereby fix the RNA on the membrane.

(3) PCR Mapping

In order to examine how a fragment from pAURGG115 (a YIp vector prepared in Example 5) is integrated into the genome, PCR was carried out using 0.3-0.6 µg of the yeast DNA prepared above as a template and a combination of synthetic oligonucleotide primers AUR-FWc and AUR-RVc, or AUR-SAL1 and AUR-SAL2. PCR conditions were as follows: 30 cycles of denaturation at 94° C. for 30 sec, annealing at 55° C. for 1 min and extension at 72° C. for 3 min.

```
AUR-FWc:
5'-TCT CGA AAA AGG GTT TGC CAT-3'  (SEQ ID NO: 98)

AUR-RVc:
5'-TCA CTA GGT GTA AAG AGG GCT-3'  (SEQ ID NO: 99)

AUR-SAL1:
5'-TGT TGA AGC TTG CAT GCC TGC-3'  (SEQ ID NO: 100)

AUR-SAL2:
5'-TTG TAA AAC GAC GGC CAG TGA-3'  (SEQ ID NO: 101)
```

(4) Preparation of DIG-Labeled Probe DNAs

As hybridization probes, Probes I, II, III and V were prepared (Table 7).

TABLE 7

Hybridization Probes

| Probe No. | Gene  | Template  | Primer 1            | Primer 2            |
|-----------|-------|-----------|---------------------|---------------------|
| I         | ERG20 | pT7ERG20  | SCFPS1              | SCFPS2              |
| II        | BTS1  | pYES2-GGPS6 | BTS1 (1-21)       | BTS1 (1008-982)     |
| III       | HMG1  | pYHMG1    | HMG1 (1267-1293)    | HMG1 (2766-2740)    |
| V         | AUR1  | pAUR123   | AUR-RV              | AUR-FW              |

Probe I:

Using pT7ERG20 prepared in section (1-1) in Example 2 as a template and SCEPS1 and SCEPS2 as primers, a DIG-labeled probe DNA was synthesized with PCR DIG Probe Synthesis Kit (Roche Diagnostics, Mannheim Germany). Experimental conditions were in accordance with the manufacturer's protocol attached to the kit. PCR was performed for 30 cycles each consisting of 30 sec at 94° C., 1 min 58° C. and 3 min at 72° C. The resultant DIG-labeled probe DNA was subjected to agarose gel electrophoresis to examine the state of synthesis.

Probe II:

A DIG-labeled probe DNA was synthesized in the same manner as described for Probe I, using synthetic oligonucleotides BSTS1(1-21) and BTS1(1008-988) as primers and pYESGGPS (see section(2-1) in Example 4) as a template.

```
BTS1 (1-21):
5'-ATG GAG GCC AAG ATA GAT GAG-3'  (SEQ ID NO: 102)

BTS1 (1008-988):
5'-TCA CAA TTC GGA TAA GTG GTC-3'  (SEQ ID NO: 103)
```

Probe III:

A DIG-labeled probe DNA was synthesized in the same manner as described for Probe I, using synthetic oligonucleotides HMG1 (1267-1293) and HMG1 (2766-2740) as primers and pYES-HMG1 (see section (3) in Example 3) as a template.

```
HMG1 (1267-1293):
                                    (SEQ ID NO: 80)
5'-AAC TTT GGT GCA AAT TGG GTC AAT GAT-3'

HMG1 (2766-2740):
                                    (SEQ ID NO: 104)
5'-TCC TAA TGC CAA GAA AAC AGC TGT CAC-3'
```

Probe V:

A DIG-labeled probe DNA was synthesized in the same manner as described for Probe I, using synthetic oligonucleotides AUR-FW and AUR-RV as primers and pAUR123 (Takara) as a template.

```
AUR-FW:
5'-ATG GCA AAC CCT TTT TCG AGA-3'  (SEQ ID NO: 105)

AUR-RV:
5'-AGC CCT CTT TAC ACC TAG TGA-3'  (SEQ ID NO: 106)
```

(5) Hybridization and Detection of Probes

Southern blot hybridization was carried out at a probe concentration of 20 ng/ml at 42° C. for 24 hr using DIG Easy Hyb (Roche). Northern blot hybridization was carried out at a probe concentration of 100 ng/ml at 50° C. for 24 hr using DIG Easy Hyb. Prior to each hybridization, prehybridization was carried out for 24 hr in DIG Easy Hyb solution at the same temperature used for each hybridization. After the hybridization, the membrane was washed 3 times with 2×SSC, 0.1% SDS at 65° C. for 10 min each, and then 2 times with 0.2× SSC, 0.1% SDS at 65° C. for 15-20 min each. Thereafter, the DIG-labeled probe in the membrane was allowed to generate chemiluminescence by using DIG Luminescent Detection Kit (Roche), followed by exposure of the blot to X-ray film for visualization.

(6) Determination of Enzyme Activities

Of the recombinants prepared, the host strain and the recombinants listed below were used in this experiment. The introduction of individual vectors into the host was carried out according to the lithium acetate method described in *Current Protocols in Molecular Biology*, John Wiley & Sons, Inc., pp. 13.7.1-13.7.2 or by a method using Frozen EZ Yeast Transformation II kit (Zymo Research, Orange, Calif.) (procedures were in accordance with the protocol attached to the kit). In the list below, clone 1-2 was obtained by introducing pYES-HMG1 into A451; clone 3-2 was obtained by introducing pYHMG044 into A451; clone 13-2 was obtained by introducing pYES-HMG1 into AURGG 101; and clone 15-2 was obtained by introducing pYHMG044 into AURGG 101.

No. 1 host strain: A451
No. 2 GAL1p-BTS1 (YIp): AURGG101 (A451, aur1::AUR1-C)
No. 3 GAL1p-BTS1 (YIp): AURGG102 (A451, aur1::BTS1-AUR1-C)
No. 4 GAL1p-HMG1 (YEp): 1-2 (pYES-HMG1/A451)
No. 5 GAL1p-HMG1Δ (YEp): 3-2 (pYHMG044/A451)
No. 6 GAL1p-HMG1 (YEp) & GAL1p-BTS1 (YIp): 13-2 (pYES-HMG1/AURGG101)
No. 7 GAL1p-HMG1Δ (YEp) & GAL1p-BTS1 (YIp): 15-2 (pYHMG044/AURGG101)
No. 8 GAL1p-HMG1 (YEp) & GAL1p-BTS1 (YIp): 24-1 (pYES-HMG1/AURGG102)
No. 9 GAL1p-HMG1Δ (YEp) & GAL1p-BTS1 (YIp): 27-2 (pYHMG045/AURGG102)
No. 10 GAL1p-HMG1Δ (YEp) & GAL1p-BTS1 (YIp): 31-2 (pYHMG076/AURGG102)

Strains/clones No. 1 to No. 10 were precultured separately at 26° C. One milliliter of the preculture was washed with physiological saline, added to 100 ml of a culture broth and cultured in a 300 ml Erlenmeyer flask at 26° C. with reciprocal shaking at 120 times/min. SD medium or SG medium (in which the glucose component of SD medium is replaced with galactose) was used for the cultivation. Recombinants retaining URA3 marker were cultured in SD-U [CSM(-URA)-added SD medium] or SG-U [CSM(-URA)-added SG medium]. AURGG strains were cultured in the presence of aureobasidin at 1 µg/ml.

$OD_{600}$ of cells was determined to monitor cell growth. Cultivation was stopped when $OD_{600}$ value reached about 3-4 (23-52 hours after the start of cultivation). The culture was cooled in ice and then subjected to the preparation of DNA, RNA and crude enzyme solution, as described below.

Cells were harvested from each culture broth by centrifugation and disrupted at 4° C. with glass beads in the same manner as in the preparation of RNA. Then, cells were suspended in sterilized water. The suspension was centrifuged at 12,000 rpm for 10 min with a refrigerated microcentrifuge, and the resultant supernatant was recovered as a crude enzyme fraction. The protein concentration in the crude enzyme fraction was determined by Bio-Rad Protein Assay (Bio-Rad, Hercules, Calif.) using BSA as a standard protein. Briefly, 10 µg of the crude enzyme fraction was reacted in 200µl of the following reaction cocktail at 37° C. for 40 min.

0.125 mM [$^{14}$C]IPP (185 GBq/mol)
0.125 mM Geranyl diphosphate (Sigma Chemical, St. Louis, MO)
100 mM Tris•HCl (pH 7.0)
10 mM NaF, 5 mM $MgCl_2$
5 mM 2-Mercaptoethanol
0.05% Triton X-100
0.005% BSA After the reaction, extended prenyl diphosphate was extracted with water-saturated butanol. An aliquot of the prenyl diphosphate was subjected to determination of radioactivity with a liquid scintillation counter. The remaining sample was dephosphorylated with potato acid phosphatase and developed by thin layer chromatography [plate: LKC18 (Whatman, Clifton, N.J.); developer: $H_2O$/acetone=1:19], followed by visualization of the autoradiogram with Bio Image Analyzer BAS2000 (Fuji Film) to determine relative radioactivity, according to the method of Koyama et al. (Koyama T., Fujii, H. and Ogura, K., 1985, *Meth. Enzymol.* 110:153-155).

(7) Results and Observations (7-1) Southern Blot Hybridization and PCR Mapping

Figure 12:
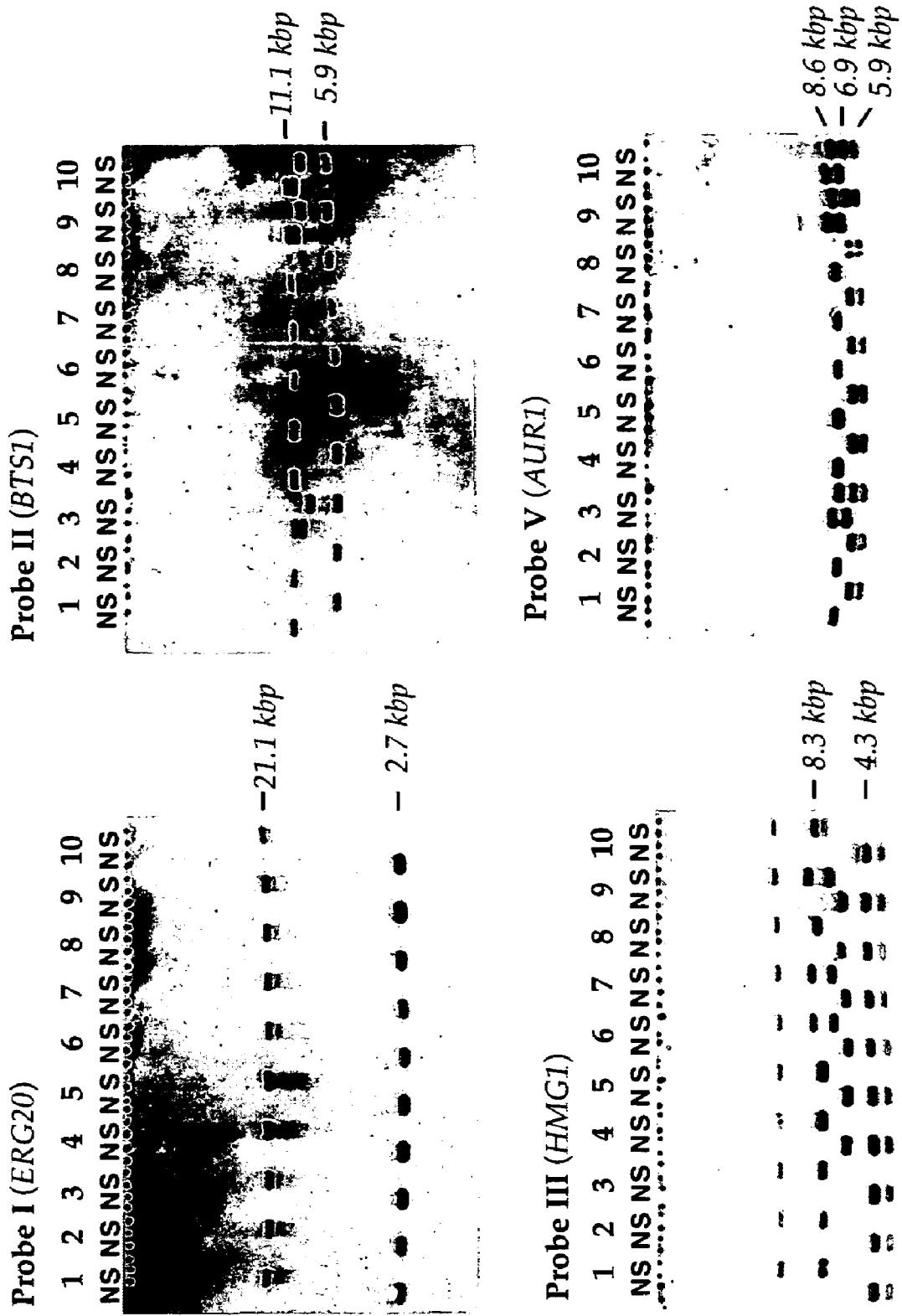
FIG. 12 presents photographs showing results of Southern blot hybridization.
Figure 13:
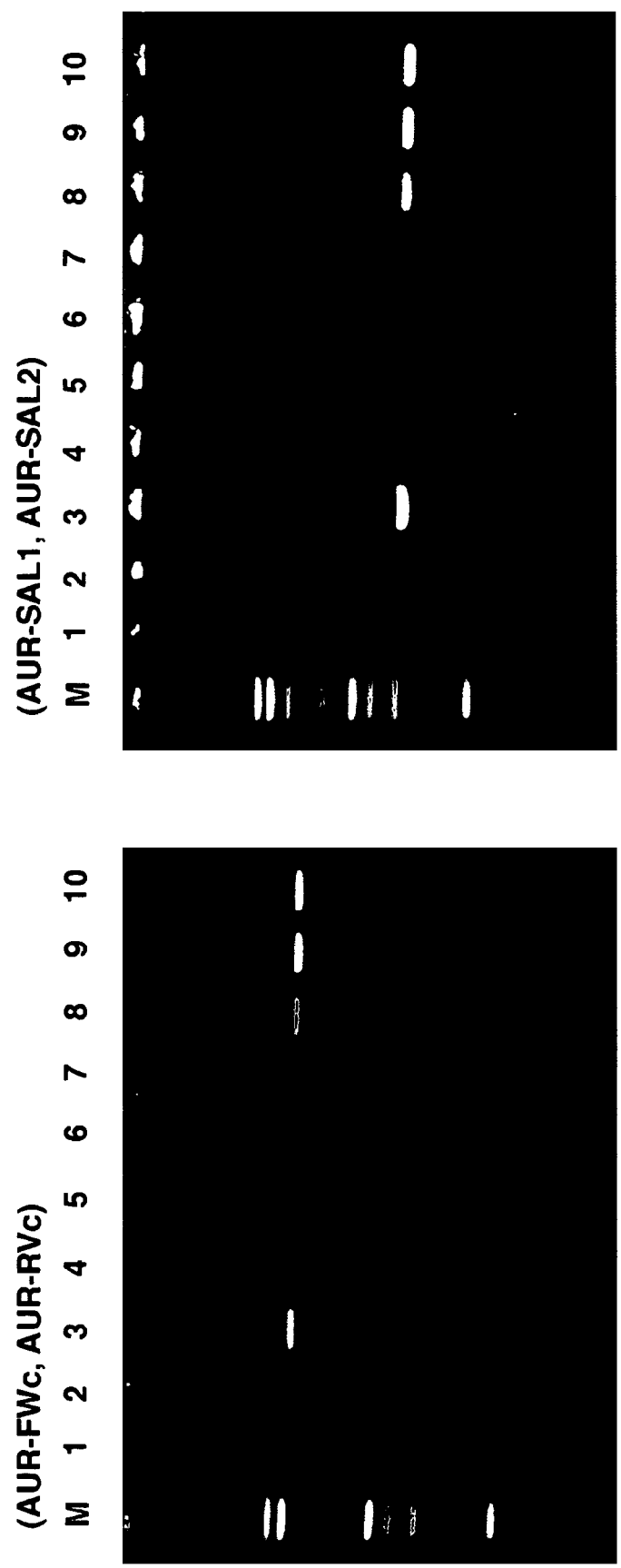
FIG. 13 presents photographs showing results of PCR mapping.

The results of southern blot hybridization are shown in FIG. 12. The results of PCR mapping in the vicinity of AUR1 are shown in FIG. 13. In FIGS. 12 and 13, lanes 1 to 10 correspond to the numbers of strains/clones (No. 1 to No. 7) used in section (6) above.

"N" appearing below each lane number represents DNA digested with NdeI; and "S" represents DNA digested with StuI. DNAs used in individual lanes were prepared from the following strains/clones.

Lane 1: A451; Lane 2: AURGG101; Lane 3: AURGG102; Lane 4: pYES-HMG1/A451; Lane 5: pYHMG044/A451; Lane 6: pYES-HMG1/AURGG101; Lane 7: pYHMG044/AURGG101; Lane 8: pYES-HMG1/AURGG102; Lane 9: pYHMG045/AURGG102; and Lane10: pYHMG076/AURGG102

It was found that ERG20 (FPP synthase gene) is identical in all of the strains/clones tested and that there is no change in the vicinity of ERG20 in the genome of each strain/clone (FIG. 12).

When BTS1 (GGPP synthase gene) and AUR1 were used as probes, it was found that BTS1 is integrated into the region of AUR1 in AURGG102, but the bands appearing in AURGG101 are the same as those appearing in the host strain A451. In AURGG101, only AUR1 gene is replaced with pAUR101-derived AUR1-C gene; it was found that the GAL1-BTS1 fragment is not integrated into the genome of this strain. When duplication of AUR1 locus resulting from genomic integration was detected by PCR, no band was detected in AURGG101 as expected, but the band was detected only in AURGG102 (FIG. 13).

In FIG. 12, when HMG1 was used as a probe, a plasmid-derived band appeared in NdeI-digested DNAs (lanes 4-7). In StuI-digested DNAs, it is expected that a 8.2 kbp band derived from the plasmid (overlapping a 8.3 kbp band derived from the genome) should appear as in clone 1-2 (No. 4). However, a band shift was observed in clone 13-2 (No. 6) and clone 15-2 (No. 7) as a result of recombination between the vicinity of HMG1 in the genome and the introduced plasmid.

From the results of Southern blot hybridization and PCR mapping, the genotypes of the strains/clones used this time can be summarized as shown in Table 8 below. In this Table, "AUR" means a medium to which aureobasidin has been added. "Medium 1" means a medium for preculture, and "Medium 2" means a medium for main culture.

(7-2) Northern Blot Hybridization

Figure 14:
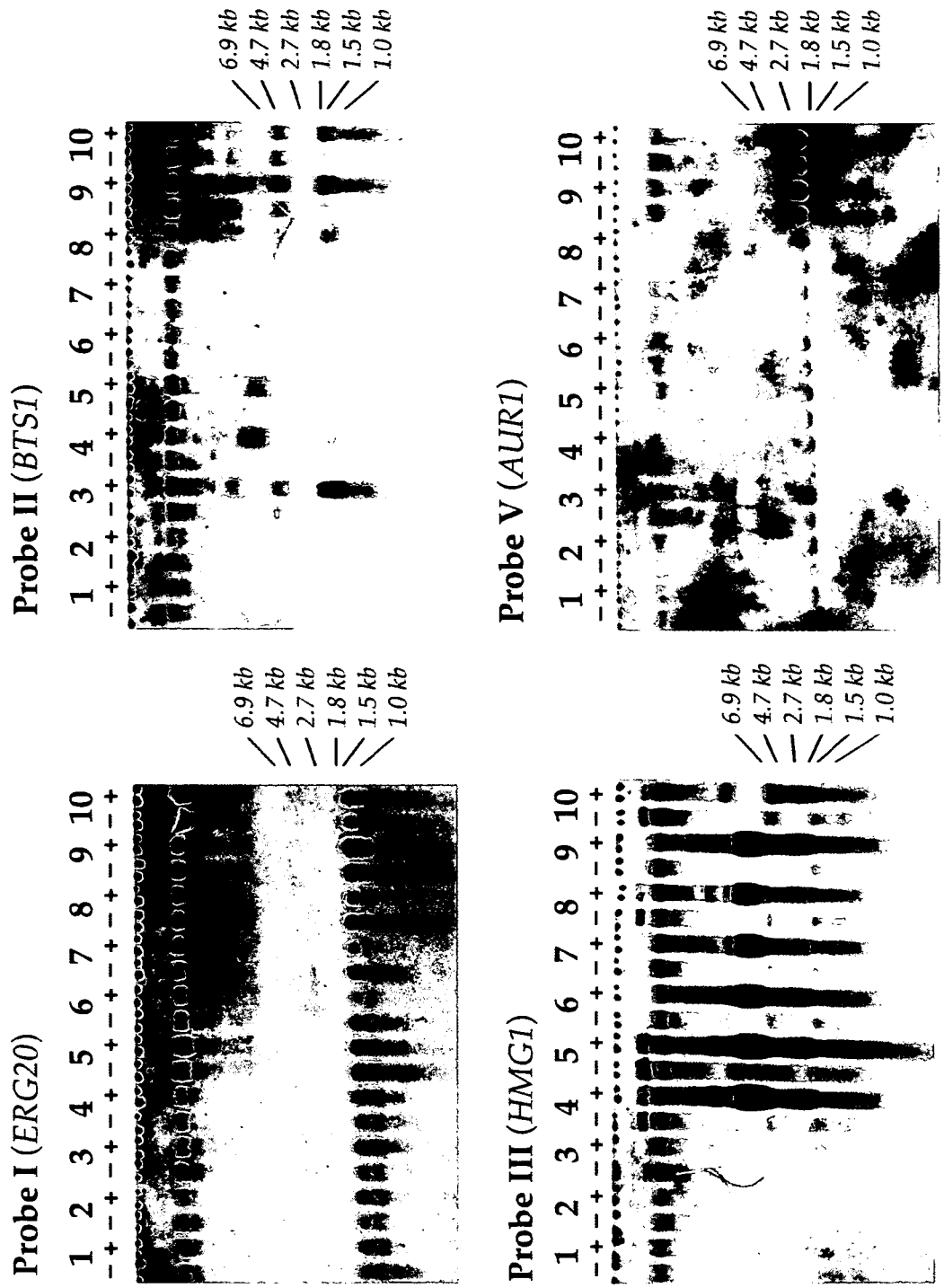
FIG. 14 presents photographs showing results of Northern blotting.

The results of Northern blot hybridization are shown in FIG. 14. Probes I, II, III and V as shown in Table 7 were used in the hybridization.

In FIG. 14, the strains/clones used in lanes 1 to 10 are the same as used in FIG. 12. Mark "−" indicates transcripts in SD medium, and mark "+" indicates transcripts in SG medium.

ERG20 transcript showed a tendency to decrease in clone 13-2 (No. 6) and clone 15-2 (No. 7) when GAL1p transcriptional induction was applied by SG medium.

When the transcription of genes under the control of GAL1 transcription promoter was induced by SG medium, BTS1 transcript increased only in a strain in which GAL1p-BTS1 fragment has been integrated into the genome, i.e., AURGG102 (No. 3).

However, when compared with HMG1 transcript, it is seen that the degree of transcription induction of BTS1 is lower. When transcription was induced by SG medium, HMG1 transcript increased remarkably in clones No. 4 to No. 7 into which GAL1p-HMG1 fragment was transferred by a plasmid.

(7-3) Prenyl Diphosphate Synthase Activities

The activities of prenyl diphosphate synthases in crude enzyme fraction was determined using geranyl diphosphate (GPP) and $^{14}C$-labeled IPP as allylic diphosphate substrates.

Briefly, individual prenyl diphosphates synthesized with GPP and [$^{14}C$] IPP as substrates were dephosphorylated and developed by TLC, followed by examination of the radioactivity of each spot. As a result, FPP synthase activity was high, and next to that, HexPP (hexaprenyl diphosphate) synthase activity was detected that was by far higher than GGPP synthase activity. Then, relative amounts of reaction products were calculated from autoradiogram, followed by calculation of specific activity per gross protein. The results are shown in FIG. 15. In FIG. 15A, the upper panel shows FPP synthase (FPS) activity and the lower panel shows GGPP synthase (GGPS) activity. In FIG. 15B, the upper panel shows HexPP synthase (HexPS) activity and the lower panel shows PTase (total prenyl diphosphate synthase) activity. Gray columns show the results in SD medium, and white columns show the results in SG medium. A large part of the total prenyl diphosphate synthase activity is FPP synthase activity. Increase in this activity caused by SG medium was observed. In particular, FPP synthase activity remarkably increased in clone 13-2 (No. 6) and clone 15-2 (No. 7). As a whole, when GPP is used as an allylic substrate, GGPP synthase activity is about 1/20000

TABLE 8

| Strain/Clone No. | Designation | Integrated gene | Gene in plasmid | Medium 1 | Medium 2 |
|---|---|---|---|---|---|
| 1 | A451 | — | — | SD | SG |
| 2 | AURGG101 | — | — | SD-AUR | SG-AUR |
| 3 | AURGG102 | BTS1 | — | SD-AUR | SG-AUR |
| 4 | 1-2 | — | HMG1 | SD-U | SG-U |
| 5 | 3-2 | — | HMG1Δ044 | SD-U | SG-U |
| 6 | 13-2 | — | HMG1 | SD-U-AUR | SG-U-AUR |
| 7 | 15-2 | — | HMG1Δ044 | SD-U-AUR | SG-U-AUR |
| 8 | 24-1 | BTS1 | HMG1 | SD-U-AUR | SG-U-AUR |
| 9 | 27-2 | BTS1 | HMG1Δ045 | SD-U-AUR | SG-U-AUR |
| 10 | 31-2 | BTS1 | HMG1Δ076 | SD-U-AUR | SG-U-AUR | of FPP synthase activity and about 1/300 of HexPP synthase activity. HexPP synthase activity decreased in SG medium.

EXAMPLE 8

DNA Transfer into Hosts and Cultivation thereof (Expression by *Saccharomyces cerevisiae*)

In this Example, in order to construct systems where mevalonate pathway-related enzyme genes are expressed permanently in *S. cerevisiae* cells, expression vectors for mevalonate pathway-related enzyme genes were prepared by transferring *S. cerevisiae*-derived genes into expression shuttle vectors comprising a constitutive promoter and various auxotrophic markers. Then, the effect of high expression of these genes upon prenyl alcohol production was evaluated.

(1) Transformation of Yeast

The resultant expression vector for each mevalonate pathway-related enzyme gene was introduced into hosts. In the newly introduced vector, each mevalonate pathway-related enzyme gene was inserted downstream of TDH3 transcription promoter TDH3p (=GAPp). As hosts, the following strains/clones were used.
A451
AURGG101
YPH499
AURGG703
YPH500
W303-1A
W303-1B
EUG5 (derived from A451)
EUG8 (derived from A451)
EUG12 (derived from YPH499)
EUG24 (derived from YPH500)
EUG27 (derived from YPH500)
15-2 (pYHMG044/AURGG101) (derived from AURGG101)

(2) Cultivation of Yeast

Each of the mevalonate pathway-related enzyme gene-transferred yeast clones was precultured in an SD selection medium corresponding to the marker gene used. Then, 25 μl of preculture broth was added to 2.5 ml of YM or SG (the glucose component of SD is replaced with galactose) medium and cultured under reciprocal shaking at 130 rpm at 26° C. for 4 days. When the preculture broth was added to SG medium, cells were washed with physiological saline in advance so that no glucose component was brought into the medium. When YPH499-derived clones were used, adenine sulfate was added to the medium to give a concentration of 40 μg/ml.

(3) Pentane Extraction

After the cultivation of mevalonate pathway-related enzyme gene-transferred yeast clones, $OD_{600}$ was determined using 30-fold dilutions of the culture. Then, 2.5 ml of methanol was added thereto and mixed. To this mixture, about 5 ml of pentane was added and agitated vigorously. Then, the resultant mixture was left stationary. The pentane layer was transferred into a fresh, glass test tube. This test tube was placed in a draft where the pentane was evaporated to concentrate the solute. Subsequently, 10μl of 1.0 ml/L undecanol was added thereto as an internal standard substance to thereby prepare a sample for GC/MS.

(4) GC/MS Analysis

The fraction extracted with pentane was separated, identified and quantitatively determined with HP6890/5973 GC/MS system (Hewlett-Packard, Wilmington, Del.). The column used was HP-5MS (0.25 mm×30 m; film thickness 0.25 μm). Analytical conditions were as described below. The same conditions were used for all the GC/MS analyses in this specification.
Inlet temperature: 250° C.
Detector temperature: 260° C.
[MS Zone Temperatures]
 MS Quad: 150° C.
 MS Source: 230° C.
 Mass scan range: 35-200
[Injection Parameters]
 Automated injection mode
 Sample volume: 2μl
 Methanol washing 3 times and hexane washing twice
 Split ratio: 1/20
 Carrier gas: helium 1.0 ml/min
Solvent retardation: 2 min
[Oven Heating Conditions]
 115° C. for 90 sec
 Heating up to 250° C. at 70° C./min and retaining for 2 min
 Heating up to 300° C. at 70° C./min and retaining for 7 min
After 0 hr
Internal standard: 0.01μl of 1-undecanol in ethanol
Reliable standards: (all-E)-Nerolidol (Eisai)
 (all-E)-Farnesol (Sigma)
 (all-E)-Geranylgeraniol (Eisai)
 Squalene (Tokyo Kasei Kogyo)

(5) Results

Relations between genes, expression vectors, hosts, culture conditions (medium, temperature and cultivation period) and maximum GGOH yields are summarized in Table 9 below.

TABLE 9

Maximum GGOH Yield

| Gene | DNA transferred | Host | Medium | Temperature (° C.) | Cultivation period (hr) | GGOH yield (mg/l) |
|---|---|---|---|---|---|---|
| HMG1 | pRS434GAP-HMG1 | Sc A451 | YM | 26 | 96 | 0.348 |
|  | pRS444GAP-HMG1 | Sc A451 | YM | 26 | 96 | 0.128 |
|  | pRS444TEF-HMG1 | Sc A451 | YM | 30 | 96 | 0.069 |
|  | pYES-HMG1 | Sc A451 | SG | 26 | 48 | 0.100 |
|  | pYES-HMG1 | Sc AURGG101 | SG | 26 | 48 | 2.20 |
|  | pRS414TPadh-HMG1 | Sc YPH499 | YM* | 26 | 96 | 0.136 |
| HMG1Δ | pYHMG044 | Sc A451 | SG | 26 | 48 | 0.053 |
|  | pYHMG056 | Sc A451 | SG | 26 | 48 | 0.070 |

TABLE 9-continued

Maximum GGOH Yield

| Gene | DNA transferred | Host | Medium | Temperature (° C.) | Cultivation period (hr) | GGOH yield (mg/l) |
|---|---|---|---|---|---|---|
| | pYHMG062 | Sc A451 | SG | 26 | 48 | 0.065 |
| | pYHMG076 | Sc A451 | SG | 26 | 48 | 0.050 |
| | pYHMG081 | Sc A451 | SG | 26 | 48 | 0.051 |
| | pYHMG112 | Sc A451 | SG | 26 | 48 | 0.064 |
| | pYHMG122 | Sc A451 | SG | 26 | 48 | 0.062 |
| | pYHMG044 | Sc AURGG101 | SG | 26 | 48 | 2.20 |
| | pYHMG044 | Sc AURGG101 | SG | 26 | 96 | 0.729 |
| | pYHMG044 | Sc AURGG101 | SG | 30 | 96 | 7.95 |
| | pYHMG062 | Sc AURGG101 | SG | 26 | 48 | 0.061 |
| | pYHMG076 | Sc AURGG101 | SG | 26 | 48 | 0.062 |
| | pYHMG081 | Sc AURGG101 | SG | 26 | 48 | 0.052 |
| HMG1 + HMG1Δ | pYHMG044 + pRS434GAP-HMG1 | Sc AURGG101 | SG | 26 | 96 | 0.927 |
| | pYHMG044 + pRS444GAP-HMG1 | Sc AURGG101 | SG | 26 | 96 | 0.739 |
| ERG20(YEp) | pRS435GAP-ERG20 | Sc A451 | YM | 26 | 96 | 0.067 |
| | pRS445GAP-ERG20 | Sc A451 | YM | 26 | 96 | 0.073 |
| BTS1(genome) | pAURGG115(Eco065I digested) | Sc A451(AURGG102) | SG | 30 | 96 | 0.075 |
| | pAURGG115(Eco065I digested) | Sc YPH499(AURGG703) | SG | 26 | 96 | 0.093 |
| BTS1(Yep vector) | pRS445GAP-BTS1 | Sc A451 | YM | 26 | 96 | 0.585 |
| | pRS435GAP-BTS1 | Sc YPH499 | YM | 26 | 96 | 0.204 |
| | pRS435GAP-BTS1(=pRS435GG) | Sc W303-1A | YM | 30 | 96 | 0.726 |
| | pRS445GAP-BTS1(=pRS445GG) | Sc W303-1A | YM | 30 | 96 | 0.189 |
| | pRS435GAP-BTS1(=pRS435GG) | Sc W303-1B | YM | 30 | 96 | 0.853 |
| | pRS445GAP-BTS1(=pRS445GG) | Sc W303-1B | YM | 30 | 96 | 0.254 |
| HMG1Δ(YEp) + ERG20(YEp) | pYHMG044 + pRS435GAP-ERG20 | Sc AURGG101 | SG | 26 | 96 | 11.3 |
| | pYHMG044 + pRS445GAP-ERG20 | Sc AURGG101 | SG | 26 | 96 | 1.24 |
| HMG1Δ(YEp) + ispA(YEp) | pYHMG044 + pRS435GAP-ispA | Sc AURGG101 | SG | 26 | 96 | 1.64 |
| | pYHMG044 + pRS445GAP-ispA | Sc AURGG101 | SG | 26 | 96 | 0.900 |
| HMG1(YEp) + BTS1(YEp) | pRS434GAP-HMG1(=pRS435GG) | Sc YPH499 | YM | 26 | 96 | 0.581 |
| | pRS434GAP-HMG1(=pRS445GG) | Sc YPH499 | YM | 26 | 96 | 0.350 |
| | pRS434TEF-HMG1(=pRS435GG) | Sc YPH499 | YM | 26 | 96 | 0.509 |
| | pRS434TEF-HMG1(=pRS445GG) | Sc YPH499 | YM | 26 | 96 | 0.630 |
| HMG1(YEp) + BTS1(genome) | pYES-HMG1 | Sc AURGG102 | SG | 26 | 48 | 0.090 |
| | pYES-HMG1 | Sc AURGG102 | SG | 26 | 96 | 1.280 |
| | pYES-HMG1 | Sc AURGG703 | SG | 26 | 96 | 0.462 |
| HMG1Δ(YEp) + BTS1(YEp) | pYHMG044(=pRS435GG) | Sc AURGG101 | SG | 26 | 96 | 9.76 |
| | pYHMG044(=pRS445GG) | Sc AURGG101 | SG | 26 | 96 | 8.82 |
| HMG1 Δ (YEp) + BTS1(genome) | pYHMG027 | Sc AURGG102 | SG | 26 | 48 | 0.078 |
| | pYHMG044 | Sc AURGG102 | SG | 26 | 48 | 0.120 |
| | pYHMG044 | Sc AURGG102 | SG | 26 | 96 | 0.415 |
| | pYHMG045 | Sc AURGG102 | SG | 26 | 48 | 0.610 |
| | pYHMG059 | Sc AURGG102 | SG | 26 | 48 | 0.099 |
| | pYHMG062 | Sc AURGG102 | SG | 26 | 48 | 0.120 |
| | pYHMG062 | Sc AURGG102 | SG | 26 | 48 | 0.418 |
| | pYHMG063 | Sc AURGG102 | SG | 26 | 48 | 0.110 |
| | pYHMG076 | Sc AURGG102 | SG | 26 | 48 | 0.400 |
| | pYHMG083 | Sc AURGG102 | SG | 26 | 48 | 0.210 |
| | pYHMG094 | Sc AURGG102 | SG | 26 | 48 | 0.170 |
| | pYHMG106 | Sc AURGG102 | SG | 26 | 48 | 0.120 |
| | pYHMG122 | Sc AURGG102 | SG | 26 | 48 | 0.160 |
| | pYHMG123 | Sc AURGG102 | SG | 26 | 48 | 0.097 |
| | pYHMG134 | Sc AURGG102 | SG | 26 | 48 | 0.110 |
| | pYHMG044 | Sc AURGG703 | SG | 26 | 96 | 0.201 |
| | pYHMG062 | Sc AURGG703 | SG | 26 | 96 | 0.243 |
| HMG1Δ (YEp) + ispAm(YEp) | pYHMG044 + pRS435GAP-ispAm | Sc AURGG101 | SG | 26 | 96 | 1.36 |
| HMG1Δ (YEp) + ORF182(YEp) | pYHMG044 + pRS435GAP-ORF182 | Sc AURGG101 | SG | 26 | 96 | 0.626 |
| | pYHMG044 + pRS445GAP-ORF182 | Sc AURGG101 | SG | 26 | 96 | 1.16 |
| HMG1Δ (YEp) + HMGS(YEp) | pYHMG044 + pRS435GAP-HMGS | Sc AURGG101 | SG | 26 | 96 | 1.30 |
| | pYHMG044 + pRS445GAP-HMGS | Sc AURGG101 | SG | 26 | 96 | 0.883 |
| HMG1Δ (YEp) + ERG12(YEp) | pYHMG044 + pRS435GAP-ERG12 | Sc AURGG101 | SG | 26 | 96 | 0.702 |
| | pYHMG044 + pRS445GAP-ERG12 | Sc AURGG101 | SG | 26 | 96 | 1.01 |
| HMG1Δ (YEp) + ERG8(YEp) | pYHMG044 + pRS435GAP-ERG8 | Sc AURGG101 | SG | 26 | 96 | 0.700 |
| | pYHMG044 + pRS445GAP-ERG8 | Sc AURGG101 | SG | 26 | 96 | 2.72 |
| HMG1Δ (YEp) + ERG10(YEp) | pYHMG044 + pRS435GAP-ERG10 | Sc AURGG101 | SG | 26 | 96 | 1.15 |
| | pYHMG044 + pRS445GAP-ERG10 | Sc AURGG101 | SG | 26 | 96 | 1.22 |
| HMG1Δ (YEp) + ERG19(YEp) | pYHMG044 + pRS435GAP-ERG19 | Sc AURGG101 | SG | 26 | 96 | 1.89 |
| | pYHMG044 + pRS445GAP-ERG19 | Sc AURGG101 | SG | 26 | 96 | 1.02 |
| fpsm(Y81M) | pFPSm21 | Ec JM109 | 2 × YT*** | 37 | 16 | 16.1 |
| ispAm(Y79M) | p16M | Ec JM109 | 2 × YT*** | 37 | 16 | 21.9 |
| ispAm(Y79D) | p15D | Ec JM109 | 2 × YT*** | 37 | 16 | 0.12 |
| ispAm(Y79E) | p4E | Ec JM109 | 2 × YT*** | 37 | 16 | 0.26 |
| ispAm(Y79M) + idi | pALispA16m + p3-47-13 | Ec JM109 | 2 × YT | 37 | 16 | 0.07 |
| — | | Sc A451** | | | | 0.02 |

TABLE 9-continued

Maximum GGOH Yield

| Gene | DNA transferred | Host | Medium | Temperature (° C.) | Cultivation period (hr) | GGOH yield (mg/l) |
|---|---|---|---|---|---|---|
| — | | Sc AURGG101 | | | | 0.02 |
| — | | Sc YPH499 | | | | 0.00 |
| — | | Sc YPH500 | | | | 0.00 |
| — | | Sc W303-1A | | | | 0.00 |
| — | | Sc W303-1B | | | | 0.00 |
| — | | Ec JM109 | | | | 0.00 |
| HMG1 | pRS434GAP-HMG1 | Sc EUG8 | YM | 30 | 96 | 0.16 |
| | pRS444GAP-HMG1 | Sc EUG8 | YM | 30 | 96 | 0.12 |
| | pRS434GAP-HMG1 | Sc EUG12 | YM | 30 | 96 | 1.03 |
| | pRS444GAP-HMG1 | Sc EUG12 | YM | 30 | 96 | 1.02 |
| | pRS434GAP-HMG1 | Sc EUG12 | YM | 30 | 96 | 0.55 |
| | pRS434GAP-HMG1 | Sc EUG27 | YM | 30 | 96 | 0.55 |
| | pRS434GAP-HMG1 | Sc EUG27 | YM | 30 | 96 | 0.63 |
| HMG1Δ | pYHMG044 | Sc AURGG101 | YMO | 26 | 157 | 3.58 |
| | pRS434GAP-HMG026 | Sc EUG5 | YM | 30 | 96 | 0.09 |
| | pRS434GAP-HMG044 | Sc EUG5 | YM | 30 | 96 | 0.09 |
| | pRS434GAP-HMG056 | Sc EUG5 | YM | 30 | 96 | 0.11 |
| | pRS434GAP-HMG062 | Sc EUG5 | YM | 30 | 96 | 0.13 |
| | pRS434GAP-HMG076 | Sc EUG5 | YM | 30 | 96 | 0.15 |
| | pRS434GAP-HMG081 | Sc EUG5 | YM | 30 | 96 | 0.14 |
| | pRS434GAP-HMG100 | Sc EUG5 | YM | 30 | 96 | 0.18 |
| | pRS434GAP-HMG112 | Sc EUG5 | YM | 30 | 96 | 0.34 |
| | pRS434GAP-HMG122 | Sc EUG5 | YM | 30 | 96 | 0.13 |
| | pRS434GAP-HMG133 | Sc EUG5 | YM | 30 | 96 | 0.71 |
| | pRS434GAP-HMG026 | Sc EUG12 | YM | 30 | 96 | 0.63 |
| | pRS434GAP-HMG044 | Sc EUG12 | YM | 30 | 96 | 0.44 |
| | pRS434GAP-HMG056 | Sc EUG12 | YM | 30 | 96 | 0.4 |
| | pRS434GAP-HMG062 | Sc EUG12 | YM | 30 | 96 | 0.45 |
| | pRS434GAP-HMG076 | Sc EUG12 | YM | 30 | 96 | 0.55 |
| | pRS434GAP-HMG081 | Sc EUG12 | YM | 30 | 96 | 0.49 |
| | pRS434GAP-HMG100 | Sc EUG12 | YM | 30 | 96 | 0.44 |
| | pRS434GAP-HMG112 | Sc EUG12 | YM | 30 | 96 | 0.53 |
| | pRS434GAP-HMG122 | Sc EUG12 | YM | 30 | 96 | 0.5 |
| | pRS434GAP-HMG133 | Sc EUG12 | YM | 30 | 96 | 0.44 |
| BTS1(Yep vector) | pRS435GG | Sc EUG8 | YM | 30 | 96 | 1.4 |
| | pRS435GG | Sc EUG12 | YM | 30 | 96 | 1.58 |
| | pRS435GG | Sc EUG27 | YM | 30 | 96 | 1.53 |
| FPS genes | pFPSm21 | Ec JM109 | 2 × YT*** | 37 | 16 | 16.1 |
| | pFPSm31 | Ec JM109 | 2 × YT*** | 37 | 16 | 6.9 |
| | p4D | Ec JM109 | 2 × YT*** | 37 | 16 | 0.09 |
| | p4E | Ec JM109 | 2 × YT*** | 37 | 16 | 0.26 |
| | p4M | Ec JM109 | 2 × YT*** | 37 | 16 | 15.5 |
| | p8M | Ec JM109 | 2 × YT*** | 37 | 16 | 0.31 |
| | p15D | Ec JM109 | 2 × YT*** | 37 | 16 | 0.12 |
| | p15E | Ec JM109 | 2 × YT*** | 37 | 16 | 0.21 |
| | p16D | Ec JM109 | 2 × YT*** | 37 | 16 | 0.06 |
| | p16E | Ec JM109 | 2 × YT*** | 37 | 16 | 0.88 |
| | p16M | Ec JM109 | 2 × YT*** | 37 | 16 | 21.9 |
| | p18E | Ec JM109 | 2 × YT*** | 37 | 16 | 0.14 |
| | p18M | Ec JM109 | 2 × YT*** | 37 | 16 | 6 |
| FPS genes + idi | p16M + p3-47-13 | Ec JM109 | 2 × YT | 37 | 16 | 0.07 |
| GGHDEL | pRS445GGHDEL | Sc YPH499 | YM | 30 | 96 | 0.23 |
| FGG fusion | pRS435FGG | Sc YPH499 | YM | 30 | 96 | 0.46 |
| | pRS435FGGHDEL | Sc YPH499 | YM | 30 | 96 | 0.29 |
| GGF fusion | pRS435GGF | Sc A451 | YM | 30 | 96 | 0.28 |
| | pRS435GGF | Sc A451 | YMO | 30 | 96 | 0.48 |
| | pRS435GGF | Sc A451 | YM | 30 | 168 | 0.28 |
| | pRS435GGF | Sc A451 | YMO | 30 | 168 | 1.01 |
| | pRS435GGF | Sc YPH499 | YM | 30 | 96 | 2.1 |
| | pRS435GGF | Sc YPH499 | YMO | 30 | 96 | 1.49 |
| | pRS435GGF | Sc YPH499 | YM | 30 | 168 | 0.37 |
| | pRS435GGF | Sc YPH499 | YMO | 30 | 168 | 2.92 |
| | pRS435GGF | Sc EUG5 | YM | 30 | 96 | 5.2 |
| | pRS435GGF | Sc EUG5 | YMO | 30 | 96 | 4.2 |
| | pRS435GGF | Sc EUG5 | YM(100) | 30 | 96 | 3.5 |
| | pRS435GGF | Sc EUG5 | YM | 30 | 168 | 7.32 |
| | pRS435GGF | Sc EUG5 | YMO | 30 | 168 | 10.1 |
| | pRS435GGF | Sc EUG12 | YM | 30 | 96 | 0.47 |
| | pRS435GGF | Sc EUG12 | YMO | 30 | 96 | 2.38 |
| | pRS435GGF | Sc EUG12 | YM(20) | 30 | 96 | 7.04 |
| | pRS435GGF | Sc EUG12 | YM | 30 | 168 | 1.43 |
| | pRS435GGF | Sc EUG12 | YMO | 30 | 168 | 5.78 |

TABLE 9-continued

Maximum GGOH Yield

| Gene | DNA transferred | Host | Medium | Temperature (° C.) | Cultivation period (hr) | GGOH yield (mg/l) |
|---|---|---|---|---|---|---|
| | pRS435GGFHDEL | Sc A451 | YMO | 30 | 96 | 0.13 |
| | pRS435GGFHDEL | Sc YPH499 | YM | 30 | 96 | 1.9 |
| | pRS435GGFHDEL | Sc YPH499 | YMO | 30 | 96 | 1.69 |
| | pRS435GGFHDEL | Sc YPH499 | YM | 30 | 168 | 0.54 |
| | pRS435GGFHDEL | Sc YPH499 | YMO | 30 | 168 | 2.5 |
| | pRS435GGFHDEL | Sc EUG5 | YM | 30 | 96 | 5.78 |
| | pRS435GGFHDEL | Sc EUG5 | YMO | 30 | 96 | 3.97 |
| | pRS435GGFHDEL | Sc EUG5 | YM(75) | 30 | 96 | 3.94 |
| | pRS435GGFHDEL | Sc EUG5 | YM | 30 | 168 | 6.99 |
| | pRS435GGFHDEL | Sc EUG5 | YMO | 30 | 168 | 10.6 |
| | pRS435GGFHDEL | Sc EUG12 | YM | 30 | 96 | 0.6 |
| | pRS435GGFHDEL | Sc EUG12 | YMO | 30 | 96 | 2.33 |
| | pRS435GGFHDEL | Sc EUG12 | YM(20) | 30 | 96 | 8.01 |
| | pRS435GGFHDEL | Sc EUG12 | YM | 30 | 168 | 1.18 |
| | pRS435GGFHDEL | Sc EUG12 | YMO | 30 | 168 | 5.78 |
| HMG1 + GGF fusion | pRS434GAP-HMG1 + pRS435GGF | Sc A451 | YM | 30 | 96 | 0.55 |
| | pRS434GAP-HMG1 + pRS435GGF | Sc A451 | YMO | 30 | 96 | 0.36 |
| | pRS434GAP-HMG1 + pRS435GGF | Sc A451 | YM | 30 | 168 | 0.93 |
| | pRS434GAP-HMG1 + pRS435GGF | Sc A451 | YMO | 30 | 168 | 1.01 |
| | pRS434GAP-HMG1 + pRS435GGF | Sc A451 | YM(50) | 30 | 168 | 4.54 |
| | pRS434GAP-HMG1 + pRS435GGF | Sc YPH499 | YM | 30 | 96 | 0.79 |
| | pRS434GAP-HMG1 + pRS435GGF | Sc YPH499 | YMO | 30 | 96 | 2.46 |
| | pRS434GAP-HMG1 + pRS435GGF | Sc YPH499 | YM(50) | 30 | 96 | 2.25 |
| | pRS434GAP-HMG1 + pRS435GGF | Sc YPH499 | YMO | 33 | 109 | 128 |
| | pRS434GAP-HMG1 + pRS435GGF | Sc YPH499 | YM | 30 | 168 | 1.28 |
| | pRS434GAP-HMG1 + pRS435GGF | Sc YPH499 | YMO | 30 | 168 | 5.66 |
| | pRS434GAP-HMG1 + pRS435GGF | Sc YPH499 | YM(100) | 30 | 168 | 2.5 |
| | pRS434GAP-HMG1 + pRS435GGFHDEL | Sc A451 | YM | 30 | 96 | 0.54 |
| | pRS434GAP-HMG1 + pRS435GGFHDEL | Sc A451 | YMO | 30 | 96 | 0.41 |
| | pRS434GAP-HMG1 + pRS435GGFHDEL | Sc A451 | YM | 30 | 168 | 0.76 |
| | pRS434GAP-HMG1 + pRS435GGFHDEL | Sc A451 | YMO | 30 | 168 | 3.49 |
| | pRS434GAP-HMG1 + pRS435GGFHDEL | Sc A451 | YM(75) | 30 | 168 | 5.74 |
| | pRS434GAP-HMG1 + pRS435GGFHDEL | Sc YPH499 | YM | 30 | 96 | 1 |
| | pRS434GAP-HMG1 + pRS435GGFHDEL | Sc YPH499 | YMO | 30 | 96 | 2.6 |
| | pRS434GAP-HMG1 + pRS435GGFHDEL | Sc YPH499 | YM(100) | 30 | 168 | 2.85 |
| | pRS434GAP-HMG1 + pRS435GGFHDEL | Sc YPH499 | YM | 30 | 168 | 2.45 |
| | pRS434GAP-HMG1 + pRS435GGFHDEL | Sc YPH499 | YMO | 30 | 168 | 6.16 |

*0.1% ADEKANOL + 5% Glc were added.
**When the host per se was cultured, GGOH was not produced under any culture conditions.
***IPP and DMAPP were added.
In the "Gene" column, "YEp" means that the gene was transferred using a YEp vector, and "genome" means the gene was transferred by genomic integration.
In the above Table, "Ec" in the host column means *E. coli* and "Sc" *S. cerevisiae*.
In the "medium" column, "YM(20)" means that this YM medium has initial sugar composition of 20% Glc-80% Gal and that Glc is further added to this medium at a final concentration of 5% on 2 day of the cultivation. Other combinations of medium and numerical value have similar meaning.

(5-1) Production of GGOH by ERG20 Expression

When pRS435GAP-ERG or pRS445GAP-ERG was introduced into A451, the recombinant produced GGOH at high efficiency. When pRS445GAP-ERG was used, 0.73 mg/L of GGOH was produced (Table 9).

(5-2) Production of GGOH by BTS1 Expression

When pRS435GAP-BTS1 or pRS445GAP-BTS1 was introduced into A451 or YPH499, GGOH yields increased (Table 9) at a high yield. When the host was A451, the recombinant produced 0.10-0.11 mg/L of GGOH on the average and 0.585 mg/L at the maximum (Table 9). Further, when pRS435GAP-BTS1 or pRS445GAP-BTS1 was introduced into W303-1A or W303-1B, 0.19-0.85 mg/L of GGOH was produced at the maximum (Table 9).

(5-3) Production of GGOH by Expression of HMG-CoA Reductase Gene or Mutant Thereof (i) GGOH Production when Constitutive Promoter-Ligated HMG1 Gene Is Transferred into A451
(expressed as "Constitutive Promoter; HMG1; A451"; this way of expression is also applied to other recombinants described below)

Figure 16:
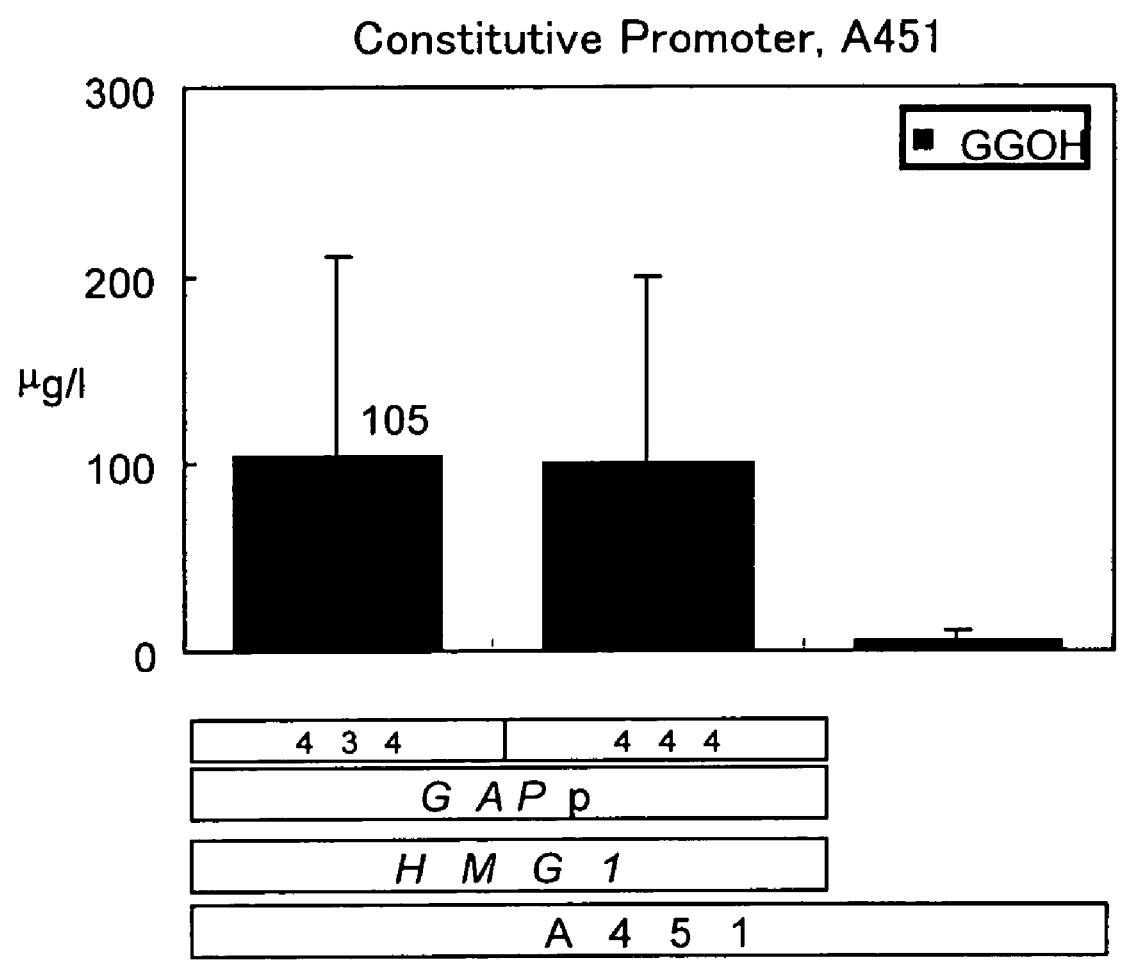
FIG. 16 is a graph showing the GGOH yields of recombinants obtained by transferring into A451 HMG1 gene to which a constitutive promoter is ligated.

The results of determination of GGOH yields are shown in FIG. 16. In FIG. 16, 434 and 444 represent the results when pRS434GAP and pRS444GAP vectors were used, respectively. The right column in this graph indicates the results when the host (A451) before gene transfer was cultured.

These results revealed that GGOH productivity was improved in pRS343GAP-HMG/A451, and that GGOH was produced at 0.105 mg/L on the average and, depending on colonies, at 0.348 mg/L at the maximum by merely activating the transcription of HMG1 gene (Table 9). Thus, this recombinant was found effective for GGOH production.

(ii) Inducible Promoter; HMG1; A451 & AURGG101

Plasmid pYES2-HMG obtained by inserting an HMG1 gene (HMG1', a PCR error type HMG1) into inducible promoter GAL1p-containing vector pYES2 was introduced into A451 and AURGG101 (A451, aur1::AUR1-C).

Figure 17:
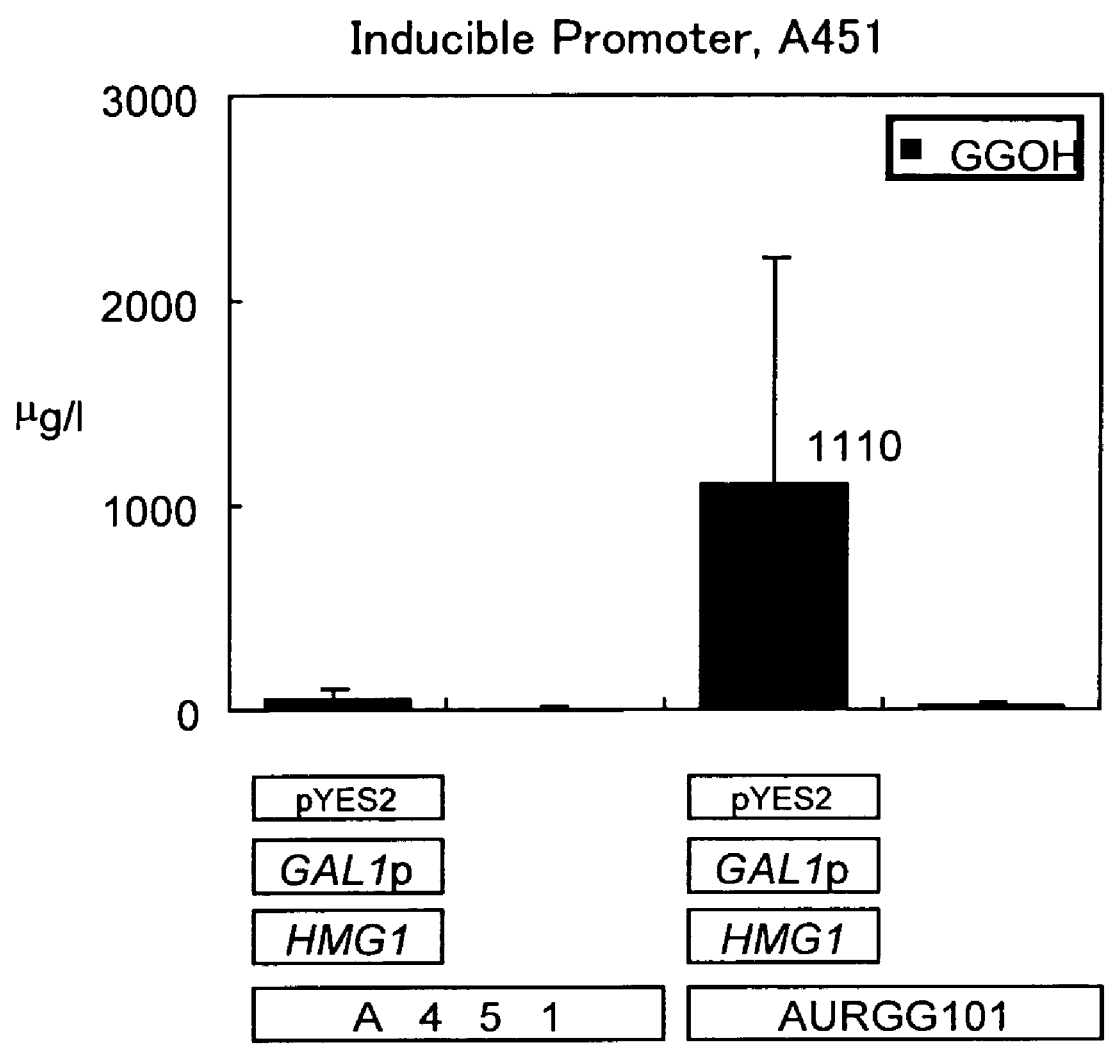
FIG. 17 is a graph showing the GGOH yield of each recombinant obtained by using A451 or AURGG101 (each retaining YEp expression vector comprising GAL1p-HMG1) as a host.

As a result, GGOH high-yielding clones were obtained. The GGOH yield of AURGG101-derived clones reached 1.1 mg/L on the average, and they produced 2.2 mg/L of GGOH at the maximum (FIG. 17).

(iii) Inducible Promoter; HMG1 & BTS1; AURGG102 & AURGG703

Plasmid pYES-HMG obtained by inserting HMG1' into inducible promoter GAL1p-containing vector pYES2 was introduced into A451-derived AURGG102 and YPH499-derived AURGG703 (BTS1 is integrated in the host genome).

Figure 18:
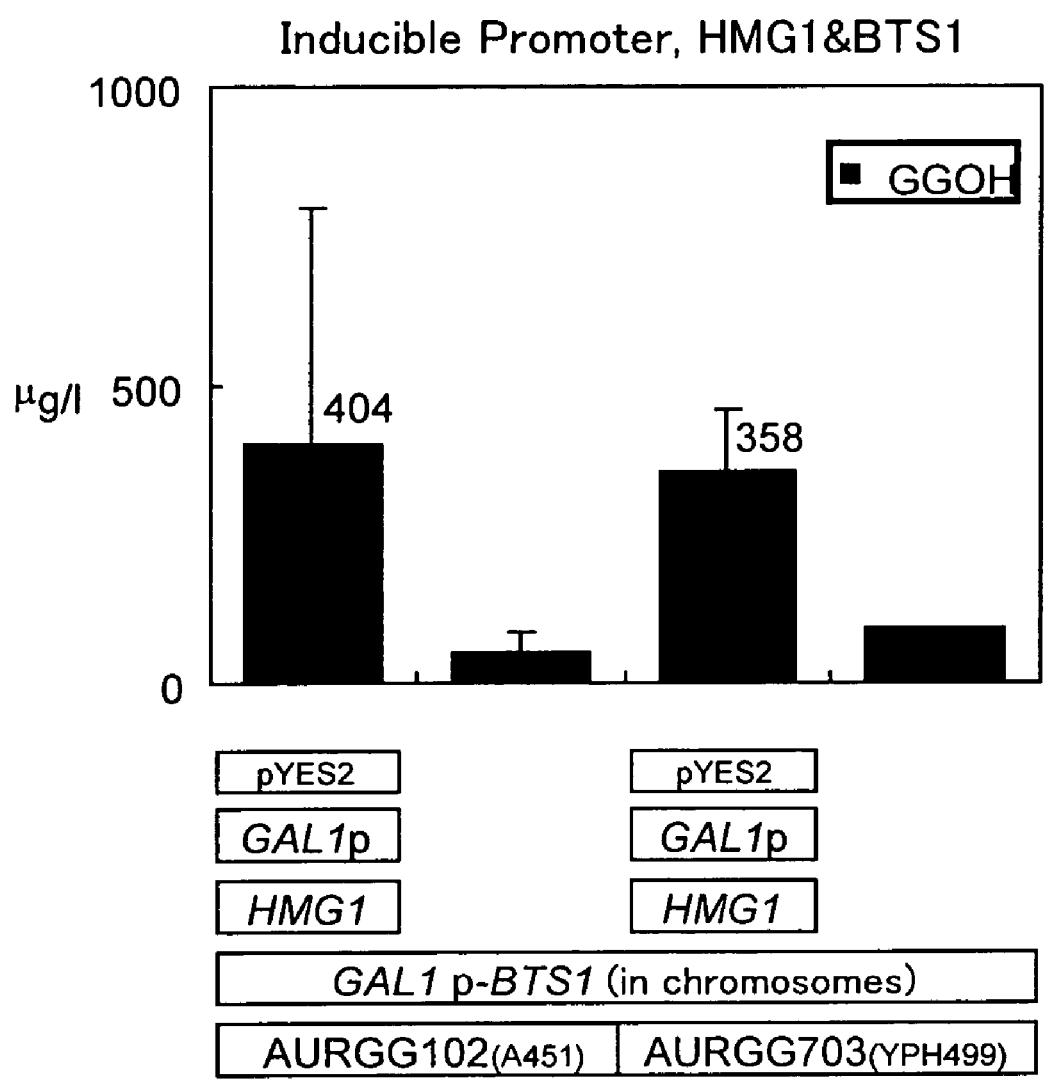
FIG. 18 is a graph showing the GGOH yield of each recombinant obtained by transferring plasmid pYES2-HMG into AURGG102 or AURGG703.

As a result, when either AURGG102 or AURGG703 was used as the host, GGOH high yielding clones were obtained as long as GAL1p was used (FIG. 18). AURGG102-derived clone produced 1.28 mg/L of GGOH at the maximum.

(iv) Inducible Type Promoter; HMG1Δ; A451

The following plasmids obtained by inserting a deletion mutant of HMG1' gene into an inducible promoter GAL1p-containing vector pYES2 were introduced separately into A451.

pYHMG026
pYHMG044
pYHMG056
pYHMG062
pYHMG076
pYHMG081
pYHMG100
pYHMG112
pYHMG122

Figure 19:
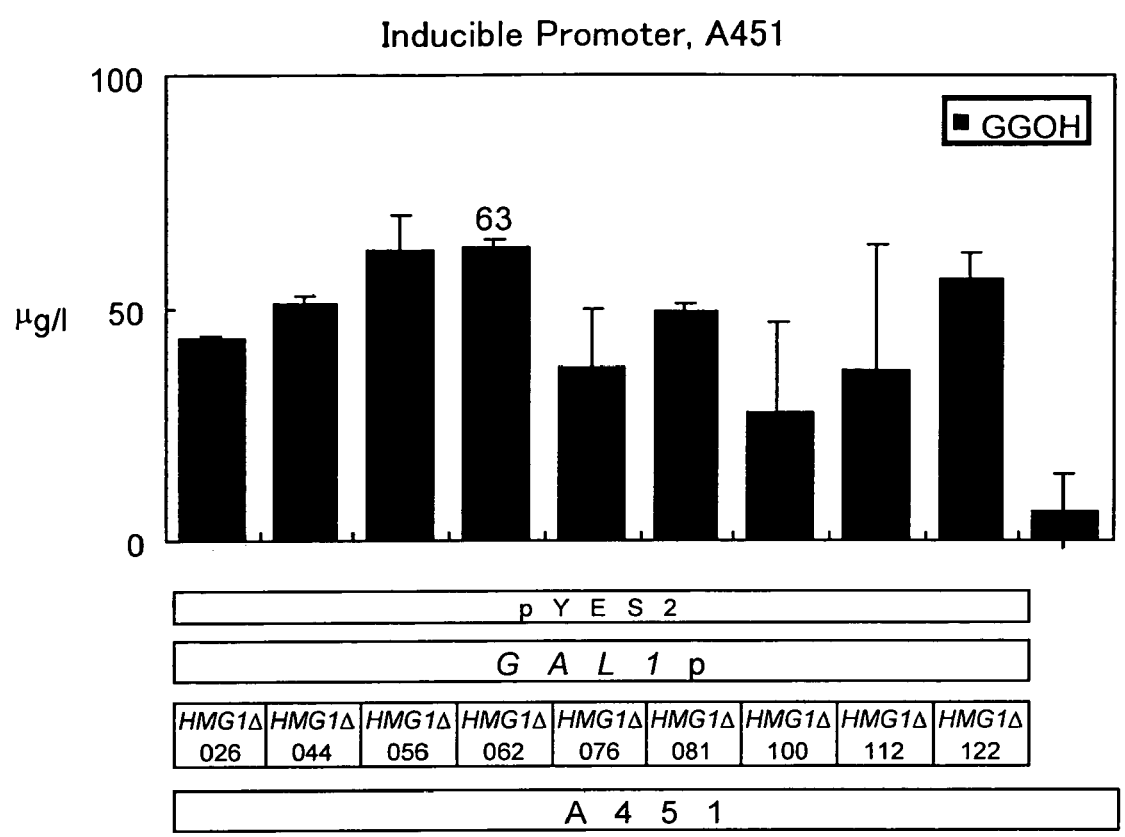
FIG. 19 is a graph showing the GGOH yield of each recombinant when a deletion-type HMG1' gene is inserted into GAL1p-containing pYES2 vector.

The resultant recombinants were cultured in SG medium, followed by determination of GGOH yields (FIG. 19). In FIG. 19, "HMG1Δ026" represents the result when pYHMG026 was introduced into A451. Introduction of other genes is expressed in the same manner.

When deletion mutants of HMG1 gene were expressed with the inducible promoter, GGOH high-yielding clones were obtained. HMG1Δ056 and HMG1Δ062 were effective for GGOH production. (HMG062/A451 clone produced 0.063 mg/L of GGOH on the average.)

(v) Inducible Promoter; HMG1Δ; AURGG101

The following plasmids obtained by inserting a deletion mutant of HMG1' gene into an inducible promoter GAL1p-containing vector pYES2 were introduced separately into AURGG101.

pYHMG026
pYHMG044
pYHMG056
pYHMG062
pYHMG076
pYHMG081
pYHMG100
pYHMG112
pYHMG122
pYHMG133

Figure 20:
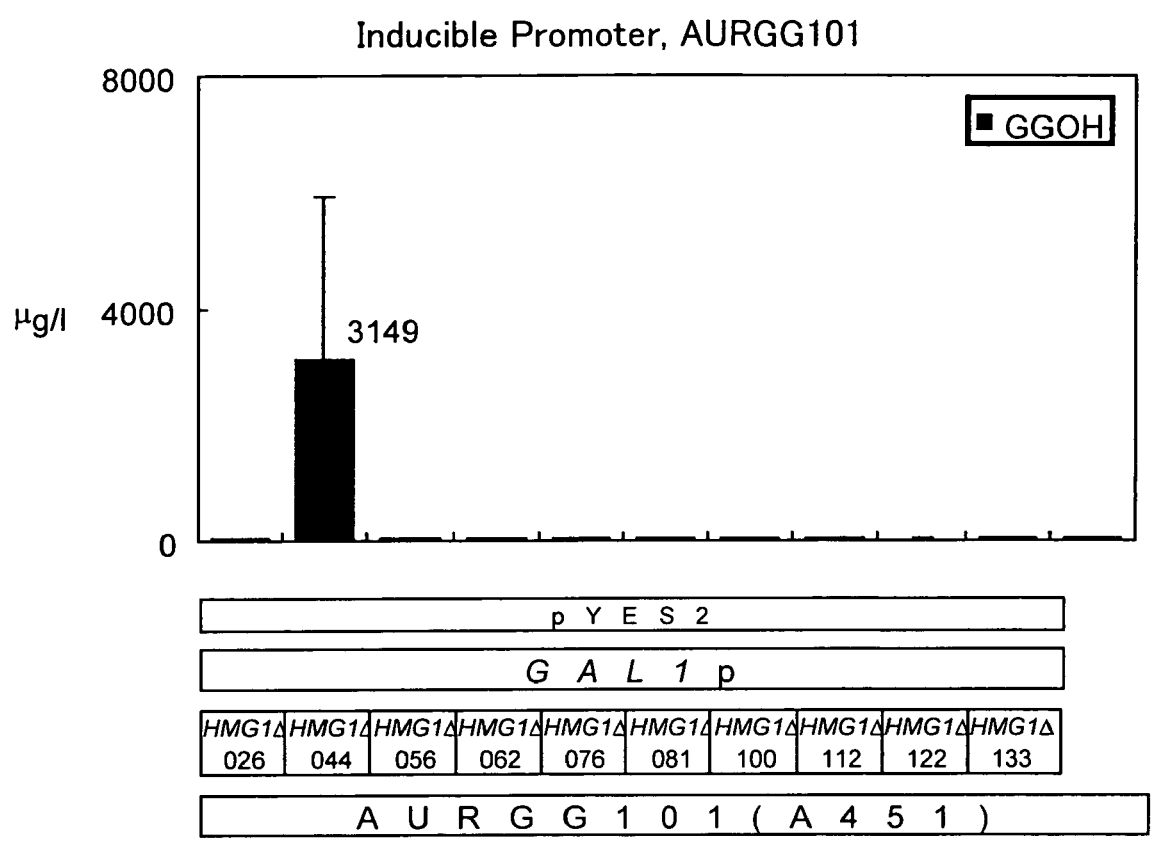
FIG. 20 is a graph showing the GGOH yield of each recombinant when a deletion-type HMG1' gene is inserted into GAL1p-containing pYES2 vector.

The resultant recombinants were cultured in SG medium, followed by determination of GGOH yields (FIG. 20). As a result, GGOH yield of approximately 3.1 mg was observed in HMG1Δ044. In FIG. 20, the right utmost column represents the GGOH yield of the host AURGG101 before gene transfer.

(vi) Inducible Promoter; HMG1Δ & BTS1; AURGG102

The following plasmids obtained by inserting a deletion mutant of HMG1' gene into an inducible promoter GAL1p-containing vector pYES2 were introduced separately into AURGG102.

pYHMG027
pYHMG044
pYHMG045
pYHMG059
pYHMG062
pYHMG063
pYHMG076
pYHMG083
pYHMG094
pYHMG106
pYHMG112
pYHMG123
pYHMG134

The resultant recombinants were cultured in SG medium, followed by determination of GGOH yields.

Figure 21:
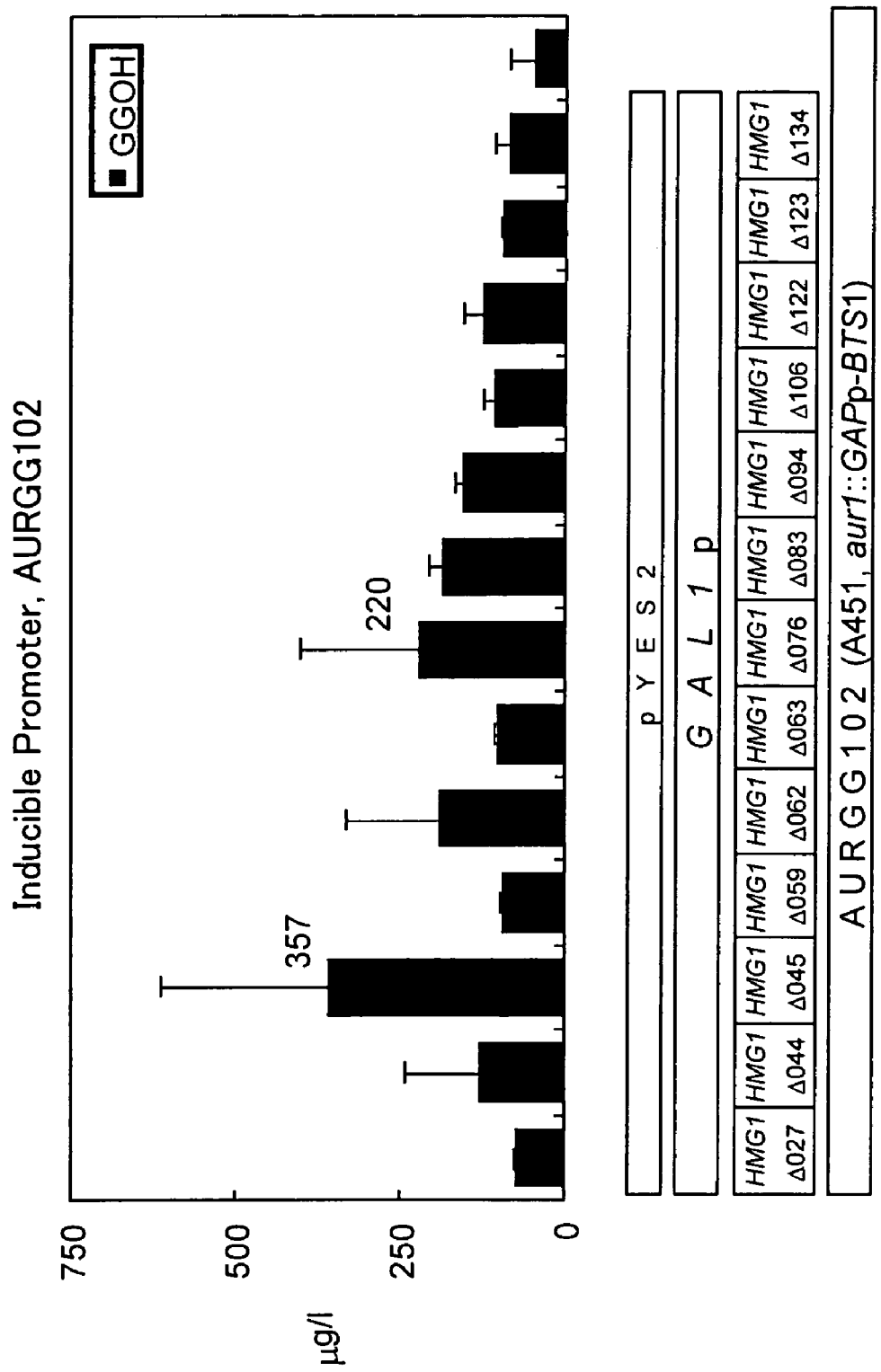
FIG. 21 is a graph showing the GGOH yield of each recombinant when a deletion-type HMG1' gene is inserted into GAL1p-containing pYES2 vector.

As a result, a clone producing 0.36 mg/L of GGOH on the average was obtained when pYHMG045 was introduced (FIG. 21).

(vii) Inducible Promoter; HMG1Δ & BTS1; AURGG703

Plasmids pYHMG044 and pYHMG062 obtained by inserting a deletion mutant of HMG1' gene into an inducible promoter GAL1p-containing vector pYES2 were introduced separately into AURGG703. The resultant recombinants were cultured in SG medium, followed by determination of GGOH yields.

Figure 22:
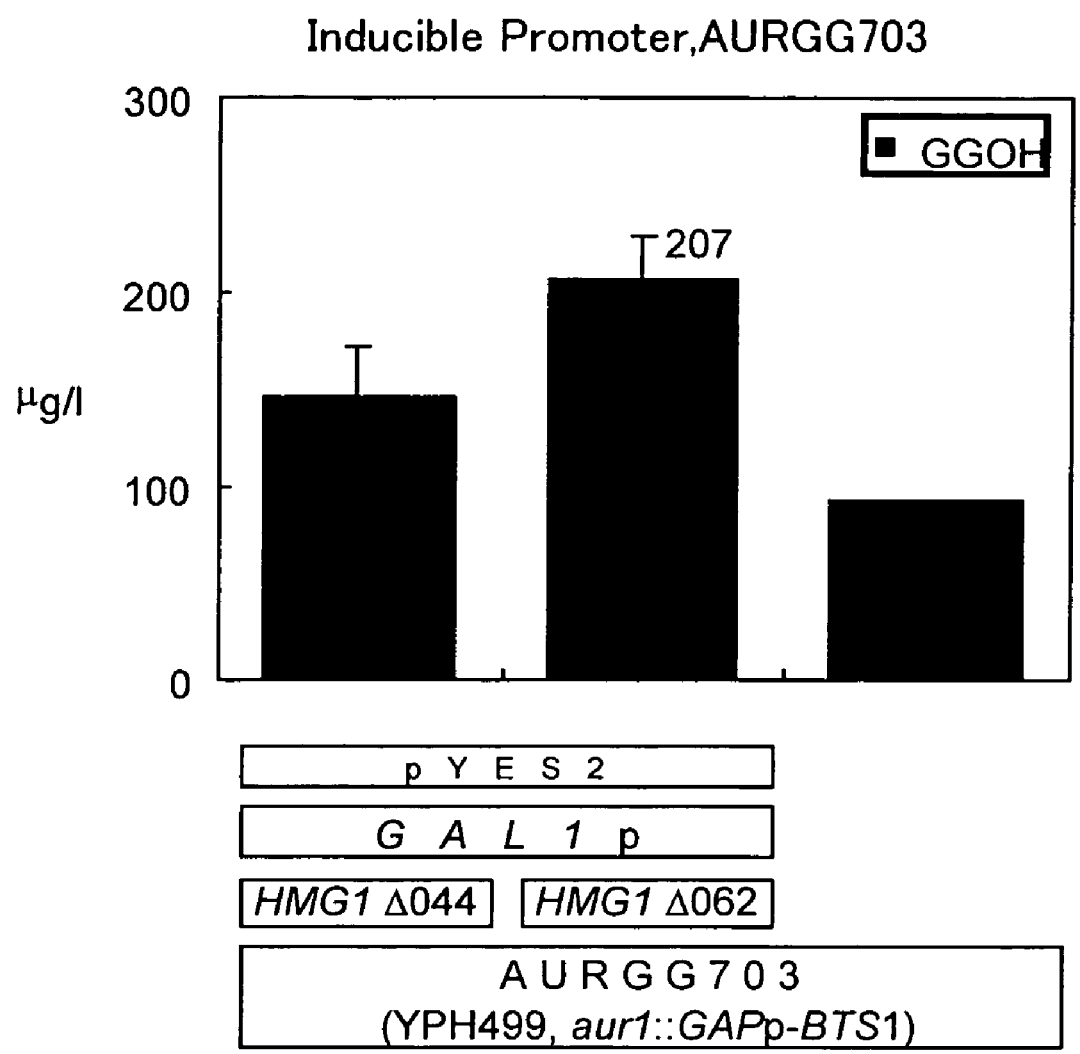
FIG. 22 is a graph showing the GGOH yield of each recombinant when a deletion-type HMG1' gene is inserted into GAL1p-containing pYES2 vector.

As a result, pYHMG062-introduced clone produced 0.21 mg/L of GGOH on the average (FIG. 22).

(5-4) Production of GGOH by Co-Expression of BTS1 and HMG-CoA Reductase Gene pRS435GAP-HMG1 or pRS445GAP-HMG1 was introduced into YPH499 together with BTS1, and GGOH yields of the resultant recombinants were determined. As a result, a clone producing 0.58 mg/L of GGOH at the maximum was obtained when pRS435GAP-HMG1 was introduced (Table 9).

(5-5) Production of GGOH by Co-Expression of ispAm, ORF182(idi), HMGS, ERG8, ERG10 or ERG19 together with a Deletion Mutant HMG-CoA Reductase Gene (HMG1Δ)

ispAm, ORF182(idi), HMGS, ERG8, ERG10 or ERG19 was transferred into AURGG101 together with HMG1Δ, and GGOH yields of the resultant recombinants were determined. As a result, clones producing 0.6-2.7 mg/L of GGOH at the maximum were obtained (Table 9).

EXAMPLE 9

DNA Transfer into Host and Cultivation of the Host

Expression in *Escherichia coli*

The following vectors were transferred into *E. coli* JM109: pALisp4, pALisp15, pALisp16 and pALisp18 as expression vectors for *E. coli* FPP synthase gene ispA; p4D, p4E, p4M, p8M, p15D, p15E, p16D, p16E, p16M, p18E and p18M as expression vector for ispA(Y79D), ispA(Y79E) and ispA(Y79M) that are GGPP synthase genes converted from ispA through a substitution mutation; and pFPSm21 and pFPSm31 as expression vectors for Y81M mutants of *B. stearothermophilus* FPP synthase gene fps. The resultant recombinants were precultured. To a 50 ml medium containing 2×YT and 1 mM IPTG in a 300 ml flask, 0.5 ml of the preculture broth was added. Antibiotics (ampicillin and chloramphenicol), if necessary, 5 mM (about 0.12% (w/v)) IPP and 5 mM DMAPP were added thereto, and the cells were cultured at 37° C. for 16 hr under shaking.

After completion of the cultivation, potato acid phosphatase was added to the culture supernatant and the precipitate disrupted by sonication, followed by extraction of prenyl alcohols with pentane as an organic solvent. Then, the prenyl alcohols were identified and quantitatively determined by GC/MS. Further, in order to ascertain whether prenyl alcohol production can be carried out without the addition of IPP and DMAPP, plasmid p16M obtained in section (1) in Example 3 (designated pALispA16m) and IPPΔ-isomerase gene idi-retaining p3-47-13 obtained in section (10-2) in Example 2 were introduced into *E. coli* JM109, which was then precultured. To a 50 ml medium containing 2×YT and 1 mM IPTG in a 300 ml flask, 0.5 ml of the preculture broth was added. Antibiotics (ampicillin and chloramphenicol) were added thereto, if necessary. Then, the cells were cultured at 37° C. for 16 hr under shaking.

Figure 23:
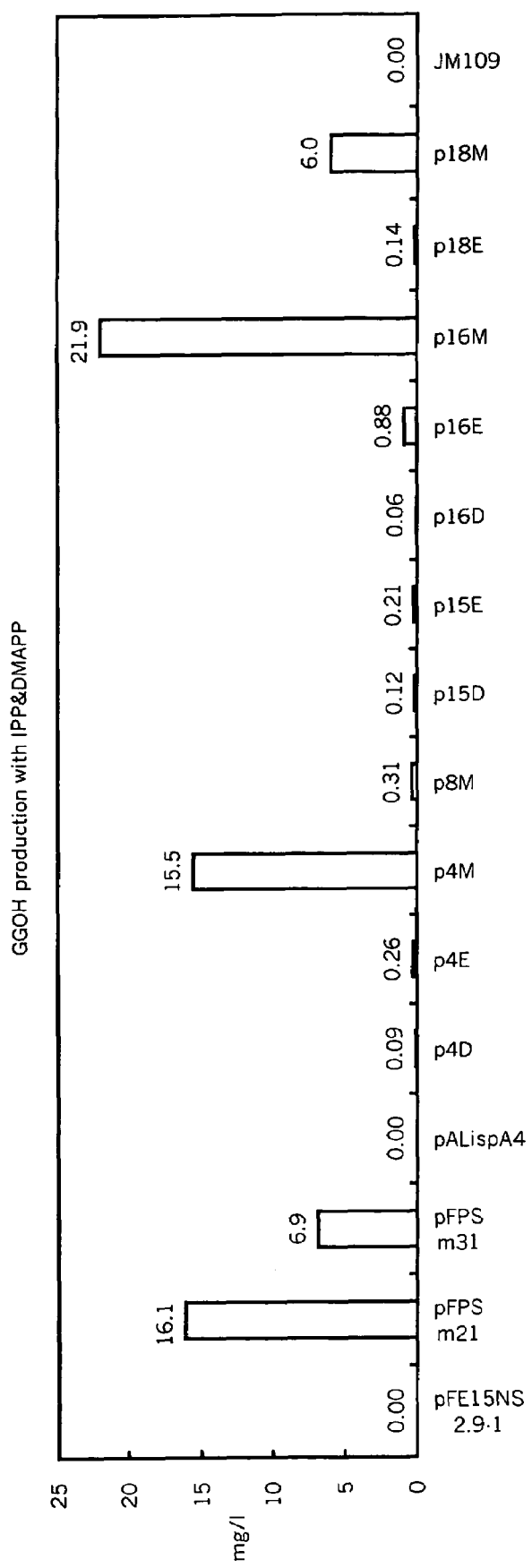
FIG. 23 is a graph showing the GGOH yields of recombinant E. coli retaining p4M, p16M, etc. when cultured in a medium containing IPP and DMAPP.

As a result, GGOH yields when IPP and DMAPP were added to the medium were as follows. When mutant fps was introduced (pFPSm21 and pFPSm31 in FIG. 23), GGOH yields were 16.1 mg/L and 6.9 mg/L. When mutant ispA was introduced, p4M-, p16M- and p18M-retaining JM109 cells produced GGOH at 15.5 mg/L, 21.9 mg/L and 6.0 mg/L, respectively (FIG. 23). In p4M and p16M where Y79M mutation is introduced, a high GGOH activity was recognized in the precipitate fraction. From these results, it is considered that pALispA4 and pALispA16 express FPP synthase gene active in *E. coli* cells, and that their substitution mutant type plasmids p4M and p16M also have sufficient expression activity.

When IPP and DMAPP were not added to the medium, the GGOH yield was 0.07 mg/L in pALispA16m-retaining JM109. When pALispA16m and p3-47-13 (retaining IPPΔ-isomerase gene) were co-expressed, prenyl alcohol productivity was 0.12 mg/L as calculated for GGOH.

EXAMPLE 10

Prenyl Alcohol Production by Expression of Fusion Genes

It is assumed that the GGPP synthase encoded by *S. cerevisiae* BTS1 prefers FPP to DMAPP (dimethyl allyl diphosphate) as a primer substrate. Therefore, it was believed that enforcement of FPP synthesis ability is required simultaneously for enforcing the ability to synthesize GGPP (the precursor of GGOH) from IPP.

In view of this, it was attempted in this Example to create fusion genes composed of BTS1 and ERG20, to express them in *S. cerevisiae* cells and to ascertain whether GGOH productivity improves or not. Further, it was also attempted to incorporate a nucleotide sequence encoding an ER transition signal downstream of BTS1, ERG20 or fusion genes thereof and to examine its effect upon prenyl alcohol production.

(1) Preparation of Plasmid DNA

PCR reactions were carried out using pYESGGPS, which is a pYES2 plasmid incorporating GGPP synthase gene BTS1, and pT7ER20, which is a pT7 plasmid incorporating FPP synthase gene ERG20, as templates. The PCR primers used are as follows.

SacII-BTS1:
(SEQ ID NO: 107)
5'-TCC CCG CGG ATG GAG GCC AAG ATA GAT-3'

BTS1-XhoI:
(SEQ ID NO: 108)
5'-CAA CTC GAG TCA CAA TTC GGA TAA GTG-3'

ERG20HDEL-XbaI:
(SEQ ID NO: 109)
5'-GCT CTA GAG TTC GTC GTG TTT GCT TCT CTT GTA AAC TT-3'

BTS1HDEL-XhoI:
(SEQ ID NO: 110)
5'-TAT CTC GAG TCA CAA TTC GTC ATG TAA ATT GG-3'

BTSI-109I:
(SEQ ID NO: 111)
5'-GCA GGG ACC CCA ATT CGG ATA AGT GGT C-3'

109I-BTS1:
(SEQ ID NO: 112)
5'-GTA GGG TCC CTG GAG GCC AAG ATA GAT G-3'

ERG20-109I:
(SEQ ID NO: 113)
5'-GCA GGG ACC CTT TGC TTC TCT TGT AAA CT-3'

109I-ERG20:
(SEQ ID NO: 114)
5'-GTA GGG TCC TCA GAA AAA GAA ATT AGG AG-3'

-21:
(SEQ ID NO: 115)
5'-TGT AAA ACG ACG GCC AGT-3'

T7:
(SEQ ID NO: 116)
5'-TAA TAC GAC TCA CTA TAG GG-3'

ERG20HDEL-XbaI:
(SEQ ID NO: 117)
5'-GCT CTA GAG TTC GTC GTG TTT GCT TCT CTT GTA AAC TT-3'

BTS1HDEL-XhoI:
(SEQ ID NO: 118)
5'-TAT CTC GAG TCA CAA TTC GTC ATG TAA ATT GG-3'

The nucleotides from position 3 to position 8 of ERG20HDEL-XbaI and the nucleotides from position 4 to position 9 of BTS1HDEL-XhoI (underlined portions) represent the SacII, XhoI or XbaI recognition site for vector ligation. The nucleotides from position 4 to position 10 of BTS1-109I, 109I-BTS1, ERG20-109I and 109I-ERG20 (underlined portions) individually represent the EcoO109I recognition site for fusion gene preparation.

The PCR was carried out in the following reaction solution.

1× KOD-Plus buffer (Toyobo)
0.2 mM dNTPs
0.25 mM MgSO₄
15 pmol Primer 1
15 pmol Primer 2
0.01-0.1 µg Template DNA
1 unit KOD-Plus DNA polymerase (Toyobo)
Total: 50 µl KOD-Plus contains 1.6 µg/µl of KOD antibody. Following an initial denaturation of 2 min at 94° C., the PCR was carried out for 30 cycles each consisting of 15 sec at 94° C., 30 sec for 55° C. and 1 min at 68° C. Then, the solution was retained at 68° C. for 2 min.

Figure 24:
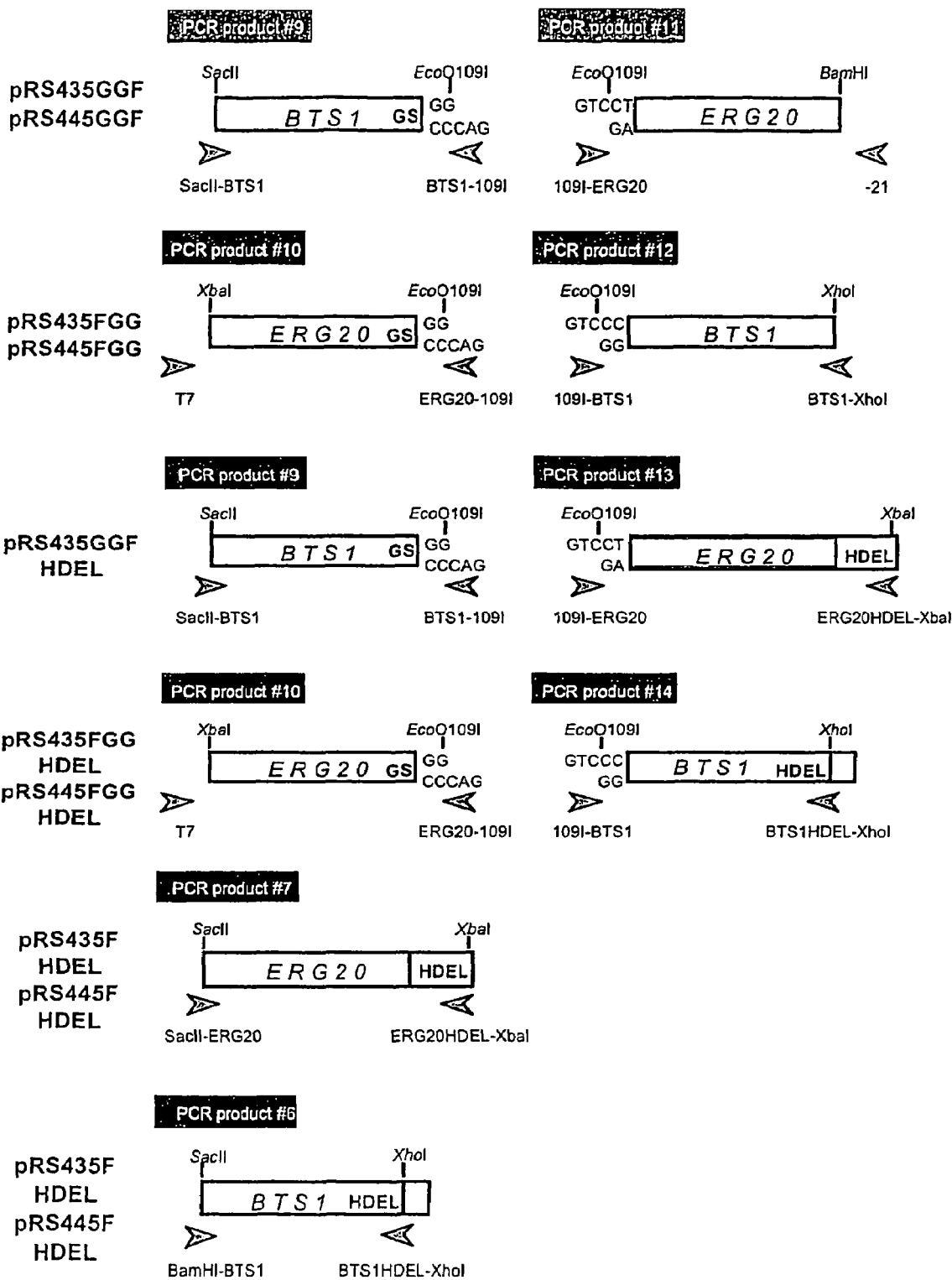
FIG. 24 is a diagram showing the primers used in the creation of BTS1-ERG20 fusion genes, as well as the locations and directions of these primers.

First PCR was carried out using the combinations of a template and primers (Primer 1+Primer 2) as indicated in Table 10 and FIG. 24. The designations of PCR products are also shown in Table 10 and FIG. 24. In FIG. 24, the designations of final plasmids are shown in the leftmost column. The sequences written in gray letters represent amino acid sequences. Of these, GS was introduced into the binding sequence of the fusion gene, and HDEL was inserted as an ER transition signal. Arrowheads indicate the location and direction of individual primers used in the PCR.

TABLE 10

| Template | Primer 1 | Primer 2 | PCR product |
|---|---|---|---|
| pT7ERG20 | SacII-BTS1 | BTS1HDEL-XhoI | #6 |
| pYESGGPS | SacII-ERG20 | ERG20HDEL-XbaI | #7 |
| pYESGGPS | SacII-BTS1 | BTS1-109I | #9 |
| pT7ERG20 | T7 | ERG20-109I | #10 |
| pT7ERG20 | 109I-ERG20 | −21 | #11 |
| pYESGGPS | 109-BTS1 | BTS1-XhoI | #12 |
| pT7ERG20 | 109I-ERG20 | ERG20HDEL-XbaI | #13 |
| pYESGGPS | 109I-BTS1 | BTS1HDEL-XhoI | #14 |

PCR products #9, #10, #11, #12, #13 and #14 were digested with the restriction enzyme Eco0109I. Then, #9 and #11, #10 and #12, #9 and #13, and #10 and #14 were ligated to each other individually. Using the resultant ligation solution as a template and combinations of SacII-BTS1 and −21, T7 and BTS1-XhoI, SacII-BTS1 and ERG20HDEL-XbaI, and T7 and BTS1HDEL-XhoI as primer 1 and primer 2, second PCR was carried out under the same conditions as in the first PCR. As a result, second PCR products #9-#11, #10-#12, #9-#13 and #10-#14 were obtained.

The product #9-#11 was digested with SacII and BamHI, and inserted into the SacII-BamHI site of pRS435GAP and pRS445GAP to obtain pRS435GGF and pRS445GGF, respectively.

The product #10-#12 was digested with XbaI and XhoI, and inserted into the XbaI-XhoI site of pRS435GAP and pRS445GAP to obtain pRS435FGG and pRS445FGG, respectively.

The product #9-#13 was digested with SacII and XbaI, and inserted into the SacII-XbaI site of pRS435GAP to obtain pRS435GGFHDEL.

The product #10-#14 was digested with XbaI and XhoI, and inserted into the XbaI-XhoI site of pRS435GAP and pRS445GAP to obtain pRS435FGGHDEL and pRS445FGGHDEL, respectively.

The product #7 was digested with SacII and XbaI, and inserted into the SacII-XbaI site of pRS435GAP and pRS445GAP to obtain pRS435FHDEL and pRS445FHDEL, respectively.

The product #6 was digested with BamHI and XhoI, and inserted into the BamHI-XhoI site of pRS435GAP and pRS445GAP to obtain pRS435GGHDEL and pRS445GGHDEL, respectively.

It was confirmed by DNA sequencing that each of the resultant plasmid DNAs has the exact nucleotide sequence as designed.

As plasmids for expressing non-fused BTS1 and ERG20 genes separately, pRS435GAP-BTS1 (called pRS435GG), pRS445GAP-BTS1 (called pRS445GG), pRS435GAP-ERG20 (called pRS435F) and pRS445GAP-ERG20 (called pRS445F) were used. As plasmids for expressing HMG1, pRS434TEF-HMG1 and pRS434GAP-HMG1 were used.

(2) Preparation of Recombinants

Recombinants were prepared by introducing the plasmid prepared above into the host using Frozen EZ yeast transformation kit (Zymo Research, Orange, Calif.). As the host, A451, YPH499, AH1 (pRS434GAP-HMG1/A451), YH1 (pRS434GAP-HMG1/YPH499), EUG5 and EUG12 were used.

(3) Determination of Prenyl Alcohol Yields

Recombinants except for EUG strains were inoculated into SD (synthetic dextrose) selection liquid medium. EUG strains were inoculated into SGR medium (a medium in which the glucose component of SD medium is replaced with galactose and raffinose). All of them were cultured at 30° C. to prepare preculture broth. Ten or 25μl of the preculture broth was added to 1.0 or 2.5 ml of YM7+ade medium (YM, pH 7, 40 μg/ml adenine sulfate) or YMO medium [YM7+ade, 1% soybean oil, 0.1% ADEKANOL LG-109 (Asahi Denka Kogyo, Tokyo, Japan)] and cultured at 30° C. for 4 days or 7 days under reciprocal shaking at 130 rpm.

After completion of the cultivation, an equal volume of methanol was added to the culture broth and mixed. Approximately 2 volumes of pentane was added to this mixture, agitated vigorously and then left stationary. The resultant pentane layer was transferred into a fresh glass tube, which was then placed in a draft. Pentane was evaporated therein to condense the solute components. Subsequently, prenyl alcohols were identified and quantitatively determined by GC/MS using undecanol as an internal standard for quantitative determination. At that time, the degree of cell growth was also examined by diluting 20μl of the culture broth 30-fold with water and measuring the absorbance at 600 nm.

For GC/MS analysis, PH6890/5973 GC/MS system (Hewlett-Packard, Wilmington, Del.) was used.

(4) Results and Observations

Maximum GGOH yields obtained by expressing fusion genes are listed in Table 11.

TABLE 11

Maximum GGOH Yield by Fusion Gene Expression

| Gene | Expression vector | Host | Medium | Temperature (° C.) | Cultivation Period (hr) | GGOH yield (mg/l) |
|---|---|---|---|---|---|---|
| 435FHDEL | pRS435FHDEL | Sc EUG5 | YM | 30 | 96 | 0.171 |
|  | pRS445FHDEL | Sc EUG5 | YM | 30 | 96 | 0.106 |
|  | pRS435FHDEL | Sc EUG12 | YM | 30 | 96 | 0.090 |
|  | pRS445FHDEL | Sc EUG12 | YM | 30 | 96 | 0.056 |

TABLE 11-continued

Maximum GGOH Yield by Fusion Gene Expression

| Gene | Expression vector | Host | Medium | Temperature (° C.) | Cultivation Period (hr) | GGOH yield (mg/l) |
|---|---|---|---|---|---|---|
| 435GGHDEL | pRS445GGHDEL + pRS434GAP-HMG1 | Sc YPH499 | YM | 30 | 96 | 0.227 |
| | pRS435GGHDEL | Sc EUG5 | YM | 30 | 96 | 0.168 |
| | pRS445GGHDEL | Sc EUG5 | YM | 30 | 96 | 0.397 |
| | pRS435GGHDEL | Sc EUG12 | YM | 30 | 96 | 0.733 |
| | pRS445GGHDEL | Sc EUG12 | YM | 30 | 96 | 0.825 |
| 435FGG | pRS435FGG | Sc YPH499 | YM | 30 | 96 | 0.271 |
| | pRS445FGG | Sc YPH499 | YM | 30 | 96 | 0.156 |
| | pRS435FGG + pRS434GAP-HMG1 | Sc YPH499 | YM | 30 | 96 | 0.462 |
| | pRS445FGG + pRS434GAP-HMG1 | Sc YPH499 | YM | 30 | 96 | 0.648 |
| | pRS435FGG | Sc EUG5 | YM | 30 | 96 | 2.46 |
| | pRS445FGG | Sc EUG5 | YM | 30 | 96 | 2.17 |
| | pRS435FGG | Sc EUG12 | YM | 30 | 96 | 4.83 |
| | pRS445FGG | Sc EUG12 | YM | 30 | 96 | 3.65 |
| 435GGF | pRS435GGF | Sc A451 | YM | 30 | 96 | 0.354 |
| | pRS435GGF | Sc A451 | YM | 30 | 168 | 0.283 |
| | pRS435GGF | Sc A451 | YMO | 30 | 96 | 0.475 |
| | pRS435GGF | Sc A451 | YMO | 30 | 168 | 1.00 |
| | pRS435GGF + pRS434GAP-HMG1 | Sc A451 | YM | 30 | 96 | 0.546 |
| | pRS435GGF + pRS434GAP-HMG1 | Sc A451 | YM | 30 | 168 | 0.929 |
| | pRS435GGF + pRS434GAP-HMG1 | Sc A451 | YMO | 30 | 96 | 0.362 |
| | pRS435GGF + pRS434GAP-HMG1 | Sc A451 | YMO | 30 | 168 | 1.01 |
| | pRS435GGF | Sc YPH499 | YM | 30 | 96 | 0.458 |
| | pRS435GGF | Sc YPH499 | YM | 30 | 168 | 0.371 |
| | pRS435GGF | Sc YPH499 | YMO | 30 | 96 | 1.49 |
| | pRS435GGF | Sc YPH499 | YMO | 30 | 168 | 2.92 |
| | pRS445GGF | Sc YPH499 | YM | 30 | 96 | 0.317 |
| | pRS435GGF + pRS434GAP-HMG1 | Sc YPH499 | YM | 30 | 96 | 2.10 |
| | pRS435GGF + pRS434GAP-HMG1 | Sc YPH499 | YM | 30 | 168 | 1.28 |
| | pRS435GGF + pRS434GAP-HMG1 | Sc YPH499 | YMO | 30 | 96 | 2.46 |
| | pRS435GGF + pRS434GAP-HMG1 | Sc YPH499 | YMO | 30 | 168 | 5.66 |
| | pRS445GGF + pRS434GAP-HMG1 | Sc YPH499 | YM | 30 | 96 | 1.01 |
| | pRS435GGF | Sc EUG5 | YM | 30 | 96 | 5.20 |
| | pRS435GGF | Sc EUG5 | YM | 30 | 168 | 7.32 |
| | pRS435GGF | Sc EUG5 | YMO | 30 | 96 | 1.20 |
| | pRS435GGF | Sc EUG5 | YMO | 30 | 168 | 10.1 |
| | pRS445GGF | Sc EUG5 | YM | 30 | 96 | 0.661 |
| | pRS435GGF | Sc EUG12 | YM | 30 | 96 | 4.67 |
| | pRS435GGF | Sc EUG12 | YM | 30 | 168 | 1.18 |
| | pRS435GGF | Sc EUG12 | YMO | 30 | 96 | 2.38 |
| | pRS435GGF | Sc EUG12 | YMO | 30 | 168 | 5.02 |
| | pRS445GGF | Sc EUG12 | YM | 30 | 96 | 3.25 |
| 435FGGHDEL | pRS435FGGHDEL | Sc YPH499 | YM | 30 | 96 | 0.121 |
| | pRS445FGGHDEL | Sc YPH499 | YM | 30 | 96 | 0.066 |
| | pRS435FGGHDEL + pRS434GAP-HMG1 | Sc YPH499 | YM | 30 | 96 | 0.294 |
| | pRS445FGGHDEL + pRS434GAP-HMG1 | Sc YPH499 | YM | 30 | 96 | 0.385 |
| | pRS435FGGHDEL | Sc EUG5 | YM | 30 | 96 | 0.786 |
| | pRS445FGGHDEL | Sc EUG5 | YM | 30 | 96 | 0.504 |
| | pRS435FGGHDEL | Sc EUG12 | YM | 30 | 96 | 2.41 |
| | pRS435FGGHDEL | Sc EUG12 | YM | 30 | 168 | 1.43 |
| | pRS445FGGHDEL | Sc EUG12 | YM | 30 | 96 | 0.521 |
| 435GGFHDEL | pRS435GGFHDEL | Sc A451 | YM | 30 | 96 | 0.072 |
| | pRS435GGFHDEL | Sc A451 | YMO | 30 | 96 | 0.126 |
| | pRS435GGFHDEL + pRS434GAP-HMG1 | Sc A451 | YM | 30 | 96 | 0.540 |
| | pRS435GGFHDEL + pRS434GAP-HMG1 | Sc A451 | YM | 30 | 168 | 0.760 |
| | pRS435GGFHDEL + pRS434GAP-HMG1 | Sc A451 | YMO | 30 | 96 | 0.414 |
| | pRS435GGFHDEL + pRS434GAP-HMG1 | Sc A451 | YMO | 30 | 168 | 3.49 |
| | pRS435GGFHDEL | Sc YPH499 | YM | 30 | 96 | 0.805 |
| | pRS435GGFHDEL | Sc YPH499 | YM | 30 | 168 | 0.541 |
| | pRS435GGFHDEL | Sc YPH499 | YMO | 30 | 96 | 1.69 |
| | pRS435GGFHDEL | Sc YPH499 | YMO | 30 | 168 | 2.50 |
| | pRS435GGFHDEL + pRS434GAP-HMG1 | Sc YPH499 | YM | 30 | 96 | 1.90 |
| | pRS435GGFHDEL + pRS434GAP-HMG1 | Sc YPH499 | YM | 30 | 168 | 2.45 |
| | pRS435GGFHDEL + pRS434GAP-HMG1 | Sc YPH499 | YMO | 30 | 96 | 2.60 |
| | pRS435GGFHDEL | Sc EUG5 | YM | 30 | 96 | 5.78 |
| | pRS435GGFHDEL | Sc EUG5 | YM | 30 | 168 | 6.99 |
| | pRS435GGFHDEL | Sc EUG5 | YMO | 30 | 96 | 3.97 |
| | pRS435GGFHDEL | Sc EUG5 | YMO | 30 | 168 | 10.6 |
| | pRS435GGFHDEL | Sc EUG12 | YM | 30 | 96 | 3.00 |
| | pRS435GGFHDEL | Sc EUG12 | YM | 30 | 168 | 1.43 |
| | pRS435GGFHDEL | Sc EUG12 | YMO | 30 | 96 | 2.33 |
| | pRS435GGFHDEL | Sc EUG12 | YMO | 30 | 168 | 5.78 |

TABLE 11-continued

Maximum GGOH Yield by Fusion Gene Expression

| Gene | Expression vector | Host | Medium | Temperature (°C.) | Cultivation Period (hr) | GGOH yield (mg/l) |
|---|---|---|---|---|---|---|
| EUG(ERG9p::URA3-GAL1p) | | | | | | |
| — | | Sc EUG5 | YM | 30 | 96 | 0.179 |
| — | | Sc EUG5 | YM | 30 | 168 | 0.230 |
| — | | Sc EUG5 | YMO | 30 | 96 | 0.232 |
| HMG1Δ | pRS434GAP-HMG026 | Sc EUG5 | YM | 30 | 96 | 0.093 |
| | pRS434GAP-HMG044 | Sc EUG5 | YM | 30 | 96 | 0.087 |
| | pRS434GAP-HMG056 | Sc EUG5 | YM | 30 | 96 | 0.106 |
| | pRS434GAP-HMG062 | Sc EUG5 | YM | 30 | 96 | 0.132 |
| | pRS434GAP-HMG076 | Sc EUG5 | YM | 30 | 96 | 0.148 |
| | pRS434GAP-HMG081 | Sc EUG5 | YM | 30 | 96 | 0.140 |
| | pRS434GAP-HMG100 | Sc EUG5 | YM | 30 | 96 | 0.184 |
| | pRS434GAP-HMG112 | Sc EUG5 | YM | 30 | 96 | 0.340 |
| | pRS434GAP-HMG122 | Sc EUG5 | YM | 30 | 96 | 0.127 |
| | pRS434GAP-HMG133 | Sc EUG5 | YM | 30 | 96 | 0.714 |
| HMG1 | pRS434GAP-HMG1 | Sc EUG8 | YM | 30 | 96 | 0.074 |
| BTS1 | pRS435GAP-BTS1 | Sc EUG8 | YM | 30 | 96 | 1.42 |
| | pRS445GAP-BTS1 | Sc EUG8 | YM | 30 | 96 | 0.067 |
| — | | Sc EUG12 | YM | 30 | 72 | 0.081 |
| — | | Sc EUG12 | YM | 30 | 96 | 0.194 |
| — | | Sc EUG12 | YM | 30 | 168 | 0.335 |
| HMG1 | pRS434GAP-HMG1 | Sc EUG12 | YM | 30 | 96 | 0.705 |
| | pRS444GAP-HMG1 | Sc EUG12 | YM | 30 | 96 | 2.05 |
| ERG20 | pRS435GAP-ERG20 | Sc EUG12 | YM | 30 | 72 | 6.63 |
| | pRS435GAP-ERG20 | Sc EUG12 | YM | 30 | 96 | 0.260 |
| | pRS445GAP-ERG20 | Sc EUG12 | YM | 30 | 96 | 0.381 |
| BTS1 | pRS435GAP-BTS1 | Sc EUG12 | YM | 30 | 96 | 1.75 |
| | pRS445GAP-BTS1 | Sc EUG12 | YM | 30 | 96 | 3.20 |
| HMG1Δ | pRS434GAP-HMG026 | Sc EUG12 | YM | 30 | 96 | 0.629 |
| | pRS434GAP-HMG044 | Sc EUG12 | YM | 30 | 96 | 0.428 |
| | pRS434GAP-HMG056 | Sc EUG12 | YM | 30 | 96 | 0.402 |
| | pRS434GAP-HMG062 | Sc EUG12 | YM | 30 | 96 | 0.445 |
| | pRS434GAP-HMG076 | Sc EUG12 | YM | 30 | 96 | 0.479 |
| | pRS434GAP-HMG081 | Sc EUG12 | YM | 30 | 96 | 0.488 |
| | pRS434GAP-HMG100 | Sc EUG12 | YM | 30 | 96 | 0.440 |
| | pRS434GAP-HMG112 | Sc EUG12 | YM | 30 | 96 | 0.534 |
| | pRS434GAP-HMG122 | Sc EUG12 | YM | 30 | 96 | 0.499 |
| | pRS434GAP-HMG133 | Sc EUG12 | YM | 30 | 96 | 0.440 |
| — | | Sc EUG27 | YM | 30 | 96 | 0.053 |
| HMG1 | pRS434GAP-HMG1 | Sc EUG27 | YM | 30 | 96 | 0.723 |
| | pRS444GAP-HMG1 | Sc EUG27 | YM | 30 | 96 | 0.205 |
| ERG20 | pRS435GAP-ERG20 | Sc EUG27 | YM | 30 | 96 | 0.661 |
| | pRS445GAP-ERG20 | Sc EUG27 | YM | 30 | 96 | 0.297 |
| BTS1 | pRS435GAP-BTS1 | Sc EUG27 | YM | 30 | 96 | 0.761 |
| | pRS445GAP-BTS1 | Sc EUG27 | YM | 30 | 96 | 0.595 |

(4-2) Expression of ERG20 and BTS1 in A451

Figure 25:
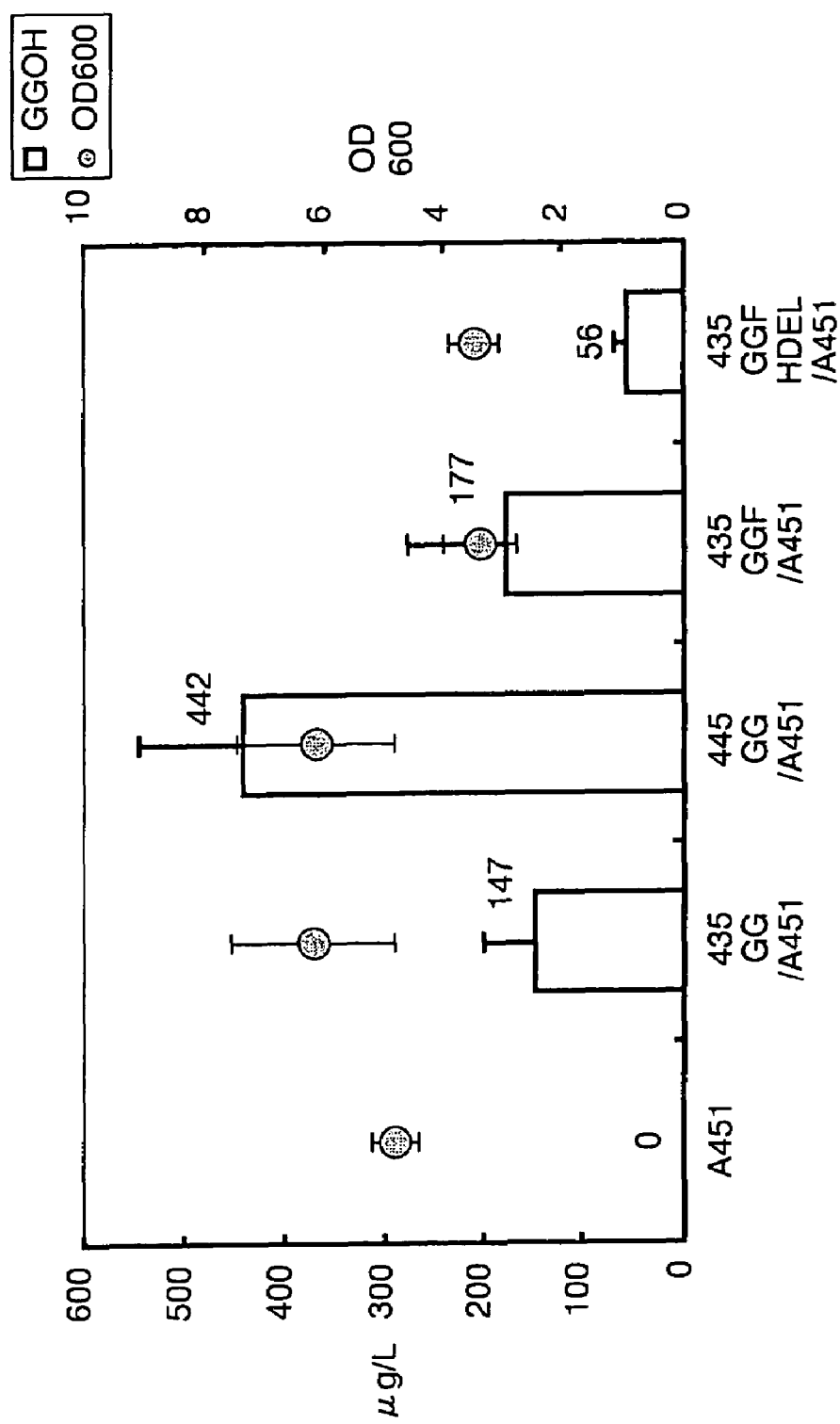
FIG. 25 is a graph showing the results of determination of GGOH yields when ERG20-BTS1 fusion genes were transferred into A451-derived clones.

Changes in prenyl alcohol yields when fusion genes were expressed in A451 are shown in FIG. 25. In FIG. 25, "435GGF" represents pRS435GGF, and "435GGFHDEL" represents pRS435GGFHDEL (in the following Figures, these terms have the same meaning). OD$_{600}$ represents absorbance at 600 nm. FIG. 25 also shows the results when an expression vector integrating non-fused BTS1 was introduced into A451 (435GG).

Even when pRS445GAP-BTS1 was introduced (expressed as "445GG/A451" in this Figure), GGOH yield of 0.44 mg/L was observed on the average.

(4-3) Expression of ERG20 and BTS1 in YPH499

Figure 26:
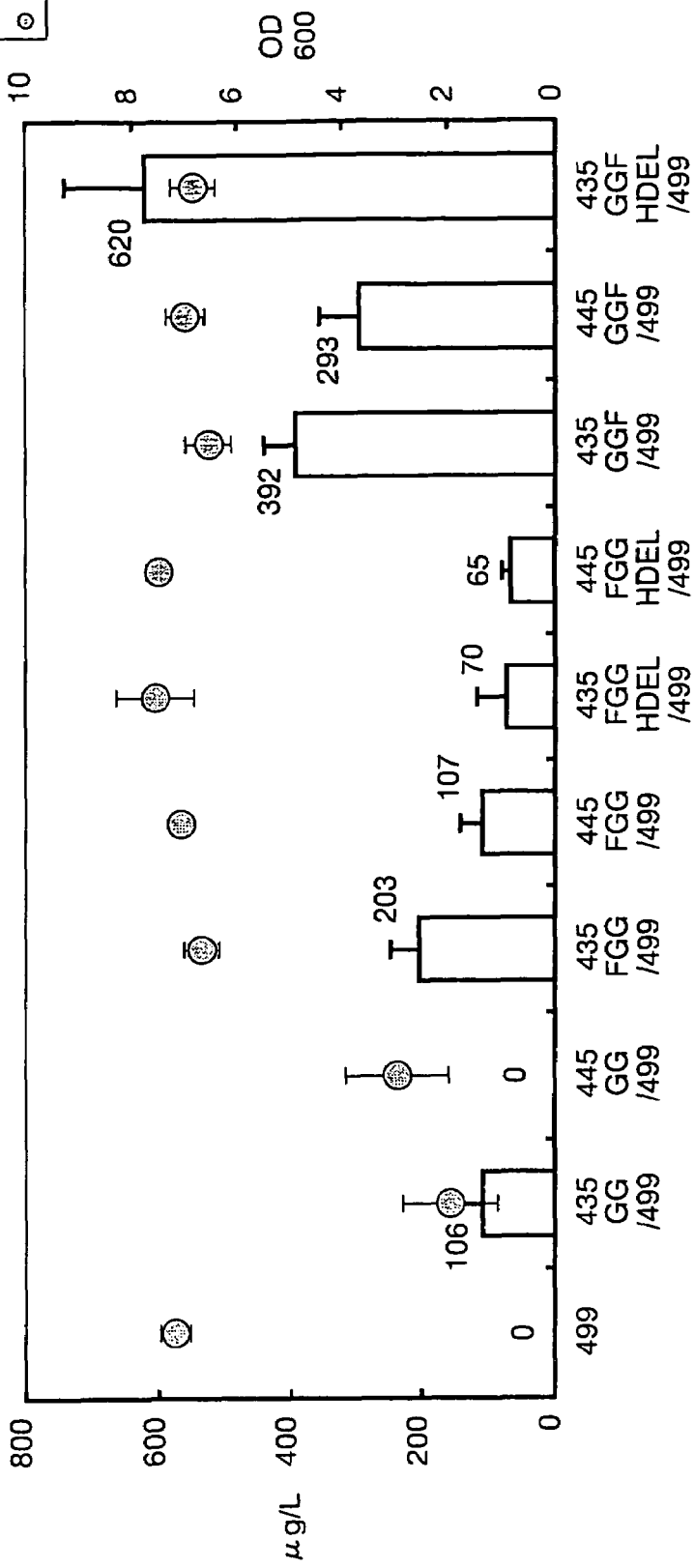
FIG. 26 is a graph showing the results of determination of GGOH yields when ERG20-BTS1 fusion genes were transferred into YPH499-derived clones.

Changes in prenyl alcohol yields when fusion genes were expressed in YPH499 are shown in FIG. 26. In FIG. 26, "499" represents YPH499; "435GGF" represents pRS435GGF; and "445GGFHDEL" represents pRS445GGFHDEL (in the following Figures, these terms have the same meaning). FIG. 26 also shows the results when non-fused BTS1-integrated expression vector was introduced into YPH499.

When pRS435GAP-BTS1 was introduced (expressed as "435GG/499" in this Figure), GGOH yield of 0.11 mg/L was observed on the average. When ERG20-BTS1 fusion gene-integrated pRS435FGG was introduced (expressed as "435FGG/499" in this Figure), GGOH yield of 0.20 mg/L was observed on the average. When pRS435GGF was introduced (expressed as "435GGF/499" in this Figure), GGOH yield of 0.39 mg/L was observed on the average. When pRS35GGFHDEL was introduced (expressed as "435GGF-HDEL/499" in this Figure), GGOH yield of 0.62 mg/L was observed on the average. Thus, it was recognized that fusion genes and HDEL sequence were effective for improving GGOH productivity.

(4-4) Expression of HMG1, ERG20 and BTS1 in YPH499

The present inventors considered that it may be possible to obtain clones of still higher GGOH productivity by co-expressing HMG1 and other gene(s) in clones pRS434GAP-HMG1/YPH499 (YH1) and pRS434TEF-HMG1/YPH499 which were obtained by introducing an HMG1 expression vector into YPH499.

Figure 27:
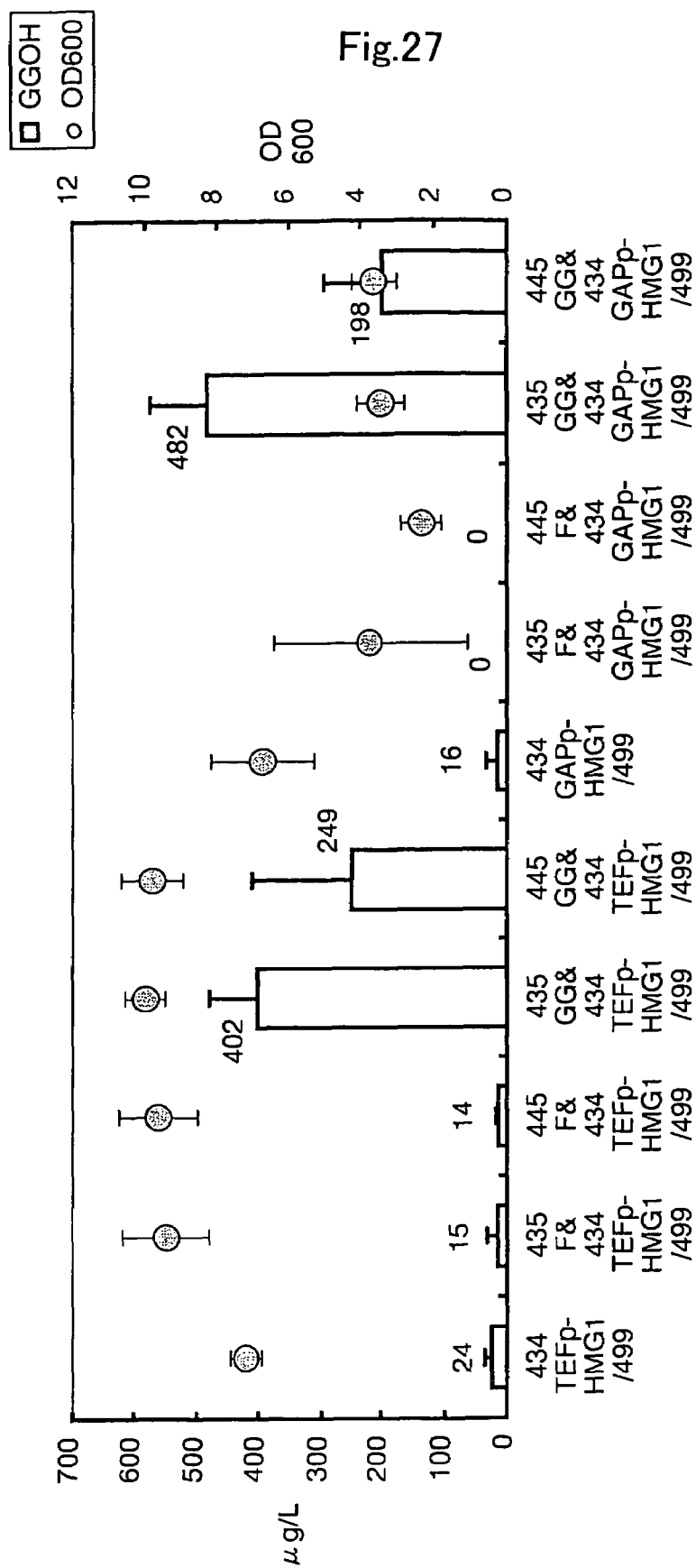
FIG. 27 is a graph showing the results of determination of GGOH yields in TEF2p-HMG1-transferred YPH499-derived clones.

FIG. 27 shows prenyl alcohol yields when a non-fused ERG20 or BTS1-integrated expression vector was further introduced into a host clone that had been already prepared by introducing pRS434TEF-HMG1 into YPH499. In FIG. 27, "434TEFp-HMG1" represents a clone to which pRS434TEF-HMG1 is introduced. TEFp is the transcription promoter of TEF2 gene. "499" represents YPH499. "435F" represents pRS435F and "445F" pRS445F. (These terms have the same meaning in the following Figures.) When BTS1 was introduced alone into YPH499, GGOH yield was only 0.11 mg/L. On the other hand, when a BTS1 expression vector was introduced into the TEF2p-HMG1-transferred clone, GGOH yield was 0.40 mg/L on the average (see "435GG & 434TEFp-HMG1/499" in FIG. 27); and when a BTS1 expression vector was introduced into the GAPp-HMG1-transferred clone, 0.49 mg/L of GGOH was produced (see "435GG & 434GAPp-HMG1/499" in FIG. 27). Thus, a possibility of prenyl alcohol mass production system by co-expression of HMG-CoA reductase gene and a prenyl diphosphate synthase gene was indicated.

Subsequently, using GAPp-HMG1-transferred YH1 (pRS434GAP-HMG1/YPH499) as a host, ERG20-BTS1 fusion genes or HDEL signal-containing genes prepared in the invention were expressed therein with TDH3 transcription promoter GAPp (TDH3p). Prenyl alcohol yields of the resultant clones were determined.

Figure 28:
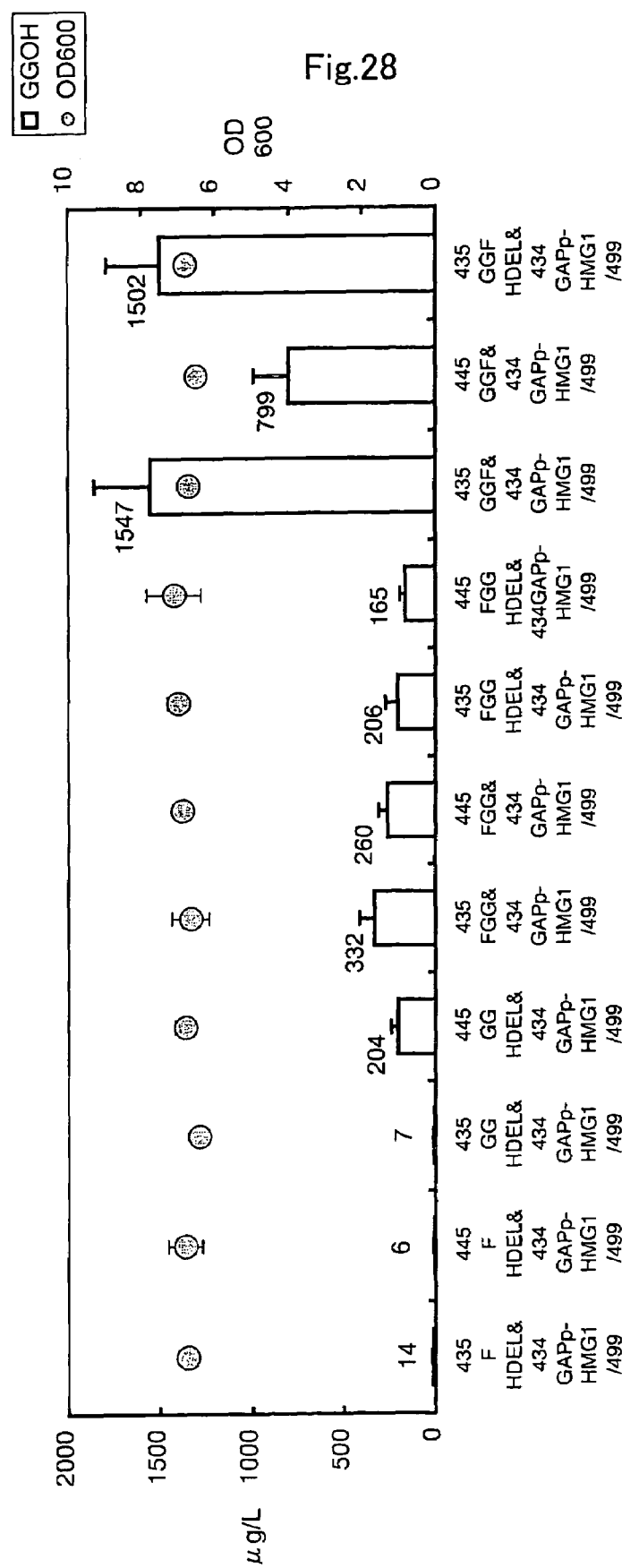
FIG. 28 is a graph showing the results of determination of GGOH yields in TDH3p-HMG1-transferred YPH499-derived clones.

The results are shown in FIG. 28. In FIG. 28, "434GAPp-HMG1" represents a clone into which pRS434GAP-HMG1 is transferred. GAPp is the transcription promoter of TDH3 gene. GGOH productivity improved when an HDEL signal-ligated prenyl diphosphate synthase gene and HMG1 were co-expressed. The productivity was further improved by the introduction of ERG20-BTS1 fusion gene. In particular, pRS435GGF- and pRS435GGFHDEL-transferred clones exhibited a remarkable improvement. They produced 1.55 mg/L and 1.50 mg/L of GGOH on the average, respectively (see "435GGF & 434GAPp-HMG1/499" and "435GGF-HEDL & 434GAPp-HMG1/499" in FIG. 28).

(4-5) Prenyl Alcohol Productivity in Soybean Oil-Containing Medium

ERG20-BTS1 fusion gene-transferred clones, which are GGOH-producing recombinants created in the invention, were cultured in YM7 (YM, pH 7) medium and YMO (YM7, 0.1% ADEKANOL LG109, 1% soybean oil) medium for 4 to 7 days, followed by determination of prenyl alcohol yields. The results obtained using A451-derived clones as hosts are shown in FIGS. 29A and 29B. The results obtained using YPH499-derived clones as hosts are shown in FIGS. 30A and 30B. In FIGS. 29A and 29B, "AH1" represents pRS434GAPp-HMG1/451, and "GGFHDEL" represents pRS435GGFHDEL. "–1" represents the yield after 4 days cultivation, and "–2" represents the yield after 7 days cultivation. Since cells are suspended in soybean oil in YMO medium, the amount of cells is expressed as the number of cells. "$10^{-3}$ cell/µl" means the number of cells per microliter divided by 1000.

While pRS435GGF/A451 produced 0.26 mg/L of GGOH on the average when cultured in YM7 medium for 7 days (FIG. 29A; upper panel; GGF/A451 –2), the yield increased to 0.98 mg/L on the average in YMO medium (FIG. 29B; upper panel; GGF/A451 –2). Also, when AH1 (pRS434GAP-HMG1-transferred A451) was used as a host, pRS435GGFHDEL-transferred recombinant produced 2.5 mg/L of GGOH on the average (FIG. 29B; middle panel; GGFHDEL/AH1 –2) and 3.5 mg/L of GGOH at the maximum in YMO medium (Table 11; see the rows coming under the gene name "435GGFHDEL"). Even when EUG5 obtained by replacing the ERG9 transcription promoter of A451 with GAL1 promoter (see Example 6) was used as a host, pRS435GGF-transferred recombinant produced more GGOH in YMO medium. This recombinant produced 6.6 mg/L of GGOH on the average when cultured in YM7 medium for 7 days (FIG. 29A; lower panel; GGF-EUG5 –2), but the yield increased to 9.6 mg/L on the average when cultured in YMO medium (FIG. 29B; lower panel; GGF/EUG5 –2).

Improvement in GGOH productivity by the use of YMO medium was also observed when YPH499-derived clones were used as hosts (FIGS. 30A and 30B). While pRS435GGF-transferred YPH499 produced 0.19 mg/L of GGOH on the average when cultured in YM7 medium for 7 days (FIG. 30A; upper panel; GGF/YPH499 –2), it produced 2.5 mg/L of GGOH on the average in YMO medium (FIG. 30B; upper panel; GGF/YPH499 –2). Further, when pRS435GGF or pRS435GGFHDEL was transferred into YH1 that co-expresses HMG1 and cultured in YMO medium for 7 days, both recombinants produced 5.6 mg/L of GGOH on the average (FIG. 30B; middle panel; GGF/YH1 –2 and GGFHDEL/YH1 –2). When EUG12 that was created from YPH499 in the same manner as used in the creation of EUG5 (see Example 6) was used as a host, pRS435GGF- or pRS435GGFHDEL-transferred recombinant produced approximately 3.7-4.0 mg/L of GGOH. Thus, it was suggested that the GGOH productivity of YPH499-derived clones can be improved with a combination of HMG1 and a prenyl diphosphate synthase gene.

EXAMPLE 11

Effects of Various Glucose-Galactose Compositions in Media Upon Prenyl Alcohol Production (1) Introduction of Vectors into Hosts and Their Cultivation In this Example, how the prenyl alcohol production in budding yeast will change with varied glucose-galactose (Glc-Gal) composition ratios is examined. In addition, effects of the expression of BTS1-ERG20 fusion genes upon prenyl alcohol production are also examined.

Vectors were introduced into yeast hosts using Frozen EZ yeast transformation II kit purchased from Zymo Research (Orange, Calif.). As expression vectors for BTS1-ERG20 fusion gene, pRS435GGF and pRS435GGFHDEL were used. As hosts, A451, YPH499, AH1, EUG5 and EUG12 were used. Each of the resultant transformants was grown on an agar plate of SGR-based selection medium that has an appropriate auxotrophy as an indicator. For the purpose of cloning, cultivation on the selection medium agar plate was carried out twice.

The transformant prepared was precultured in SGR selection medium. Then, 0.01-0.05 ml of the preculture broth was added to 1-5 ml of YM7 medium and cultured in a test tube 18 mm in diameter at 30° C. under reciprocal shaking at 130 rpm. Five types of YM7 medium having the following sugar components (Glc-Gal composition ratios) were prepared in advance: 0% Glc-100% Gal; 20% Glc-80% Gal; 50% Glc-50% Gal; 75% Glc-25% Gal; and 100% Glc-0% Gal. First, cells were cultured in these media at 30° C. under reciprocal shaking at 130 rpm. Two days after the start of cultivation, Glc was added further to each medium to give a final concentration of 5% (w/v). Cells were cultured further up to day 7.

(2) Results (2-1) GGOH Production by A451

Figure 31A:
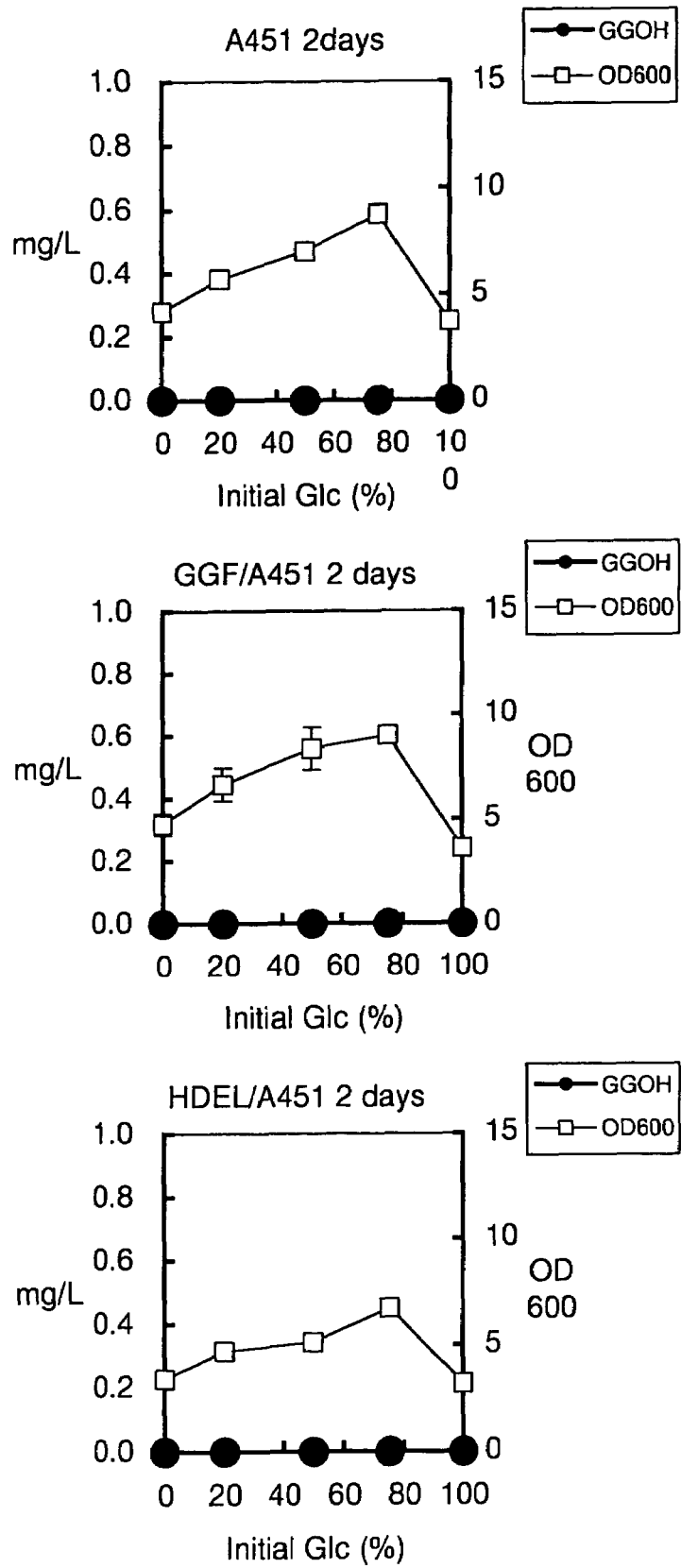
FIG. 31A is a graph showing the GGOH yields of pRS435GGF- or pRS435GGFHDEL-transferred A451 strain when cultured for 2 days with indicated sugar compositions.
Figure 31B:
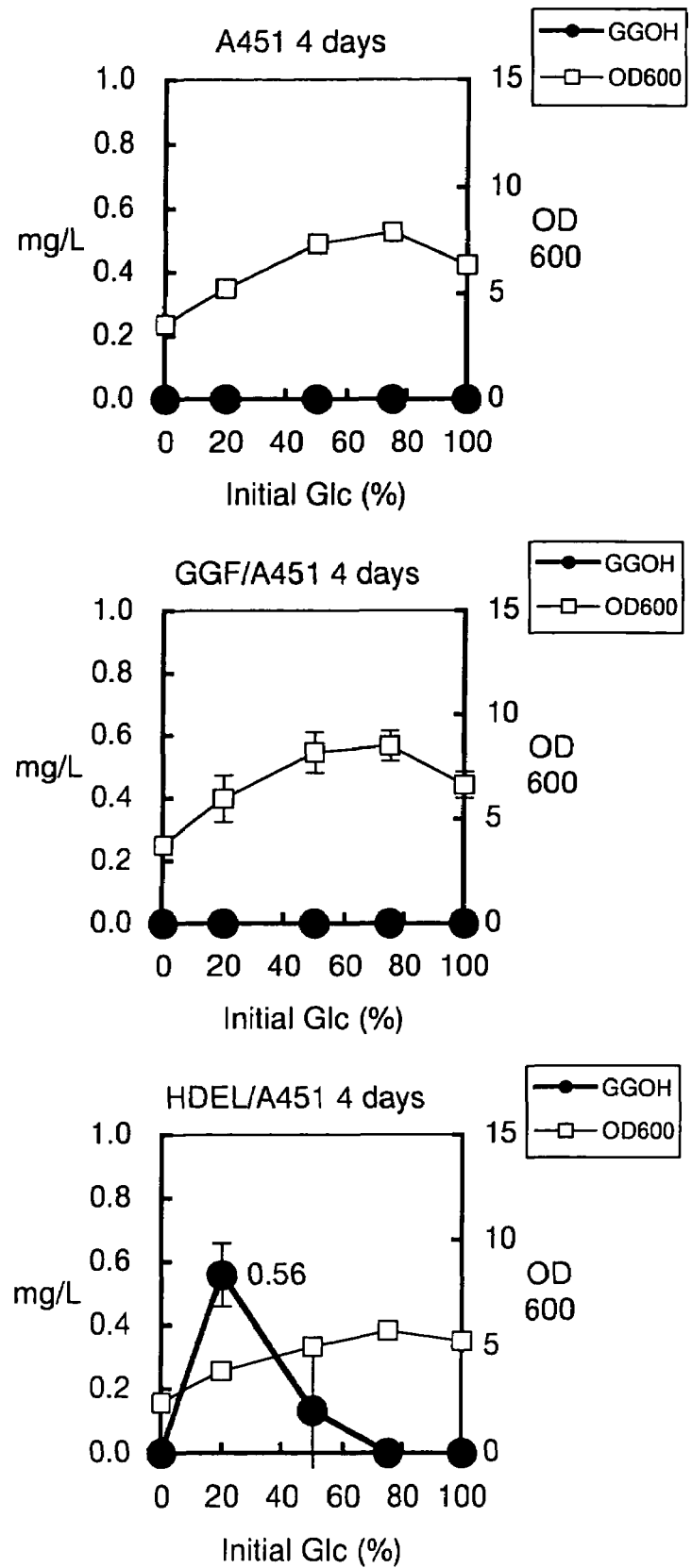
FIG. 31B is a graph showing the GGOH yields of pRS435GGF- or pRS435GGFHDEL-transferred A451 strain when cultured for 4 days with indicated sugar compositions.
Figure 31C:
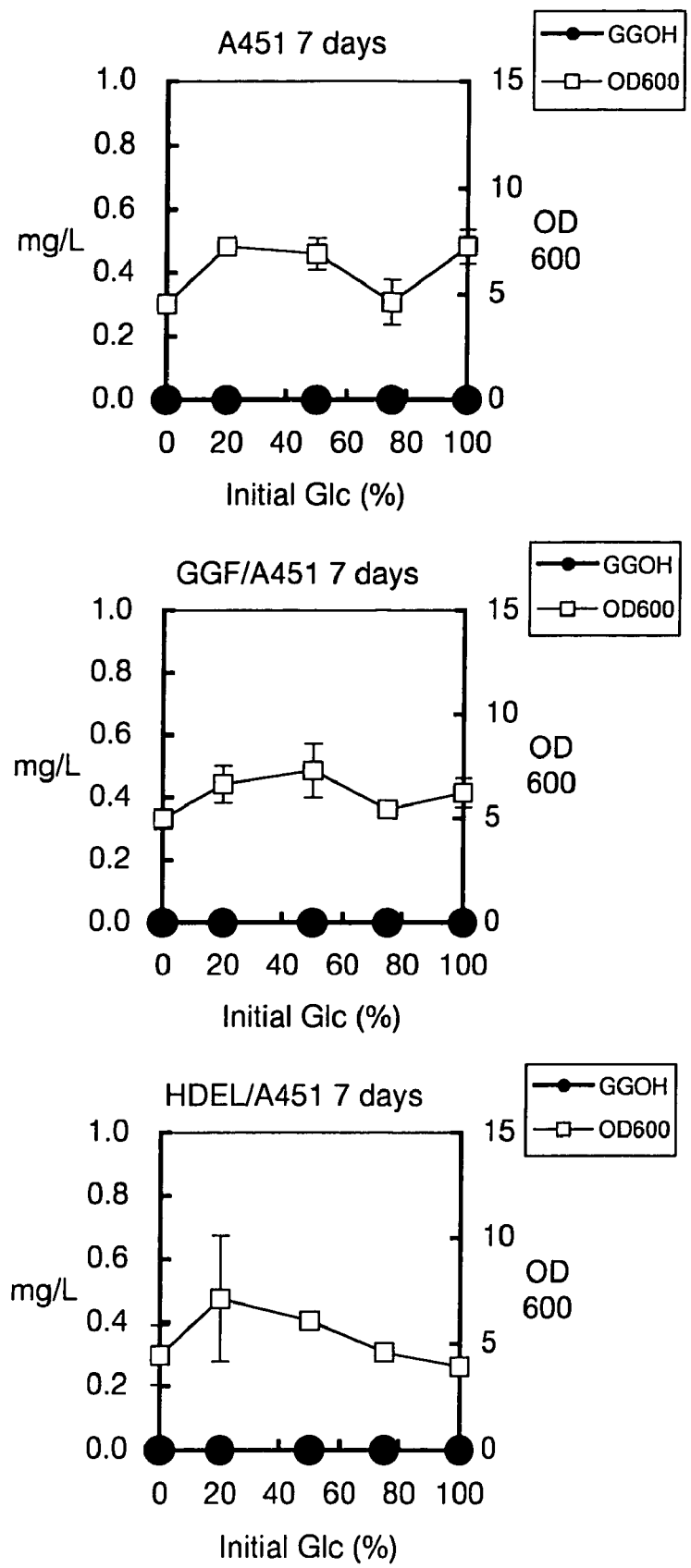
FIG. 31C is a graph showing the GGOH yields of pRS435GGF- or pRS435GGFHDEL-transferred A451 strain when cultured for 7 days with indicated sugar compositions.

GGOH yields when pRS435GGF and pRS435GGFHDEL were transferred into A451 separately are shown in FIGS. 31A-31C. In both cases, GGOH was detected little. Characteristically, pRS435GGFHDEL/A451 cultured for 4 days exhibited the highest GGOH yield (0.56 mg/L on the average) when the initial Glc ratio was 20%.

(2-2) GGOH Production by AH1

Figure 32A:
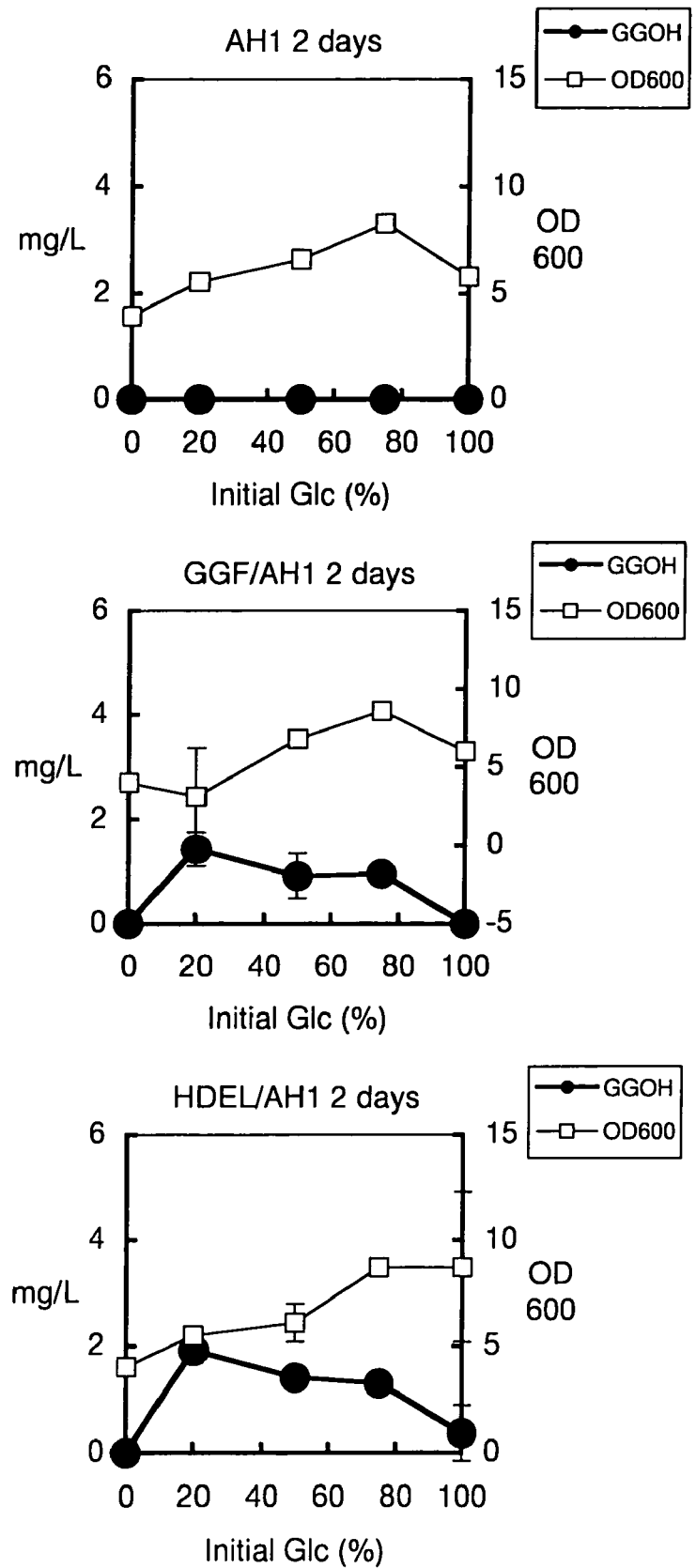
FIG. 32A is a graph showing the GGOH yields of pRS435GGF- or pRS435GGFHDEL-transferred AH1 strain when cultured for 2 days with indicated sugar compositions.
Figure 32B:
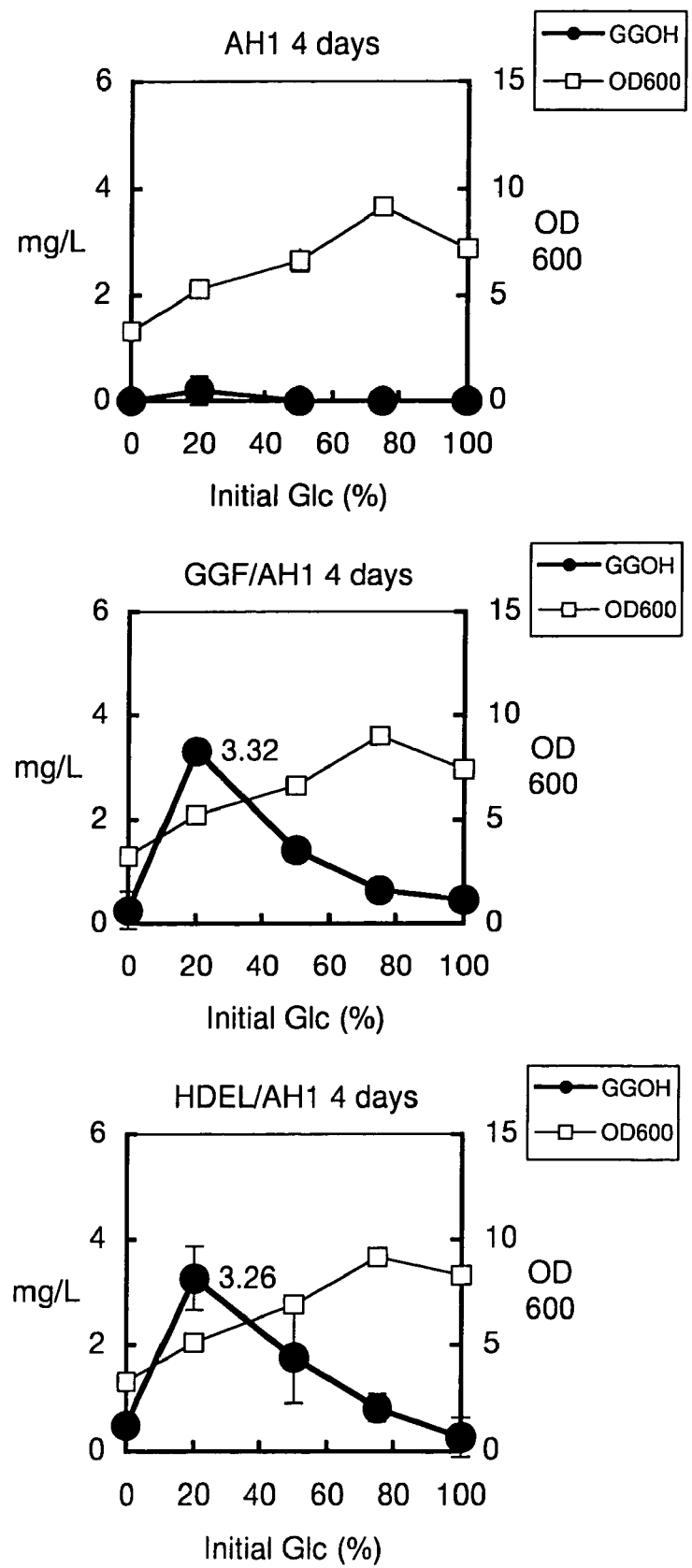
FIG. 32B is a graph showing the GGOH yields of pRS435GGF- or pRS435GGFHDEL-transferred AH1 strain when cultured for 4 days with indicated sugar compositions.
Figure 32C:
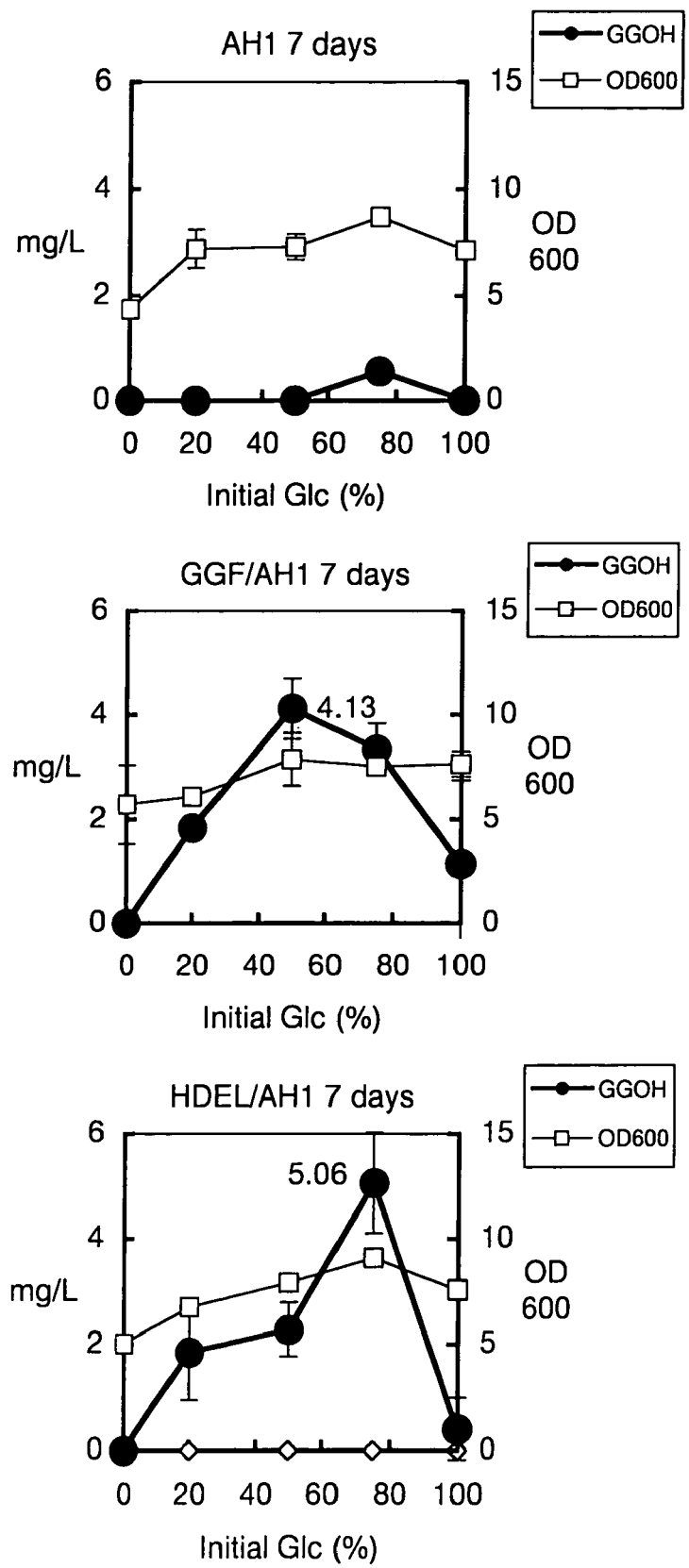
FIG. 32C is a graph showing the GGOH yields of pRS435GGF- or pRS435GGFHDEL-transferred AH1 strain when cultured for 7 days with indicated sugar compositions.
Figure 33A:
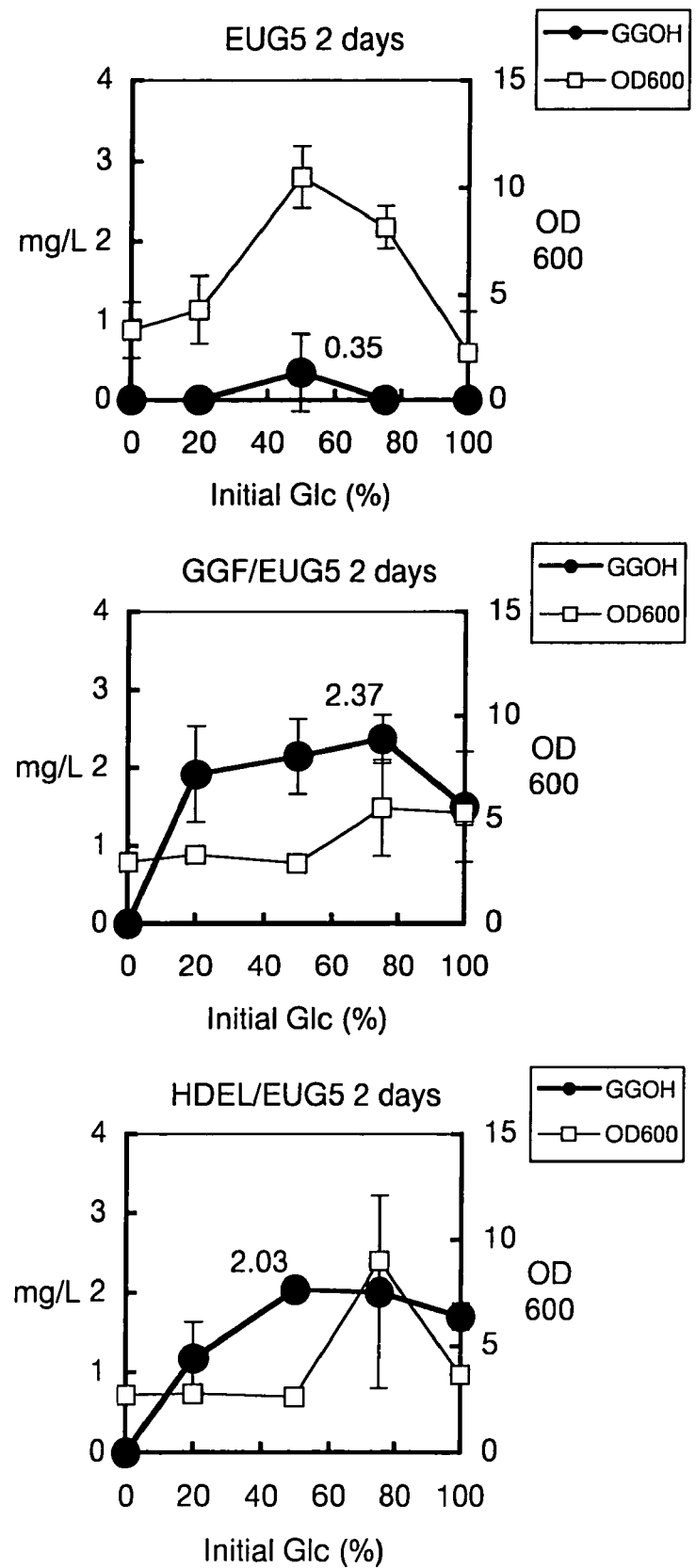
FIG. 33A is a graph showing the GGOH yields of pRS435GGF- or pRS435GGFHDEL-transferred EUG5 strain when cultured for 2 days with indicated sugar compositions.

GGOH yields when pRS435GGF and pRS435GGFHDEL were transferred into AH1 separately are shown in FIGS. 33A-32C. BTS1-ERG20 fusion gene-transferred AH1 clones cultured for 2-4 days also exhibited the highest GGOH yield (3.32 mg/L) when the initial Glc ratio was 20%. When these clones were cultured for 7 days, they exhibited the highest GGOH yield (4.13 mg/L on the average) when the initial Glc ratio was 50-80%.

(2-3) GGOH Production by EUG5

Figure 33B:
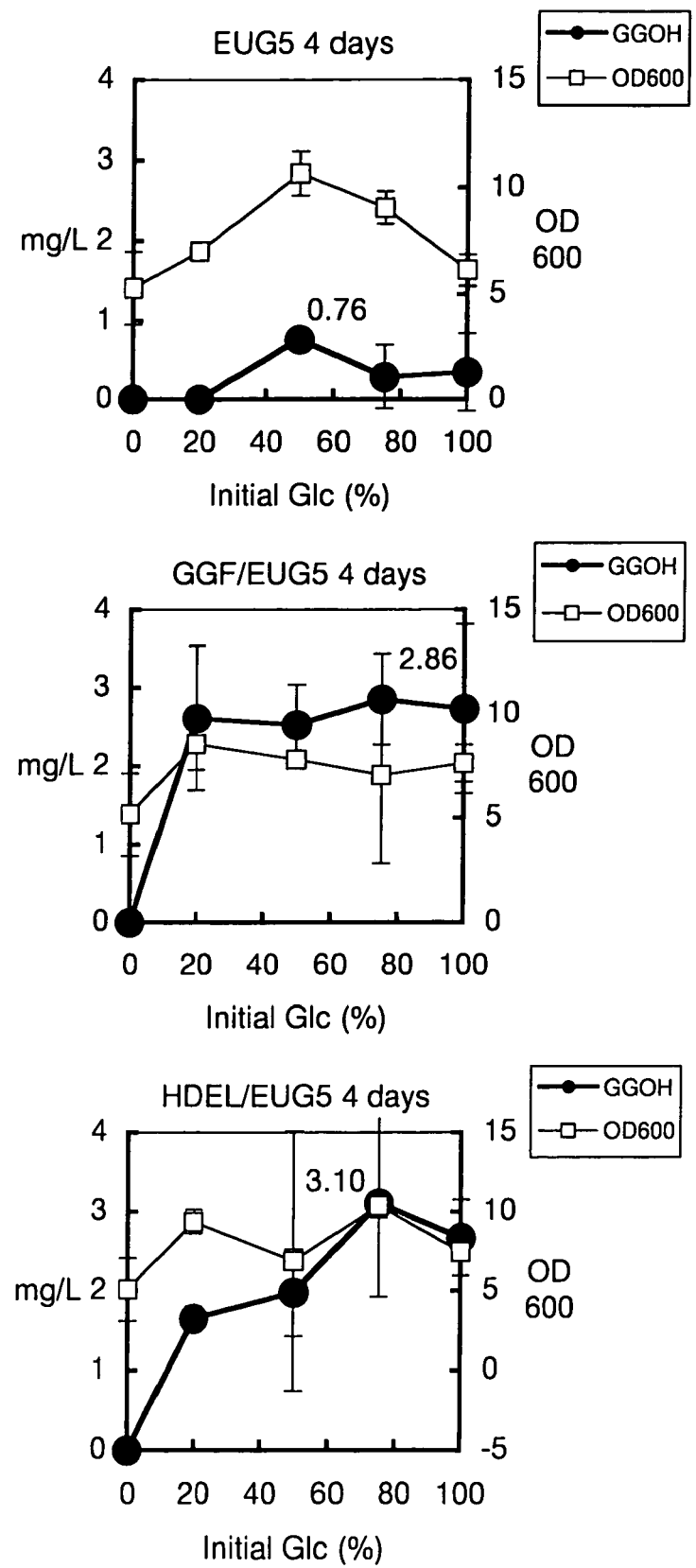
FIG. 33B is a graph showing the GGOH yields of pRS435GGF- or pRS435GGFHDEL-transferred EUG5 strain when cultured for 4 days with indicated sugar compositions.
Figure 33C:
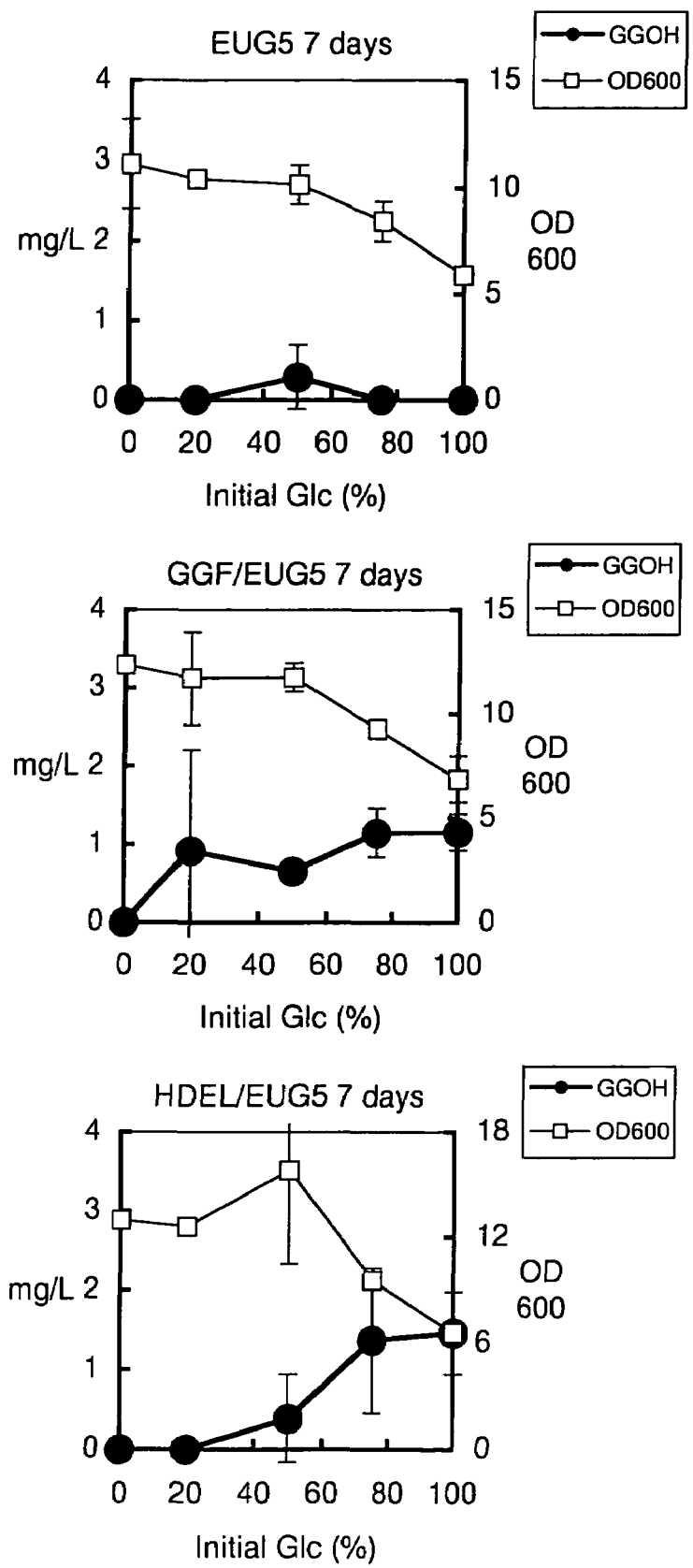
FIG. 33C is a graph showing the GGOH yields of pRS435GGF- or pRS435GGFHDEL-transferred EUG5 strain when cultured for 7 days with indicated sugar compositions.

GGOH yields when pRS435GGF and pRS435GGFHDEL were transferred into EUG5 separately are shown in FIGS. 33A-33C. In both pRS435GGF-transferred clone and pRS435GGFHDEL-transferred clone, good results were obtained when they were cultured for 2-4 days with the initial Glc ratio of 20-80%.

(2-4) GGOH Production by YPH499

Figure 34A:
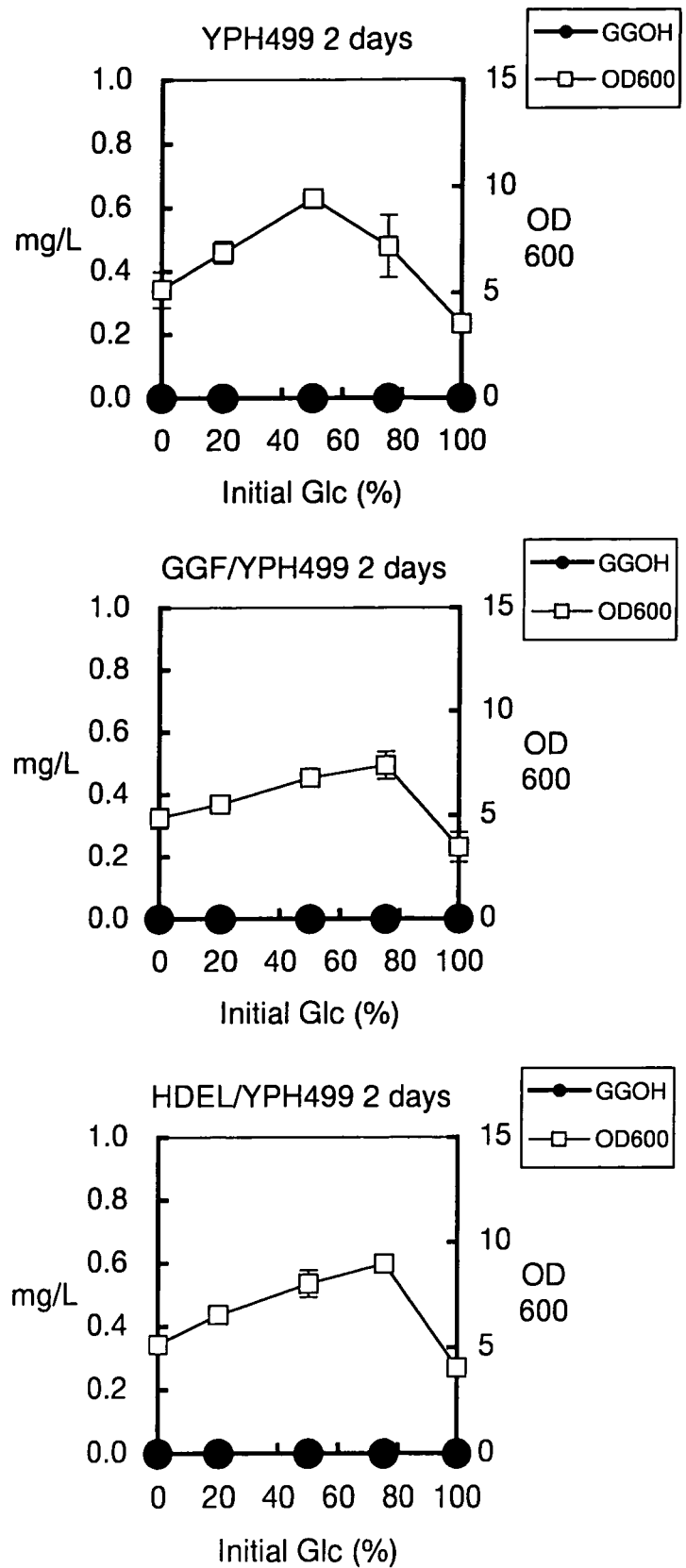
FIG. 34A is a graph showing the GGOH yields of pRS435GGF- or pRS435GGFHDEL-transferred YPH499 strain when cultured for 2 days with indicated sugar compositions.
Figure 34B:
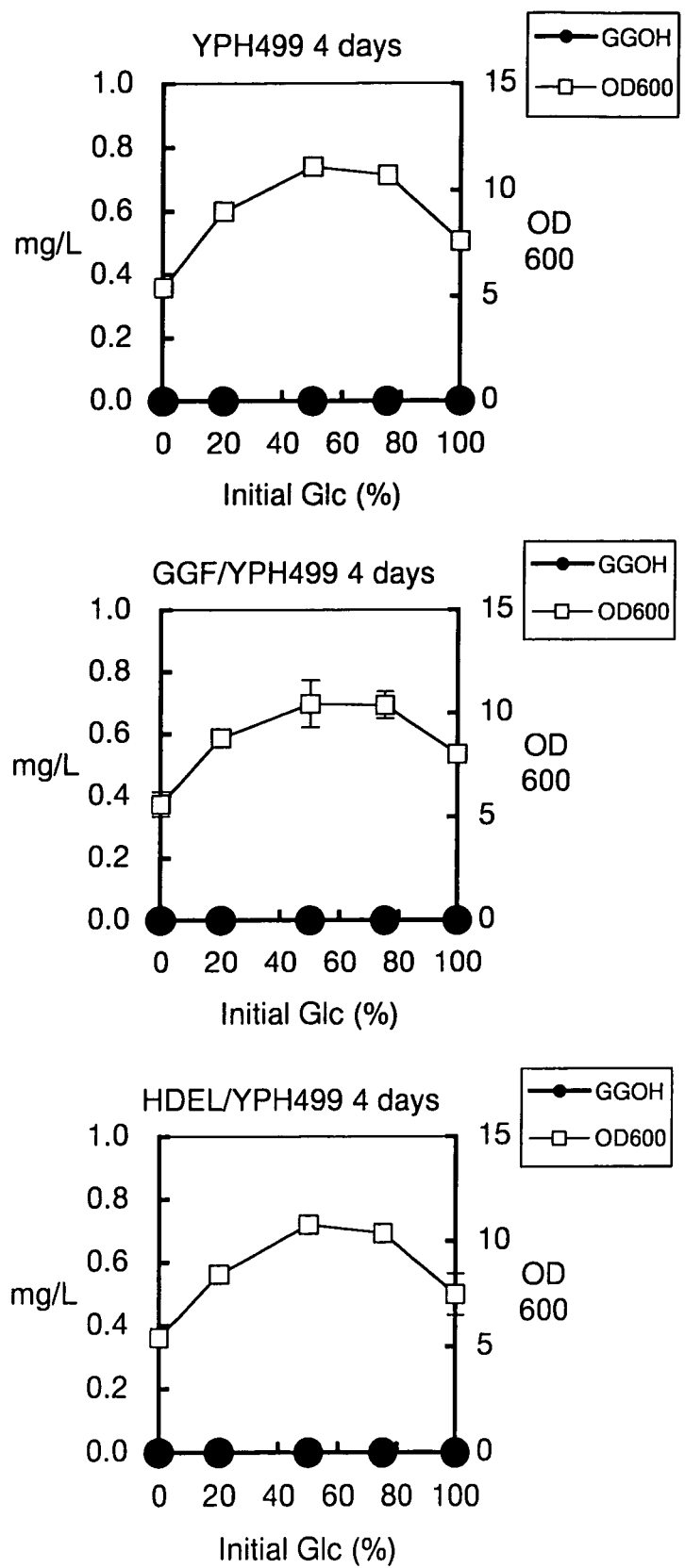
FIG. 34B is a graph showing the GGOH yields of pRS435GGF- or pRS435GGFHDEL-transferred YPH499 strain when cultured for 4 days with indicated sugar compositions.
Figure 34C:
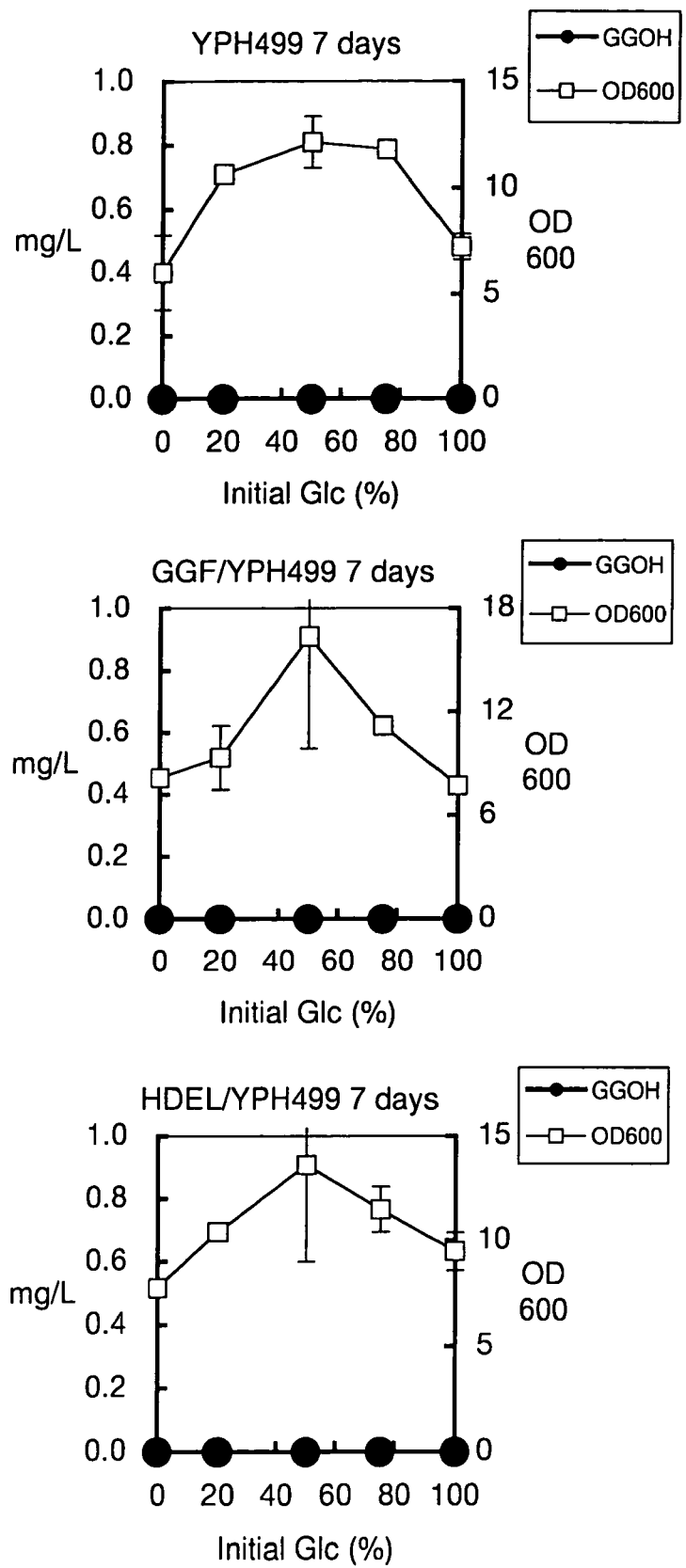
FIG. 34C is a graph showing the GGOH yields of pRS435GGF- or pRS435GGFHDEL-transferred YPH499 strain when cultured for 7 days with indicated sugar compositions.

GGOH yields when pRS435GGF and pRS435GGFHDEL were transferred into YPH499 separately are shown in FIGS. 34A-34C. Like in the case where A451 was used, GGOH was detected little.

(2-5) GGOH Production by YH1

Figure 35A:
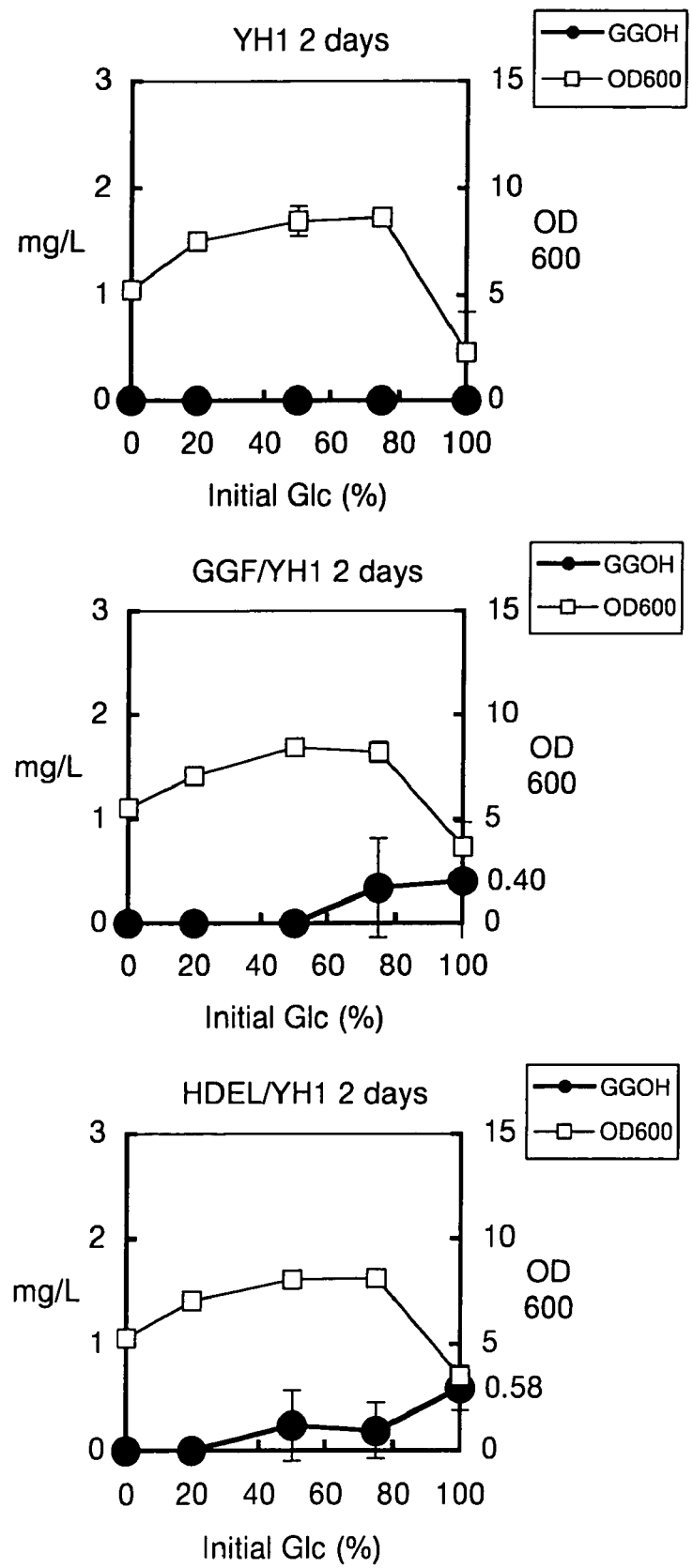
FIG. 35A is a graph showing the GGOH yields of pRS435GGF- or pRS435GGFHDEL-transferred YH1 strain when cultured for 2 days with indicated sugar compositions.
Figure 35C:
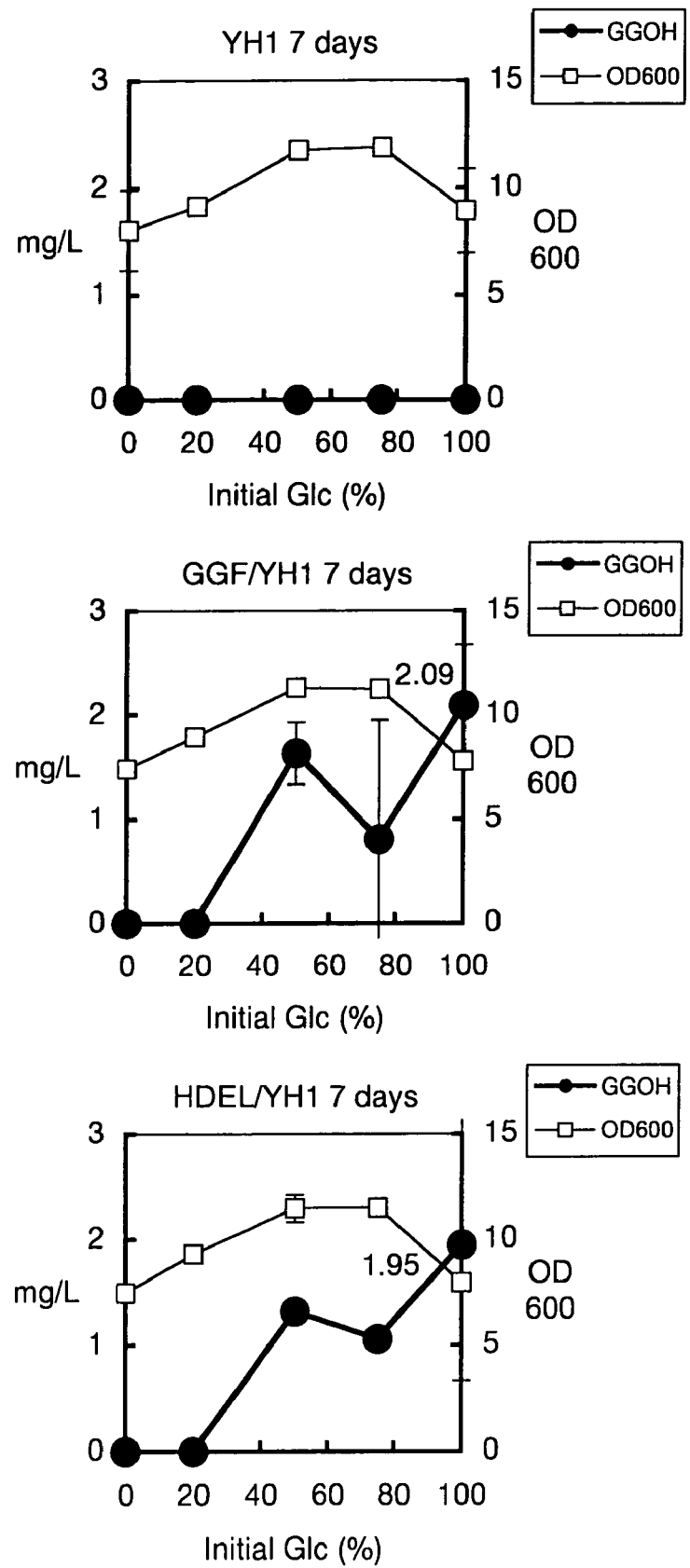
FIG. 35C is a graph showing the GGOH yields of pRS435GGF- or pRS435GGFHDEL-transferred YH1 strain when cultured for 7 days with indicated sugar compositions.

GGOH yields when pRS435GGF and pRS435GGFHDEL were transferred into YH1 separately are shown in FIGS. 35A-35C. When the recombinant clones were cultured for 7 days, high GGOH yields were obtained with the initial Glc ratio of 100%.

(2-6) GGOH Production by EUG12

Figure 36A:
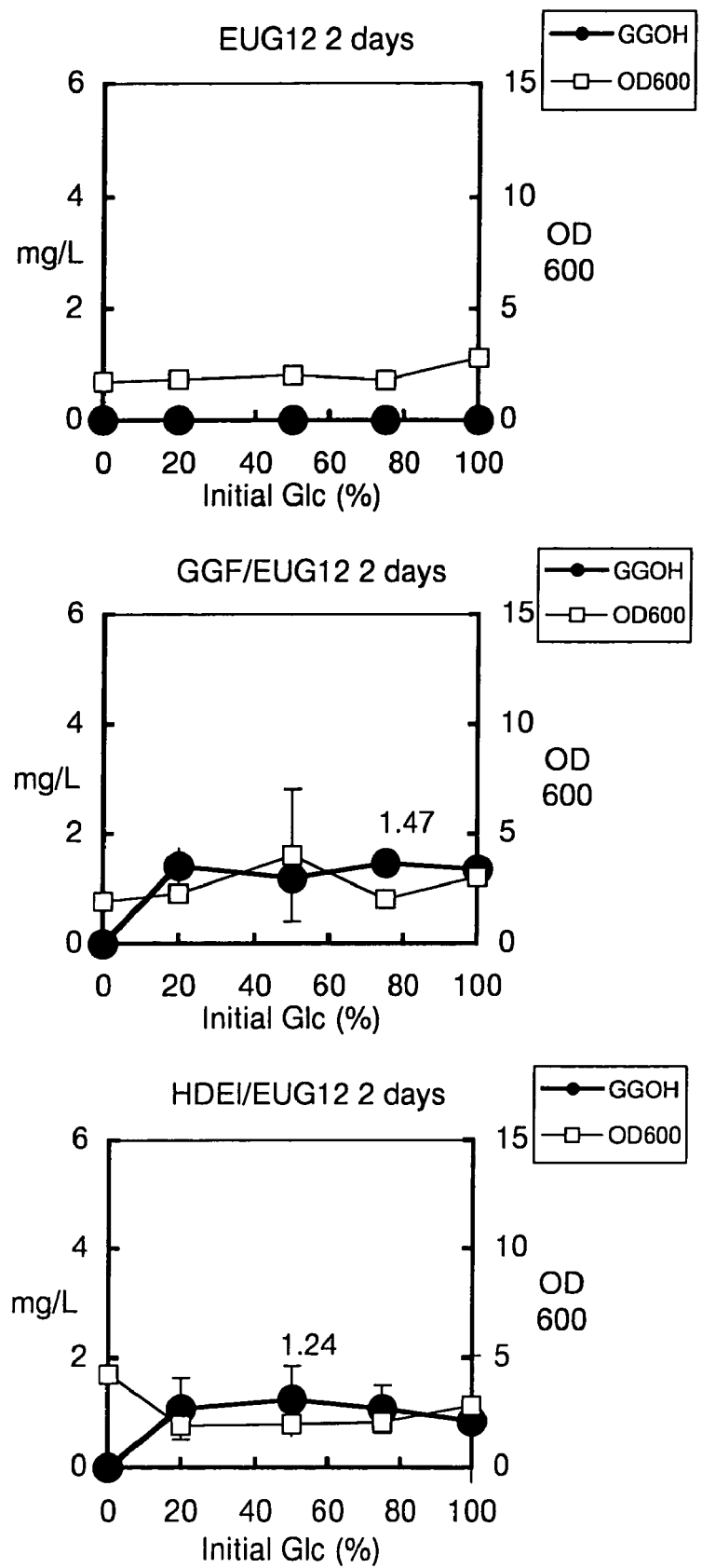
FIG. 36A is a graph showing the GGOH yields of pRS435GGF- or pRS435GGFHDEL-transferred EUG12 strain when cultured for 2 days with indicated sugar compositions.
Figure 36B:
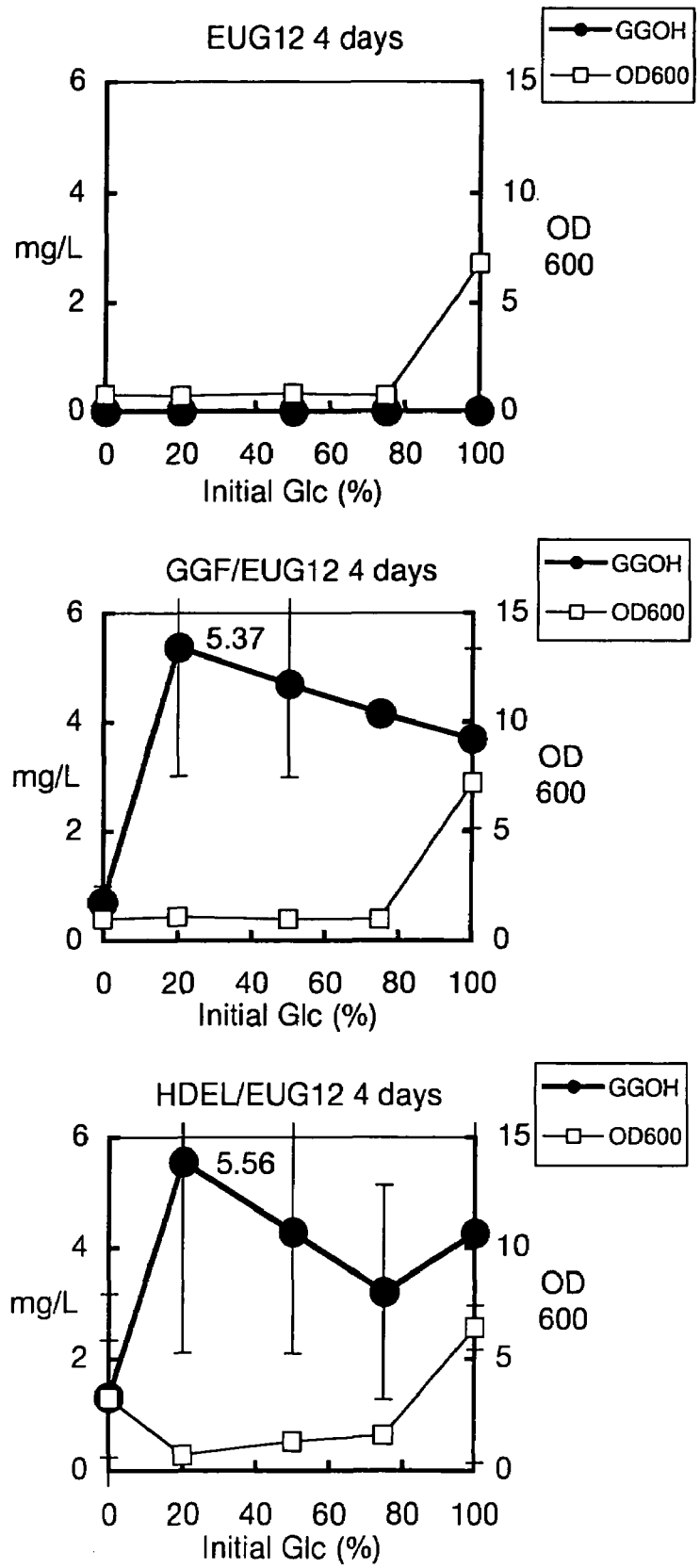
FIG. 36B is a graph showing the GGOH yields of pRS435GGF- or pRS435GGFHDEL-transferred EUG12 strain when cultured for 4 days with indicated sugar compositions.
Figure 36C:
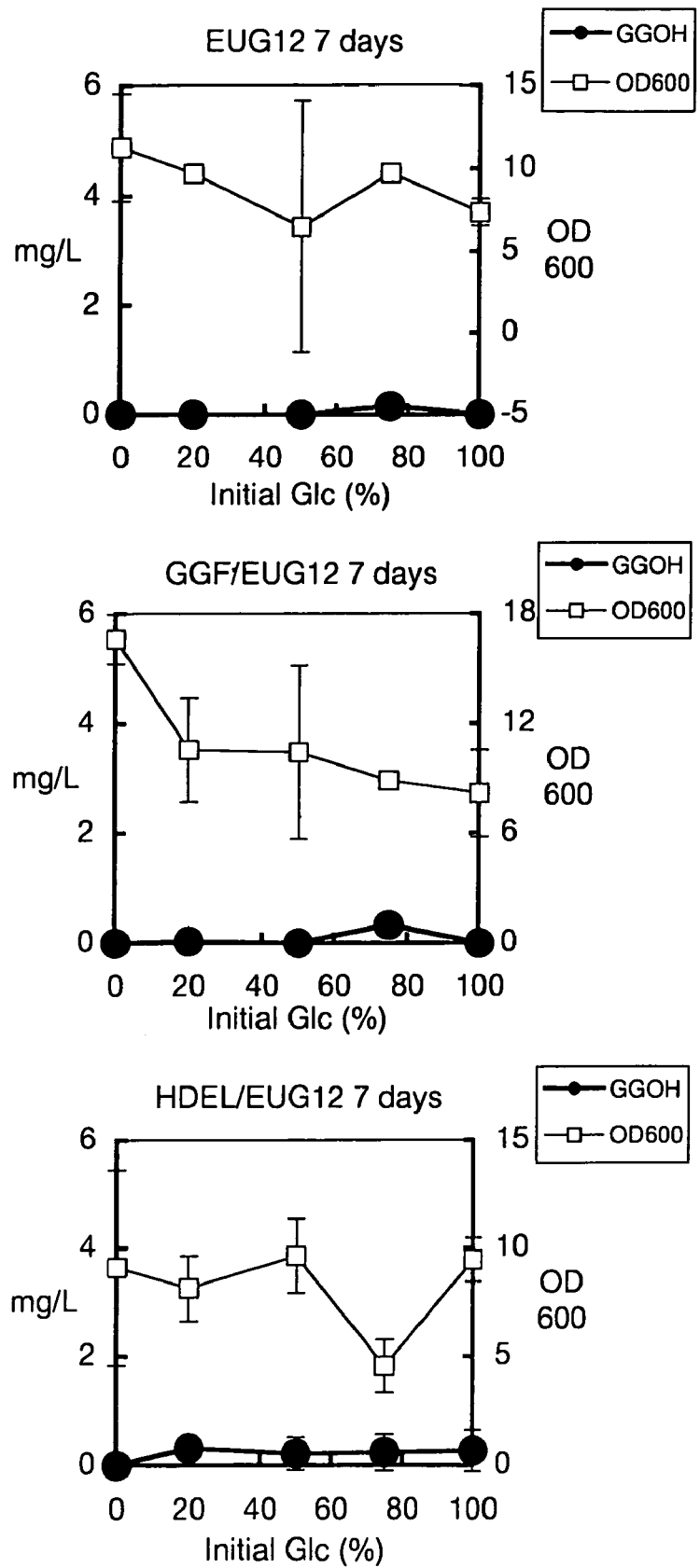
FIG. 36C is a graph showing the GGOH yields of pRS435GGF- or pRS435GGFHDEL-transferred EUG12 strain when cultured for 7 days with indicated sugar compositions.

GGOH yields when pRS435GGF and pRS435GGFHDEL were transferred into EUG12 separately are shown in FIGS. 36A-36C. When the initial Glc ratio was 20%, both of the recombinant clones exhibited high prenyl alcohol productivity. When pRS435GGF/EUG12 was cultured for 4 days with the initial Glc ratio of 20%, this clone produced 7.6 mg/L of FOH and 5.4 mg/L of GGOH though the amount of cells corresponded to $OD_{600}$=1.1. It is believed that these production results are very efficient as productivity per cell.

EXAMPLE 12

Jar Fermenter Cultivation of pRS435GGF/YH1 and 15-2

(1) pRS435GGF/YH1

In order to produce GGOH in a large quantity, pRS435GGF/YH1 clone that had produced GGOH preferentially at 5.6 mg/L (see Example 10) was cultured in a jar fermenter under the conditions described below.

<Fermenter Medium>
5% glucose (YM itself contains 1% glucose. Thus, the final concentration of glucose becomes 6%.)
YM broth (Difco)
3% soybean oil (Nacalai Tesque)
0.1 % ADEKANOL LG109 (Asahi Denka)

<Operational Conditions>
Cultivation apparatus: MSJ-U 10 L Cultivation Apparatus (B. E. Marubishi)
Medium volume: 5 L
Cultivation temperature: 33° C.
Aeration rate: 1 vvm
Agitation: 300 rpm
pH: controlled proportionally with the following parameters using 4 N sodium hydroxide solution and 2N hydrochloric acid solution:

| | |
|---|---|
| Proportional Band | 1.00 |
| Non Sensitive Band | 0.15 |
| Control Period | 16 Sec |
| Full Stroke | 1 Sec |
| Minimum Stroke | 0 Sec |

Figure 37:
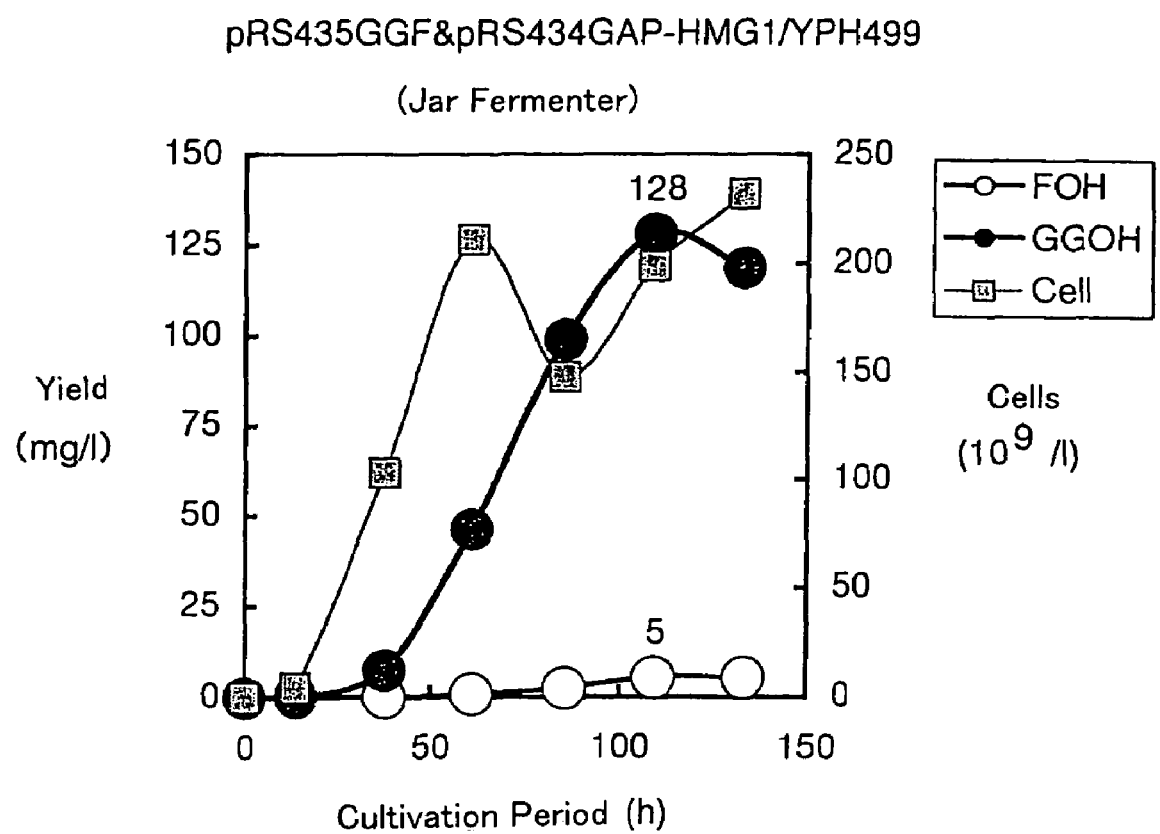
FIG. 37 is a graph showing the results of determination of prenyl alcohol yields in pRS435GGF/YH1 (pRS434GAP-HMG1/YPH499) clone when cultured in a soybean oil-containing medium in a jar fermenter.

As a result, RS435GGF/YH1 clone could produce 128 mg/L of GGOH when cultured for 115 hr. At that time, yields of squalene (SQ), FOH and nerolidol (NOH) were 15 mg/L, 5 mg/L and almost 0, respectively. Thus, the inventors have succeeded to create a system that produces GGOH alone in a large quantity by fermentation (FIG. 37).

(2) 15-2 Clone 15-2 Clone (pYHMG044-retaining AURGG101) described in Example 7 was inoculated from a slant into GSM-URA (BIO101)+DOB (BIO101) medium (200 ml in a 500 ml three-necked flask equipped with a baffle) and cultured at 30° C. at 130 rpm for 2 days. Subsequently, centrifugation (1500 rpm, 5 min, 4° C.) and washing with sterilized physiological saline were repeated 3 times to completely remove the glucose contained in the culture broth. Then, 50 ml of this preculture broth was cultured in a jar fermenter under the same conditions as used in (1) above for pRS435GGF/YH1. However, the medium used was as described below and the cultivation temperature was 26° C.

<Fermenter Medium>
5% galactose (YM contains 1% glucose. Thus, the final sugar concentration becomes 6%.)
YMB without Amino Acids (Difco)
1% soybean oil (Nacalai Tesque)
0.1% ADEKANOL LG 109 (Asahi Denka)

Figure 38:
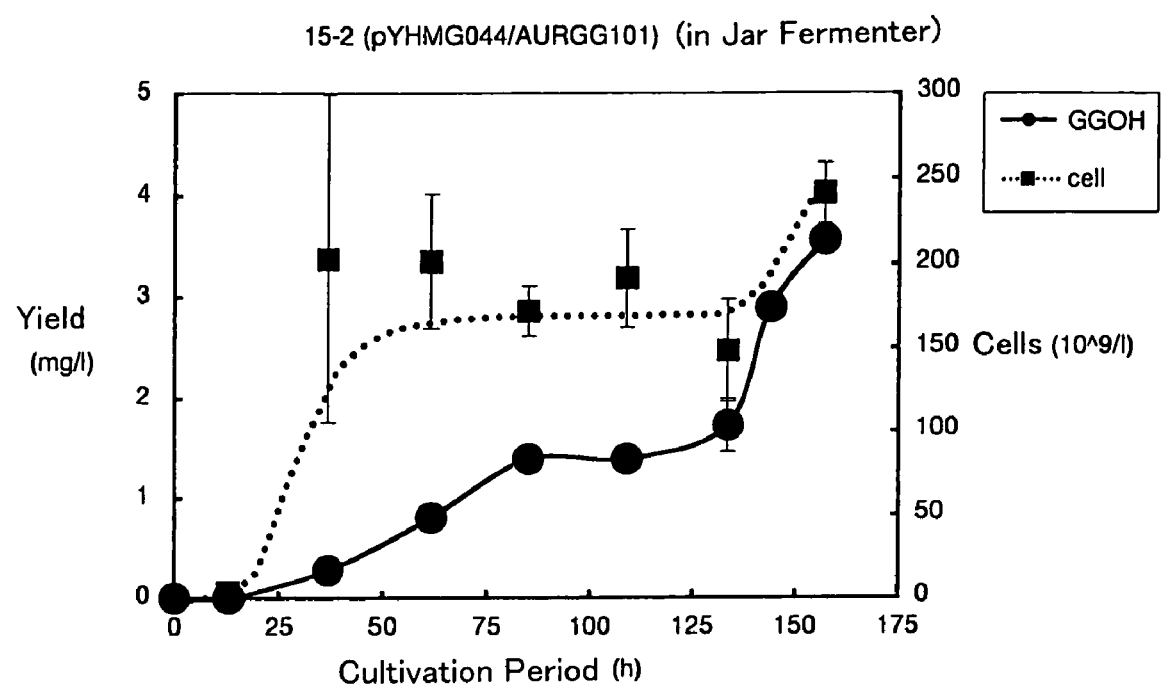
FIG. 38 is a graph showing the results of determination of prenyl alcohol yields in 15-2 clone when cultured in a soybean oil-containing medium in ajar fermenter.

As a result, 15-2 clone could produce 3 mg/L of GGOH when cultured for 150 hr (FIG. 38).

EXAMPLE 13

Expression of Fusion Genes

In order to examine whether pRS435GGF-transferred cells and pRS435GGFHDEL-transferred cells are expressing the respective fusion gene products or not, analysis of transcription products and translation products were carried out by Northern blot hybridization and Western blotting.

(1) Northern Blot Hybridization

FIG. 39 shows the results of Northern blot hybridization analysis of transcription products in YPH499-derived recombinants to which pRS435GGF and pRS435GGFHDEL are transferred separately and YH1-derived recombinants to which pRS435GGF and pRS435GGFHDEL are transferred separately. As probes, a DNA fragment located in the coding region of TUB1 gene encoding α-tubulin and the ERG20 probe, BTS1 probe and HMG1 probe described in Table 7 in Example 7. The TUB1 probe was prepared in the same manner as described in Example 7 using oligonucleotides TUB1f-2 and TUB1r-2 described below. The preparation of RNA and Northern blot hybridization were performed in the same manner as described in Example 7.

```
TUB1f-2:
5'-ACG GTA AGA AAT CCA AGC-3'    (SEQ ID NO: 119)

TUB1r-2:
5'-TAT GAG TCG GCA CCC ACT-3'    (SEQ ID NO: 120)
```

In FIG. 39, "-" indicates RNA samples from those cells into which prenyl diphosphate synthase gene-retaining plasmids are not transferred; "GGF" indicates RNA samples from pRS435GGF-transferred recombinants; "HDEL" indicates RNA samples from pRS435GGFHDEL-transferred recombinants; and "HMG1" indicates RNA samples from YH1-derived recombinants. From the results obtained with probe TUB1 (tubulin α gene), it is understood that an almost equal amount of messenger RNA is obtained from every sample prepared. When probe ERG20 and probe BTS1 were used, an over-expressed, common 3.1 kb band is detected, indicating that fusion genes are transcribed efficiently. The 1.8 kb band detected with probe ERG20 is believed to be the transcription product of the wild-type ERG20 gene in the genome. The results obtained with probe HMG1 show that 4.1 kb RNA (a transcription product of plasmid-derived HMG1) is detected in a large quantity in all of the pRS434GAP-HMG1-pretransferred clones (i.e., YH1-derived clones; lanes marked with "HMG1" in FIG. 39). This indicates that the transcription of HMG1 is performed efficiently even if a prenyl diphosphate synthase expression plasmid is introduced further as a second plasmid.

(2) Western Blotting

According to the C-terminal sequences of the polypeptides encoded by ERG20 and BTS1, polypeptides having the amino acid sequences described below were chemically synthesized. Using these polypeptides as antigens, mouse antibodies were prepared by conventional methods (described in common experimental manuals such as F. M. Ausubel et al. Eds, Short Protocols in Molocular Biology, 4th Edition, (1999) John Wiley & Sons, Inc., New York). Two milligrams of each of the following peptides was crosslinked to KLH (Keyhole Limpet Hemocyanin) and used as an antigen.

```
BTS1-C:
                                 (SEQ ID NO: 121)
NH2 Cys Tyr Ile Ile Asp His Leu Ser Glu Leu COOH

ERG20-C:
                                 (SEQ ID NO: 122)
NH2 Cys Leu Asn Lys Val Tyr Lys Arg Ser Lys COOH
```

Protein was prepared from the 6 strains/clones of YPH499, pRS435F/YPH499, pRS435GGF/YPH499, pRS435FGG/YPH499, pRS435GGFHDEL/YPH499 and pRS435GGF/YH1 as described below and subjected to Western blot analysis. Briefly, preculture broth (absorbance at 600 nm was measured, and each broth was diluted with physiological saline to have an equal amount of cells) of each strain/clone was inoculated into a selection medium [for YPH499, SD medium DOB (dropout base: minimum medium whose carbon source is glucose) to which CSM (complete supplement mixture) is added as amino acid or nucleic acid component; for pRS435F/YPH499, SD-L medium (SD medium minus Leu); for pRS435GGF/YPH499, SD-L medium; for pRS435FGG/YPH499, SD-L medium; for pRS435GGFHDEL/YPH499, SD-L medium; for pRS435GGF/YH1, SD-LW medium (SD medium minus Leu and Trp)] and cultured at 30° C. under shaking at 130 rpm for 4 days. After harvesting cells with a centrifuge, 2 ml of Y-PER (PIERCE, Rockford, Ill.) was added per 1 g (wet weight) of cells and agitated vigorously at room temperature for 1 hr to prepare a total protein solution. Twenty micrograms of the resultant total protein was separated on the basis of molecular weights by SDS-polyacrylamide gel electrophoresis (SDS-PAGE; for procedures, see Short Protocols in Molecular Biology, 4th Edition, (1999) John Wiley & Sons, Inc., New York), and examined the state of expression of the gene transferred into the relevant recombinant by Western blotting (see Short Protocols in Molecular Biology, 4th Edition, (1999) John Wiley & Sons, Inc., New York). The Western blotting technique used this time was partially modified in the following points.

1) Conditions for treating PVDF membrane with primary antibody
   In the routine procedures, PVDF membrane is shaken in a 10- to 1000-fold dilution of primary antibody in TBST for 30-60 min.
   In the modified procedures, PVDF membrane is shaken in a 2000-fold dilution of the above-mentioned anti-peptide antibody in TBST for 60 min.

2) PVDF membrane washing conditions
   In the routine procedures, the membrane is washed 4 times with 200 ml of TBST solution for 15 min each time.
   In the modified procedures, the membrane is washed 5 times with 80 ml of TBST solution for 5 min each time.

3) Treatment of PVDF membrane with secondary antibody
   In the routine procedures, anti-IgG (H+L)-alkali phosphatase conjugate is diluted 200- to 2000-fold with a blocking solution, and then PVDF membrane is soaked and shaken for 30-60 min.
   In the modified procedures, PVDF membrane is soaked in a 4000-fold dilution of anti-IgG (H+L)-alkali phosphatase conjugate in TBST and shaken for 30 min.

4) Method of detection of antigen protein bands
   In the routine procedures, PVDF membrane washed with TBST and TBS is soaked in BCIP (4-bromo-4-chloro-3-indoxyl-phosphate)/NBT (nitro blue tetrazolium) mixture for 30 min for color formation.
   In the modified procedures, PVDF membrane washed with TBST and TBS is soaked in ProtoBlot II AP System with Stabilized Substrate Mouse solution (Promega, Madison, Wis.) for 20-40 sec for color formation.

The results of Western blot analysis are shown in FIG. 40. In FIG. 40, "M" represents the lane of molecular markers. "F", "GGF", "FGG", "GGFHDEL" and "GGF/YH1" represent those lanes in which proteins from pRS435F/YPH499, pRS435GGF/YPH499, pRS435FGG/YPH499, pRS435GGFHDEL/YPH499 and pRS435GGF/YH1, respectively, were electrophoresed.

When anti-BTS1-C mouse antibody that detects the polypeptide encoded by BTS1 was used, polypeptides corresponding to approx. 79 kDa fusion proteins (GGF, FGG and GGFHDEL, respectively) were detected (in FIG. 40, the bands showing the mobility marked with an open triangle). From these results, it was found that an FPP synthase-GGPP synthase fusion protein derived from ERG20-BTS1 fusion gene is actually expressed in pRS435GGF-transferred and pRS435GGFHDEL-transferred recombinants. Also, it was expected that the GGPP synthase encoded by BTS1 gene is expressed little in non-recombinant cells because no band was detected in the protein from YPH499.

When anti-ERG20-C mouse antibody that detects the polypeptide encoded by ERG20 was used, it was shown that the expression level of a protein having a molecular weight (approx. 40 kDa) corresponding to the FPP synthase encoded by ERG20 is elevated in pRS435F-transferred clone (lane "F") (the band showing the mobility marked with a filled triangle). In pRS435GGF-transferred clone (lane "GGF") and pRS435GGFHDEL-transferred clone (lane "GGFH-DEL"), polypeptides corresponding to fusion proteins (GGF and GGFHDEL) were detected (the bands showing the mobility corresponding to approx. 79 kDa; marked with an open triangle). The fusion gene that should be expressed in pRS435FGG-transferred clone was not detected with the anti-ERG20-C antibody. It is believed that this occurred because the anti-ERG20-C antibody that recognizes a C-terminal portion of FPP synthase could not recognize the fusion enzyme well since GGPP synthase is fused to the C-terminal of FPP synthase in the fusion enzyme. Of the other bands detected with the anti-ERG20-C antibody, an approx. 45 kDa band is believed to be a non-specifically detected protein. Less than 40 kDa bands are believed to be non-specifically detected proteins or degradation products of proteins comprising the amino acid sequence encoded by ERG20 gene.

EXAMPLE 14

GGOH Production When HMG-CoA Reductase Gene and GGF Fusion Gene are Co-Expressed In order to ascertain whether it is also possible to obtain industrially useful GGOH-producing clones from strains other than YPH499 (ATCC76625, MATa ura3-52 lys2-801 ade2-101 trp1Δ63 his3Δ200 leu2Δ2) by enhancing the expression of HMG-CoA reductase gene and BTS1-ERG20 fusion gene encoding GGPP synthase-FPP synthase fusion protein, the following strains were transformed with pRS434GAP-HMG1, pRS435GGF and pRS435GGFHDEL.
INVSc1 (MATa/MATα ura3-52/ura3-52 trp1-289/trp1-289 his3Δ1/his3Δ1 leu2/leu2)
YPH500 (ATCC76626, MATα ura3-52 lys2-801 ade2-101 trp1×63 his3Δ200 leu2Δ1)
YPH501 (ATCC6627, MATa/MATα ura3-52/ura3-52 lys2-801/lys2-801 ade2-101/ade2-101 trp1Δ63/trp1-Δ63 his3Δ200/his3Δ200 leu2Δ1/leu2Δ1)
W303-1A (ATCC208352, MATa leu2-3 leu2-112 his3-11 ade2-1 ura3-1 trp1-1 can1-100)
W303-1B (ATCC208353, MATα leu2-3 leu2-112 his3-11 ade2-1 ura3-1 trp1-1 can1-100)

Figure 41A:
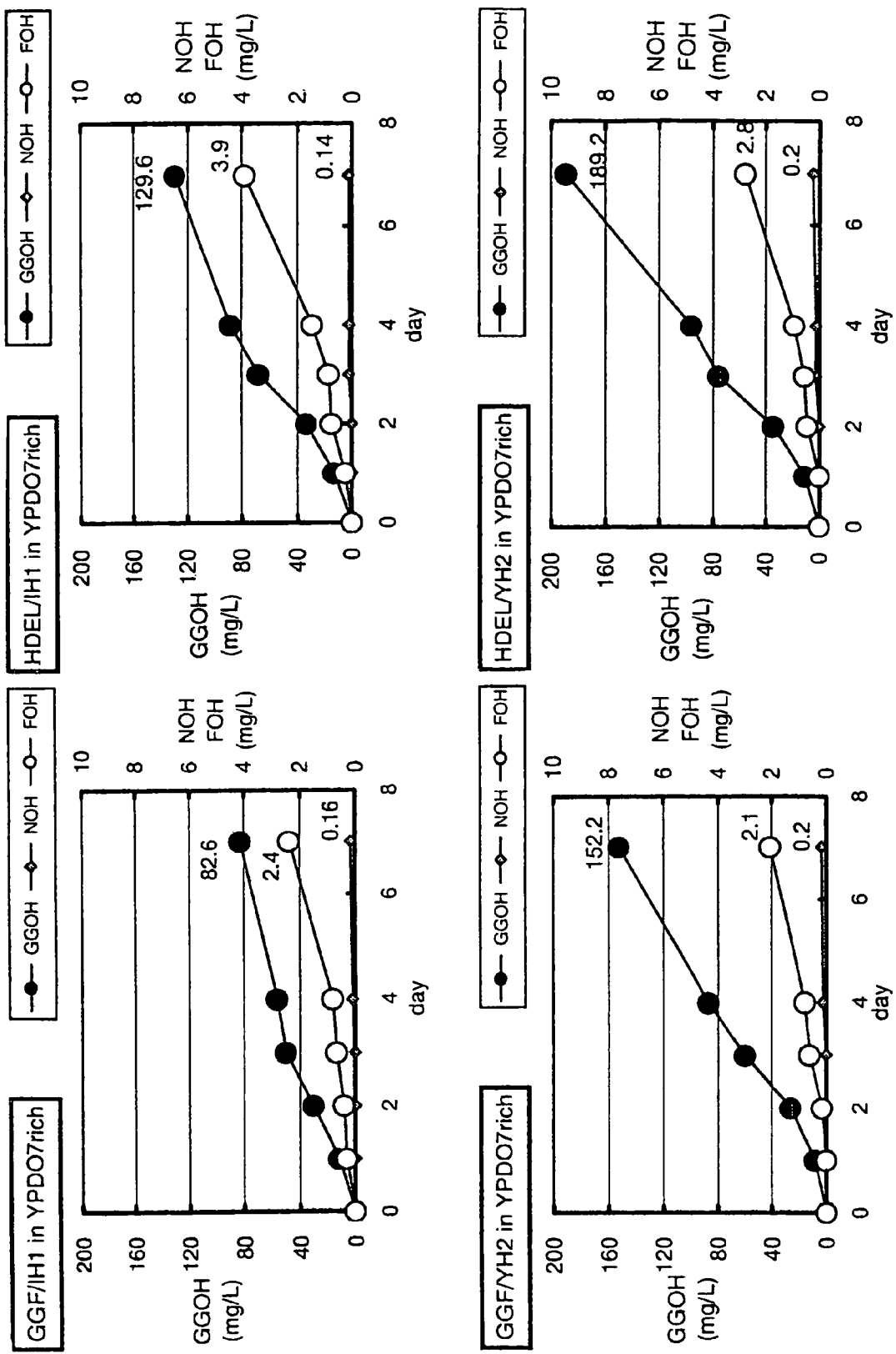
FIG. 41A presents graphs showing the results of determination of GGOH yields in clones co-expressing HMG-CoA reductase gene and a fusion gene composed of GGPP synthase gene and FPP synthase gene.
Figure 41B:
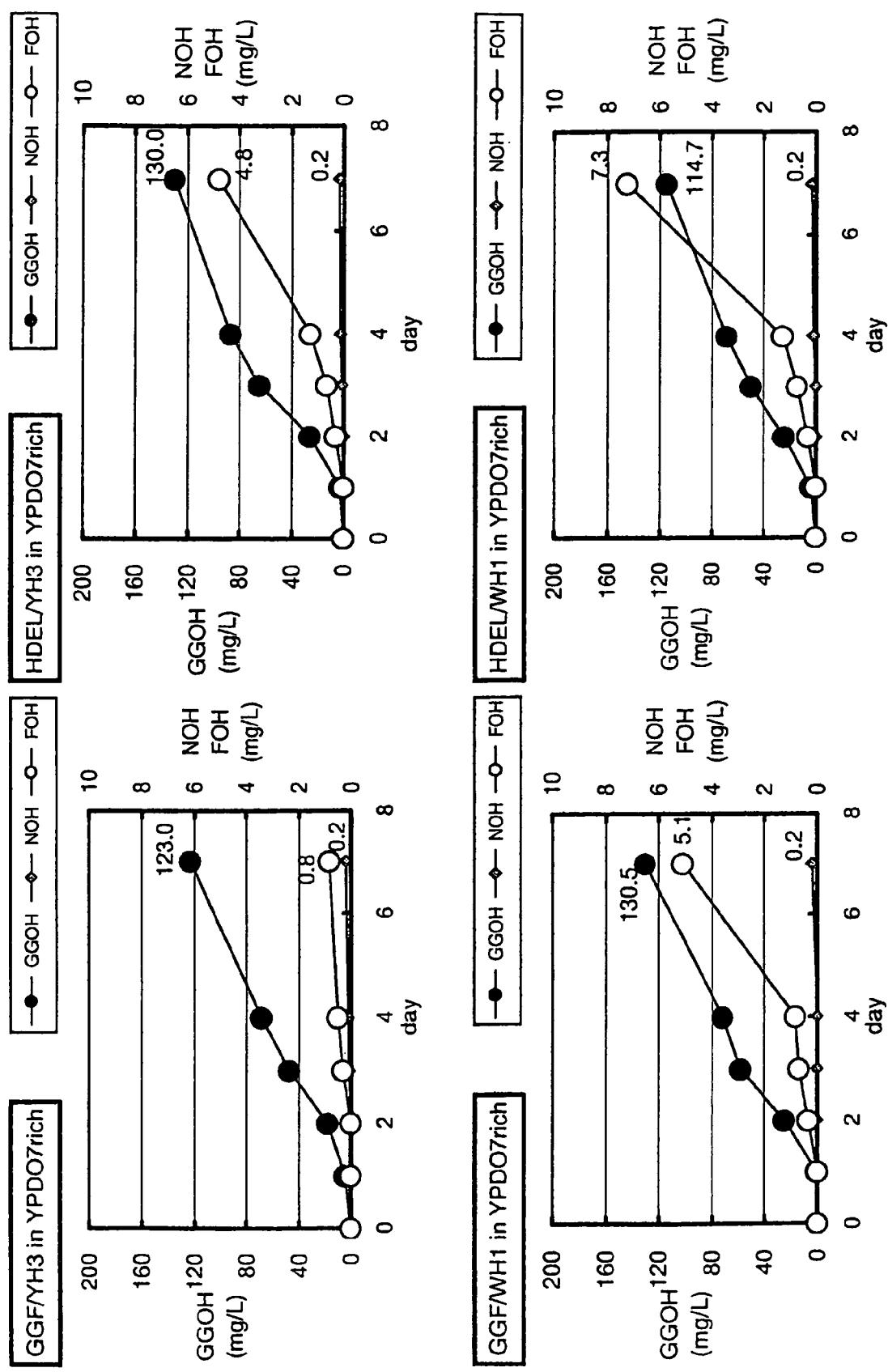
FIG. 41B presents graphs showing the results of determination of GGOH yields in clones co-expressing HMG-CoA reductase gene and a fusion gene composed of GGPP synthase gene and FPP synthase gene.
Figure 41C:
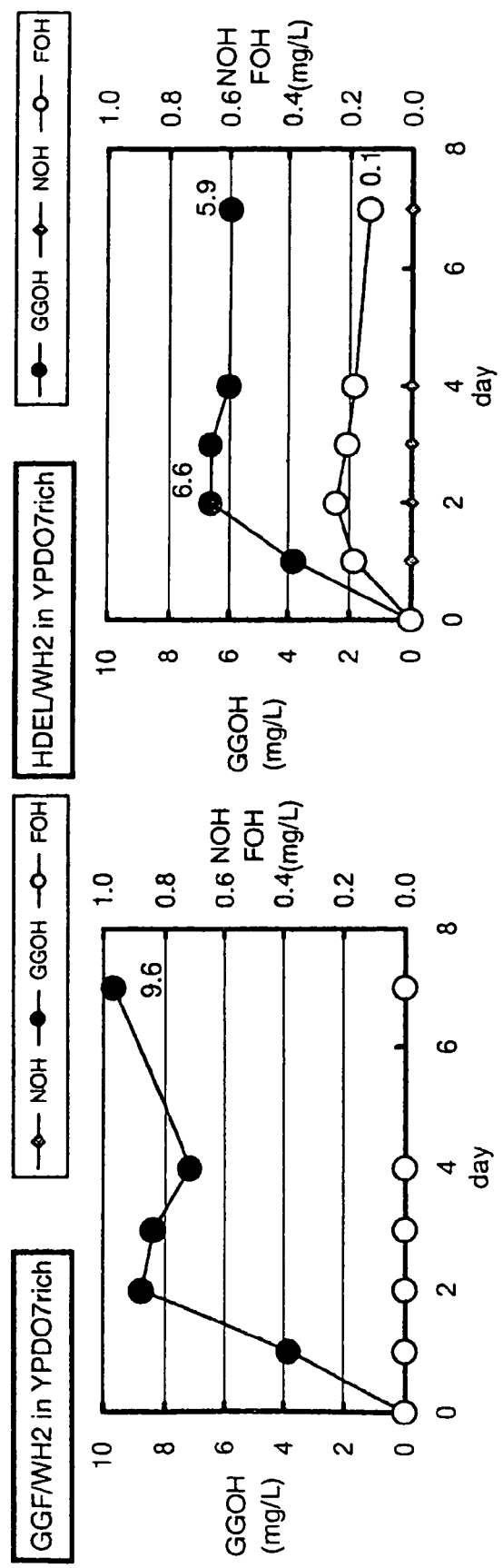
FIG. 41C presents graphs showing the results of determination of GGOH yields in clones co-expressing HMG-CoA reductase gene and a fusion gene composed of GGPP synthase gene and FPP synthase gene.

Briefly, pRS434GAP-HMG1 was transferred into INVSc1, YPH500, YPH501, W303-1A and W303-1B to prepare IH1, YH2, YH3, WH1 and WH2, respectively. Using these recombinants as hosts, pRS435GGF was transferred thereinto to obtain GGF/IH1, GGF/YH2, GGF/YH3, GGF/WH1 and GGF/WH2. Also, pRS435GGFHDEL was transferred into those hosts to obtain HDEL/IH1, HDEL/YH2, HDEL/YH3, HDEL /WH1 and HDEL/WH2. These recombinants were cultured in YPDO7rich medium, followed by determination of prenyl alcohol productivity. The results are shown in FIG. 41. Every recombinant produced GGOH preferentially, and most of them produced 100 mg/L or more of GGOH. In particular, HDEL/YH2 clone produced 189 mg/L of GGOH at the maximum.

EXAMPLE 15

GGOH Production When a Clone Co-Expressing HMG-Co Reductase Gene and GGF Fusion Gene is Converted into a Prototroph and then Diploidized A GGOH-producing clone GGF/YH1 was converted into a prototroph (a strain capable of growing without supplementation of specific nutrients to the medium) by replacing its mutant genes causing auxotrophy with corresponding wild-type genes, and then diploidized by mating with a YPH500-derived clone to thereby obtain GGF/YH3-AHKU clone. The preparation procedures are as described below.

(1) Introduction of HIS3 and ADE2 into GGF/YH1 and Introduction of LYS2 and URA3 into YPH500

A HIS3 fragment was prepared by PCR using pRS403GAP digested with PvuII and XhoI as a template and oligonucleotides HIS3-L (5' TTT TAA GAG CTT GGT GAG CGC 3' (SEQ ID NO: 123)) and HIS3-R (5' TCG AGT TCA AGA GAA AAA AAA 3' (SEQ ID NO: 124)) as primer DNAs under the following conditions.

| | |
|---|---|
| 0.1 μg/L Template DNA | 1 μL |
| 100 pmol Primer DNA 1 | 1 μL |
| 100 pmol Primer DNA 2 | 1 μL |
| 10x Pyrobest buffer | 10 μL |
| 2 mM dNTPmix | 8 μL |
| 5 u/μL Pyrobest DNA polymerase | 0.5 μL |
| $H_2O$ | 78.5 μL |

In the same manner, an URA3 fragment was prepared using pRS406GAP digested with PvuII and XhoI as a template and oligonucleotides URA3-L (5' TTC AAT TCA TCA TTT TTT TTT 3' (SEQ ID NO: 125)) and URA3-R (5' GGG TAA TAA CTG ATA TAA TTA 3' (SEQ ID NO: 126)) as primer DNAs.

An ADE2 fragment and a LYS2 fragment were also prepared under similar reaction conditions using A451 genomic DNA as a template and ADE-1 (5' ATG GAT TCT AGA ACA GTT GGT 3' (SEQ ID NO: 127)) and ADE-2 (5' TTA CTT GTT TTC TAG ATA AGC 3' (SEQ ID NO: 128)) or LYS-1 (5' ATG ACT AAC GAA AAG GTC TGG 3' (SEQ ID NO: 129)) and LYS-2 (5' TTA AGC TGC TGC GGA GCT TCC 3' (SEQ ID NO: 130)) as primer DNAs. The resultant HIS3 fragment and ADE2 fragment were introduced into pRS435GGF/YH1 successively to thereby obtain pRS435GGF/YH1-AH that exhibited non-histidine requirement and non-adenine requirement as phenotypes. On the other hand, the LYS2 fragment and URA3 fragment were introduced into YPH500 successively to thereby obtain YPH500-KU that exhibited non-lysine requirement and non-uracil requirement as phenotypes.

(2) Mating pRS435GGF/YH1-AH and YPH500-KU were cultured in YM medium at 30° C. and streaked onto DOB (dropout base) agar plate medium so that the two clones were crossed with each other. Then, the cells were incubated at 30° C. for 3 days. Colonies appearing on the plate were picked up and cultured on a presporulation plate medium (containing 1.6 g of yeast extract, 0.6 g of polypeptone, 100 ml of 20% glucose and 4 g of agar per liter), followed by cultivation on a sporulation plate medium (containing 2 g of potassium acetate, 0.2 g of yeast extract, 500μl of 20% glucose and 4 g of agar per liter). Sporulation was confirmed by microscopic observation. A clone was confirmed to have been converted into a prototroph because it grows on DOB plate (a minimum medium) and also confirmed to have been diploidized because it forms spores on the sporulation medium. This clone was designated GGF/YH3-AHKU.

EXAMPLE 16

GGOH Production by Fed-Batch Culture (1)

GGF/YH3-AHKU was subjected to fed-batch culture under the conditions described below, and GGOH yield was determined.

(1) Pre-seed Culture

The medium composition was as follows: yeast extract 5 g/L, malt extract 5 g/L, Bacto-Peptone 10 g/L, and glucose 5 g/L.

The pH of the medium was not adjusted. Fifty milliliters of the medium was placed in a 500 ml Sakaguchi flask and sterilized at 120° C. for 20 min. One platinum loopful of GGF/YH3-AHKU was scratched from a slant and cultured at 30° C. under reciprocal shaking at 120 rpm for 24 hr. OD (in 26-fold dilution, at 562 nm) reached 0.4.

(2) Seed Culture

The medium composition was as follows: glucose 20 g/L, MAMENO (Ajinomoto Co., Inc.) 310 mg/L (as calculated for the amount of total nitrogen), $KH_2PO_4$ 3 g/L, $MgSO_4$ 0.5 g/L, ammonium sulfate 5 g/L, $CaCl_2$ 0.5g/L, and defoaming agent 0.1 ml/L. If the total nitrogen concentration in MAMENO is 63 g/L, the amount of MAMENO per se added to the medium is 4.9 ml/L.

After dissolving the medium components completely, the pH of each component was adjusted to 5.0 with a KOH solution. After adjusting the liquid volume, each component was sterilized at 120° C. for 20 min.

A one liter mini-jar was used for seed culture. Three hundred milliliters of the medium was placed in the jar, to which 0.06-1 ml of the pre-seed culture was inoculated. Prior to the inoculation, the pH of the medium was adjusted to 5.5. Aeration rate was ½ vvm, and the temperature was set at 30° C. The pH was controlled to 5.5 with ammonia. Agitation, which started at 500 rpm, was put under cascade control so that dissolved oxygen (DO) was >20%. Seed culture was terminated at the time point when pH rose. OD (in 51-fold dilution, at 562 nm) reached to 0.18-0.2. The amount of dissolved oxygen mentioned above was calculated taking the amount at saturation as 100%.

(3) Main Culture

The medium composition was as shown in Table 12 below. The liquid volumes of plot A, plot B, plot C and plot D to the total volume of main culture were 20%, 20%, 30% and 20%, respectively. Corn steep liquor (CSL) was treated with sulfuric acid to adjust the pH to 2.0 and then pre-sterilized at 80° C. for 1 hr. The concentration of CSL appearing in Table 12 is expressed in terms of the amount of total nitrogen. CSL per se is added at 31.4 g/L to give this concentration. Each plot was sterilized at 120° C. for 20 min and mixed together. After adjustment of the liquid volume, the mixture was put into a vessel.

TABLE 12

| Component | Concentration | Plot |
| --- | --- | --- |
| Glucose | 2 g/l | Plot A |
| $MgSO_4$ | 1.7 g/l | Plot B |
| Ammonia sulfate | 3 g/l | |
| $KH_2PO_4$ | 10 g/l | |

TABLE 12-continued

| Component | Concentration | Plot |
| --- | --- | --- |
| CSL | 2.3 g/l | Plot C |
| Defoaming agent | 0.26 ml/l | |
| $H_2SO_4$ | pH = 2.0 | |
| Pre-sterilization | 80° C. × 60 min | |
| $CaCl_2$ | 0.7 g/l | Plot D |

Figure 42:
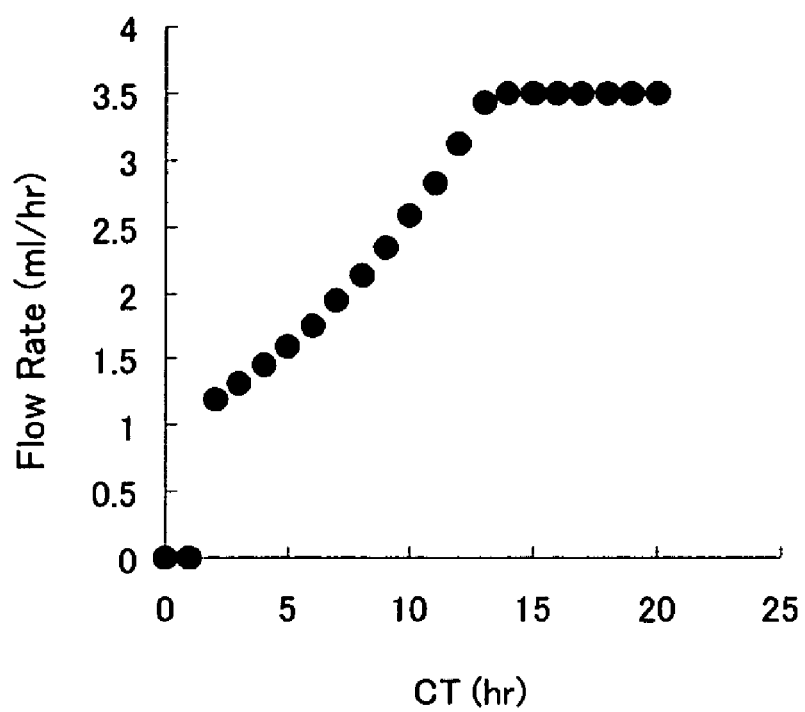
FIG. 42 is a graph showing flow rate conditions of a feed solution.

A one liter mini-jar was used for main culture. The total volume of main culture in the jar was made 300 ml by adding 10% seed culture to the above mixture. Since the pH of the medium after sterilization was around 2.6, it was raised prior to seed inoculation. Aeration rate was ½ vvm, and the temperature was set at 30° C. The pH was controlled to 5.5 with ammonia. Agitation, which started at 500 rpm, was put under cascade control so that dissolved oxygen (DO) was >20%. The feeding of glucose was started 2 hr after the start of cultivation, and conducted in such a manner that the flow rate was increased gradually, as shown in FIG. 42. The maximum flow rate was 3.5 ml/hr, which corresponds to approx. 5.8 g of glucose/L/hr. When it was difficult to secure sufficient dissolved oxygen (DO>20%) by agitation, aeration volume was increased. About 20 hours after the start of cultivation, the predetermined amount of feed was fed. At this time, OD (in 101-fold dilution at 562 nm) reached 0.9-1.0.

Thereafter, feed and other parameters were changed according to culture conditions.

(4) Examination of Culture Conditions

Cells were grown under the same conditions up to 20 hr after the start of cultivation, and then effects of glucose and ethanol upon GGOH production were examined.

Briefly, 400 g/L of ethanol solution (plot 1) and 500 g/L of glucose solution (plot 2) were fed to the culture. Further, the ethanol solution of plot 1 and the glucose solution of plot 2 were mixed 1:1 to prepare plot 3. The flow rate of feed solutions was set at 3.5 ml/hr at the maximum, and controlled so that the substrate concentration in the culture broth was 1.0 g/L or less. The amounts of accumulated GGOH are shown in Table 13. It was found that GGOH accumulation increases by feeding ethanol as a carbon source.

TABLE 13

| | GGOH accumulation (g/l) |
| --- | --- |
| Plot 1 | 1.16 |
| Plot 2 | 0.47 |
| Plot 3 | 0.58 |

EXAMPLE 17

GGOH Production by Fed-Batch Culture (2)

GGF/YH3-AHKU clone was inoculated into 200 ml of DOB (dropout base) glucose minimum medium (Q·BIOgene, Carlsbad, Calif.) and cultured at 30° C. under rotating for 3 days. Subsequently, the total volume of the resultant culture was inoculated into 3.35 L of a medium (preadjusted to pH 5.5 with aqueous ammonia) containing 0.09% glucose, 0.075% $KH_2PO_4$, 0.14% magnesium sulfate, 0.45% ammonium sulfate, 5.4% corn steep liquor, 0.031% calcium chloride and 0.15% ADEKANOL LG109 (Asahi Denka), and cultured under the conditions described below. Bach culture was conducted using Jar 1, Jar 2 and Jar 3.

Cultivation apparatus: MSJ-U2W (10 L fermenter) (B. E. Marubishi, Chiyoda-ku, Tokyo)

Cultivation temperature: 33° C.

Aeration rate: 0.74 vvm

Agitation rate: 900 rpm pH 5.5 (adjusted with 4 N sodium hydroxide solution and 2 N hydrochloric acid solution)

Four hours after the start of cultivation, feeding of 40% glucose solution was started. Twenty-one hours after the start of cultivation, the feed solution to Jar 2 was changed to 40% glucose+3.3% ammonium acetate solution; and the feed solution to Jar 3 was changed to 1.65% ammonium acetate+50% ethanol+20% glucose solution. Then, cells were cultured further. Culture broth samples were taken aseptically to analyze and quantitatively determine prenyl alcohols in the same manner as in Example 8. In order to maintain the sugar concentration in the medium at 0.1% or below, the feeding rate was adjusted (18.7 g/h at the maximum).

The results revealed that this method minimizes the generation of FOH and enables efficient production of GGOH by microorganisms (Table 14). By feeding ethanol and ammonium acetate in addition to glucose, GGOH concentration in the medium reached 2.5 g/L.

TABLE 14

| | Cultivation period (hr) | | | | | |
|---|---|---|---|---|---|---|
| | 0 | 21 | 45 | 69 | 93 | 117 | 165 |
| Jar 1 (Feed solution: 40% glucose) | | | | | | |
| FOH(mg/L) | 0.0 | 2.0 | 1.0 | 8.0 | 19 | 24 | 23 |
| GGOH(mg/L) | 0.0 | 27 | 35 | 190 | 660 | 840 | 890 |
| OD600 | 0.0 | 52 | 86 | 93 | 120 | 120 | 110 |

TABLE 14-continued

| | Cultivation period (hr) | | | | | |
|---|---|---|---|---|---|---|
| | 0 | 21 | 45 | 69 | 93 | 117 | 165 |
| Jar 2 (Feed solution: 40% glucose, 3.3% ammonium acetate) | | | | | | |
| FOH(mg/L) | 0.0 | 1.0 | 1.0 | 1.0 | 0.3 | 0.8 | 5.0 |
| GGOH(mg/L) | 0.0 | 26 | 56 | 120 | 37 | 100 | 710 |
| OD600 | 0.0 | 49 | 91 | 120 | 120 | 120 | 170 |
| Jar 3 (Feed solution: 20% glucose, 1.65% ammonium acetate, 50% ethanol) | | | | | | |
| FOH(mg/L) | 0.0 | 2.0 | 4.0 | 17 | 33 | 38 | 77 |
| GGOH(mg/L) | 0.0 | 30 | 210 | 550 | 830 | 1000 | 2500 |
| OD600 | 0.0 | 63 | 160 | 160 | 120 | 140 | 120 |

All publications, patents and patent applications cited herein are incorporated herein by reference in their entity.

INDUSTRIAL APPLICABILITY

According to the present invention, methods of producing prenyl alcohols are provided. Since it is possible to obtain prenyl alcohols (in particular geranylgeraniol) in large quantities according to the present invention, they can be utilized for the production of substances important in vivo and also utilized as reagents for discovering novel physiological activities of active prenyl alcohols. Thus, the methods of the invention are useful.

Sequence Listing Free Text

SEQ ID NO: 24: synthetic peptide
SEQ ID NOS: 25-120: synthetic DNA
SEQ ID NO: 121: synthetic peptide
SEQ ID NO: 122: synthetic peptide
SEQ ID NOS: 123-130: synthetic DNA

The invention claimed is:

1. A method of producing a geranylgeraniol in a yeast host, wherein the concentration of said geranylgeraniol accumulated in a culture is at least 0.1 g/L, said method comprising creating a recombinant by transferring into the host:

(a) a recombinant DNA for expression or a DNA for genomic integration each comprising a fusion gene comprising in the following order (i) a geranylgeranyl diphosphate (GGPP) synthase gene encoding a polypeptide having the amino acid sequence set forth in SEQ ID NO:6 or a polypeptide having GGPP synthase activity and an amino acid sequence derived from the amino acid sequence set forth in SEQ ID NO:6 by deletion, substitution, or addition of from one to ten amino acids, and (ii) a farnesyl diphosphate (FPP) synthase gene encoding a polypeptide having the amino acid sequence set forth in SEQ ID NO:2 or 4 or a polypeptide having FPP synthase activity and an amino acid sequence derived from the amino acid sequence set forth in SEQ ID NO:2 or 4 by deletion, substitution, or addition of from one to ten amino acids, and (b) a recombinant DNA for expression or a DNA for genomic integration each comprising a hydroxymethylglutaryl-CoA (HMG-CoA) reductase gene encoding a polypeptide having the amino acid sequence set forth in SEQ ID NO:10 or a polypeptide having HMG-CoA reductase activity and an amino acid sequence derived from the amino acid sequence set forth in SEQ ID NO:10 by deletion, substitution, or addition of from one to ten amino acids, culturing the resultant recombinant, and recovering the geranylgeraniol from the resultant culture.

2. The method according to claim 1, wherein the fusion gene further comprises a nucleotide sequence encoding a peptide of amino acid sequence His-Asp-Glu-Leu as set forth in SEQ ID NO:24.

3. A method of producing a geranylgeraniol according to claim 1, comprising culturing the yeast using a medium comprising:

(i) a mixture of
(a) a carbon source component comprising a sugar and/or an alcohol,
(b) a nitrogen source component comprising ammonia gas, aqueous ammonia and/or an ammonium salt, and
(c) inorganic salts assimilable by the yeast;
(ii) a mixture of $KH_2PO_4$, magnesium sulfate, ammonium sulfate, corn steep liquor, calcium chloride and a surfactant; or
(iii) a mixture of (i) and (ii);
and recovering the geranylgeraniol from the resultant culture.

4. The method according to claim 1, wherein the host is cultured using a feed solution comprising the following component (i), (ii) or (iii) or a mixture of two or more of said components:

(i) a sugar
(ii) an alcohol
(iii) ammonia gas, aqueous ammonia and/or an ammonium salt.

5. The method according to claim 1, wherein the host is cultured using a feed solution which comprises a carbon source component consisting of glucose alone up to 12-24 hours after the start of cultivation, and then the carbon source component is shifted to a component containing ethanol.

6. The method according to claim 5, wherein the ratio of ethanol to the total carbon source component of the feed solution is 50% or more after 12-24 hours after the start of cultivation.

7. The method according to claim 3, wherein the host is cultured using a feed solution which comprises a carbon source component consisting of ethanol alone after 12-24 hours after the start of cultivation.

8. The method according to claim 3, wherein the concentration of said geranylgeraniol accumulated in the culture is at least 1 g/L.

9. The method according to claim 3, wherein the host is *Saccharomyces cerevisiae*.

10. The method according to claim 9, wherein the *Saccharomyces cerevisiae* is *Saccharomyces cerevisiae* A451 strain, YPH499 strain, YPH500 strain, W303-1A strain or W303-1B strain, or a strain derived from any one of said strains.

11. The method according to claim 3, wherein the host is a prototroph.

12. The method according to claim 3, wherein the host is a diploid cell.

13. The method according to claim 3, wherein the host is a prototroph and a diploid cell.

14. The method according to claim 3, wherein the pH of the medium is controlled.

15. The method according to claim 14, wherein the pH control is carried out using ammonium gas, an ammonium salt solution, a sodium hydroxide solution or sulfuric acid.

16. The method according to claim 1, wherein the hydroxymethylglutaryl-CoA reductase gene encodes a hydroxymethylglutaryl-CoA reductase including a transmembrane domain.

* * * * *